US012790308B2

(12) United States Patent
Del Valle et al.

(10) Patent No.: US 12,790,308 B2
(45) Date of Patent: Nov. 10, 2026

(54) INHIBITORS OF THE IRE-1/XBP-1 PATHWAY AND METHODS OF USING THEREOF

(71) Applicant: H. LEE MOFFITT CANCER CENTER AND RESEARCH INSTITUTE, INC., Tampa, FL (US)

(72) Inventors: Juan R. Del Valle, Tampa, FL (US); Chih-Chi Andrew Hu, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 0 days.

(21) Appl. No.: 18/402,910

(22) Filed: Jan. 3, 2024

(65) Prior Publication Data

US 2024/0294487 A1 Sep. 5, 2024

Related U.S. Application Data

(63) Continuation of application No. 16/356,318, filed on Mar. 18, 2019, now Pat. No. 11,945,789, which is a (Continued)

(51) Int. Cl.

| | |
|---|---|
| ***A61K 9/00*** | (2006.01) |
| ***A01K 67/0276*** | (2024.01) |
| ***A61K 31/37*** | (2006.01) |
| ***A61K 31/395*** | (2006.01) |
| ***A61K 31/436*** | (2006.01) |
| ***A61K 31/519*** | (2006.01) |
| ***A61K 31/52*** | (2006.01) |
| ***A61K 31/55*** | (2006.01) |

(Continued)

(52) U.S. Cl.

CPC ........ *C07D 311/16* (2013.01); *A01K 67/0276* (2013.01); *A61K 31/37* (2013.01); *A61K 31/395* (2013.01); *A61K 31/436* (2013.01); *A61K 31/519* (2013.01); *A61K 31/52* (2013.01); *A61K 31/55* (2013.01); *A61K 33/243* (2019.01); *A61K 45/06* (2013.01); *C07D 311/18* (2013.01); *C07D 491/052* (2013.01); *A01K 2217/075* (2013.01); *A01K 2217/077* (2013.01); *A01K 2227/105* (2013.01); *A01K 2267/0331* (2013.01)

(58) Field of Classification Search

CPC .................................................... A61K 33/243

See application file for complete search history.

(56) References Cited

U.S. PATENT DOCUMENTS

| | | | |
|---|---|---|---|
| 4,404,138 | A | 9/1983 | Connor et al. |
| 4,493,719 | A | 1/1985 | Wintermantel et al. |

OTHER PUBLICATIONS

Shiraish, Highly sensitive cyanide anion detection with a coumarin-spiropyran conjugate as a fluorescent receptor, Chem. Commun., 2011, 47, 4953-4955 (Year: 2011).*

(Continued)

*Primary Examiner* — Paul W Dickinson

(74) *Attorney, Agent, or Firm* — Meunier Carlin & Curfman LLC

(57) ABSTRACT

Disclosed are XBP-1/IRE-1 inhibitors having formula disclosed herein. Methods of making and using these inhibitors for the treatment of cancer, in particular B cell cancers, are also disclosed. Also disclosed is a genetic XBP-1-knockout cancer mouse model.

13 Claims, 67 Drawing Sheets

Specification includes a Sequence Listing.

Related U.S. Application Data continuation of application No. 14/786,561, filed as application No. PCT/US2014/035164 on Apr. 23, 2014, now Pat. No. 10,323,013.

(60) Provisional application No. 61/975,563, filed on Apr. 4, 2014, provisional application No. 61/875,080, filed on Sep. 8, 2013, provisional application No. 61/814,883, filed on Apr. 23, 2013.

(51) Int. Cl.

| | |
|---|---|
| ***A61K 33/243*** | (2019.01) |
| ***A61K 45/06*** | (2006.01) |
| ***C07D 311/16*** | (2006.01) |
| ***C07D 311/18*** | (2006.01) |
| ***C07D 491/052*** | (2006.01) |

(56) References Cited

OTHER PUBLICATIONS

Advani, R.H., et al. Bruton tyrosine kinase inhibitor ibrutinib (PCI-32765) has significant activity in patients with relapsed/refractory B-cell malignancies. *J Clin Oncol* 31, 88-94 (2013).
Bertilaccio, M.T., et al. Xenograft models of chronic lymphocytic leukemia: problems, pitfalls and future directions. *Leukemia* 27, 534-540 (2013).
Bichi, R., et al. Human chronic lymphocytic leukemia modeled in mouse by targeted TCL1 expression. *Proc Natl Acad Sci U S A* 99, 6955-6960 (2002).
Blažević, N., et al. Hexamethylenetetramine, a versatile reagent in Organic Synthesis. *Synthesis*, 161-176 (1979).
Boes, M., et al. Enhanced B-1 Cell Development, But Impaired IgG Antibody Responses in Mice Deficient in Secreted IgM. *J Immunol* 160, 4776-4787 (1998).
Burger, J.A. & Buggy, J.J. Bruton tyrosine kinase inhibitor ibrutinib (PCI-32765). *Leuk Lymphoma* (2013).
Byrd, J.C., et al. Targeting BTK with Ibrutinib in Relapsed Chronic Lymphocytic Leukemia. *The New England Journal of Medicine* 369, 32-42 (2013).
Calfon, M., et al. IRE1 couples endoplasmic reticulum load to secretory capacity by processing the XBP-1 mRNA. *Nature* 415, 92-96 (2002).
Capitani, N., et al. S1P1 expression is controlled by the pro-oxidant activity of p66Shc and is impaired in B-CLL patients with unfavorable prognosis. *Blood* 120, 4391-4399 (2012).
Carrasco, D.R., et al. The Differentiation and Stress Response Factor XBP-1 Drives Multiple Myeloma Pathogenesis. *Cancer Cell* 11, 349-360 (2007).
Chou, T.C. Theoretical Basis, Experimental Design, and Computerized Simulation of Synergism and Antagonism in Drug Combination Studies. *Pharmacol Rev* 58, 621-681 (2006).
Cross, B.C., et al. The molecular basis for selective inhibition of unconventional mRNA splicing by an IRE1-binding small molecule. *Proc Natl Acad Sci U S A* 109, E869-878 (2012).
Ellgaard, L. & Helenius, A. Quality Control in the Endoplasmic Reticulum. *Nat Rev Mol Cell Biol* 4, 181-191 (2003).
Feldman, D. E., et al. The Unfolded Protein Response: A Novel Component of the Hypoxic Stress Response in Tumors. *Mol. Cancer Res.* 2005, 3, 597-605 (2005).
Gangadhar (Synthesis, spectral characterization, electrochemical and biological studies of Co(II), Ni(II) and Cu(II) complexes with thiocarbohydrazone, Journal of Coordination Chemistry, 2008, 61(17), 2793-2806. (Year: 2008).
Gururajan, M., et al. Cutting Edge: Constitutive B Cell Receptor Signaling Is Critical For Basal Growth of B Lymphoma. *J Immunol* 176, 5715-5719 (2006).
Hamblin, T.J. The TCL1 mouse as a model for chronic lymphocytic leukemia. *Leuk Res* 34, 135-136 (2010).
Herling, M., et al. TCL1 shows a regulated expression pattern in chronic lymphocytic leukemia that correlates with molecular subtypes and proliferative state. *Leukemia* 20, 280-285 (2006).
Hertlein, E., et al. 17-DMAG targets the nuclear factor-κB family of proteins to induce apoptosis in chronic lymphocytic leukemia: clinical implications of HSP90 inhibition. *Blood* 116, 45-53 (2010).
Hetz, C., et al. Targeting the unfolded protein response in disease. *Nat. Rev. Drug Discovery*, 12, 703-19 (2013).
Hu, C., et al. XBP-1 regulates signal transduction, transcription factors and bone marrow colonization in B cells. *EMBO J.*, 28, 1624-36 (2009).
Huang, Access to a large stokes shift in functionalized fused coumarin derivatives by increasing the geometry relaxation upon photoexcitation: An experimental and theoretical study, Dyes and Pigments,2012, 95, 732-742 (Year: 2012).
Huang, et al., "Study on the Anticancer Activity of Coumarin Derivatives by Molecular Modeling", Chem. Biol. Drug. Des., 2011, 78, 651-658.
International Search Report and Written Opinion for PCT/US2014/035164 dated Sep. 29, 2014.
International Preliminary Report on Patentability dated Oct. 27, 2015, from International Application No. PCT/US2014/035164 filed Apr. 23, 2014, 5 pages.
Johnson, A.J., et al. Characterization of the TCL-1 transgenic mouse as a preclinical drug development tool for human chronic lymphocytic leukemia. *Blood* 108, 1334-1338 (2006).
Kriss, C.L., et al. Overexpression of TCL1 activates the endoplasmic reticulum stress response: a novel mechanism of leukemic progression in mice. *Blood* 120, 1027-1038 (2012).
Laine, J., et al. The Protooncogene TCL1 Is an Akt Kinase Coactivator. *Mol Cell* 6:395-407.(2000).
Lapalombella, R., et al. Selective inhibitors of nuclear export show that CRM1/XPO1 is a target in chronic lymphocytic leukemia. *Blood* 120, 4621-4634 (2012).
Lucas, D.M., et al. The novel plant-derived agent silvestrol has B-cell selective activity in chronic lymphocytic leukemia and acute lymphoblastic leukemia in vitro and in vivo. *Blood* 113, 4656-4666 (2009).
Luo, J., et al. Principles of Cancer Therapy: Oncogene and Non-Oncogene Addiction. *Cell* 2009, 136, 823-37.
Martinon, F., et al. Toll-like receptor activation of XBP1 regulates innate immune responses in macrophages. *Nat. Immunol.* 2010, 11, 411-18.
Mimura, N., et al. Blockade of XBP1 splicing by inhibition of IRE1α is a promising therapeutic option in multiple myeloma. *Blood* 119, 5772-5781 (2012).
Ogata, Y., et al. Kinetics and Mechanism of the Duff Reaction. *Tetrahedron* 1968, 24, 5001-5010.
Pan Z., et al. Discovery of Selective Irreversible Inhibitors for Bruton's Tyrosine Kinase. *ChemMedChem* 2, 58-61 (2007).
Papandreou, I., et al. Identification of an Ire1alpha endonuclease specific inhibitor with cytotoxic activity against human multiple myeloma. *Blood* 117, 1311-1314 (2011).
Pekarsky, Y., et al. Tcl1 enhances Akt kinase activity and mediates its nuclear translocation. *Proc Natl Acad Sci U S A* 97:3028-3033 (2000).
Ponader, S., et al. The Bruton tyrosine kinase inhibitor PCI-32765 thwarts chronic lymphocytic leukemia cell survival and tissue homing in vitro and in vivo. *Blood* 119, 1182-1189 (2012).
PubChem Compound Summary for CID 10899435, Create date Oct. 26, 2006, retrieved on Aug. 28, 2014 from <URL:https://pubchem.ncbi.nlm.nih.gov/summary/summary.cgi?cid=10899435&loc=ec_rcs>.
Ri, M., et al. Identification of Toyocamycin, an agent cytotoxic for multiple myeloma cells, as a potent inhibitor of ER stress-induced XBP1 mRNA splicing. *Blood Cancer J.* (2012).
Romero-Ramirez, L, et al. XBP1 is Essential for Survival under Hypoxic Conditions and Is Required for Tumor Growth. *Cancer Res.* 64, 5943-7 (2004).
Rutkowsi, D. T., et al. Regulation of basal cellular physiology by the homeostatic unfolded protein response. *J. Cell Biol.*, 189, 783-94. (2010).

(56) References Cited

OTHER PUBLICATIONS

Sawant, Synthesis and Characterization of Transition Metal Complexes of Novel Schiff Base 8-[(Z)-{[3-(N-Methylamino) Propyl] Imino}Methyl]-7-Hydroxy-4-Methyl-2H-Chromen-2-One][Nmapimhmc] and Their Biological Activities, International Journal of Research in Pharmacy and Chemistry, 3(3), 2013, 636-644 (Year: 2013).
Shen, X., et al. Complementary Signaling Pathways Regulate the Unfolded Protein Response and Are Required For C. Elegans Development. *Cell* 107, 893-903 (2001).
Singh, J., et al. The resurgence of covalent drugs. *Nat. Rev. Drug Discovery* 10, 307-17 (2011).
Suljagic, M., et al. The Syk inhibitor fostamatinib disodium (R788) inhibits tumor growth in the Eμ-TCL1 transgenic mouse model of CLL by blocking antigen-dependent B-cell receptor signaling. *Blood* 116, 4894-4905 (2010).
Todd, D. J., et al. XBP1 governs late events in plasma cell differentiation and is not required for antigen-specific memory B cell development. *J. Exp. Med.* 206, 2151-9 (2009).
Tomasio, S., et al. Selective inhibition of the unfolded protein response: targeting catalytic sites for Schiff base modification. *Mol. Biosys.* 9, 2408-16 (2013).
Volkmann, K., et al. Potent and Selective Inhibitors of the Inositol-requiring Enzyme 1 Endoribonuclease. *J Biol Chem* 286, 12743-12755 (2011).
Walter, P. et al. The Unfolded Protein Response: From Stress Pathway to Homeostatic Regulation. *Science* 334, 1081-6. (2011).
Wang et al. “Endoplasmic reticulum stress response in cancer: molecular mechanism and therapeutic potential” Am J Transl Res 2(1):65-74 (2010).
Wang, L., et al. Divergent allosteric control of the IREIα endoribonuclease using kinase inhibitors. *Nat. Chem. Biol.*, 8, 982-9 (2012).
Wang, M.L., et al. Targeting BTK with Ibrutinib in Relapsed or Refractory Mantle-Cell Lymphoma. *The New England Journal of Medicine* 369, 507-516 (2013).
Wang, S., et al. The impact of the unfolded protein response on human disease. *J. Cell Biol.*, 197, 857-67 (2012).
Wiseman, R.L., et al. Flavonol activation defines an unanticipated ligand-binding site in the kinase-RNase domain of IRE1. *Mol Cell* 38, 291-304 (2010).
Woyach, J., et al. The B-cell receptor signaling pathway as a therapeutic target in CLL. *Blood* 120, 1175-1184 (2012).
Yan, X.J., et al. B cell receptors in TCL1 transgenic mice resemble those of aggressive, treatment-resistant human chronic lymphocytic leukemia. *Proc Natl Acad Sci U S A* 103, 11713-11718 (2006).
Yoshida, H., et al. XBP1 mRNA Is Induced by ATF6 and Spliced by IRE1 in Response to ER Stress to Produce a Highly Active Transcription Factor. *Cell* 107, 881-891 (2001).
Yu, C., et al. Flavivirus Infection Activates the XBP1 Pathway of the Unfolded Protein Response To Cope with Endoplasmic Reticulum Stress. *J. Virol.*, 80, 11868-80 (2006).
Zanesi, N., et al. Effect of Rapamycin on Mouse Chronic Lymphocytic Leukemia and the Development of Nonhematopoietic Malignancies in Eμ-TCL1 Transgenic Mice. *Cancer Res* 66, 915-920 (2006).
Zenz, T., et al From pathogenesis to treatment of chronic lymphocytic leukaemia. *Nat Rev Cancer* 10, 37-50 (2010).

* cited by examiner

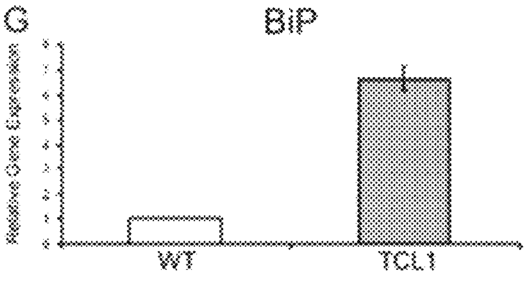

Figure 6G

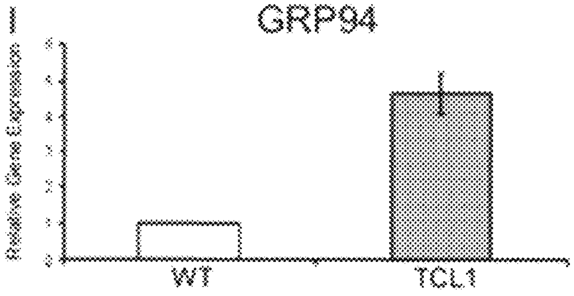

Figure 6I

K. Sequences of primers used for quantitative real-time PCR

| | | |
|---|---|---|
| IRE-1+ | AGC GCT GTG GAT ATC TTC TCC | (SEQ ID NO:11) |
| IRE-1- | ACC TTG TCA TGG GTC TCT TCC | (SEQ ID NO:12) |
| XBP-1t+ | TGG CCG GGT CTG CTG AGT CCG | (SEQ ID NO:13) |
| XBP-1t- | GTC CAT GGG AAG ATG TTC TGG | (SEQ ID NO:14) |
| XBP-1s+ | CTG AGT CCG AAT CAG GTG CAG | (SEQ ID NO:15) |
| XBP-1s- | GTC CAT GGG AAG ATG TTC TGG | (SEQ ID NO:16) |
| Derlin-1+ | AGC TGA ACA GAG ACC TGA TCG | (SEQ ID NO:17) |
| Derlin-1- | AAT TCC TTC CTC CCA AGT CC | (SEQ ID NO:18) |
| Derlin-2+ | TAA TGC TGG TCT ACG TGT GG | (SEQ ID NO:19) |
| Derlin-2- | ATG TGC CCA ACT GCA ATA CC | (SEQ ID NO:20) |
| Derlin-3+ | CAC CAC CTT CCT CTT CTT CG | (SEQ ID NO:21) |
| Derlin-3- | CTA ACA GGT CTG TGA CAA CCG | (SEQ ID NO:22) |
| BiP+ | TCA TCG GAC GCA CTT GGA A | (SEQ ID NO:23) |
| BiP- | CAA CCA CCT TGA ATG GCA AGA | (SEQ ID NO:24) |
| PDI+ | CAA GAT CAA GCC CCA CCT GAT | (SEQ ID NO:25) |
| PDI- | AGT TCG CCC CAA CCA GTA CTT | (SEQ ID NO:26) |
| GRP94+ | TGG GCC TCT GCT GTG TCC TGC | (SEQ ID NO:27) |
| GRP94- | GGC TTT TAC CCA GGT CCT CTT CCA CTG | (SEQ ID NO:28) |

Figure 6K

A-106
A-107
STF-083010(STF)
B-A05

C
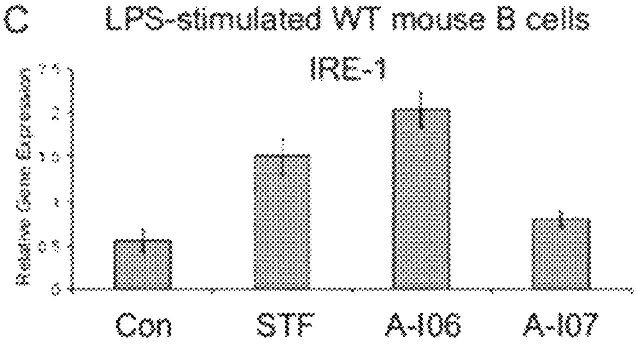
Figure 11C
D
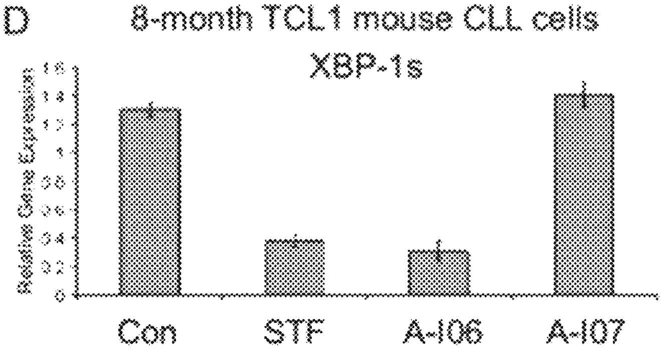
Figure 11D
E
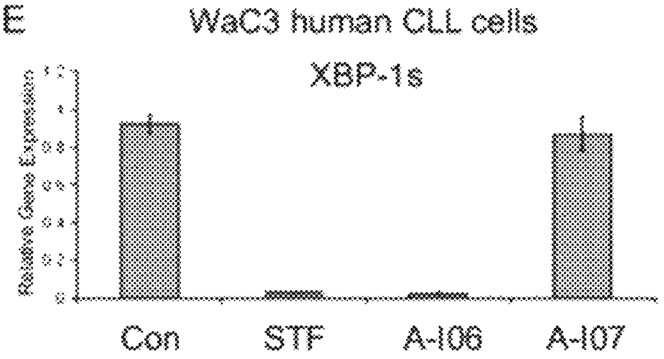
Figure 11E
F
Human XBP-1s+:
CTG AGT CCG AAT CAG GTG CAG (SEQ ID NO:29)
Human XBP-1s-:
ATC CAT GGG GAG ATG TTC TGG (SEQ ID NO:30)
Figure 11F

8

9

10

11

12

13

14

15

16

| compound | $IC_{50}$ (nM) | 95% CI (nM) |
|---|---|---|
| **1** | 9939 | (3692 - 26760) |
| **2** | 9732 | (5057 - 18730) |
| **5** | 206 | (142 - 297) |
| **8** | >20000 | - |
| **9** | >20000 | - |
| **10** | >20000 | - |
| **11** | >20000 | - |
| **12** | >20000 | - |
| **13** | >20000 | - |
| **14** | >20000 | - |
| **15** | >20000 | - |
| **16** | >20000 | - |

17a-d 21a-d 20a-d 19a-d

| substrate | conditions[a] | product | % yield |
|---|---|---|---|
| **19a** | A | **20a** | 4 |
| **19a** | B | **20a** | 4 |
| **19a** | C | **20a** | 4 |
| **19b** | A | **20b** | 10 |
| **19b** | B | **21b** | 22 |
| **19b** | C | **21b** | 41 |
| **19c** | A | **20c** | 13 |
| **19c** | B | **21c** | 18 |
| **19c** | C | **21c** | 17 |
| **19d** | A | **20d** | 15 |
| **19d** | B | **21d** | 3 |
| **19d** | C | **21d** | 9 |

[a]Reaction conditions: (A) 3 eq. hexamine, AcOH, 95-100 °C, 24h, (B) 3 eq. hexamine, TFA, 75 °C, 24h, (C) $Ac_2O$, pyridine, DCM, then 3 eq. hexamine, TFA, 75 °C, 24h. All conditions were followed by acidic workup.

| compound | $IC_{50}$ (nM) | 95% CI (nM) |
| --- | --- | --- |
| **5** | 206 | (142 - 297) |
| **20a** | 472 | (229 - 971) |
| **20b** | 296 | (151 - 580) |
| **20c** | 181 | (156 - 210) |
| **20d** | 118 | (93 - 148) |
| **21b** | 111 | (76 - 162) |
| **21c** | 118 | (105 - 197) |
| **21d** | 150 | (126 - 178) |

F

Mino

| compound | $IC_{50}$ (μM) | 95% CI (μM) |
|---|---|---|
| **5** | 1.62 | (1.07 - 2.42) |
| **21b** | 1.63 | (0.30 - 8.95) |
| **29** | 0.69 | (0.37 - 1.28) |
| **30** | 0.57 | (0.42 - 0.77) |

G

Jeko

| compound | $IC_{50}$ (μM) | 95% CI (μM) |
|---|---|---|
| **5** | 1.57 | (1.05 - 2.35) |
| **21b** | 6.25 | (4.89 - 8.00) |
| **29** | 1.38 | (0.97 - 1.97) |
| **30** | 0.98 | (0.61 - 1.58) |

A

B

20a

20b

20c

20d

21b

21c

21d

22

23

24

25

26

27

28

29

30

31

32

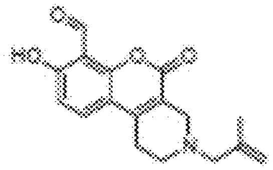
33
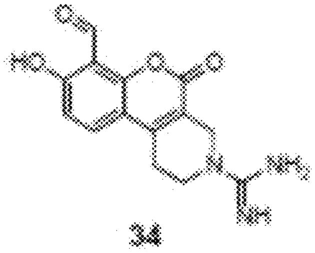
34
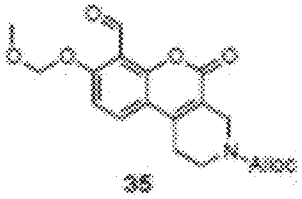
35
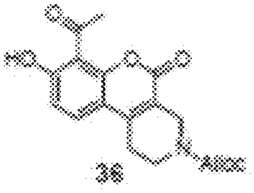
36
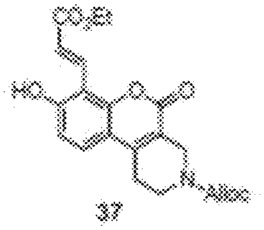
37
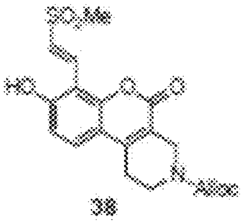
38
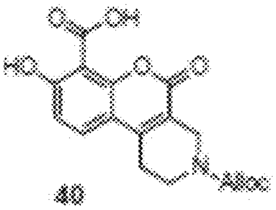
40
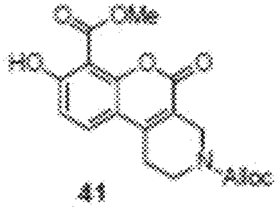
41
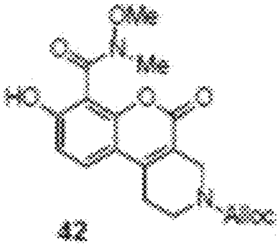
42
Figure 42 (cont.)
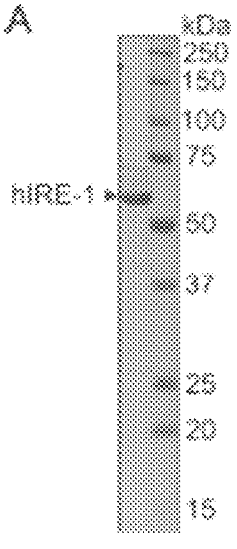
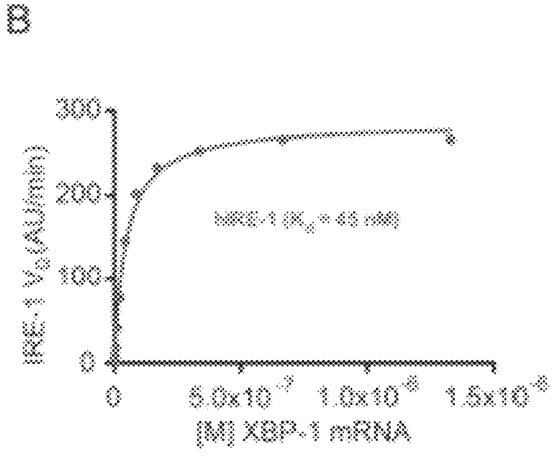
Figure 43A Figure 43B

B

| compound | $IC_{50}$ (nM) | 95% CI (nM) |
|---|---|---|
| **C-D04** | 472 | (229 - 971) |
| **B-H10** | 296 | (151 - 580) |
| **C-F01** | 181 | (156 - 210) |
| **C-F03** | 118 | (93 - 148) |
| **C-C09** | 118 | (105 - 197) |
| **C-F04** | 150 | (126 - 178) |
| **B-H09** | 111 | (76 - 162) |
| **C-D07** | >20000 | - |
| **C-D09** | >20000 | - |
| **B-I08** | 3051 | (2031 - 4584) |
| **B-J02** | 16210 | (12900 - 20360) |
| **C-C03** | >20000 | - |
| **C-C04** | >20000 | - |
| **B-I09** | 1230 | (704 - 2148) |
| **C-C05** | 312 | (222 - 439) |
| **C-D06** | 200 | (149 - 268) |
| **C-D02** | 113 | (62 - 207) |
| **C-C10** | 303 | (181-500) |
| **C-D03** | 255 | (183 -354) |
| **C-D01** | 47 | (35 - 64) |
| **C-C07** | >20000 | - |
| **C-G01** | >20000 | - |
| **C-C06** | 1718 | (1289 - 2288) |
| **C-D05** | >20000 | - |
| **C-C08** | 4109 | (3099 - 5448) |
| **C-D08** | 5644 | (3902 - 8162) |
| **C-F02** | >20000 | - |

Figure 47B substituted 1,3-dioxanes azaspirocyclic 1,3-dioxanes subsituted oxazolidines N-acyl hydrazones

*O*-acyl derivatives

SEQUENCE LISTING

```
Sequence total quantity: 31
SEQ ID NO: 1            moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 1
gagttaagac agcgcttggg                                              20

SEQ ID NO: 2            moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 2
actgggtcca agttgtccag                                              20

SEQ ID NO: 3            moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 3
ctgagcgtgg ctactccttc                                              20

SEQ ID NO: 4            moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 4
ggcatacagg tccttcctga                                              20

SEQ ID NO: 5            moltype = DNA  length = 20
FEATURE                 Location/Qualifiers
misc_feature            1..20
                        note = Synthetic Construct
source                  1..20
```

-continued

```
                         mol_type = other DNA
                         organism = synthetic construct
SEQUENCE: 5
gatcctgacg aggttccaga                                                20

SEQ ID NO: 6             moltype = DNA  length = 20
FEATURE                  Location/Qualifiers
misc_feature             1..20
                         note = Synthetic Construct
source                   1..20
                         mol_type = other DNA
                         organism = synthetic construct
SEQUENCE: 6
acagggtcca acttgtccag                                                20

SEQ ID NO: 7             moltype = DNA  length = 20
FEATURE                  Location/Qualifiers
misc_feature             1..20
                         note = Synthetic Construct
source                   1..20
                         mol_type = other DNA
                         organism = synthetic construct
SEQUENCE: 7
agccatgtac gtagccatcc                                                20

SEQ ID NO: 8             moltype = DNA  length = 20
FEATURE                  Location/Qualifiers
misc_feature             1..20
                         note = Synthetic Construct
source                   1..20
                         mol_type = other DNA
                         organism = synthetic construct
SEQUENCE: 8
ctctcagctg tggtggtgaa                                                20

SEQ ID NO: 9             moltype = RNA  length = 15
FEATURE                  Location/Qualifiers
misc_feature             1..15
                         note = Synthetic Construct
source                   1..15
                         mol_type = other RNA
                         organism = synthetic construct
SEQUENCE: 9
cagtccgcag cactg                                                     15

SEQ ID NO: 10            moltype = DNA  length = 20
FEATURE                  Location/Qualifiers
misc_feature             1..20
                         note = Synthetic Construct
source                   1..20
                         mol_type = other DNA
                         organism = synthetic construct
SEQUENCE: 10
ggatgatgtt ctggagagcc                                                20

SEQ ID NO: 11            moltype = DNA  length = 21
FEATURE                  Location/Qualifiers
misc_feature             1..21
                         note = Synthetic Construct
source                   1..21
                         mol_type = other DNA
                         organism = synthetic construct
SEQUENCE: 11
agcgctgtgg atatcttctc c                                              21

SEQ ID NO: 12            moltype = DNA  length = 21
FEATURE                  Location/Qualifiers
misc_feature             1..21
                         note = Synthetic Construct
source                   1..21
                         mol_type = other DNA
                         organism = synthetic construct
SEQUENCE: 12
accttgtcat gggtctcttc c                                              21

SEQ ID NO: 13            moltype = DNA  length = 21
FEATURE                  Location/Qualifiers
misc_feature             1..21
                         note = Synthetic Construct
```

-continued

```
source                  1..21
                        mol_type = other DNA
                        organism = synthetic construct
SEQUENCE: 13
tggccgggtc tgctgagtcc g                                            21

SEQ ID NO: 14           moltype = DNA  length = 21
FEATURE                 Location/Qualifiers
misc_feature            1..21
                        note = Synthetic Construct
source                  1..21
                        mol_type = other DNA
                        organism = synthetic construct
SEQUENCE: 14
gtccatggga agatgttctg g                                            21

SEQ ID NO: 15           moltype = DNA  length = 21
FEATURE                 Location/Qualifiers
misc_feature            1..21
                        note = Synthetic Construct
source                  1..21
                        mol_type = other DNA
                        organism = synthetic construct
SEQUENCE: 15
ctgagtccga atcaggtgca g                                            21

SEQ ID NO: 16           moltype = DNA  length = 21
FEATURE                 Location/Qualifiers
misc_feature            1..21
                        note = Synthetic Construct
source                  1..21
                        mol_type = other DNA
                        organism = synthetic construct
SEQUENCE: 16
gtccatggga agatgttctg g                                            21

SEQ ID NO: 17           moltype = DNA  length = 21
FEATURE                 Location/Qualifiers
misc_feature            1..21
                        note = Synthetic Construct
source                  1..21
                        mol_type = other DNA
                        organism = synthetic construct
SEQUENCE: 17
agctgaacag agacctgatc g                                            21

SEQ ID NO: 18           moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 18
aattccttcc tcccaagtcc                                              20

SEQ ID NO: 19           moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 19
taatgctggt ctacgtgtgg                                              20

SEQ ID NO: 20           moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 20
atgtgcccaa ctgcaatacc                                              20

SEQ ID NO: 21           moltype = DNA  length = 20
FEATURE                 Location/Qualifiers
misc_feature            1..20
```

```
                      note = Synthetic Construct
source                1..20
                      mol_type = other DNA
                      organism = synthetic construct
SEQUENCE: 21
caccaccttc ctcttcttcg                                             20

SEQ ID NO: 22         moltype = DNA  length = 21
FEATURE               Location/Qualifiers
misc_feature          1..21
                      note = Synthetic Construct
source                1..21
                      mol_type = other DNA
                      organism = synthetic construct
SEQUENCE: 22
ctaacaggtc tgtgacaacc g                                           21

SEQ ID NO: 23         moltype = DNA  length = 19
FEATURE               Location/Qualifiers
misc_feature          1..19
                      note = Synthetic Construct
source                1..19
                      mol_type = other DNA
                      organism = synthetic construct
SEQUENCE: 23
tcatcggacg cacttggaa                                              19

SEQ ID NO: 24         moltype = DNA  length = 21
FEATURE               Location/Qualifiers
misc_feature          1..21
                      note = Synthetic Construct
source                1..21
                      mol_type = other DNA
                      organism = synthetic construct
SEQUENCE: 24
caaccacctt gaatggcaag a                                           21

SEQ ID NO: 25         moltype = DNA  length = 21
FEATURE               Location/Qualifiers
misc_feature          1..21
                      note = Synthetic Construct
source                1..21
                      mol_type = other DNA
                      organism = synthetic construct
SEQUENCE: 25
caagatcaag ccccacctga t                                           21

SEQ ID NO: 26         moltype = DNA  length = 21
FEATURE               Location/Qualifiers
misc_feature          1..21
                      note = Synthetic Construct
source                1..21
                      mol_type = other DNA
                      organism = synthetic construct
SEQUENCE: 26
agttcgcccc aaccagtact t                                           21

SEQ ID NO: 27         moltype = DNA  length = 21
FEATURE               Location/Qualifiers
misc_feature          1..21
                      note = Synthetic Construct
source                1..21
                      mol_type = other DNA
                      organism = synthetic construct
SEQUENCE: 27
tgggcctctg ctgtgtcctg c                                           21

SEQ ID NO: 28         moltype = DNA  length = 27
FEATURE               Location/Qualifiers
misc_feature          1..27
                      note = Synthetic Construct
source                1..27
                      mol_type = other DNA
                      organism = synthetic construct
SEQUENCE: 28
ggcttttacc caggtcctct tccactg                                     27

SEQ ID NO: 29         moltype = DNA  length = 21
FEATURE               Location/Qualifiers
```

-continued

```
misc_feature           1..21
                       note = Synthetic Construct
source                 1..21
                       mol_type = other DNA
                       organism = synthetic construct
SEQUENCE: 29
ctgagtccga atcaggtgca g                                        21

SEQ ID NO: 30          moltype = DNA  length = 21
FEATURE                Location/Qualifiers
misc_feature           1..21
                       note = Synthetic Construct
source                 1..21
                       mol_type = other DNA
                       organism = synthetic construct
SEQUENCE: 30
atccatgggg agatgttctg g                                        21

SEQ ID NO: 31          moltype = DNA  length = 20
FEATURE                Location/Qualifiers
misc_feature           1..20
                       note = Synthetic Construct
source                 1..20
                       mol_type = other DNA
                       organism = synthetic construct
SEQUENCE: 31
catcaccatc ttccaggagc                                          20
```

INHIBITORS OF THE IRE-1/XBP-1 PATHWAY AND METHODS OF USING THEREOF

CROSS-REFERENCE TO RELATED APPLICATIONS

This application is a continuation of U.S. application Ser. No. 16/356,318 filed Mar. 18, 2019, which is a continuation of U.S. application Ser. No. 14/786,561, filed Oct. 23, 2015 (now U.S. Pat. No. 10,323,013), which is a national stage application filed under 35 U.S.C. § 371 of PCT/US2014/035164, filed Apr. 23, 2014, which claims benefit of U.S. Provisional Application No. 61/814,883, filed Apr. 23, 2013, U.S. Provisional Application No. 61/875,080, filed Sep. 8, 2013, and U.S. Provisional Application No. 61/975,563 filed Apr. 4, 2014, which are all hereby incorporated herein by reference in their entireties.

SEQUENCE LISTING

A Sequence Listing conforming to the rules of WIPO Standard ST.26 is hereby incorporated by reference. Said Sequence Listing has been filed as an electronic document via PatentCenter encoded as XML in UTF-8 text. The electronic document, created on May 15, 2024, is entitled "10110-068US3_ST26.xml", and is 40,317 bytes in size.

TECHNICAL FIELD

This application relates generally to treating chronic lymphocytic leukemia (CLL). Specifically, the application related to a method of diagnosing leukemia and methods of treating chronic lymphocytic leukemia.

BACKGROUND

Chronic lymphocytic leukemia (CLL) represents 30% of adult leukemia and is an incurable B cell malignancy. Malignant CLL cells use a limited repertoire of immunoglobulin heavy and light chain genes to manufacture their B cell receptors (BCR) (Hamblin et al., *Blood,* 94(6), 1848-1854 (1999); Murray et al., *Blood,* 111(3), 1524-1533 (2008); Widhopf et al., *Blood,* 111(6), 3137-3144 (2008)), and are very responsive to in vitro anti-IgM stimulation (Chen et al., *Blood,* 100(13), 4609-4614 (2002); Lanham et al., *Blood,* 101(3), 1087-1093 (2003)). Thus, antigen stimulation has been proposed to drive malignant progression of CLL.

The functional role of the endoplasmic reticulum (ER) stress response in mature B-cell leukemia or lymphoma has been largely overlooked because leukemia and lymphoma cells do not expand their ER like that of multiple myeloma cells. Recently, chronic lymphocytic leukemia (CLL), the most common adult leukemia, was shown to require activation of the ER stress response for their survival (Kriss, C. L., et al. *Blood* 120, 1027-1038 (2012)).

The IRE-1/XBP-1 pathway represents the most conserved ER stress response pathway. IRE-1 contains a luminal stress-sensor domain, and a cytoplasmic kinase/RNase domain (FIG. 1). The RNase domain splices 26 nucleotides from the XBP-1 mRNA, causing a frame shift in translation (Shen, X., et al. *Cell* 107, 893-903 (2001); Yoshida, H., Matsui, T., Yamamoto, A., Okada, T. & Mori, K. *Cell* 107, 881-891 (2001); Calfon, M., et al. *Nature* 415, 92-96 (2002)). The spliced XBP-1 mRNA encodes a functional 54-kDa XBP-1s transcription factor. While most transcription factors remain undruggable, the specific activation mechanism of XBP-1 renders IRE-1 an attractive target for therapeutic intervention for cancer.

On tissue injury, inflammatory cells (e.g., neutrophils and macrophages) are recruited to the site of damage, leading to the production of inflammatory cytokines and generation of ROS. Such factors could trigger ER stress. It has been shown that activation of TLR signal can activate IRE1 and its downstream target XBP1, which is required for the production of proinflammatory cytokines such as TNF-α, MCP-1, IL-6, IL-8, and CXCL3 in macrophages and endothelial cells, resulting in enhanced TLR responses contributing to inflammation. XBP1 is also required for the differentiation of B lymphocytes and dendritic cells, both of which are critical in mediating inflammatory response and production of cytokines.

There is a need to develop small molecules with improved potency and cellular efficacy as inhibitors of the IRE-1 RNase activity. The subject matter disclosed herein addresses these and other needs.

SUMMARY

In accordance with the purposes of the disclosed materials, compounds, compositions, articles, devices, and methods, as embodied and broadly described herein, the disclosed subject matter relates to compositions and methods of making an using the compositions. In more specific aspects, the disclosed subject matter relates to compounds having activity as XBP-1/IRE-1 inhibitors, methods of making and using the compounds, and compositions comprising the compounds. In certain aspects, the disclosed subject matter relates to compounds having the chemical structure shown in Formulas I-VII, in particular formulas III-A, IV-A, IV-B and IV-C (also referred to as B-H10, B-H09, B-I08, and B-I09 in examples and in FIG. 24D), as defined herein. In still further aspects, the disclosed subject matter relates to methods for treating oncological and inflammatory disorders in a patient. For example, disclosed herein are methods whereby an effective amount of a compound or composition disclosed herein is administered to a patient having an oncological disorder, for example B-cell chronic lymphocytic leukemia (CLL), and who is in need of treatment thereof. XBP-1 deficiency causes leukemic cells to acquire phenotypes that are disadvantageous for their survival, such as compromised BCR signaling capability and increased surface expression of S1P1. Since, the expression of XBP-1 requires RNase activity of IRE-1, inhibition of IRE-1 represents an attractive method for treating such B-cell cancers. Methods of using the disclosed compounds to inhibit or kill tumor cells and to inhibit XBP-1/IRE-1 are also disclosed.

Additional advantages will be set forth in part in part in the description that follows and the Figures, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DESCRIPTION OF FIGURES

FIG. 6G: relative gene expression levels of BiP in CD5−/B220+ wild-type B cells and CD5+/B220+ Eμ-TCL1 CLL cells that were stimulated with LPS for 1 day and lysed for purification of total RNA and synthesis of cDNA.

FIG. 6I: relative gene expression levels of GRP94 in CD5−/B220+ wild-type B cells and CD5+/B220+ Eμ-TCL1 CLL cells that were stimulated with LPS for 1 day and lysed for purification of total RNA and synthesis of cDNA.

FIG. 6K: The sequences of primers used for detection of each indicated ER stress response molecule in real-time quantitative PCR.

FIG. 11C: Wild-type B cells were stimulated with LPS (20 μg/ml) for 48 h and subsequently treated with DMSO (control), STF-083010 (50 μM), A-I06 (50 μM), or A-I07 (50 μM) for 24 h. Cells were lysed for purification of RNA and synthesis of cDNA. The mRNA expression levels of IRE-1 were measured by real-time quantitative PCR, performed in triplicate in each experiment (n=3).

FIG. 11D: CLL cells isolated from 8-month old Eμ-TCL1 mice were cultured in the presence of LPS, in combination with DMSO (control), STF-083010 (50 μM), A-I06 (50 μM), or A-I07 (50 μM) for 48 h. Cells were lysed for purification of RNA and synthesis of cDNA. The mRNA expression level of XBP-1 was measured by real-time quantitative PCR (n=3).

FIG. 11E: Human WaC3 CLL cells were treated with DMSO (control), STF-083010 (50 μM), A-I06 (50 μM), or A-I07 (50 μM) for 72 h, and subsequently lysed for RNA extraction and cDNA synthesis. The mRNA expression level of XBP-1 was measured by real-time quantitative PCR (n=3).

FIG. 11F: Primer sequences used to analyze the XBP-1 mRNA expression levels in human WaC3 CLL cells shown in FIG. 11E.

Figure 24A:
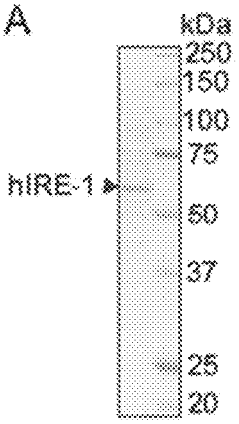
FIG. 24A: Recombinant human IRE-1 (hIRE-1) was expressed in insect cells and purified using Ni-NTA column chromatography. Purified hIRE-1 was analyzed by SDS-PAGE and stained with Coomassie Brilliant Blue G-250.
Figure 24B:
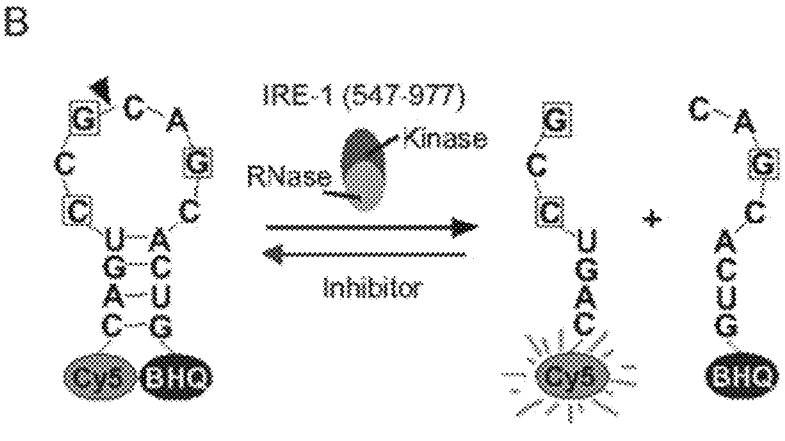
FIG. 24B: A diagram depicting the mini-XBP-1 stem-loop RNA and its cleavage by hIRE-1. IRE-1 inhibitors block hIRE-1 from cleaving the XBP-1 stem-loop RNA substrate.
Figure 24C:
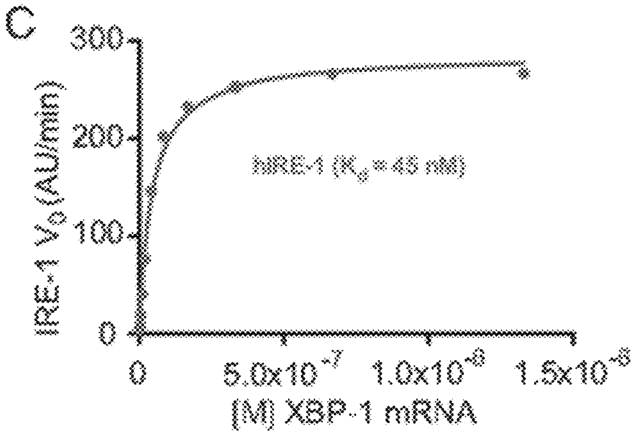
FIG. 24C: The Michaelis-Menten curve for hIRE-1 showing catalytic RNase activity in a FRET assay. Initial reaction rates are plotted as a function of different XBP-1 stem-loop RNA concentrations in the presence of 5 nM hIRE-1.
Figure 24D:
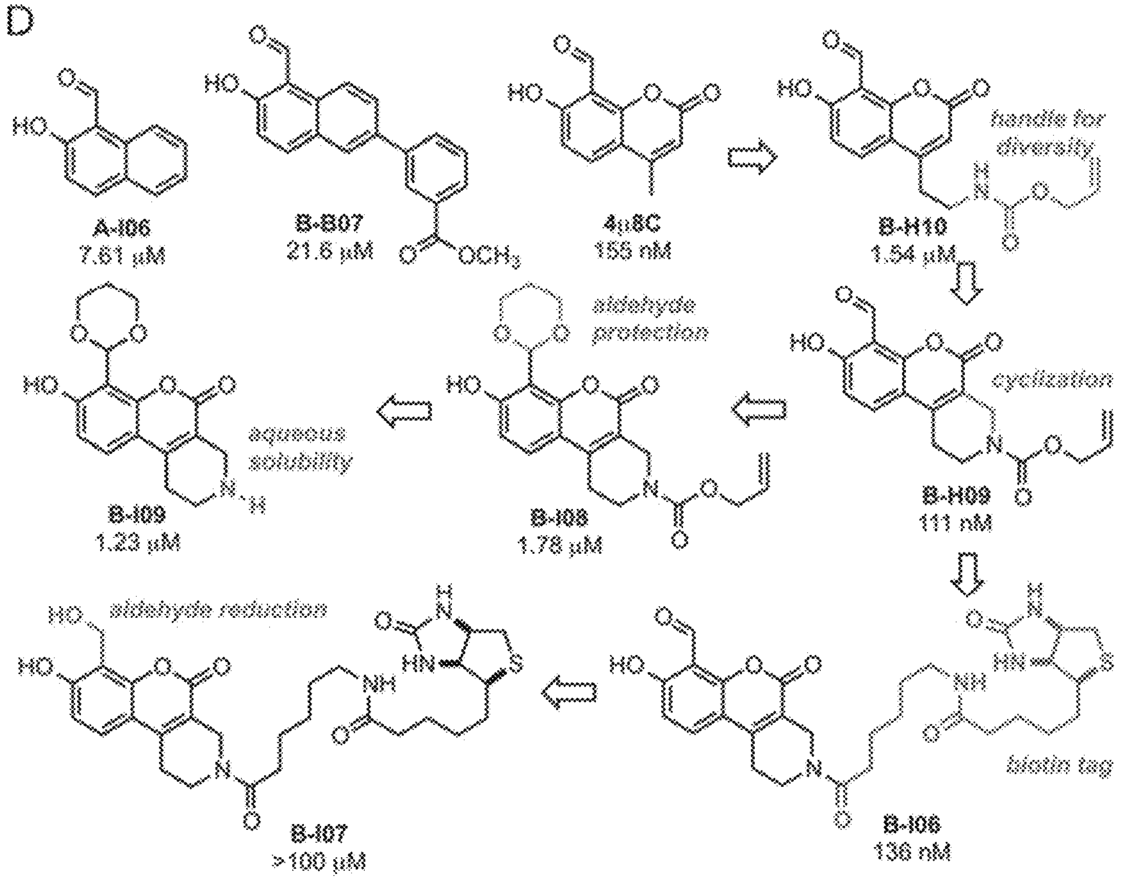

FIG. 24D: Structures of IRE-1 inhibitors with in vitro $IC_{50}$ values obtained from FRET-suppression assays.

Figure 24E:
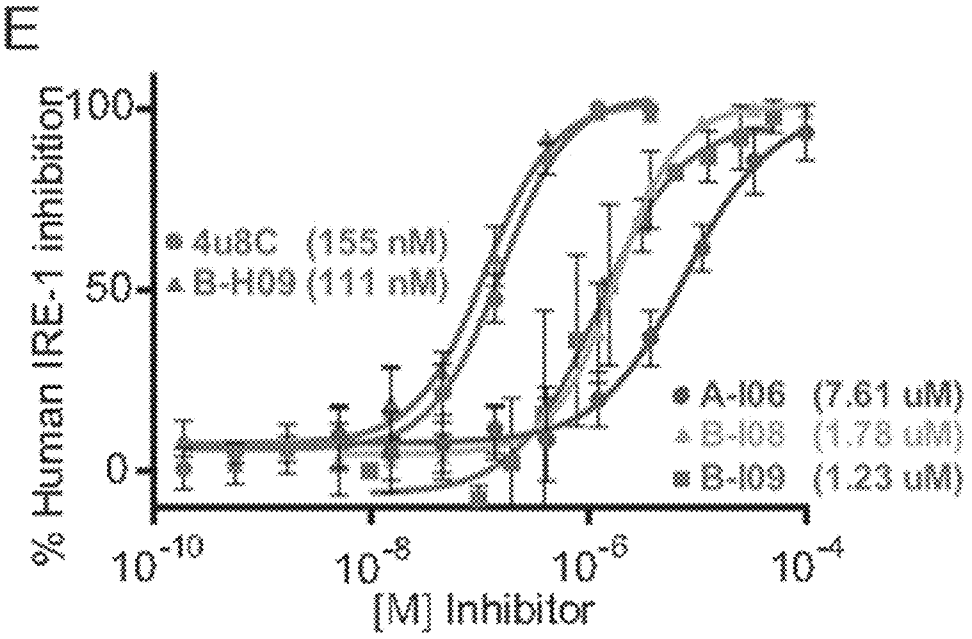

FIG. 24E: Dose-response curves were generated from FRET-suppression assays. Dose-response experiments were carried out a minimum of 3 times on different days, and $IC_{50}$ values were calculated from the mean inhibition value at each concentration. Shown here are representative curves for selected IRE-1 inhibitors.

Figure 24F:
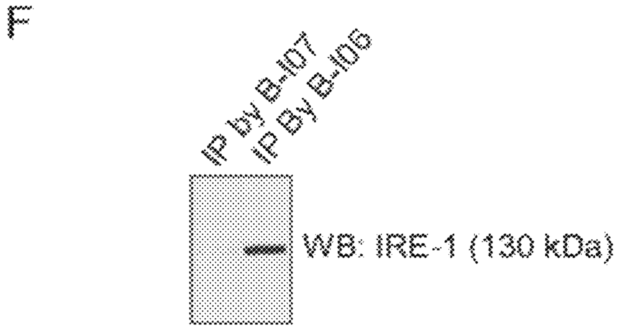

FIG. 24F: LPS-stimulated XBP-1-deficient B cells were treated with B-I06 or B-I07 (control) for 24 h, and lysed for immunoprecipitations using an anti-biotin antibody and protein G-conjugated agarose. Immunoprecipitates were analyzed by SDS-PAGE and immunoblotted for IRE-1.

Figure 24G:
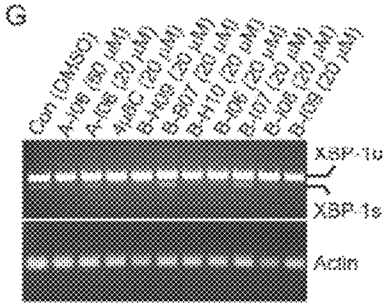

FIG. 24G: Human WaC3 CLL cells were treated with indicated compounds for 24 h and lysed for RNA extraction. The expression of human unspliced XBP-1 (XBP-1u), spliced XBP-1 (XBP-1s) and actin was detected by RT-PCR using specific primers.

Figure 24H:
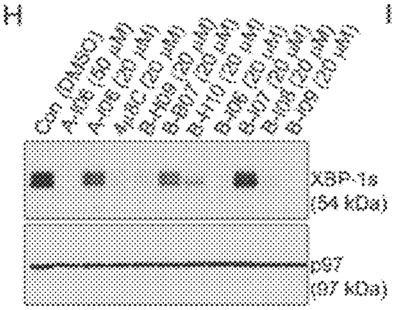

FIG. 24H: Mouse B cells were stimulated with LPS for 48 h to allow for the expression of XBP-1s, and then treated with indicated inhibitors for 24 h. Cell lysates were analyzed for the expression of XBP-1s and p97 by immunoblots.

Figure 24I:
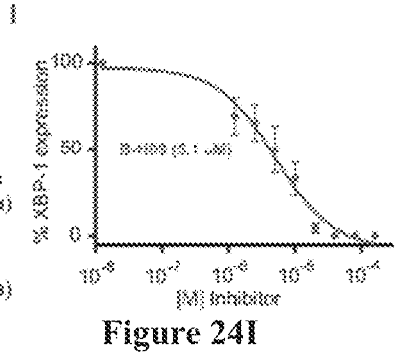

FIG. 24I: To determine the capability of IRE-1 inhibitors in suppressing the expression of XBP-1s, LPS-stimulated B cells were treated with 0, 1.25, 2.5, 5, 10, 20, 40, 80 and 160 mM B-H09 for 24 h. Equal amounts of lysates were analyzed by SDS-PAGE and immunoblotted for XBP-1s. The intensity of the XBP-1s protein band from each treated condition was determined using ImageJ, and compared with that from the untreated to determine the percentage in inhibition.

Figure 24J:
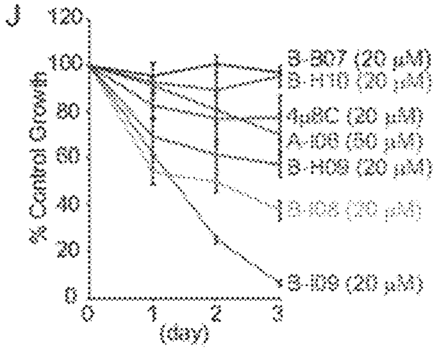

FIG. 24J: Purified mouse CD3-IgM+CD5+ Eμ-TCL1 CLL cells were treated with DMSO or indicated inhibitors, and subjected to XTT assays each day for a course of 3 days. Percentages of growth were determined by comparing inhibitor-treated with DMSO-treated groups.

Figure 24K:
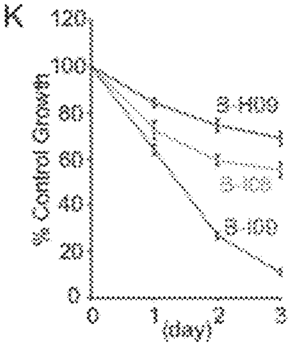

FIG. 24K: Primary CLL cells from a human patient were treated with DMSO or indicated inhibitors (20 μM) for a course of 3 days, subjected to XTT assays, and analyzed.

Figure 24L:
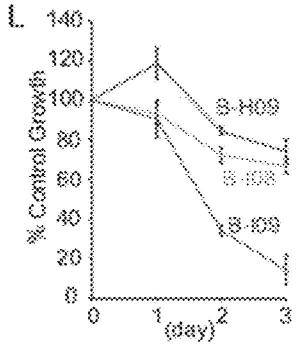

FIG. 24L: Primary CLL cells from a human patient were treated with DMSO or indicated inhibitors (20 μM) for a course of 3 days, subjected to XTT assays, and analyzed.

Figure 25A:
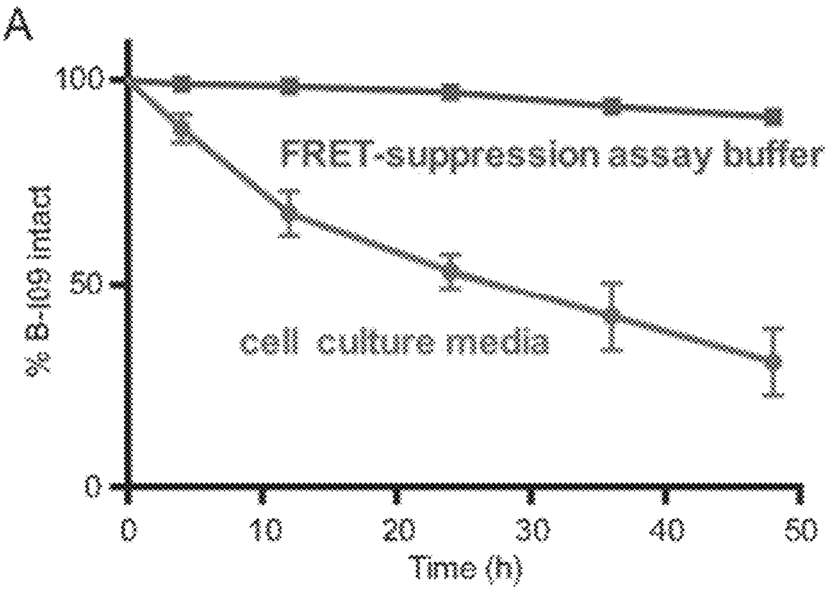

FIG. 25A displays the degradation of B-I09 is plotted as function of time upon exposure to FRET-suppression assay buffer at room temperature (blue) or cell culture media 37° C. (red). Aliquots were injected onto LCMS (UV monitored at 320 nm) and the peaks integrated. The 1,3-dioxane protecting group in B-I09 is stable to the FRET-suppression assay buffer at room temperature, whereas it exhibits a $t_{1/2}$ of approximately 30 h in cell culture media (37° C.).

Figure 25B:
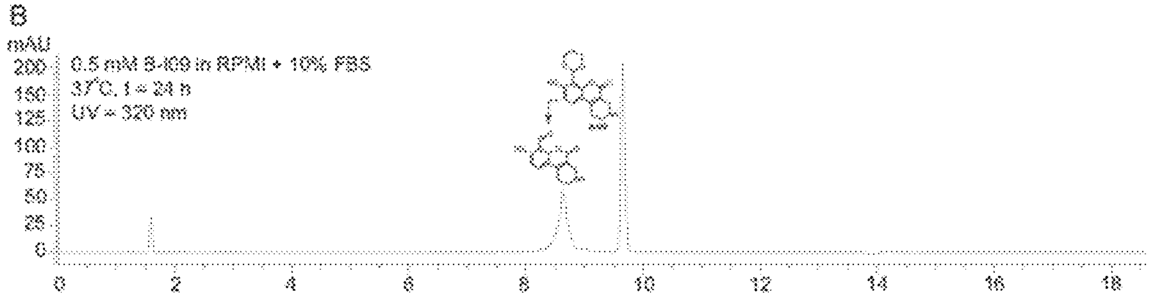

FIG. 25B: Representative HPLC trace at t=24 h for B-I09 in cell culture media, showing the partial degradation of B-I09 and formation of the corresponding aldehyde.

Figure 25C:
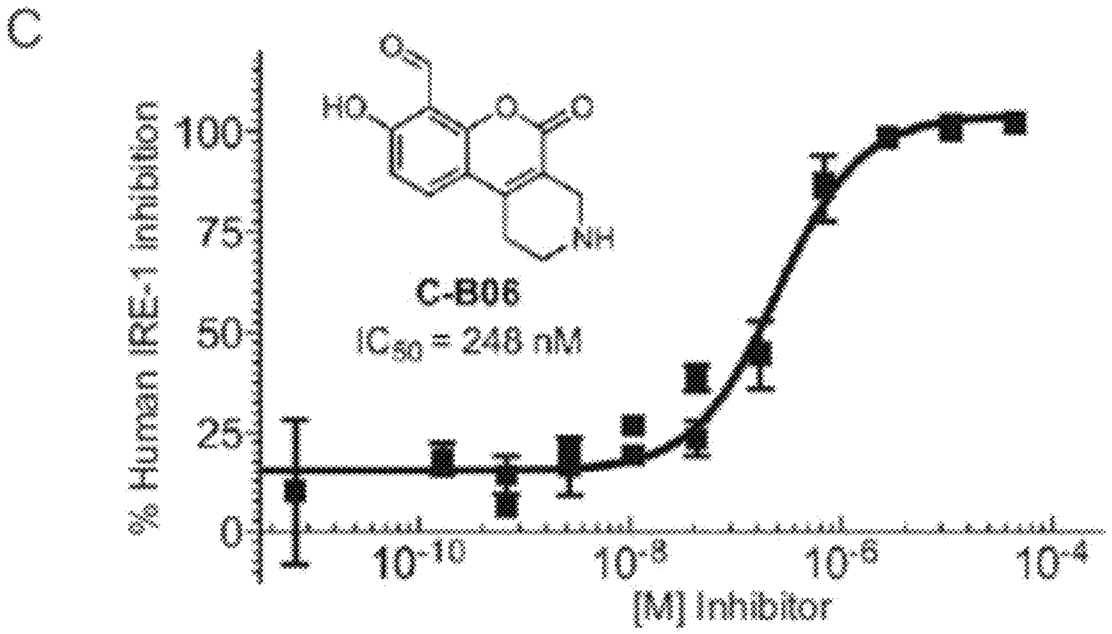

FIG. 25C: The dose-response curve of C-B06 in inhibiting human IRE-1 RNase from cleaving mini-XBP-1 stem-loop RNA. Dose-response FRET-suppression experiments were carried out a minimum of 3 times on different days, and IC50 values were calculated from the mean inhibition value at each concentration.

Figure 25D:
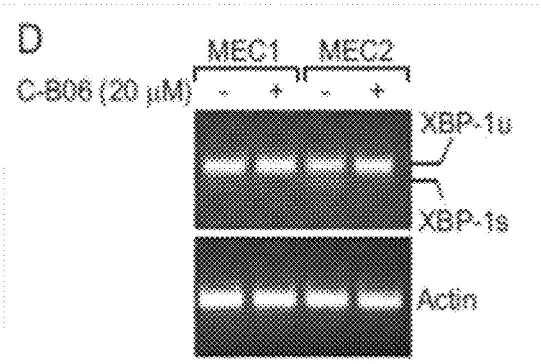

FIG. 25D: MEC1 and MEC2 human CLL cells were treated with DMSO (control) or C-B06 (20 μM) for 48 h. Cells were lysed and RNA was extracted for RT-PCR. The expression of human unspliced XBP-1 (XBP-1u), spliced XBP-1 (XBP-1s) and actin was detected using specific primers.

Figure 25E:
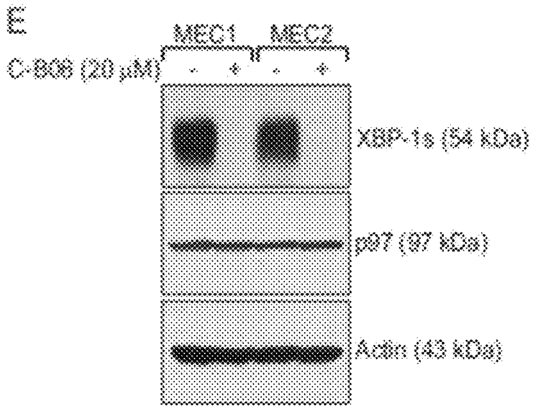

FIG. 25E: Human MEC1 and MEC2 CLL cells were cultured for 48 h in the presence of DMSO (control) or CB-06 (20 μM). Cells were lysed for analysis of the expression of XBP-1s, p97 and actin by immunoblots using specific antibodies.

Figure 26A:
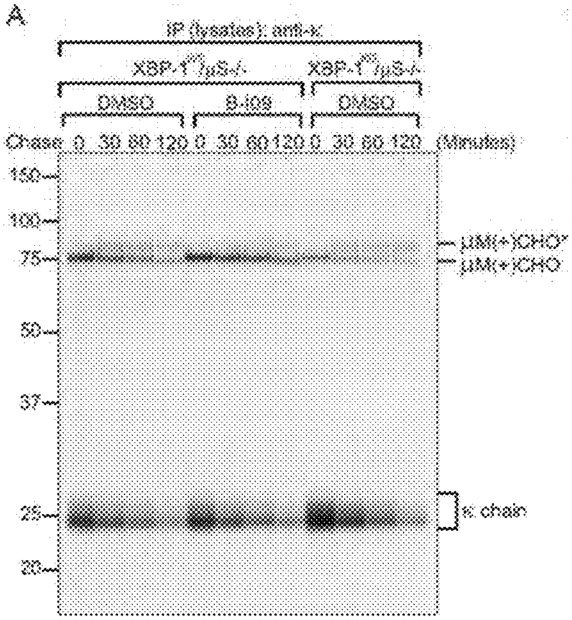

FIG. 26A: XBP-$1^{WT}$/μS−/− B cells were stimulated with LPS for 2 days and subsequently treated with DMSO (control) or B-I09 (20 μM) for additional 1 day. DMSO-, or B-I09-treated XBP-$1^{WT}$/μS−/− B cells and DMSO-treated XBP-$1^{KO}$/μS−/− B cells were radiolabeled for 15 min, chased for indicated time and lysed. Intracellular mIgM and κ light chain were immunoprecipitated from lysates using an anti-κ antibody. Immunoprecipitates were analyzed by SDS-PAGE. μM represents the membrane-bound μ chain. CHO and CHO* represent high mannose-type glycans and complex-type glycans, respectively.

Figure 26B:
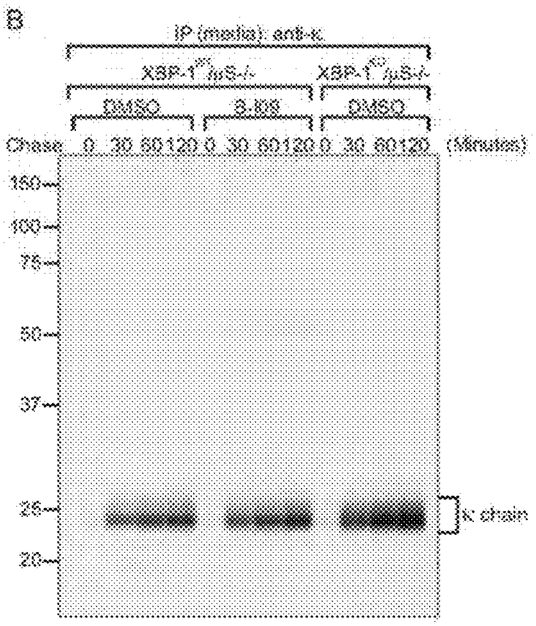

FIG. 26B: XBP-$1^{WT}$/μS−/− B cells were stimulated with LPS for 2 days and subsequently treated with DMSO (control) or B-I09 (20 μM) for additional 1 day. DMSO-, or B-I09-treated XBP-$1^{WT}$/μS−/− B cells and DMSO-treated XBP-$1^{KO}$/μS−/− B cells were radiolabeled for 15 min, chased for indicated time and lysed. Secreted free κ chains were immunoprecipitated from culture media using an anti-κ antibody. Immunoprecipitates were analyzed by SDS-PAGE. μM represents the membrane-bound μ chain. CHO and CHO* represent high mannose-type glycans and complex-type glycans, respectively.

Figure 26C:
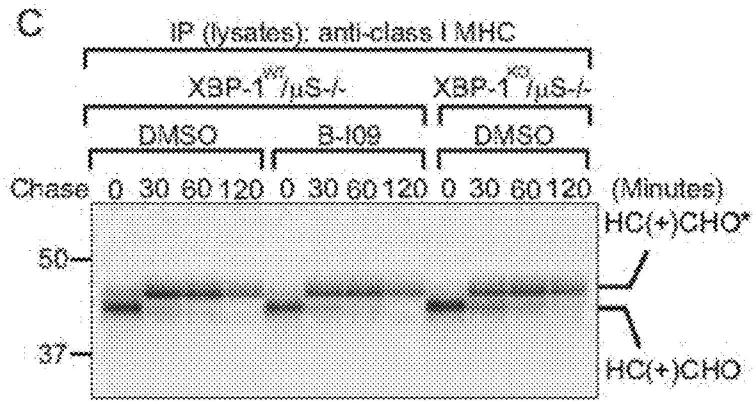

FIG. 26C: Similar lysates as those in FIG. 26A were immunoprecipitated using an antibody against the class I MHC heavy chain (HC), and immunoprecipitates were analyzed by SDS-PAGE.

Figure 26D:
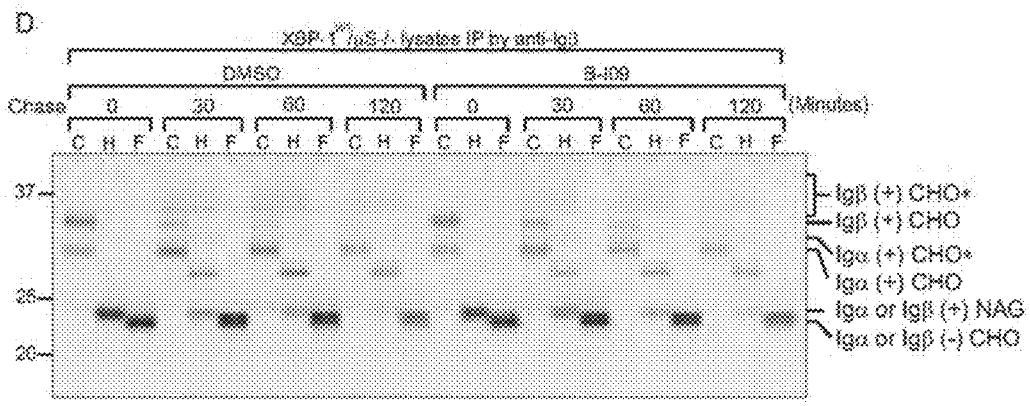

FIG. 26D: Using similar lysates as those in FIG. 26A, immunoprecipitations were performed using an anti-Ig antibody to retrieve the Igα/Igβ heterodimers. Immunoprecipitated Igα/Igβ proteins were eluted from the beads and treated with endo-H or PNGase F before being analyzed by SDS-PAGE. CHO, CHO*, NAG represent high mannose-type glycans, complex-type glycan and N-acetylglucosamines, respectively.

Figure 27A:
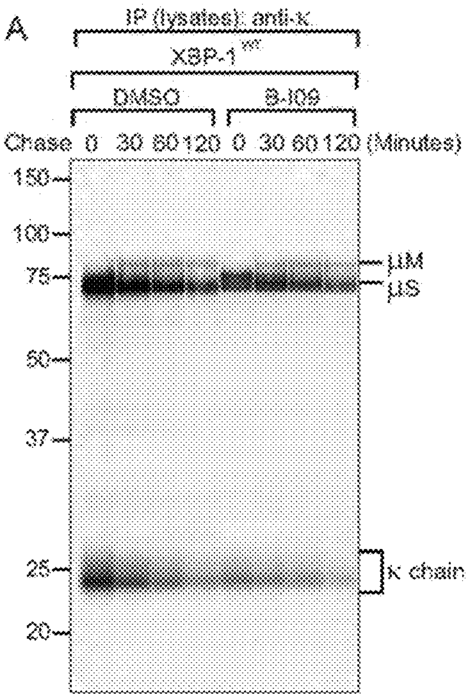

FIG. 27A: Wild-type B cells were stimulated with LPS for 2 days and subsequently treated with DMSO (control) or B-I09 (20 μM) for additional 1 day. DMSO- or B-I09-treated wild-type B cells were radiolabeled for 15 min, chased for indicated times and lysed. Intracellular membrane-bound μ chain (μM), secretory μ chain (μM) and κ light chain was immunoprecipitated from lysates using an anti-κ antibody. Immunoprecipitates were analyzed by SDS-PAGE.

Figure 27B:
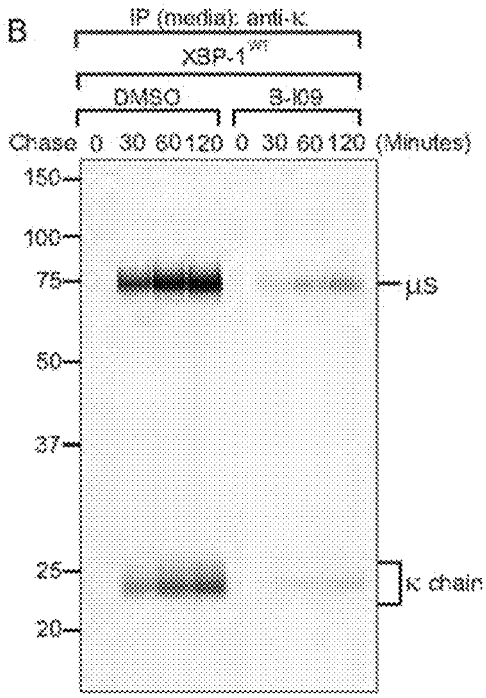

FIG. 27B: Wild-type B cells were stimulated with LPS for 2 days and subsequently treated with DMSO (control) or B-I09 (20 μM) for additional 1 day. DMSO- or B-I09-treated wild-type B cells were radiolabeled for 15 min, chased for indicated times and lysed. Secreted μ and κ chains were immunoprecipitated from culture media using an anti-κ antibody. Immunoprecipitates were analyzed by SDS-PAGE.

Figure 27C:
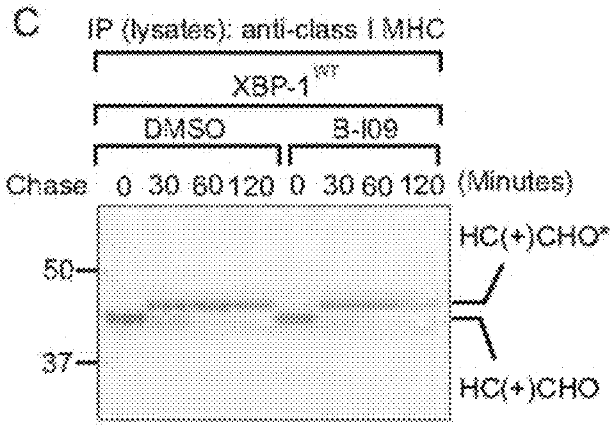

FIG. 27C: Similar lysates as those in FIG. 27A were immunoprecipitated using an antibody against the class I MHC heavy chain (HC), and immunoprecipitates were analyzed by SDS-PAGE. CHO and CHO* denote high mannose-type glycans and complex-type glycans, respectively.

Figure 27D:
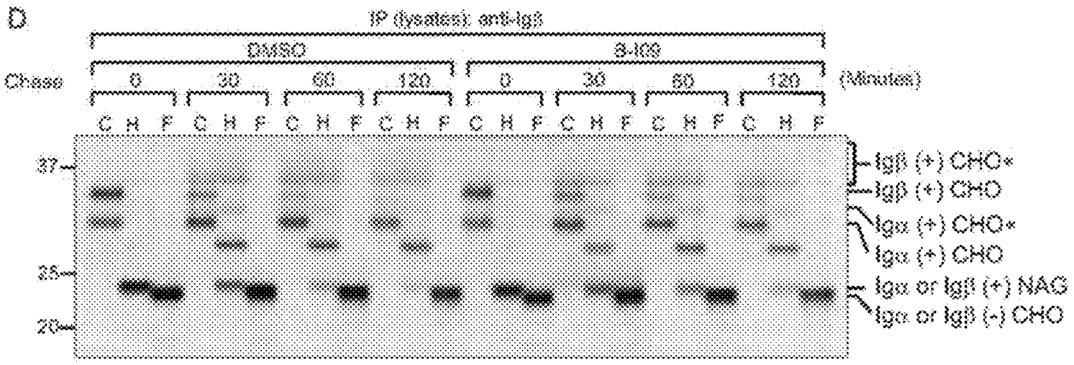

FIG. 27D: From similar lysates as those in FIG. 27A, Igα/Igβ heterodimers were immunoprecipitated using an anti-Ig antibody. Immunoprecipitated Igα/Igβ heterodimers were eluted from the beads and treated with endo-H or PNGase F before analyzed by SDS-PAGE. CHO, CHO*, NAG indicate high mannose-type glycans, complex-type glycan and N-acetylglucosamines, respectively.

Figure 28A:
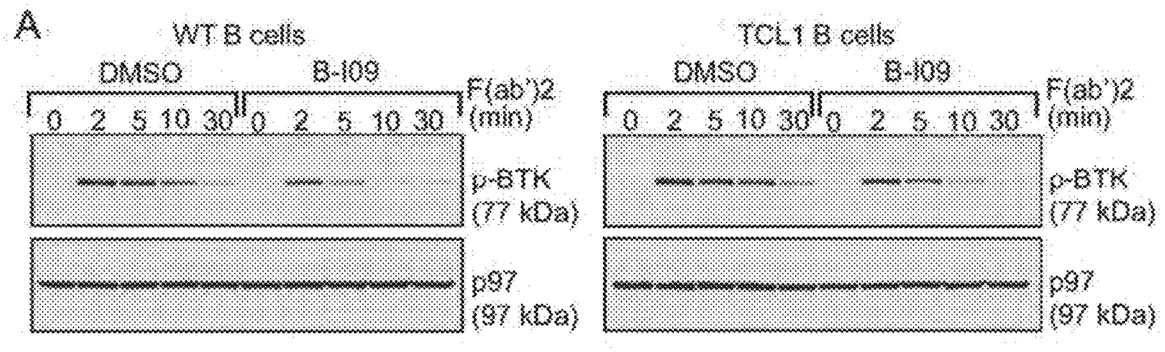

FIG. 28A: Wild-type and Eμ-TCL1 B cells were stimulated with LPS for 2 days and subsequently treated with DMSO or B-I09 (20 μM) for additional 1 day. To activate the BCR, cells were stimulated with F(ab')2 anti-mouse IgM for indicated times and lysed for analysis of phospho-BTK and p97 by immunoblots.

Figure 28B:
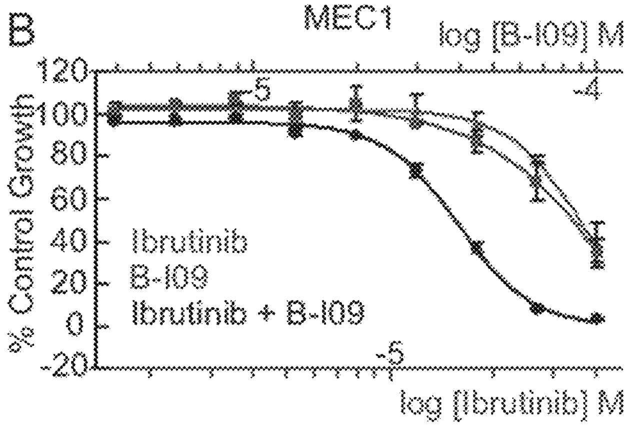

FIG. 28B: Dose-dependent growth inhibition curves of MEC1 human CLL cells treated for 48 h with B-I09, ibrutinib, or the combination were determined by CellTiter Blue assays. The concentration ranges for B-I09 and ibrutinib are 3.9 μM~100 μM and 1.56 μM~40 μM, respectively.

Figure 28C:
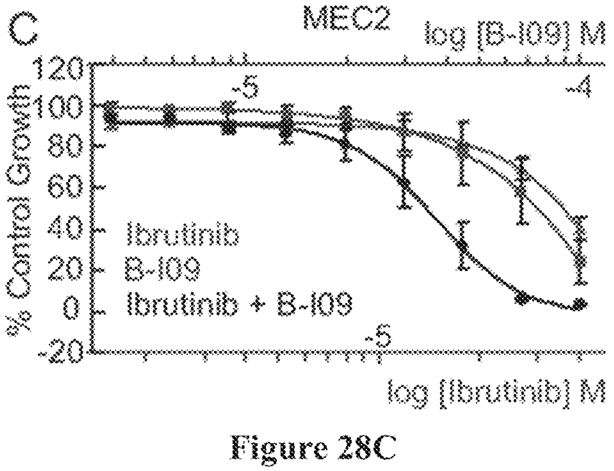

FIG. 28C: Dose-dependent growth inhibition curves of MEC2 human CLL cells treated for 48 h with B-I09, ibrutinib, or the combination were determined by CellTiter Blue assays. The concentration ranges for B-I09 and ibrutinib are 3.9 μM~100 μM and 1.56 μM~40 μM, respectively.

Figure 28D:
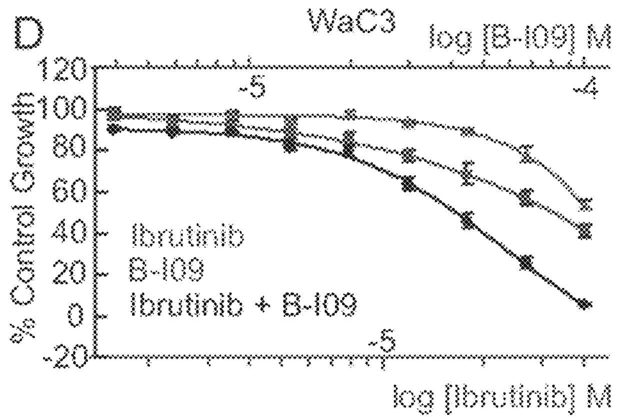

FIG. 28D: Dose-dependent growth inhibition curves of WaC3 human CLL cells treated for 48 h with B-I09, ibrutinib, or the combination were determined by CellTiter Blue assays. The concentration ranges for B-I09 and ibrutinib are 3.9 μM~100 μM and 1.56 μM~40 μM, respectively.

Figure 28E:
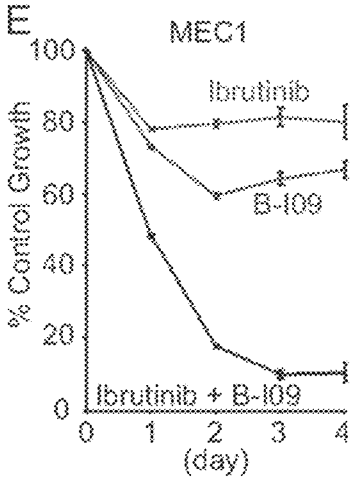

FIG. 28E: MEC1 human CLL cells were treated with DMSO (control), B-I09 (20 μM), ibrutinib (10 μM), or the combination of both for a course of 4 days, and subjected to XTT assays. Percentages of growth were determined by comparing inhibitor-treated groups with control groups.

Figure 28F:
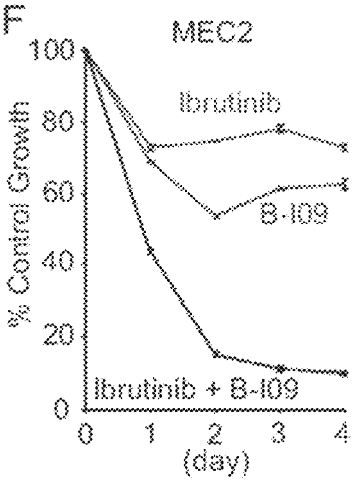

FIG. 28F: MEC2 human CLL cells were treated with DMSO (control), B-I09 (20 μM), ibrutinib (10 μM), or the combination of both for a course of 4 days, and subjected to XTT assays. Percentages of growth were determined by comparing inhibitor-treated groups with control groups.

Figure 28G:
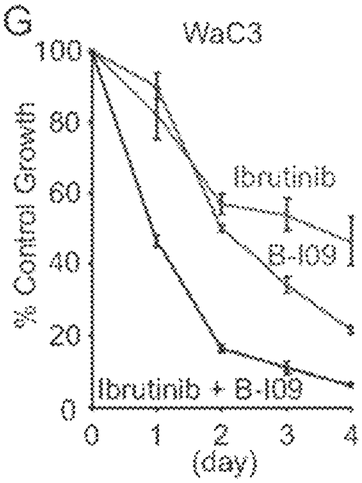

FIG. 28G: WaC3 human CLL cells were treated with DMSO (control), B-I09 (20 μM), ibrutinib (10 μM), or the combination of both for a course of 4 days, and subjected to XTT assays. Percentages of growth were determined by comparing inhibitor-treated groups with control groups.

Figure 28H:
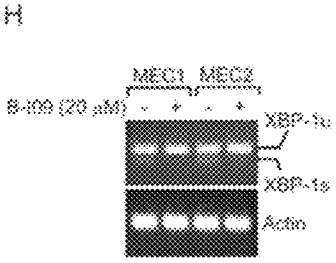

FIG. 28H: MEC1 and MEC2 human CLL cells were treated with DMSO (control) or B-I09 (20 μM) for 48 h. Cells were lysed and RNA was extracted for RT-PCR. The expression of human unspliced XBP-1 (XBP-1u), spliced XBP-1 (XBP-1s) and actin was detected using specific primers.

Figure 28J:
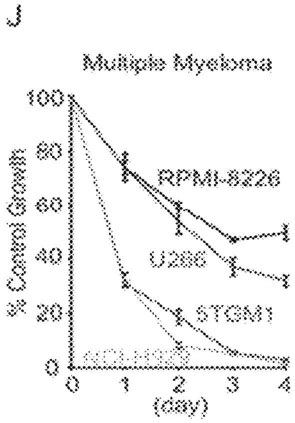
Figure 28K:
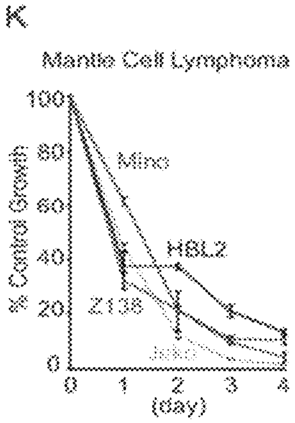
Figure 28I:
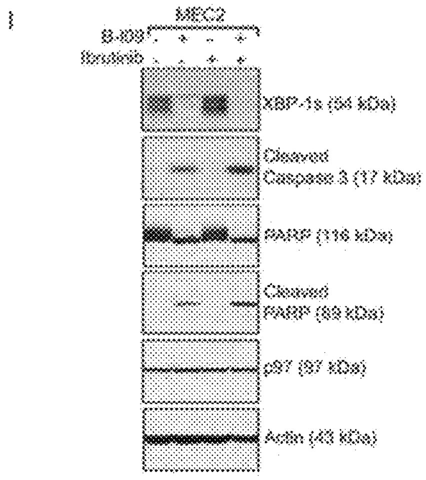

FIG. 28I: Human MEC2 CLL cells were cultured for 72 h in the presence of DMSO (control), B-I09 (20 μM), ibrutinib (10 μM), or the combination of B-I09 and ibrutinib. Cells were lysed for analysis of the expression of XBP-1s, cleaved caspase-3, PARP, cleaved PARP, p97 and actin by immunoblots using specific antibodies.

FIG. 28J: Multiple myeloma cell lines were treated with DMSO or the combination of B-I09 (20 μM) and ibrutinib (10 μM) for a course of 4 days, and subjected to XTT assays at the end of each day. Percentages of growth were determined by comparing treated groups with control groups.

FIG. 28K: Mantle cell lymphoma cell lines were treated with DMSO or the combination of B-I09 (20 μM) and ibrutinib (10 μM) for a course of 4 days, and subjected to XTT assays at the end of each day. Percentages of growth were determined by comparing treated groups with control groups.

Figure 28L:
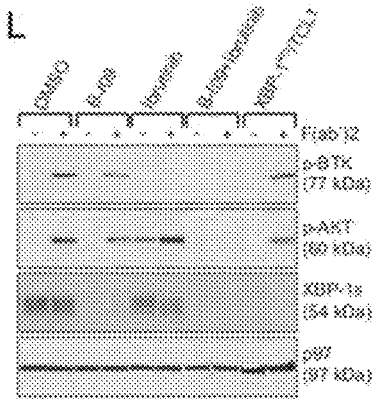

FIG. 28L: Eμ-TCL1 B cells were stimulated with LPS for 2 days and subsequently treated with DMSO, B-I09 (20 μM), ibrutinib (10 μM), or B-I09 in combination with ibrutinib for another day. LPS-stimulated XBP-1KO/Eμ-TCL1 B cells serve as controls. After stimulation with F(ab')2 anti-mouse IgM for 5 min, cells were lysed for analysis of indicated proteins by immunoblots.

Figure 28M:
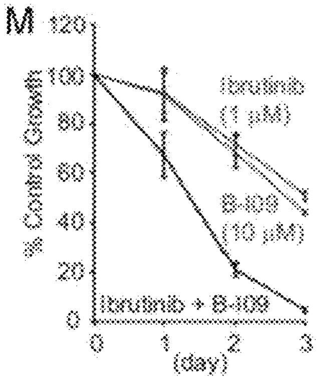

FIG. 28M: Eμ-TCL1 CLL cells were treated with DMSO (control), B-I09 (10 μM), ibrutinib (1 μM), or the combination of both for 3 days, and subjected to XTT assays. Percentages of growth were determined by comparing inhibitor-treated groups with control groups.

Figure 29A:
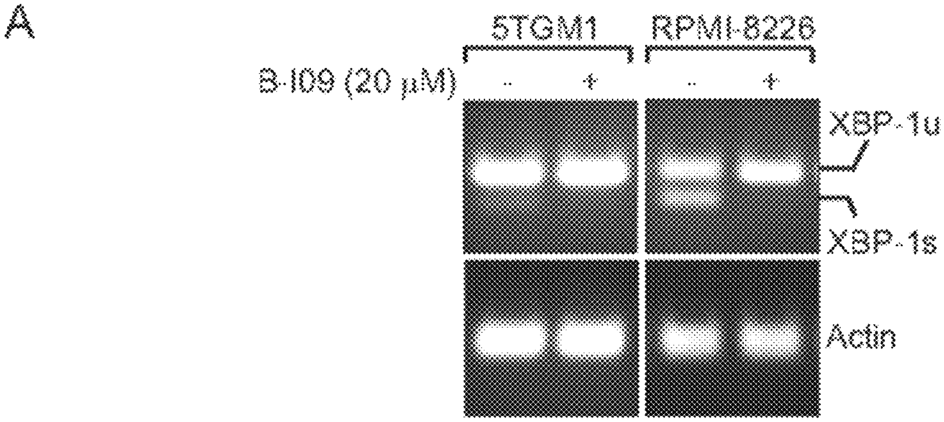

FIG. 29A: Mouse 5TGM1 MM cells and human RPMI-8226 MM cells were treated with DMSO (control) or B-I09 (20 μM) for 48 h. Cells were lysed to extract RNA for RT-PCR. The expression of mouse and human unspliced XBP-1 (XBP-1u), spliced XBP-1 (XBP-1s) and actin was detected using specific primers. XBP-1 splicing was inhibited by B-I09 in both mouse and human MM cells.

Figure 29B:
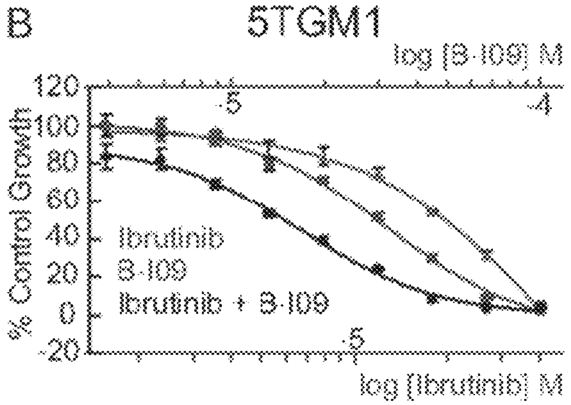

FIG. 29B: Dose-dependent growth inhibition curves of mouse 5TGM1 MM cell lines treated for 48 h with B-I09, ibrutinib, or the combination were determined by CellTiter Blue assays. The concentration ranges for B-I09 and ibrutinib are 3.9 μM~100 μM and 1.56 μM~40 μM, respectively.

Figure 29C:
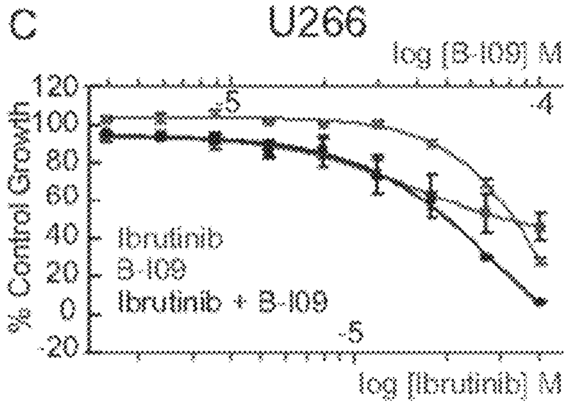

FIG. 29C: Dose-dependent growth inhibition curves of human U266 MM cell lines treated for 48 h with B-I09, ibrutinib, or the combination were determined by CellTiter Blue assays. The concentration ranges for B-I09 and ibrutinib are 3.9 μM~100 μM and 1.56 μM~40 μM, respectively.

Figure 29D:
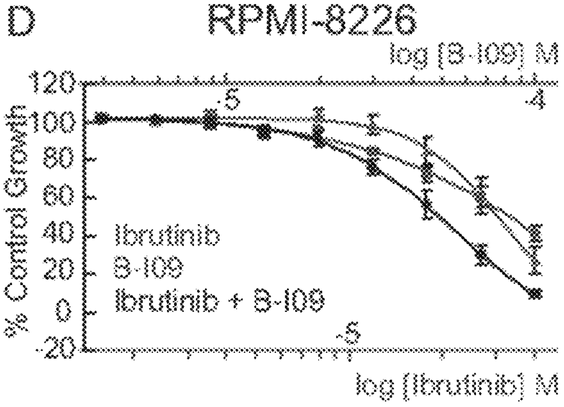

FIG. 29D: Dose-dependent growth inhibition curves of mouse human RPMI-8226 MM cell lines treated for 48 h with B-I09, ibrutinib, or the combination were determined by CellTiter Blue assays. The concentration ranges for B-I09 and ibrutinib are 3.9 μM~100 μM and 1.56 μM~40 μM, respectively.

Figure 29E:
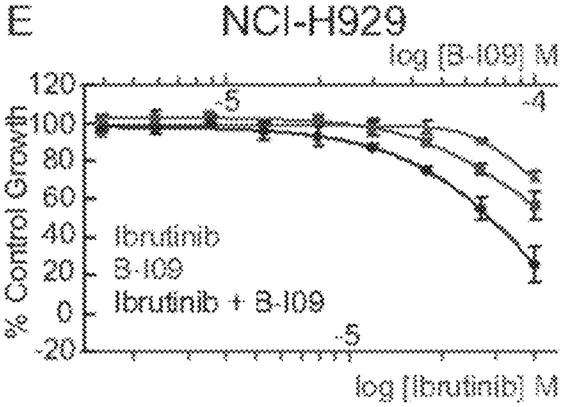

FIG. 29E: Dose-dependent growth inhibition curves of human NCI-H929 MM cell lines treated for 48 h with B-I09, ibrutinib, or the combination were determined by CellTiter Blue assays. The concentration ranges for B-I09 and ibrutinib are 3.9 μM~100 μM and 1.56 μM~40 μM, respectively.

Figure 30A:
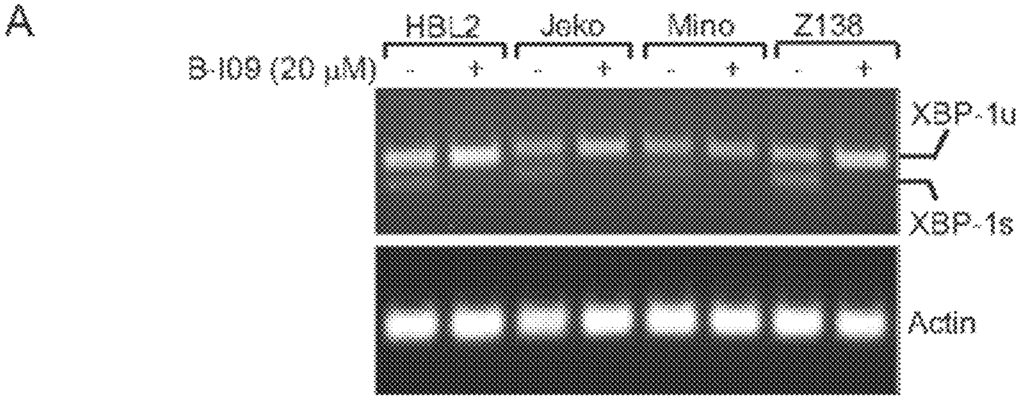

FIG. 30A: Human HBL2, Jeko, Mino and Z138 MCL cell lines were treated with DMSO (control) or B-I09 (20 μM) for 48 h. Cells were lysed and RNA was extracted for RT-PCR. The expression of human unspliced XBP-1 (XBP-1u), spliced XBP-1 (XBP-1s) and actin was detected using specific primers. XBP-1 splicing was inhibited by B-I09 in all 4 human MCL cell lines.

Figure 30B:
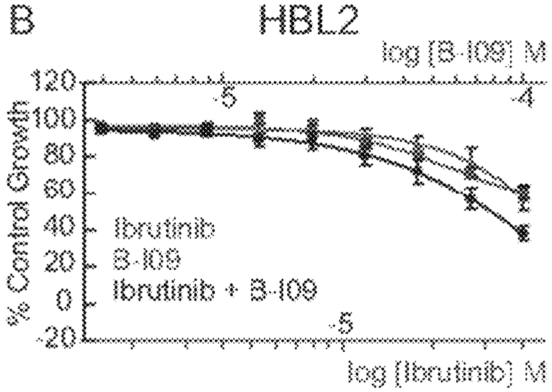

FIG. 30B: Dose-dependent growth inhibition curves of human HBL2 MCL cell lines treated for 48 h with B-I09, ibrutinib, or the combination were determined by CellTiter Blue assays. The concentration ranges for B-I09 and ibrutinib are 3.9 μM~100 μM and 1.56 μM~40 μM, respectively.

Figure 30C:
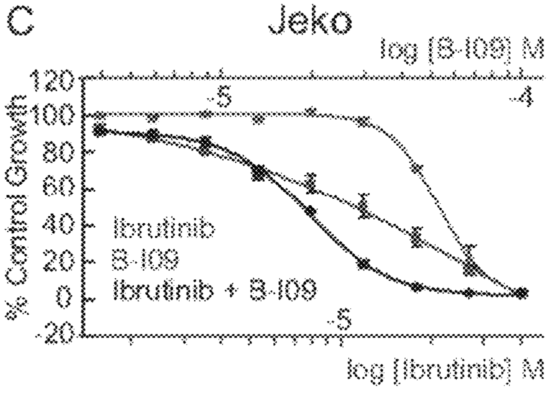

FIG. 30C: Dose-dependent growth inhibition curves of human Jeko MCL cell lines treated for 48 h with B-I09, ibrutinib, or the combination were determined by CellTiter Blue assays. The concentration ranges for B-I09 and ibrutinib are 3.9 μM~100 μM and 1.56 μM~40 μM, respectively.

Figure 30D:
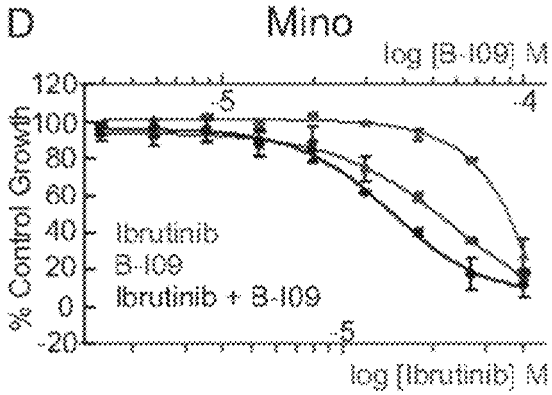

FIG. 30D: Dose-dependent growth inhibition curves of human Mino MCL cell lines treated for 48 h with B-I09, ibrutinib, or the combination were determined by CellTiter Blue assays. The concentration ranges for B-I09 and ibrutinib are 3.9 μM~100 μM and 1.56 μM~40 μM, respectively.

Figure 30E:
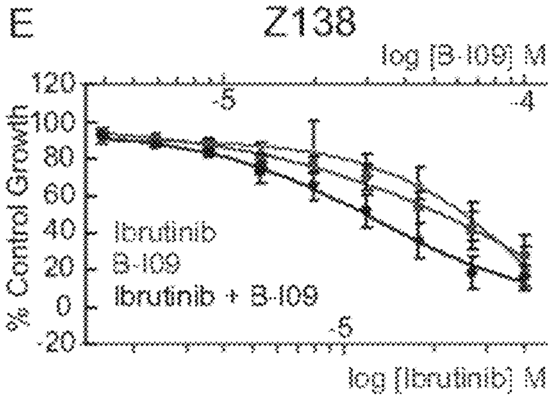

FIG. 30E: Dose-dependent growth inhibition curves of human Z138 MCL cell lines treated for 48 h with B-I09, ibrutinib, or the combination were determined by CellTiter Blue assays. The concentration ranges for B-I09 and ibrutinib are 3.9 μM~100 μM and 1.56 μM~40 μM, respectively.

Figure 31A:
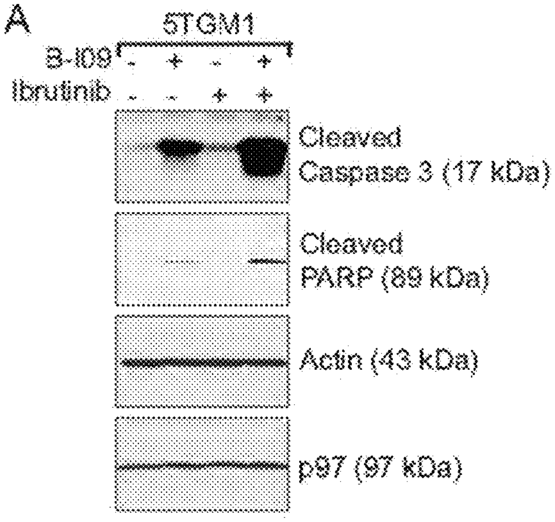

FIG. 31A: Mouse 5TGM1 MM cells were cultured in the presence of DMSO (control), B-I09 (20 μM), ibrutinib (10 μM), or the combination for 48 h (5TGM1) or 72 h (Mino). Cells were lysed for analysis of the expression of XBP-1s, cleaved caspase-3, cleaved PARP, p97 and actin by immunoblots using specific antibodies.

Figure 31B:
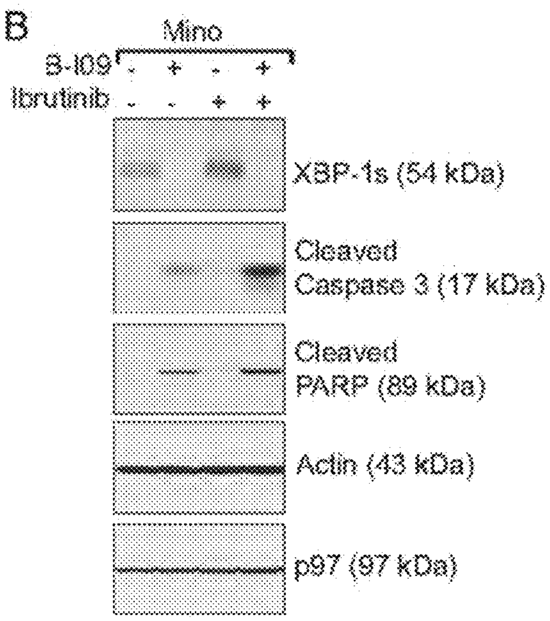

FIG. 31B: Human Mino MCL cells (B) were cultured in the presence of DMSO (control), B-I09 (20 μM), ibrutinib (10 μM), or the combination for 48 h (5TGM1) or 72 h (Mino). Cells were lysed for analysis of the expression of XBP-1s, cleaved caspase-3, cleaved PARP, p97 and actin by immunoblots using specific antibodies.

Figure 32A:
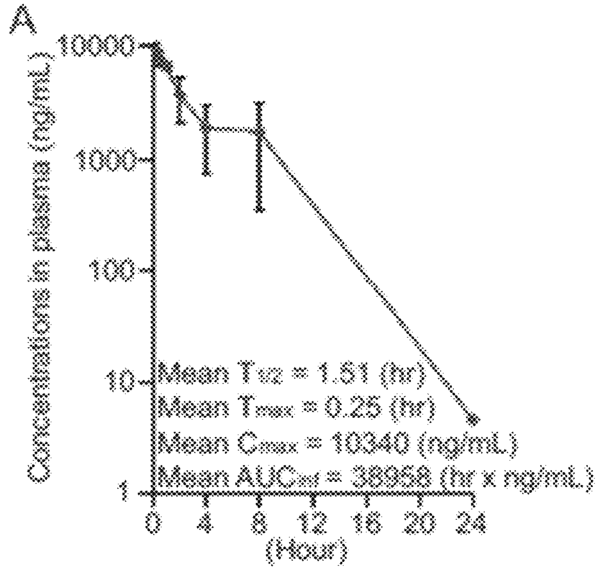

FIG. 32A: Pharmacokinetic analysis of B-I09 (n=3; mean±SEM). The terminal half-life ($T_{1/2}$), time of peak concentration ($T_{max}$), maximum concentration ($C_{max}$) and area under the concentration versus time calculated using zero to infinity ($AUC_{inf}$) of B-I09 in mouse plasma are indicated.

Figure 32B:
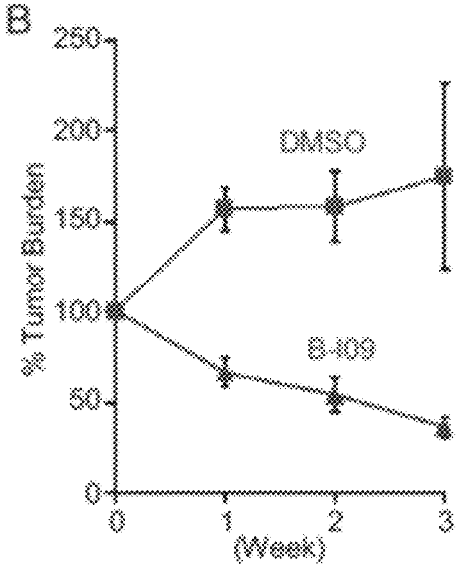

FIG. 32B: CLL-bearing Eμ-TCL1 mice were intraperitoneally injected with DMSO (n=3) or B-I09 (50 mg/kg in DMSO, n=8) daily for the first 5 days weekly for three weeks. Blood was collected to measure lymphocyte numbers using a HemaTrue Hematology Analyzer (HESKA). Data were compared with lymphocyte counts prior to B-I09 injections, and plotted as mean±SEM.

Figure 32C:
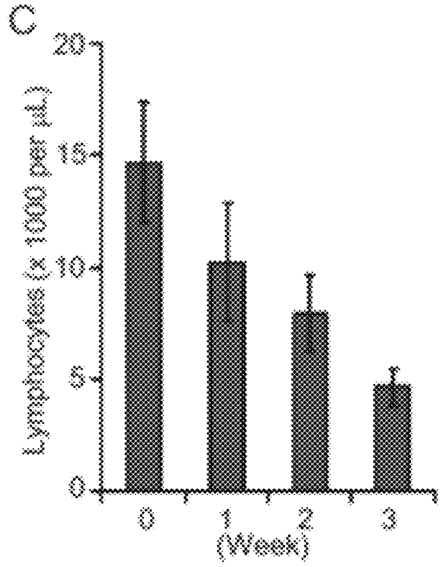

FIG. 32C: Lymphocyte counts in the peripheral blood of B-I09-treated Eμ-TCL1 mice (n=8) were plotted as mean±SEM.

Figure 32D:
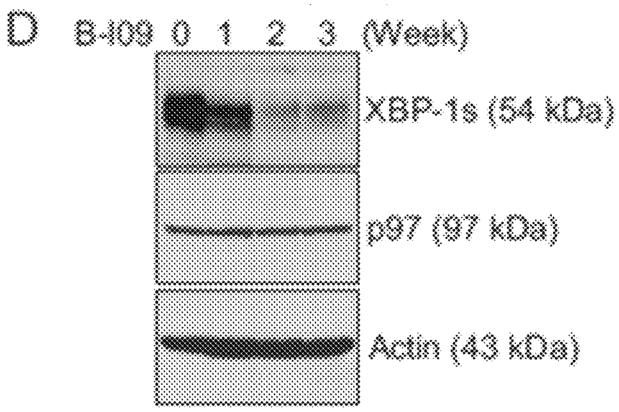

FIG. 32D: PBMCs from B-I09 mice, before and after injections, were lysed for analysis of indicated proteins.

Figure 32E:
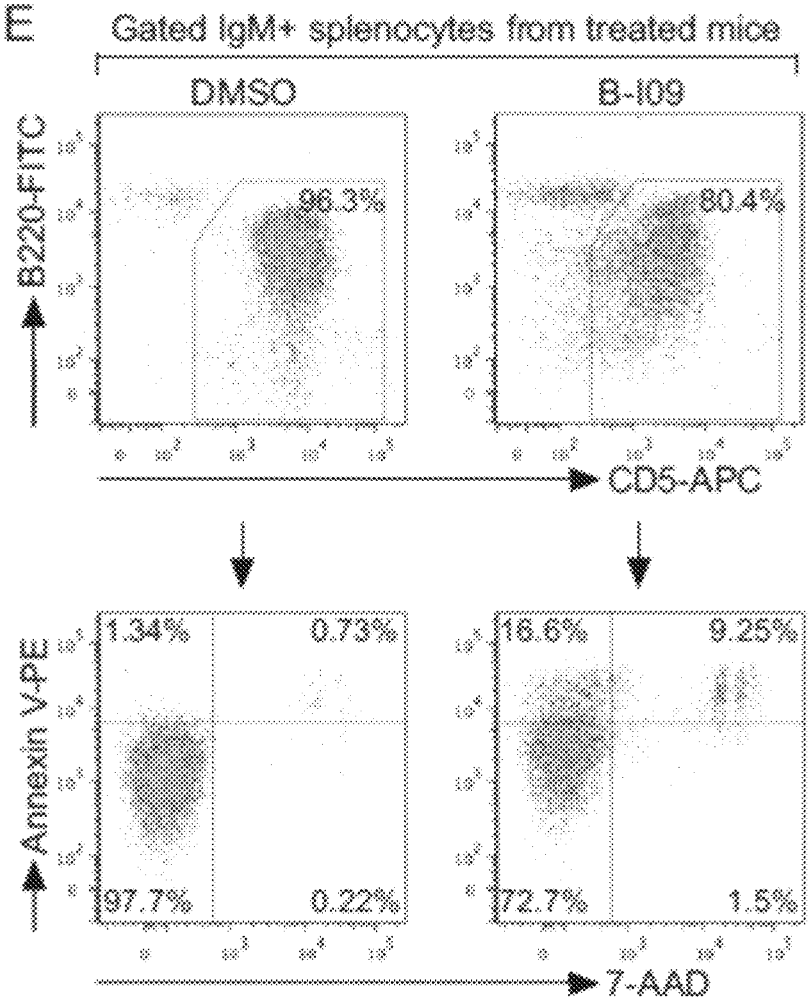

FIG. 32E: Splenocytes from DMSO- or B-I09-injected Eμ-TCL1 mice were stained with IgM-PE-Cy7, B220-FITC, CD5-APC, Annexin V-PE and 7-AAD. Gated IgM+/B220+/CD5+ splenic CLL cells were analyzed for Annexin V- and/or 7-AAD-positive populations.

Figure 32F:
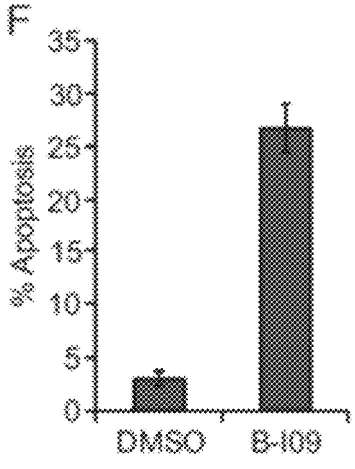

FIG. 32F: Percentages of apoptotic cells in gated $IgM^+$/B220+/CD5+ CLL populations from spleens of DMSO-injected (n=3) or B-I09-injected (n=8) Eμ-TCL1 mice were plotted as mean±SEM.

Figure 32G:
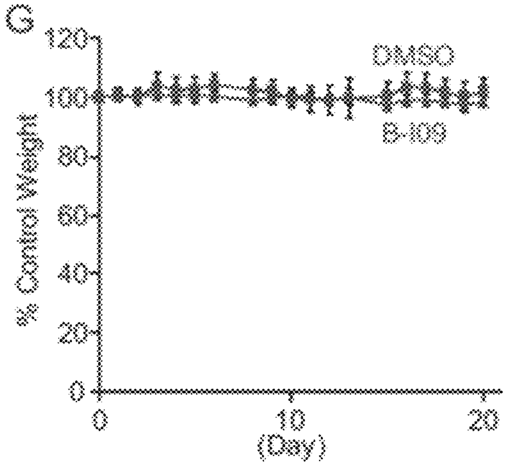

FIG. 32G: Weight of DMSO-injected (n=3) or B-I09-injected (n=8) Eμ-TCL1 mice was plotted as mean±SD.

Figure 32H:
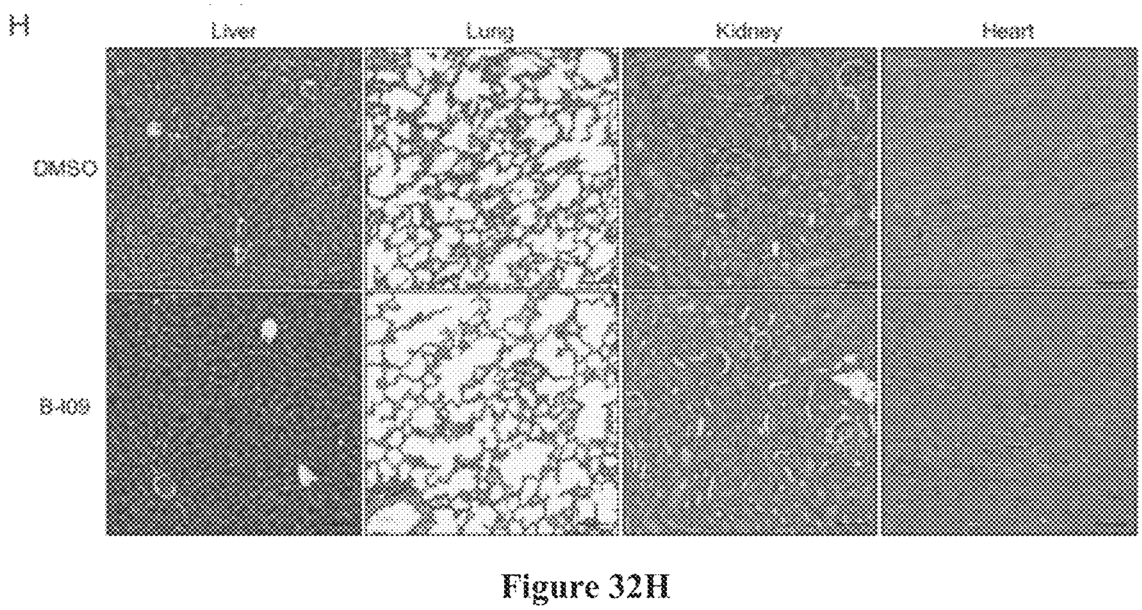

FIG. 32H: Paraffin-embedded sections of indicated organs from Eμ-TCL1 mice receiving three weeks of injections with DMSO or B-I09 were stained with hematoxylin and eosin. Bar=80 μm.

Figure 33:
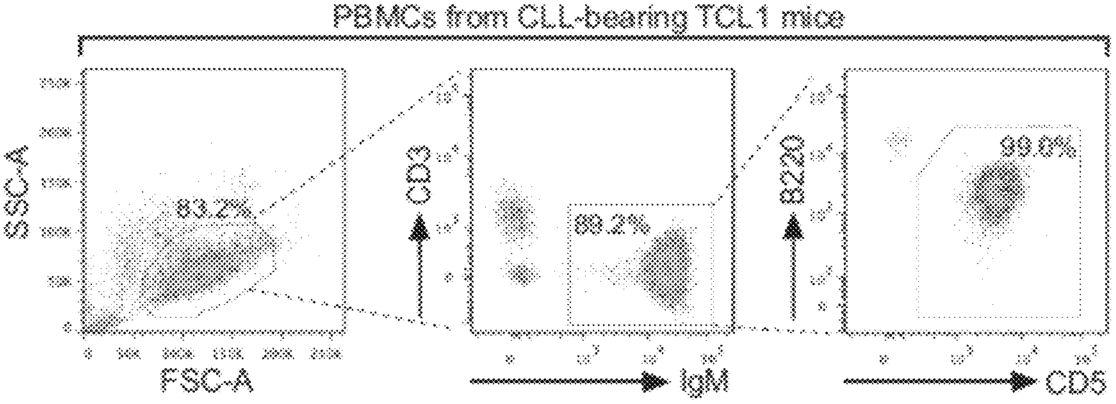

FIG. 33 displays PBMCs from CLL-bearing Eμ-TCL1 mice were stained with CD3-APC-Cy7, IgM-PE-Cy7, B220-FITC and CD5-APC monoclonal antibodies. Gated lymphocyte populations in PBMCs (left panel) were analyzed for CD3+/IgM− T cells, CD3−/IgM− non-B/non-T cells, and CD3−/$IgM^+$ B cells (middle panel). Gated CD3−/$IgM^+$ B cells were analyzed for the expression of B220 and CD5 (right panel).

Figure 34:
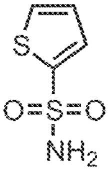
Figure 34:
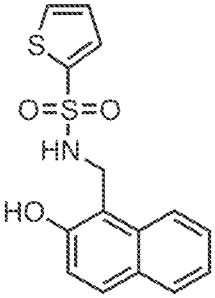
Figure 34:
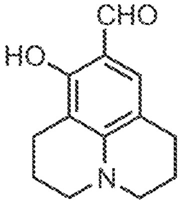
Figure 34:
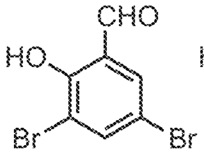
Figure 34:
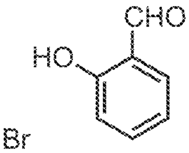
Figure 34:
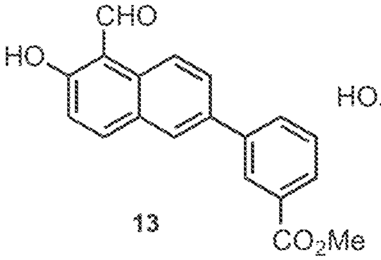
Figure 34:
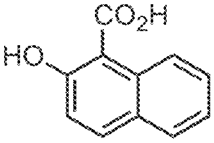
Figure 34:
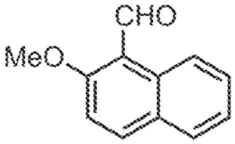
Figure 34:
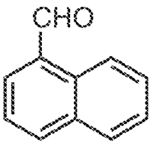

FIG. 34 displays compounds evaluated for anti-IRE-1 RNase activity by FRET-suppression assay. $IC_{50}$ and CI values are reported as the mean of 4 separate experiments.

Figure 35:
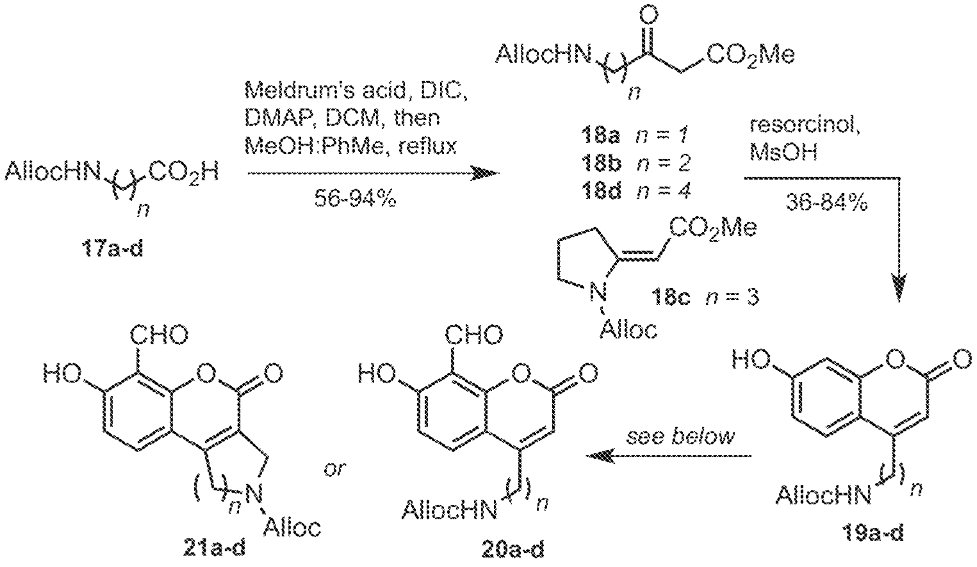

FIG. 35 displays a synthetic scheme for substituted bicyclic and tricyclic 8-formyl chromenones.

Figure 36:
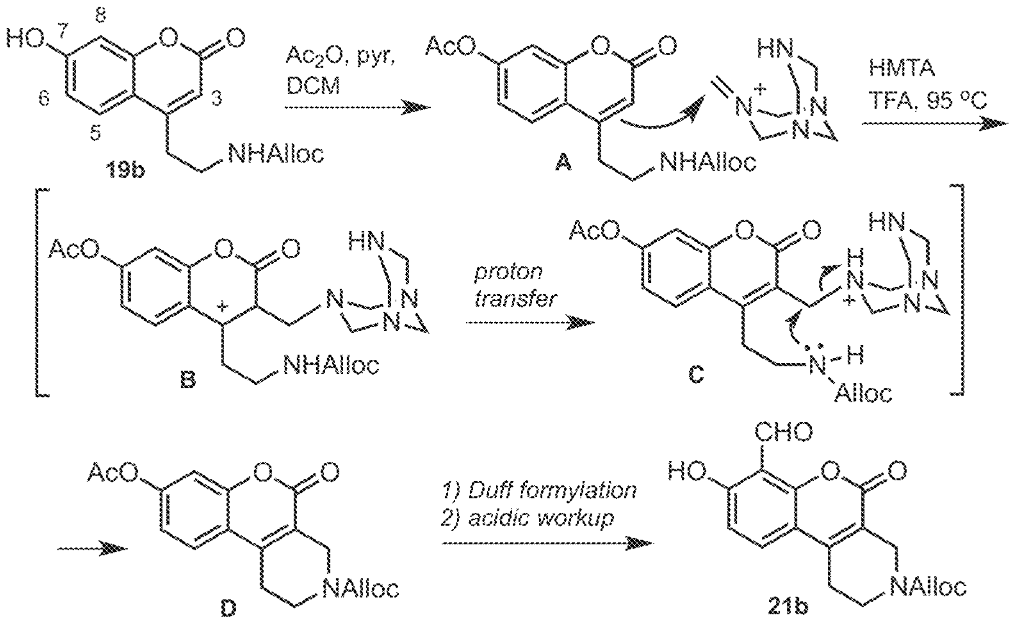

FIG. 36 displays a proposed mechanism of annulation during Duff formylation.

Figure 37:
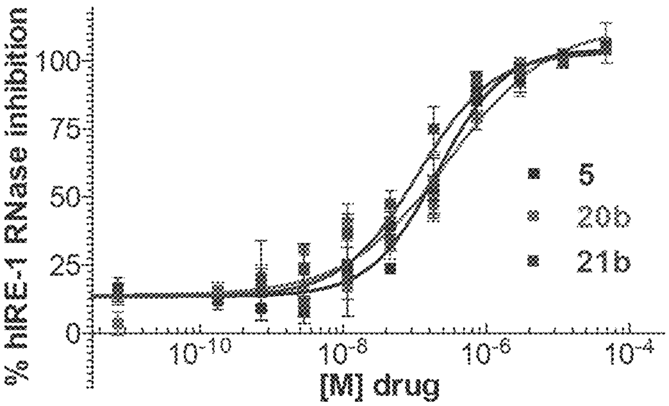

FIG. 37 displays the in vitro inhibition of IRE-1 RNase activity by compounds 20 and 21. $IC_{50}$ and CI values are reported as the mean of 4 separate experiments.

Figure 38:
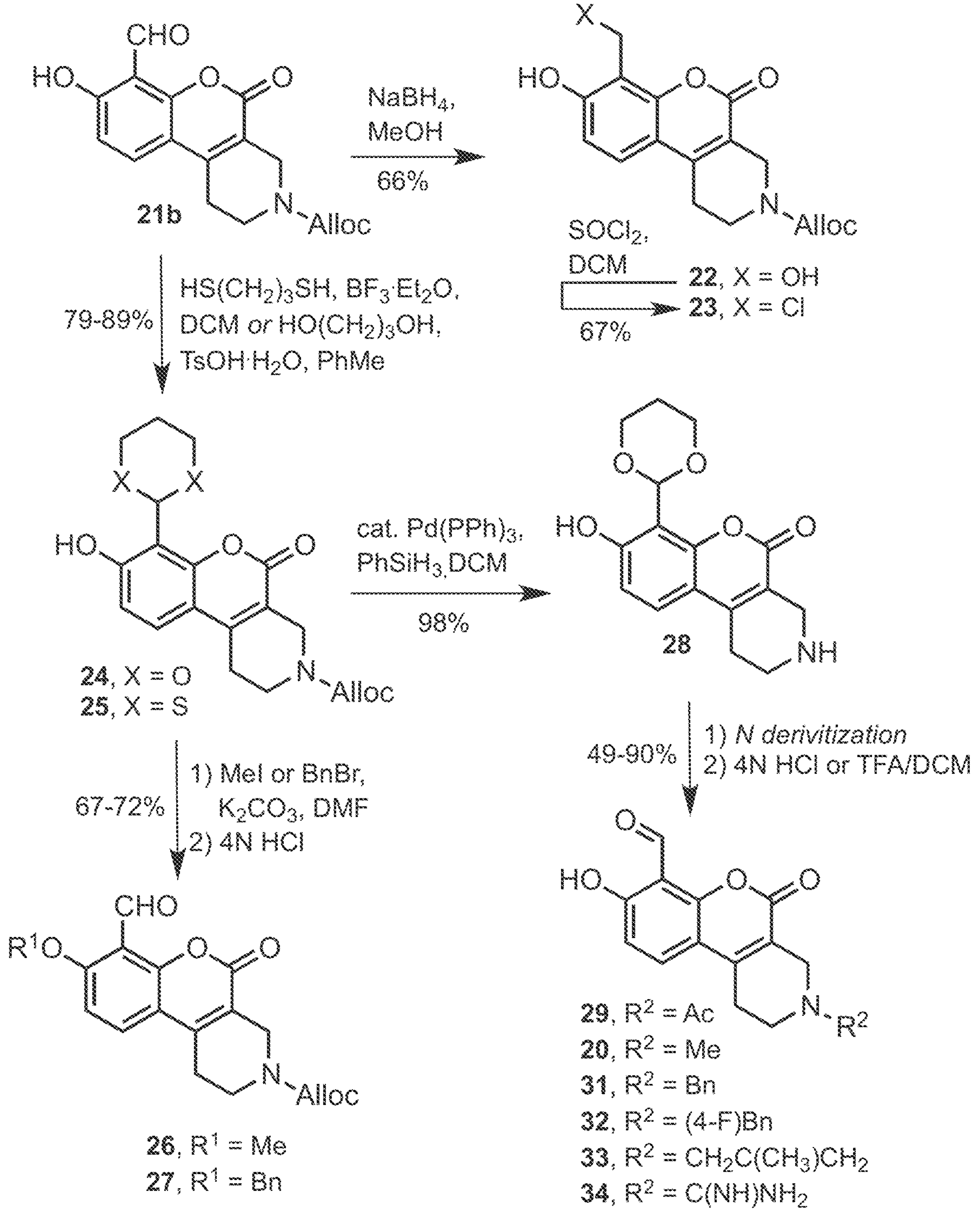

FIG. 38 displays a synthetic scheme for O- and N-substituted analogs.

Figure 39:
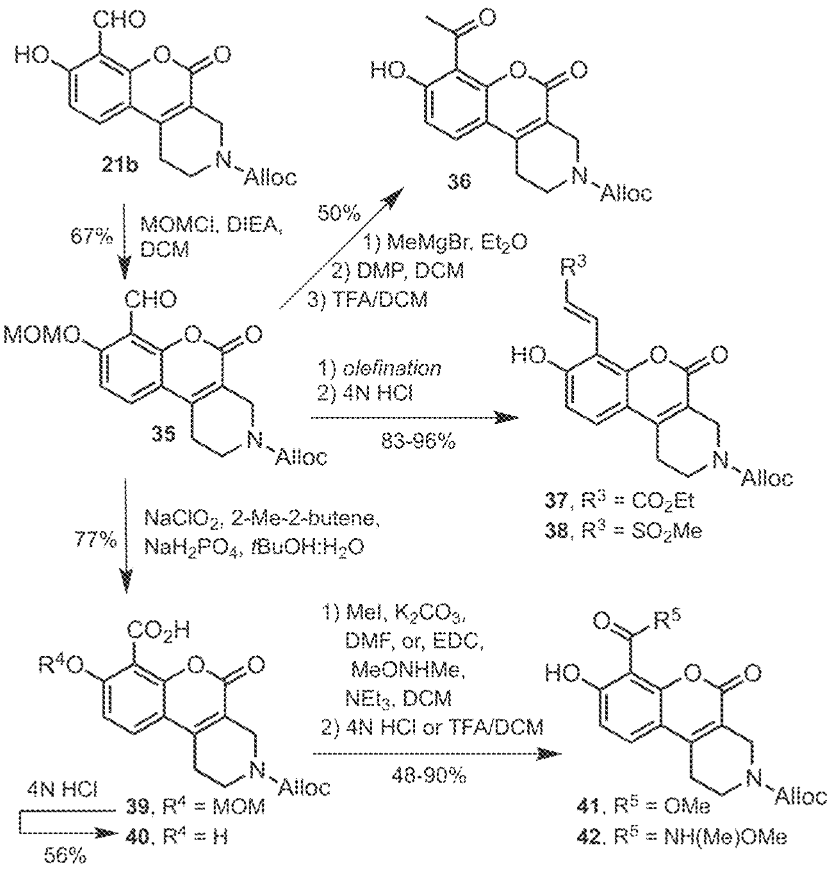

FIG. 39 displays a synthetic scheme for analogs with aldehyde surrogates.

Figure 40A:
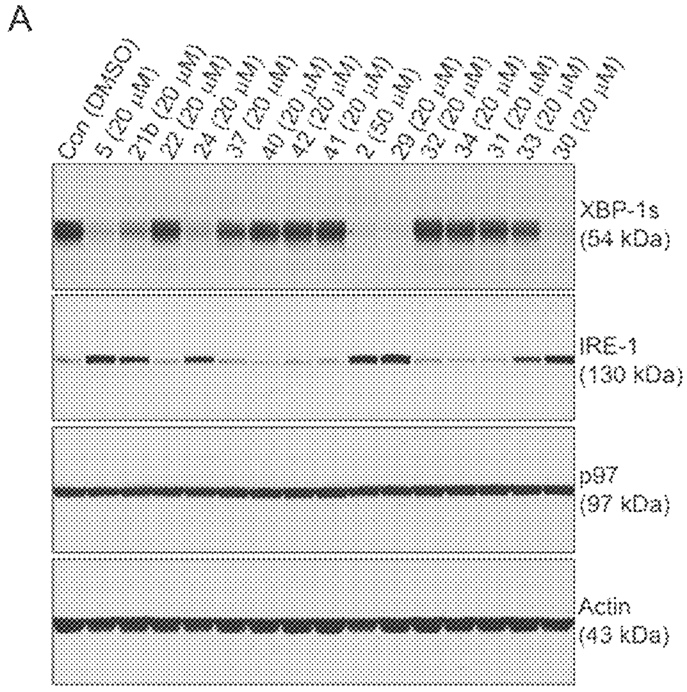

FIG. 40A displays the inhibition of XBP-1s expression in whole cells. B cells were purified from the spleens of wild-type mice, stimulated with LPS for 48 h, treated with the indicated inhibitors at 20 μM for 24 h, lysed and analyzed for expression of the indicated proteins by immunoblots.

Figure 40B:
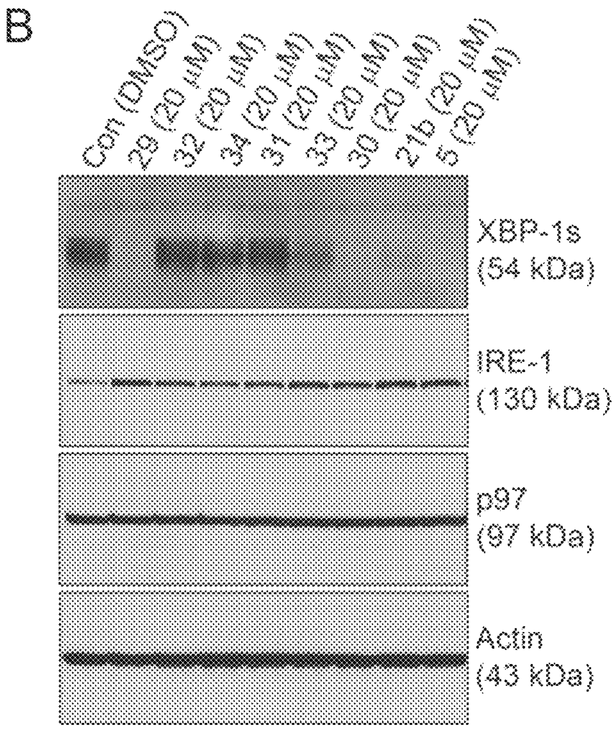

FIG. 40B displays the inhibition of XBP-1s expression in whole cells. Mino cells were treated with the indicated inhibitors at 20 μM for 24 h, lysed and analyzed for the expression of indicated proteins by immunoblots.

Figure 40C:
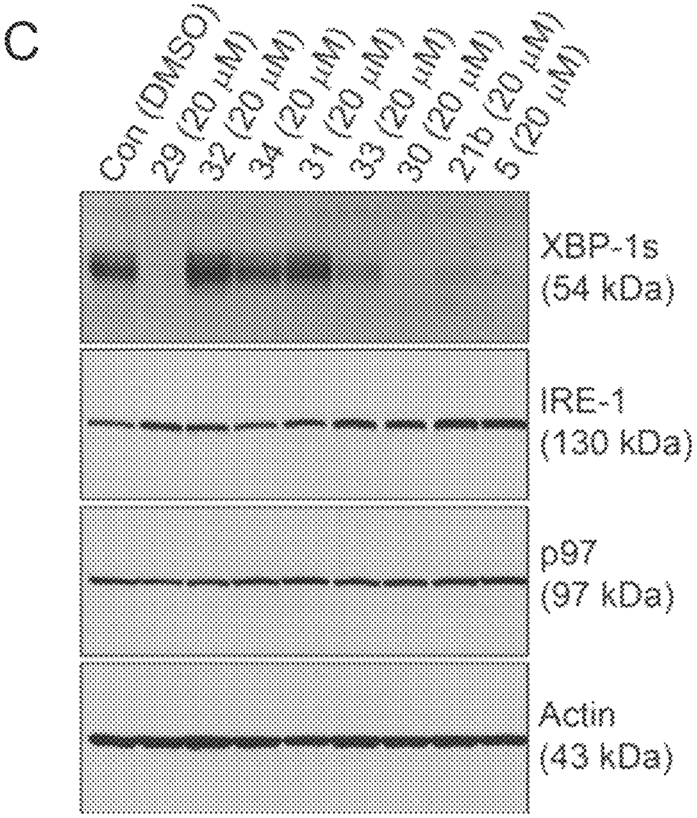

FIG. 40C displays the inhibition of XBP-1s expression in whole cells. Jeko cells were treated with the indicated inhibitors at 20 μM for 24 h, lysed and analyzed for the expression of indicated proteins by immunoblots.

Figure 40D:
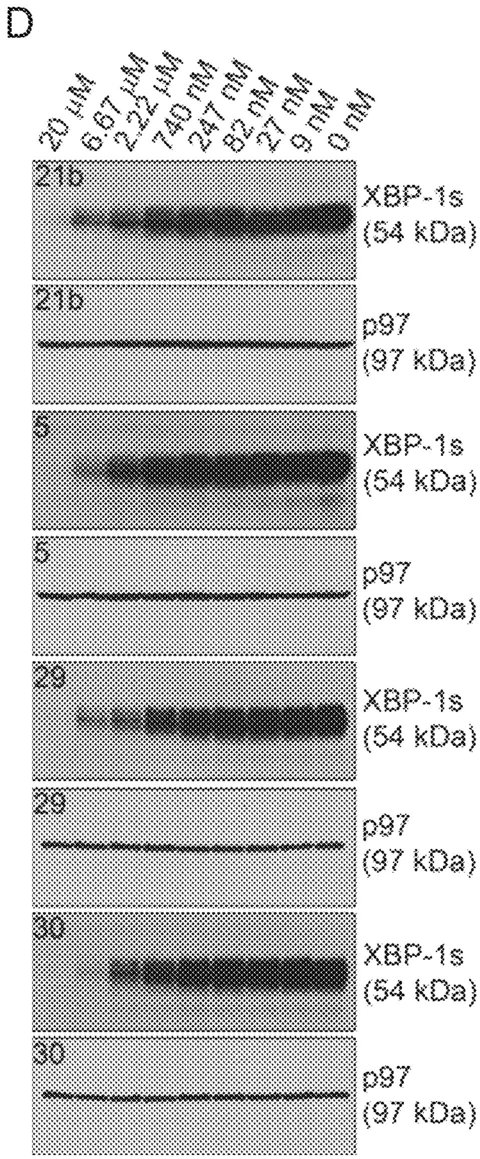

FIG. 40D displays the inhibition of XBP-1s expression in whole cells. Mino cells were treated with the indicated inhibitors at various doses for 48 h, lysed and analyzed for the expression of indicated proteins by immunoblots.

Figure 40E:
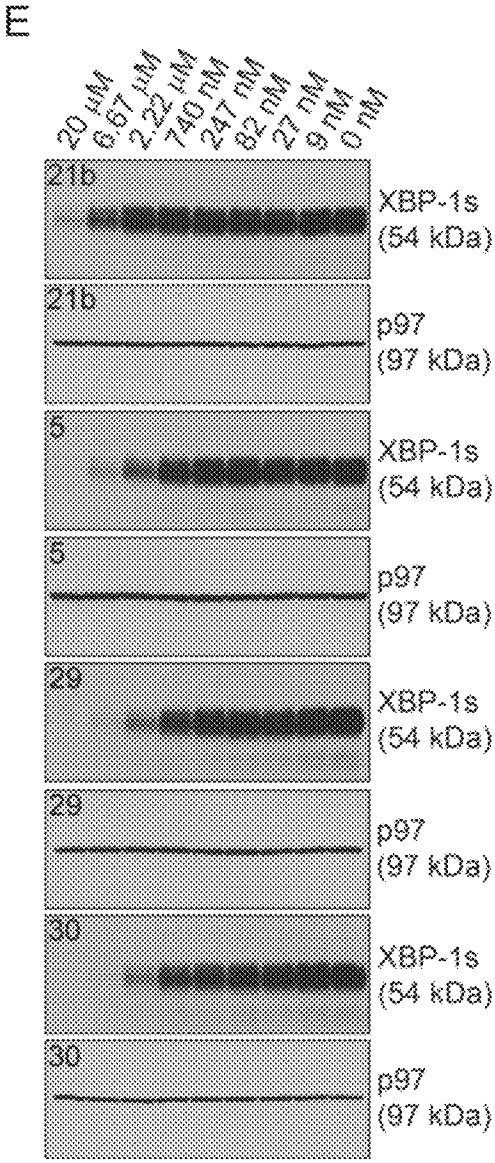

FIG. 40E displays the inhibition of XBP-1s expression in whole cells. Jeko cells were treated with the indicated inhibitors at various doses for 48 h, lysed and analyzed for the expression of indicated proteins by immunoblots.

Figure 40F:
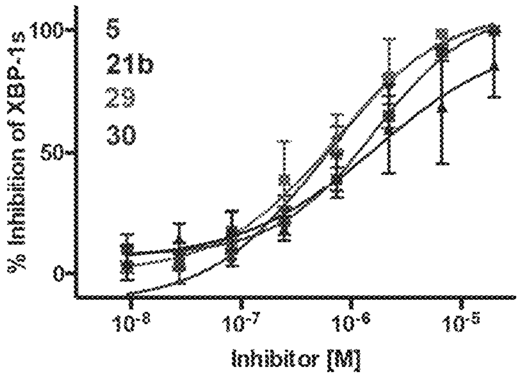

FIG. 40F displays the inhibition of XBP-1s expression in whole cells. Mino dose-response curves and IC50 values for inhibition of XBP-1s expression by indicated inhibitors as determined by immunoblots and densitometry (N=3).

Figure 40G:
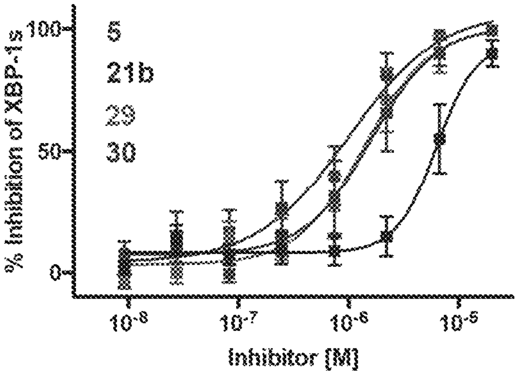

FIG. 40G displays the inhibition of XBP-1s expression in whole cells. Jeko dose-response curves and IC50 values for inhibition of XBP-1s expression by indicated inhibitors as determined by immunoblots and densitometry (N=3).

Figure 41A:
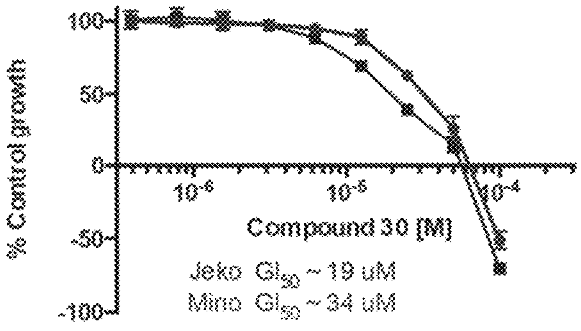

FIG. 41A displays the growth inhibition and induction of apoptosis by 30. Human Mino and Jeko cells were cultured in the presence of 30 at various concentrations for 48 h and subjected to XTT assay. Percentages of cell growth were calculated relative to DMSO-treated (control) groups.

Figure 41B:
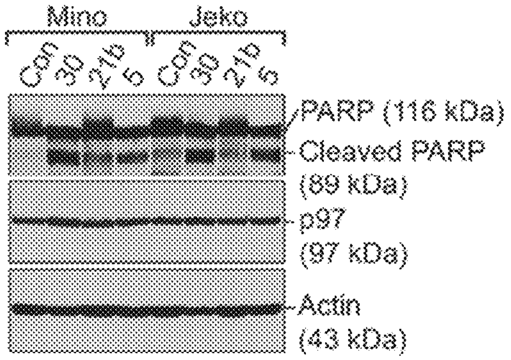

FIG. 41B displays the growth inhibition and induction of apoptosis by 30. Human Mino and Jeko cells were cultured for 72 h in the presence of DMSO (control), 30 (50 μM), 21b (50 μM), and 5 (50 μM). Cells were lysed for the analysis of the indicated proteins by immunoblot.

Figure 42:
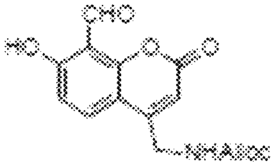
Figure 42:
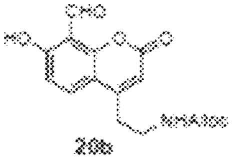
Figure 42:
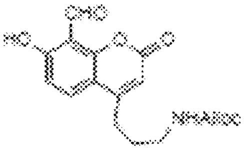
Figure 42:
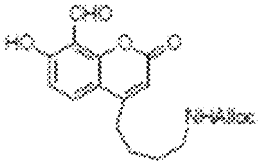
Figure 42:
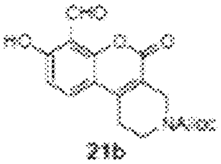
Figure 42:
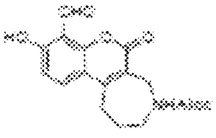
Figure 42:
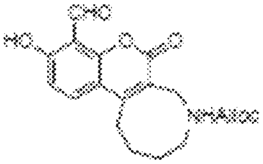
Figure 42:
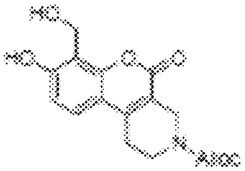
Figure 42:
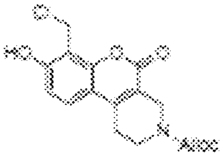
Figure 42:
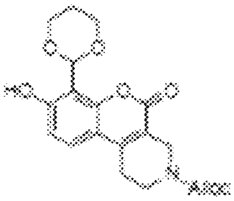
Figure 42:
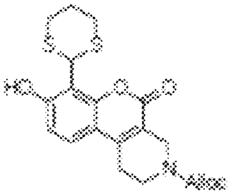
Figure 42:
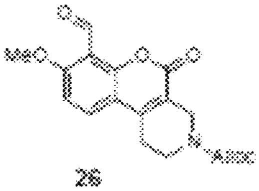
Figure 42:
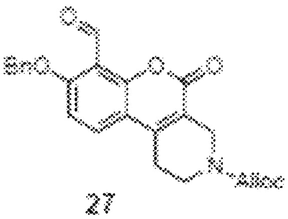
Figure 42:
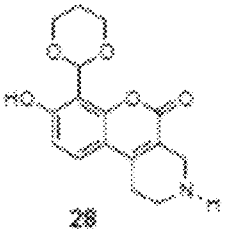
Figure 42:
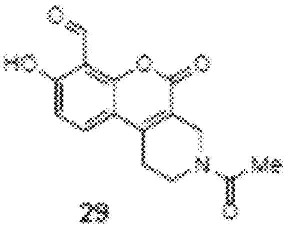
Figure 42:
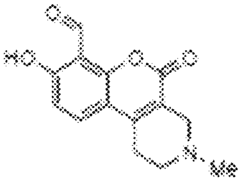
Figure 42:
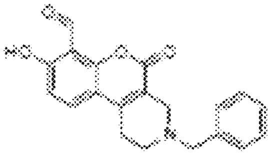
Figure 42:
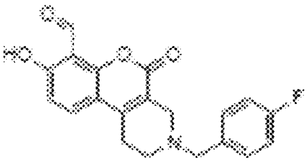

FIG. 42 displays the structure of compounds 20a-42.

FIG. 43A displays the purification and RNase activity of recombinant IRE-1. Human IRE-1 was expressed in SF21 insect cells and purified using Ni-NTA column chromatography. Purified IRE-1 was analyzed by SDS-PAGE and stained with Coomassie Brilliant Blue G-250.

FIG. 43B displays the purification and RNase activity of recombinant IRE-1. The Michaelis-Menten curve for IRE-1 showing catalytic RNase activity in a FRET assay. Initial reaction velocity plotted as a function of different XBP-1 stem-loop RNA concentration in the presence of 5 nM IRE-1.

Figure 44A:
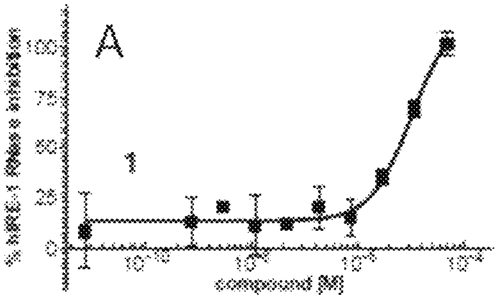

FIG. 44A displays the FRET-suppression assay dose-response curves for the active inhibitors of IRE-RNase activity as determined by FRET-suppression assay. All data points are reported as the mean of at least 4 independent experiments. The compound evaluated for the assay is 1, as shown on the plot.

Figure 44B:
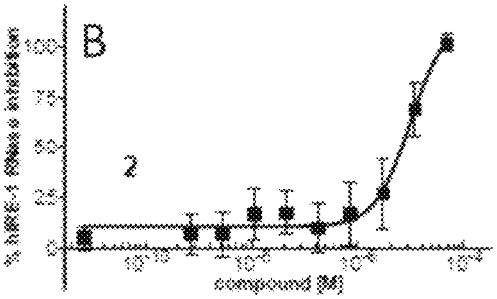

FIG. 44B displays the FRET-suppression assay dose-response curves for the active inhibitors of IRE-RNase activity as determined by FRET-suppression assay. All data points are reported as the mean of at least 4 independent experiments. The compound evaluated for the assay is 2, as shown on the plot.

Figure 44C:
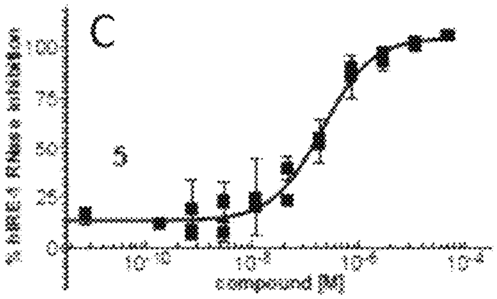

FIG. 44C displays the FRET-suppression assay dose-response curves for the active inhibitors of IRE-RNase activity as determined by FRET-suppression assay. All data points are reported as the mean of at least 4 independent experiments. The compound evaluated for the assay is 5, as shown on the plot.

Figure 44D:
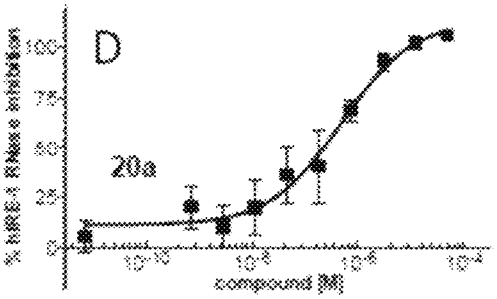

FIG. 44D displays the FRET-suppression assay dose-response curves for the active inhibitors of IRE-RNase activity as determined by FRET-suppression assay. All data points are reported as the mean of at least 4 independent experiments. The compound evaluated for the assay is 20a, as shown on the plot.

Figure 44E:
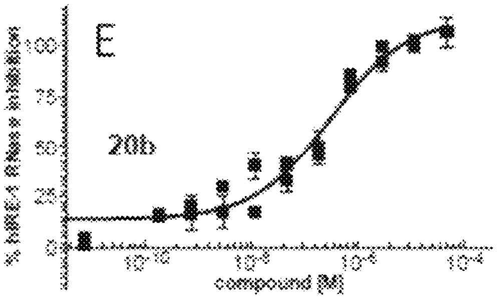

FIG. 44E displays the FRET-suppression assay dose-response curves for the active inhibitors of IRE-RNase activity as determined by FRET-suppression assay. All data points are reported as the mean of at least 4 independent experiments. The compound evaluated for the assay is 20b, as shown on the plot.

Figure 44F:
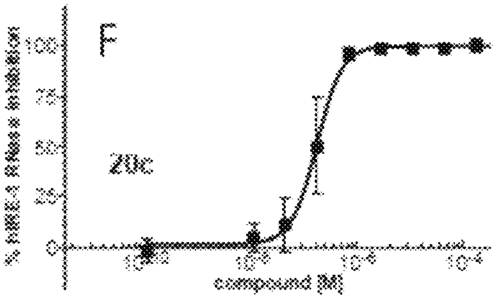

FIG. 44F displays the FRET-suppression assay dose-response curves for the active inhibitors of IRE-RNase activity as determined by FRET-suppression assay. All data points are reported as the mean of at least 4 independent experiments. The compound evaluated for the assay is 20c, as shown on the plot.

Figure 44G:
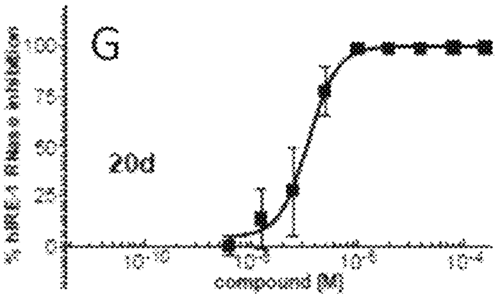

FIG. 44G displays the FRET-suppression assay dose-response curves for the active inhibitors of IRE-RNase activity as determined by FRET-suppression assay. All data points are reported as the mean of at least 4 independent experiments. The compound evaluated for the assay is 20d, as shown on the plot.

Figure 44H:
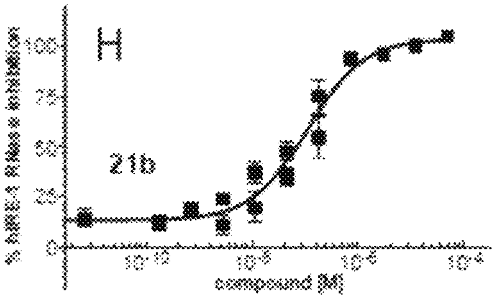

FIG. 44H displays the FRET-suppression assay dose-response curves for the active inhibitors of IRE-RNase activity as determined by FRET-suppression assay. All data points are reported as the mean of at least 4 independent experiments. The compound evaluated for the assay is 21b, as shown on the plot.

Figure 44I:
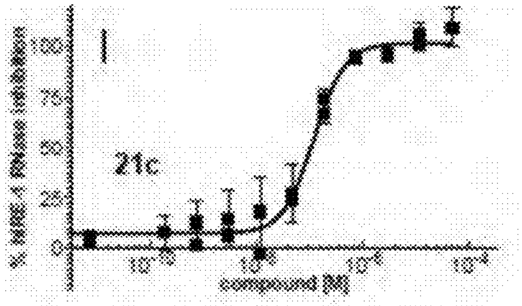

FIG. 44I displays the FRET-suppression assay dose-response curves for the active inhibitors of IRE-RNase activity as determined by FRET-suppression assay. All data points are reported as the mean of at least 4 independent experiments. The compound evaluated for the assay is 21c, as shown on the plot.

Figure 44J:
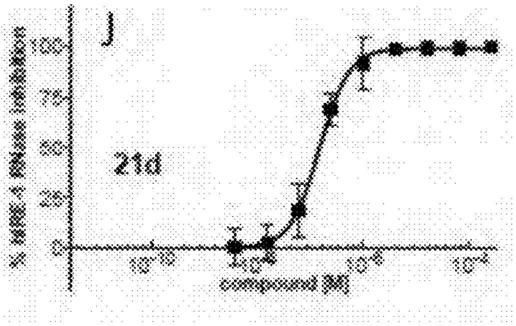

FIG. 44J displays the FRET-suppression assay dose-response curves for the active inhibitors of IRE-RNase activity as determined by FRET-suppression assay. All data points are reported as the mean of at least 4 independent experiments. The compound evaluated for the assay is 21d, as shown on the plot.

Figure 44K:
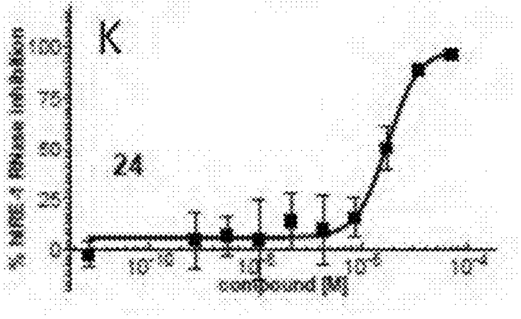

FIG. 44K displays the FRET-suppression assay dose-response curves for the active inhibitors of IRE-RNase activity as determined by FRET-suppression assay. All data points are reported as the mean of at least 4 independent experiments. The compound evaluated for the assay is 24, as shown on the plot.

Figure 44L:
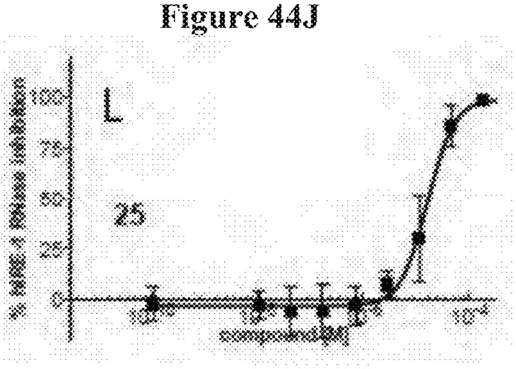

FIG. 44L displays the FRET-suppression assay dose-response curves for the active inhibitors of IRE-RNase activity as determined by FRET-suppression assay. All data points are reported as the mean of at least 4 independent experiments. The compound evaluated for the assay is 25, as shown on the plot.

Figure 44M:
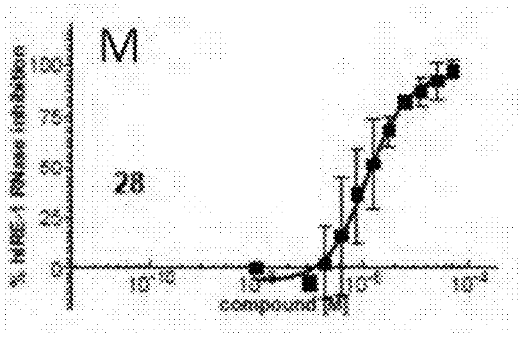

FIG. 44M displays the FRET-suppression assay dose-response curves for the active inhibitors of IRE-RNase activity as determined by FRET-suppression assay. All data points are reported as the mean of at least 4 independent experiments. The compound evaluated for the assay is 28, as shown on the plot.

Figure 44N:
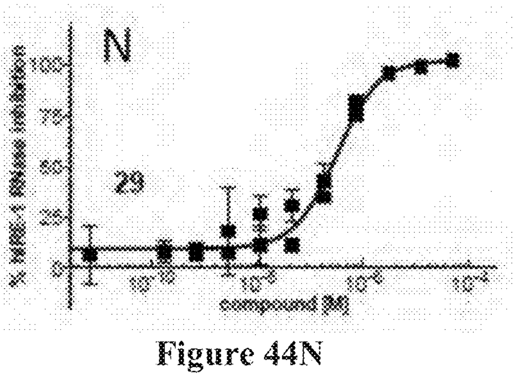

FIG. 44N displays the FRET-suppression assay dose-response curves for the active inhibitors of IRE-RNase activity as determined by FRET-suppression assay. All data points are reported as the mean of at least 4 independent experiments. The compound evaluated for the assay is 29, as shown on the plots.

Figure 44O:
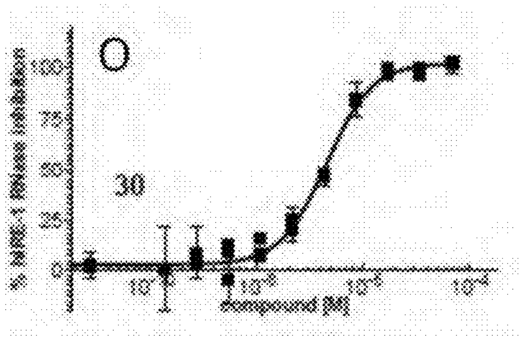

FIG. 44O displays the FRET-suppression assay dose-response curves for the active inhibitors of IRE-RNase activity as determined by FRET-suppression assay. All data points are reported as the mean of at least 4 independent experiments. The compound evaluated for the assay is 30, as shown on the plot.

Figure 44P:
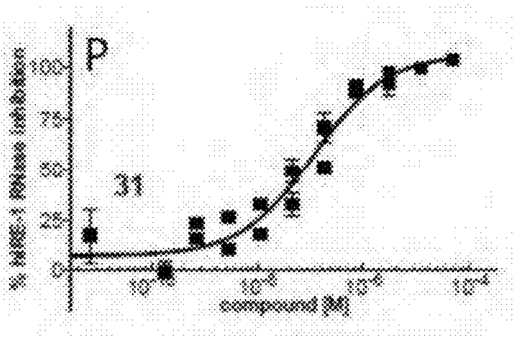

FIG. 44P displays the FRET-suppression assay dose-response curves for the active inhibitors of IRE-RNase activity as determined by FRET-suppression assay. All data points are reported as the mean of at least 4 independent experiments. The compound evaluated for the assay is 31, as shown on the plot.

Figure 44Q:
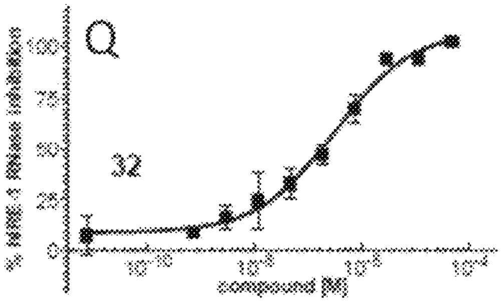

FIG. 44Q displays the FRET-suppression assay dose-response curves for the active inhibitors of IRE-RNase activity as determined by FRET-suppression assay. All data points are reported as the mean of at least 4 independent experiments. The compound evaluated for the assay is 32, as shown on the plot.

Figure 44R:
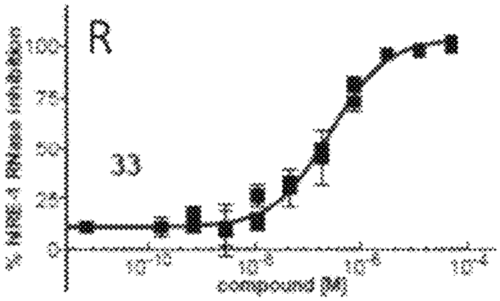

FIG. 44R displays the FRET-suppression assay dose-response curves for the active inhibitors of IRE-RNase activity as determined by FRET-suppression assay. All data points are reported as the mean of at least 4 independent experiments. The compound evaluated for the assay is 33, as shown on the plot.

Figure 44S:
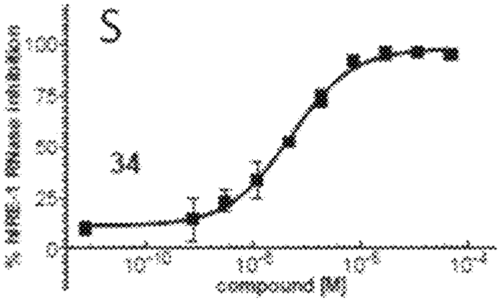

FIG. 44S displays the FRET-suppression assay dose-response curves for the active inhibitors of IRE-RNase activity as determined by FRET-suppression assay. All data points are reported as the mean of at least 4 independent experiments. The compound evaluated for the assay is 34, as shown on the plot.

Figure 44T:
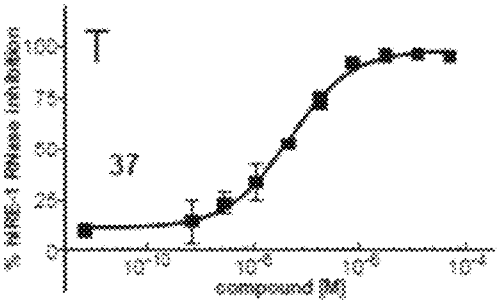

FIG. 44T displays the FRET-suppression assay dose-response curves for the active inhibitors of IRE-RNase activity as determined by FRET-suppression assay. All data points are reported as the mean of at least 4 independent experiments. The compound evaluated for the assay is 37, as shown on the plot.

Figure 44U:
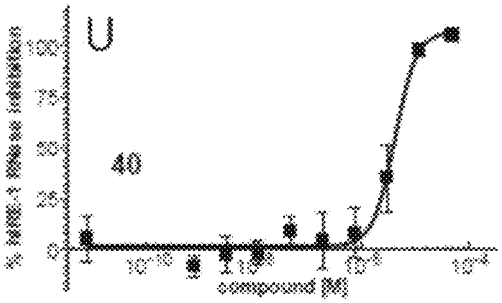

FIG. 44U displays the FRET-suppression assay dose-response curves for the active inhibitors of IRE-RNase activity as determined by FRET-suppression assay. All data points are reported as the mean of at least 4 independent experiments. The compound evaluated for the assay is 40, as shown on the plot.

Figure 44V:
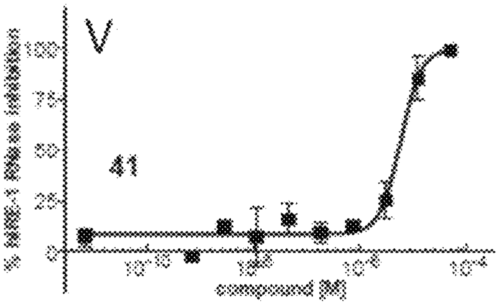

FIG. 44V displays the FRET-suppression assay dose-response curves for the active inhibitors of IRE-RNase activity as determined by FRET-suppression assay. All data points are reported as the mean of at least 4 independent experiments. The compound evaluated for the assay is 41, as shown on the plot.

Figure 45:
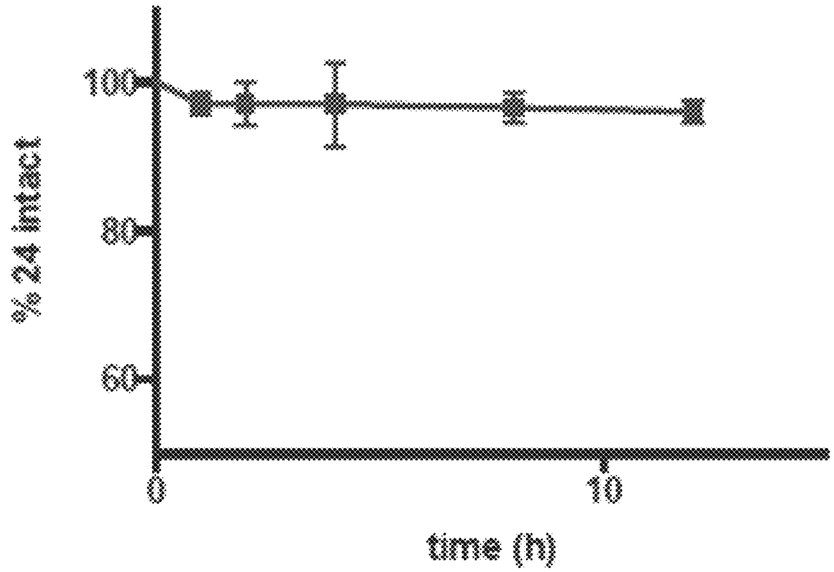

FIG. 45 displays the chemical stability of analog 24. The degradation of analog 24 was plotted as a function of time upon exposure to FRET-suppression assay buffer at rt. Aliquots were partitioned with MeOH and injected onto LCMS (UV monitored at 320 nm) and peaks integrated relative to internal standard.

Figure 46:
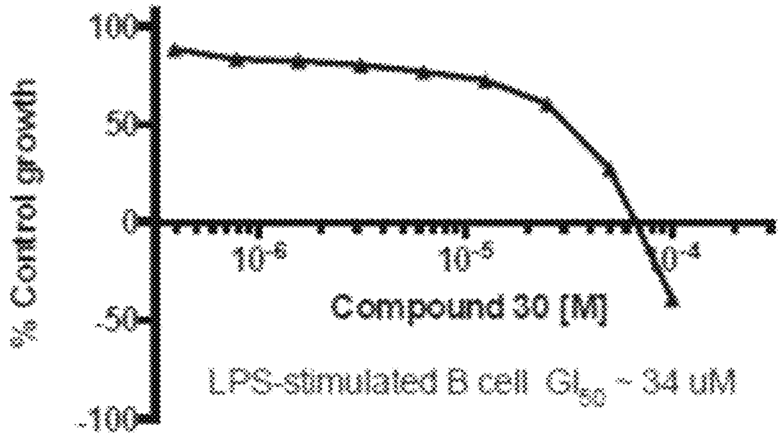

FIG. 46 displays the XTT assay with LPS-stimulated mouse B cells treated with analog 30. B cells were purified from the spleens of wild type mice, cultured in the presence LPS (20 μg/mL) and 30 at various concentrations for 72 h, and subjected to XTT assay. Percentages of cell growth were calculated relative to DMSO-treated (control) groups.

Figure 47A:
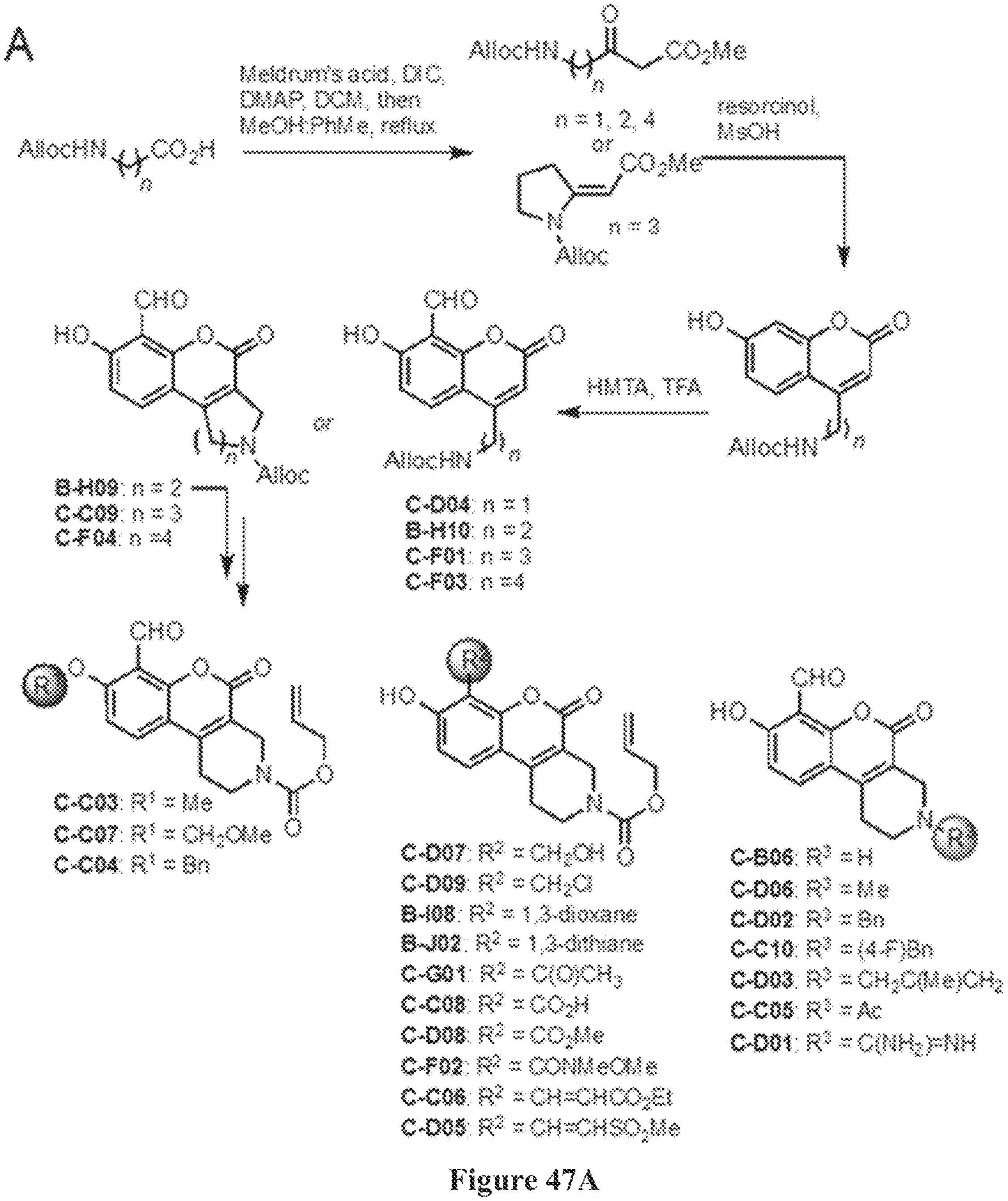

FIG. 47A displays the inhibitors of XBP-1s expression. Synthetic scheme for exemplary B-H09 analogs.

FIG. 47B displays the inhibitors of XBP-1s expression. In vitro inhibition of IRE-1 RNAse activity by FRET-suppression assay.

Figure 47C:
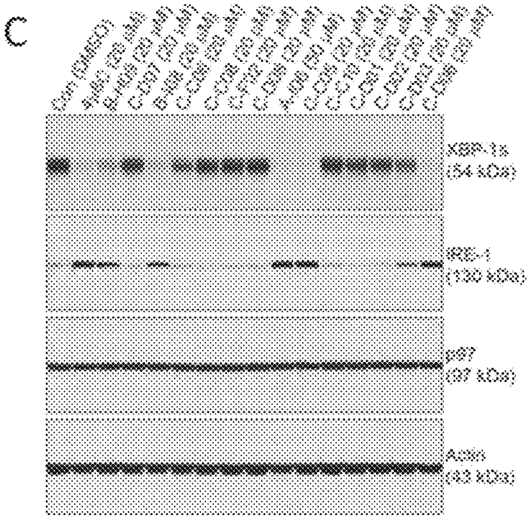

FIG. 47C displays the inhibitors of XBP-1s expression. Wild-type MD4 mouse B cells were stimulated with LPS for 48 h, then treated with the indicated inhibitors at 20 μM for 24 h. The cells were then lysed and analyzed for expression of the indicated protein immunoblots.

Figure 47D:
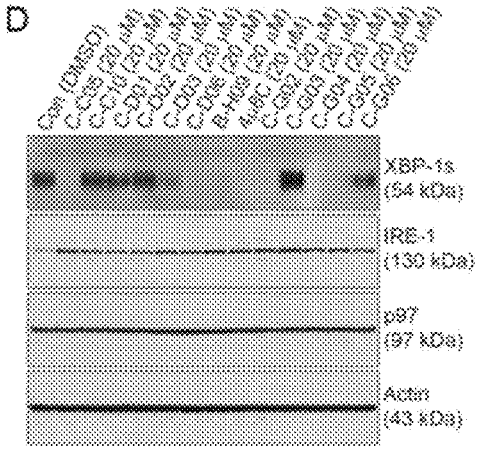

FIG. 47D displays the inhibitors of XBP-1s expression. Mino cells were treated with the indicated inhibitors at 20 μM for 24 h, lysed and analyzed for expression of the indicated protein immunoblots.

Figure 47E:
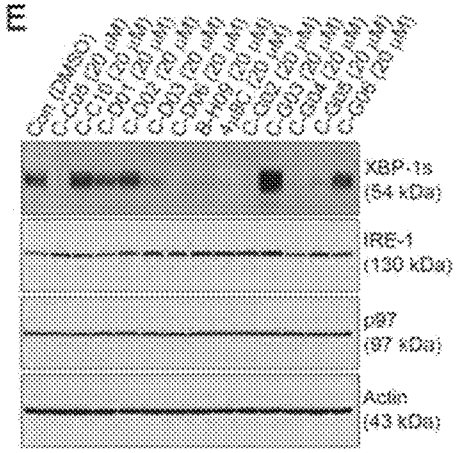

FIG. 47E displays the inhibitors of XBP-1s expression. Jeko cells were treated with the indicated inhibitors at 20 μM for 24 h, lysed and analyzed for expression of the indicated protein immunoblots.

Figure 47F:
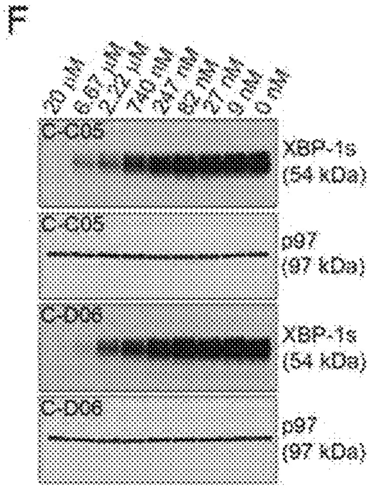

FIG. 47F displays the inhibitors of XBP-1s expression. Mino cells were treated with C-CO5 and C-DO6 at various doses for 24 h, lysed and analyzed for expression of the indicated protein immunoblots.

Figure 47G:
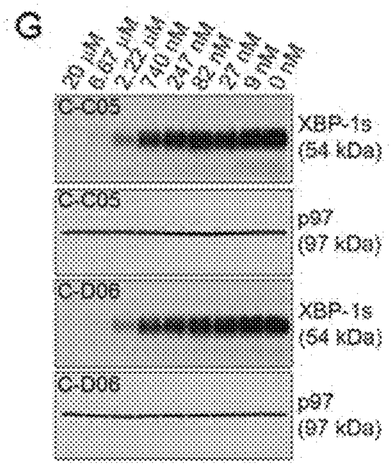

FIG. 47G displays the inhibitors of XBP-1s expression. Jeko cells were treated with C-CO5 and C-DO6 at various doses for 24 h, lysed and analyzed for expression of the indicated protein immunoblots.

Figure 47H:
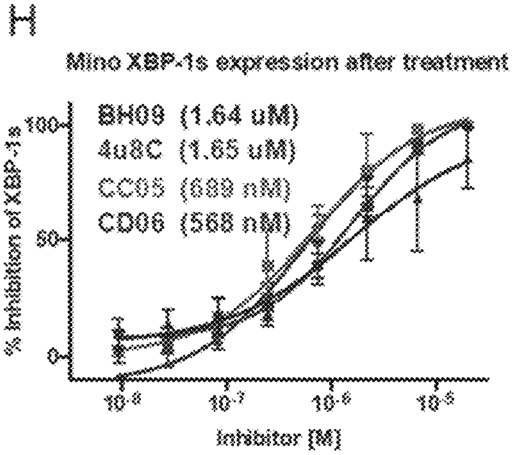

FIG. 47H displays the inhibitors of XBP-1s expression. Mino dose-response curves for inhibition of XBP-1s expression by inhibitors as determined by immunoblots and densitometry.

Figure 47I:
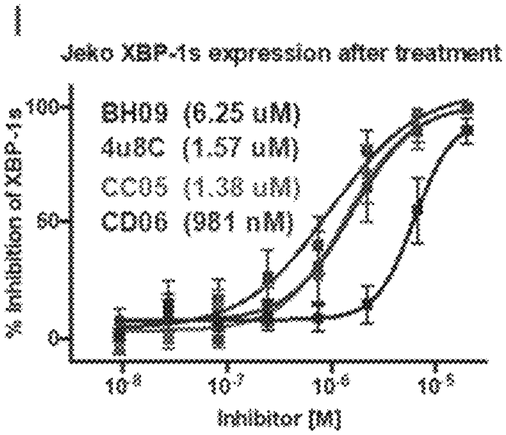

FIG. 47I displays the inhibitors of XBP-1s expression. Jeko dose-response curves for inhibition of XBP-1s expression by inhibitors as determined by immunoblots and densitometry.

Figure 48:
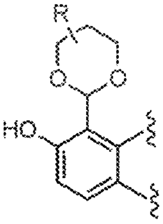
Figure 48:
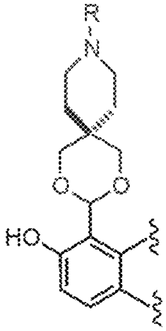
Figure 48:
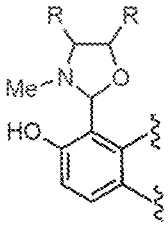
Figure 48:
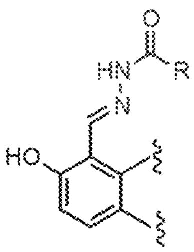
Figure 48:
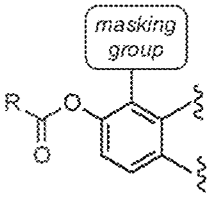

FIG. 48 displays the structures of exemplary aldehyde and phenol prodrug moieties.

DETAILED DESCRIPTION

The materials, compounds, compositions, articles, devices, and methods described herein may be understood more readily by reference to the following detailed description of specific aspects of the disclosed subject matter and the Examples and Figures included therein.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The term "inhibit" refers to a decrease in an activity, response, condition, disease, or other biological parameter. This can include but is not limited to the complete ablation of the activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

The term "anticancer" refers to the ability to treat or control cellular proliferation and/or tumor growth at any concentration.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, for example 1 to 3, 1 to 4, 1 to 5, 1 to 6, 1 to 7, 1 to 8, 1 to 9, 1 to 10, or 1 to 15 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms, for example, 2 to 5, 2 to 10, 2 to 15, or 2 to 20 carbon atoms, with a structural formula containing at least one carbon-carbon double bond. Asymmetric structures such as $(Z^1Z^2)C{=}C(Z^3Z^4)$ are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms, for example 2 to 5, 2 to 10, 2 to 15, or 2 to 20 carbon atoms, with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "carbonyl as used herein is represented by the formula —$C(O)Z^1$ where $Z^1$ can be a hydrogen, hydroxyl, alkoxy, alkyl, halogenated alkyl, alkenyl, alkynyl, aryl, heteroaryl, cycloalkyl, cycloalkenyl, heterocycloalkyl, or heterocycloalkenyl group described above. Throughout this specification "C(O)" or "CO" is a short hand notation for C═O.

The term "aldehyde" as used herein is represented by the formula —C(O)H.

The terms "amine" or "amino" as used herein are represented by the formula —$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —$C(O)NZ^1Z^2$.

The term "carboxylic acid" as used herein is represented by the formula —C(O)OH. A "carboxylate" or "carboxyl" group as used herein is represented by the formula —C(O)O—.

The term "ester" as used herein is represented by the formula —OC(O)$Z^1$ or —C(O)O$Z^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —Si$Z^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —$S(O)_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH$—.

The term "thiol" as used herein is represented by the formula —SH.

The term "thio" as used herein is represented by the formula —S—.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

The compounds disclosed herein are potent polycyclic IRE-1 RNase inhibitors. As such, disclosed herein are compounds having Formula I:

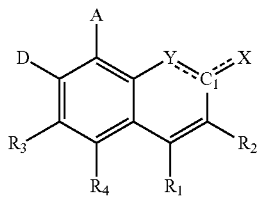

I wherein the dotted lines between Y and $C_1$ and $C_1$ and X represent single or double bonds, as valency permits;

A is a chalcogen containing moiety;

D is chosen from hydrogen, hydroxyl, carbonyl, alkoxy, halogen, thiol, thioalkyl, or alkyl;

$R^3$ and $R^4$ are independently chosen from hydrogen, halogen, hydroxy, amino, alkyl, alkenyl, alkynyl, haloalkyl, cycloalkyl, heterocycloalkyl, alkylaryl, aryl, alkylheteroaryl, or heteroaryl, any of which is optionally substituted with carbonyl, alkyl, amino, amido, —$NR^6R^7$, —C(O)$NR^6R^7$, alkoxy, alkylhydroxy, cycloalkyl, heterocycloalkyl, aryl, heteroaryl, carbonyl, halo, hydroxy, thiol, cyano, or nitro;

Y is chosen from S, N, O or C, wherein when Y is C, the dotted line between Y and $C_1$ in the ring represents a double bond and the dotted line between $C_1$ and X is a single bond; and wherein when Y is S, N or O, the dotted line between Y and $C_1$ in the ring represents a single bond and the dotted line between $C_1$ and X represents a double bond;

X represents, as valency permits, hydrogen, oxygen, halogen, hydroxy, amino, thiol, thioalkyl, alkyl, alkenyl, alkynyl, haloalkyl, cycloalkyl, heterocycloalkyl, alkylaryl, aryl, alkylheteroaryl, or heteroaryl, any of which is optionally substituted with acetyl, alkyl, amino, amido, —$NR^6R^7$, —C(O)$NR^6R^7$, alkoxy, alkylhydroxy, cycloalkyl, heterocycloalkyl, aryl, heteroaryl, carbonyl, halo, hydroxy, thiol, cyano, or nitro;

$R^1$ and $R^2$ are independently chosen from hydrogen, benzoate, alkyl, alkenyl, alkynyl, haloalkyl, cycloalkyl, heterocycloalkyl, alkylaryl, aryl, alkylheteroaryl, or heteroaryl, any of which is optionally substituted with acetyl, alkyl, amino, amido, —$NR^6R^7$, —C(O)$NR^6R^7$, alkoxy, alkylhydroxy, cycloalkyl, heterocycloalkyl, aryl, heteroaryl, carbonyl, halo, hydroxy, thiol, cyano, or nitro; or $R^1$ and $R^2$ together with the atoms to which they are attached form a 5-7 membered cyclic moiety wherein any of the additional atoms can be heteroatoms and the 5 to 7-membered ring is, optionally, a heterocyclic structure that is optionally substituted; and $R^6$ and $R^7$ are independently H, alkyl; or $R^6$ and $R^7$ together with the atoms to which they are attached form a 3-7 membered cyclic moiety wherein any of the additional atoms can be heteroatoms and the 3 to 7-membered ring is optionally a heterocyclic structure that is optionally substituted;

or a pharmaceutically acceptable salt or prodrug thereof.

Example chalcogen containing moieties are aldehyde, protected aldehyde (e.g., dioxane and dithiane), reduced aldehyde, benzoate, ester, ketone, carbonyl, ether, carboxylic acid, alcohol, or alkoxyl groups. Also, chalcogen containing moieties can include amine, amide, sulfonamide, sulfonyl, sulfinyl, halogenated alkyl, CH═CH—$CO_2R^6$, CH═$CHSO_2R^6$; where $R^6$ is H, OH, or alkyl. Example benzoate groups are methyl benzoate.

In some examples of Formula I, D is OH, $R^3$ and $R^4$ are both hydrogen, Y is C and X is H, resulting in compounds of Formula II:

II

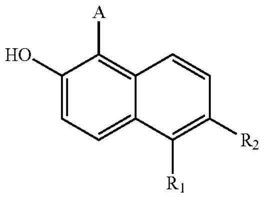

wherein A, $R^1$ and $R^2$ are as defined in Formula I.

In some examples of Formula I, D is OH, $R^3$ and $R^4$ are both hydrogen, Y is O and X is O, resulting in compounds of Formula III:

III

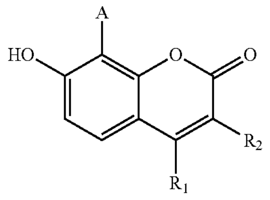

wherein A, $R^1$ and $R^2$ are as defined in Formula I.

In some examples of Formula III, A is an aldehyde, a protected aldehyde or a reduced aldehyde. In some examples of Formula III, $R^2$ is hydrogen and $R^1$ is a carbamate.

In further examples of Formula III, the disclosed compounds can have Formula III-A

III-A

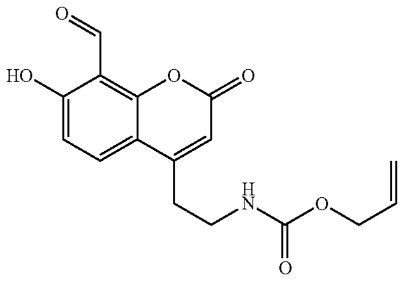

In some examples of Formula I, D is OH, $R^3$ and $R^4$ are both hydrogen, Y and X are both O, and $R^1$ and $R^2$ form a 6-membered heterocycle with nitrogen resulting in compounds of Formula IV:

IV

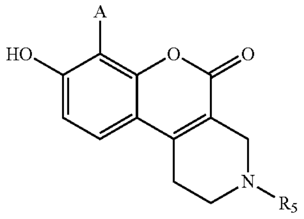

wherein

A is as defined above $R^5$ is chosen from hydrogen, benzoate, alkyl, alkenyl, alkynyl, haloalkyl, cycloalkyl, heterocycloalkyl, alkylaryl, aryl, alkylheteroaryl, or heteroaryl, any of which is optionally substituted with acetyl, alkyl, amino, amido, —$NR^6R^7$, —C(O)$NR^6R^7$, alkoxy, alkylhydroxy, cycloalkyl, heterocycloalkyl, aryl, heteroaryl, carbonyl, halo, hydroxy, thiol, cyano, or nitro; or a pharmaceutically acceptable salt or prodrug thereof.

In some examples of Formula IV, A is an aldehyde, a protected aldehyde or a reduced aldehyde. In some examples of Formula IV, $R^5$ is an ester.

In some examples, the disclosed compounds can have Formula IV-A

IV-A

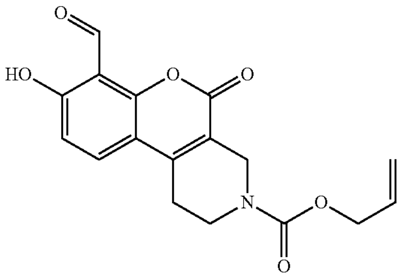

In some examples, the disclosed compounds can have Formula IV-B

IV-B

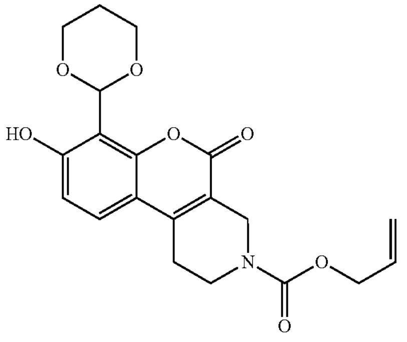

In some examples, the disclosed compounds can have Formula IV-C

IV-C

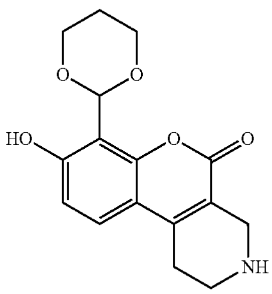

In some examples of Formula I, A is an aldehyde, D is OH, $R^3$ and $R^4$ are both hydrogen, Y and X are both O, and $R^1$ and $R^2$ form a 6-membered heterocycle with nitrogen resulting in compounds of Formula V:

V

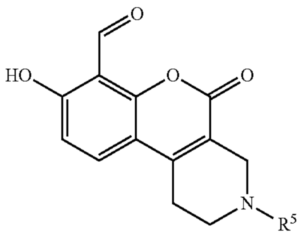

wherein $R^5$ is chosen from hydrogen, benzyl, substituted benzyl, acetate, alkyl, substituted alkyl, amidine, or substituted amindine; or a pharmaceutically acceptable salt or prodrug thereof.

In some examples of Formula I, A is an aldehyde, $R^3$ and $R^4$ are both hydrogen, Y and X are both O, and $R^1$ and $R^2$ form a 6-membered heterocycle with nitrogen resulting in compounds of Formula VI:

VI

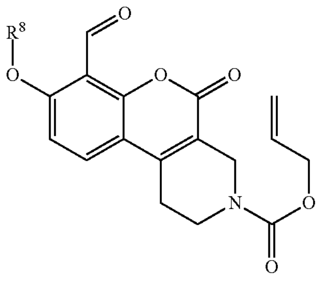

wherein $R^8$ is chosen from hydrogen, carbonyl, alkoxy, halogen, thiol, thioalkyl, aryl, alkylaryl, or alkyl; or a pharmaceutically acceptable salt or prodrug thereof.

In some examples of Formula I, D is OH, $R^3$ and $R^4$ are both hydrogen, Y and X are both O, and $R^1$ and $R^2$ form a 6-membered heterocycle with nitrogen resulting in compounds of Formula VII:

VII

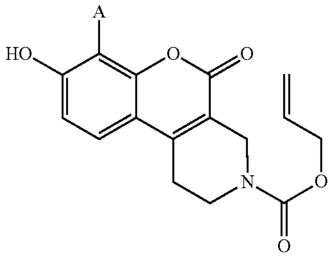

wherein

A is chosen from hydroxyl, hydroxyl, alkoxy, carboxyl, carboxylic acid, ether, ester, amine, amide, dioxane, dithiane, ketone, aldehyde, sulfonamide, sulfonyl, sulfinyl, halogenated alkyl, $CH{=}CH{-}CO_2R^6$, $CH{=}CHSO_2R^6$; where $R^6$ is H, OH, or alkyl; or a pharmaceutically acceptable salt or prodrug thereof.

In any of Formulas I-VII, D can be preferably OH. Also, in any of Formulas I-VII $R^3$ and $R^4$ are preferably both H.

In some specific examples, the disclosed compounds can have any one of the following structures:

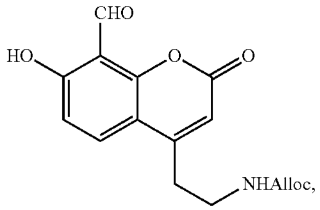

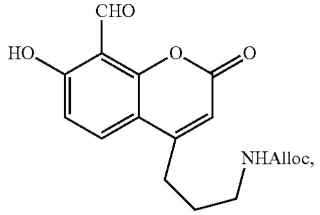

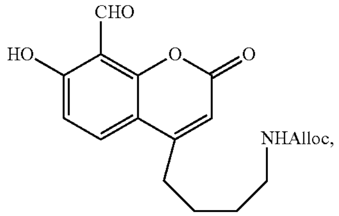

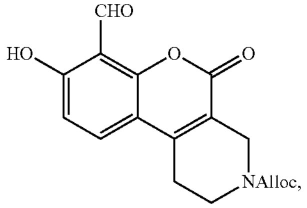

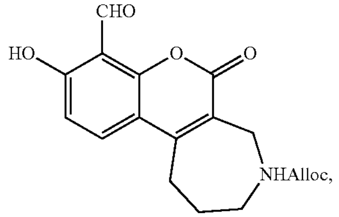

-continued
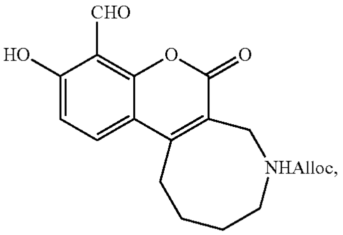
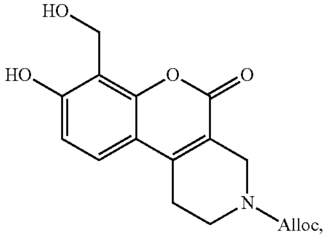
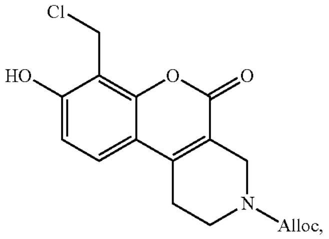
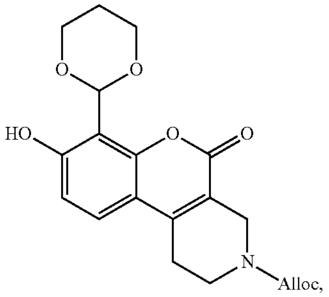
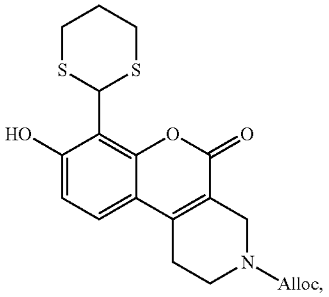
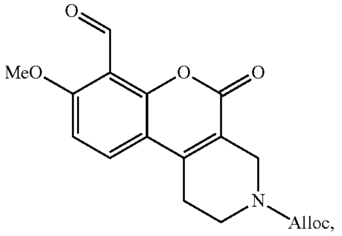
-continued
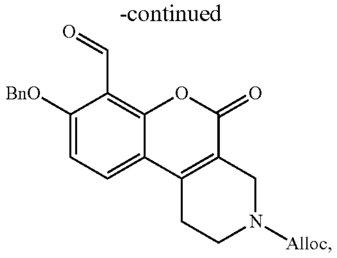
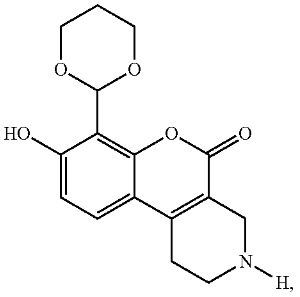
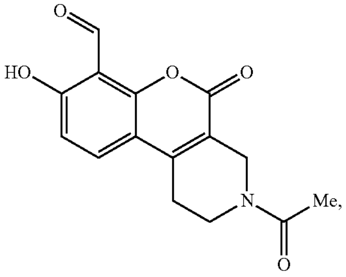
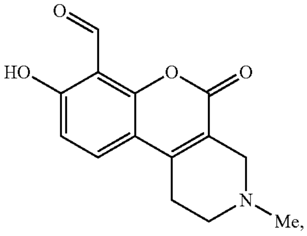
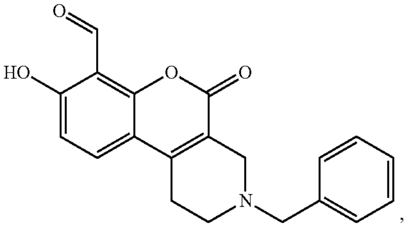
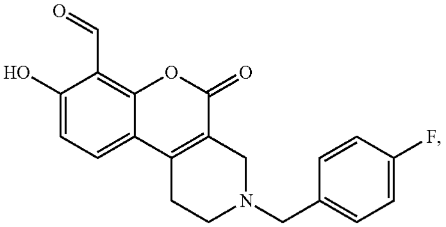
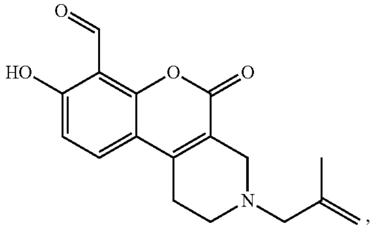

-continued

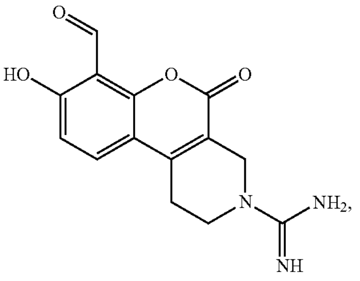

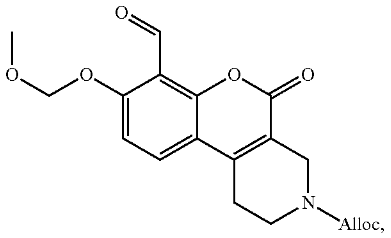

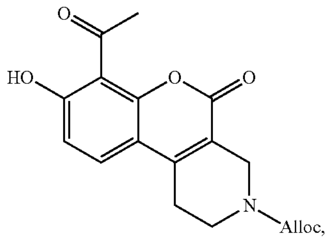

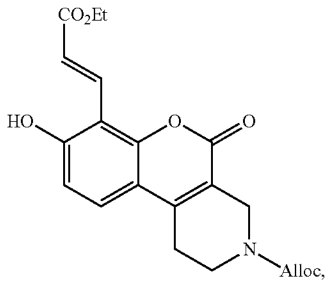

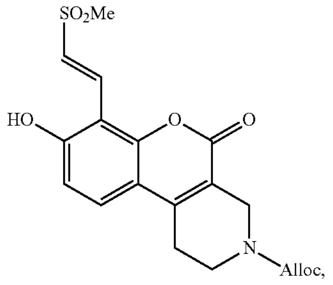

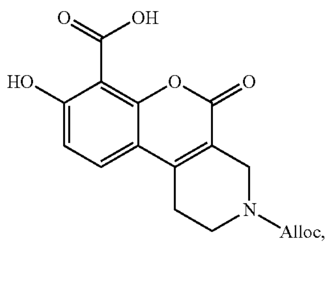

-continued

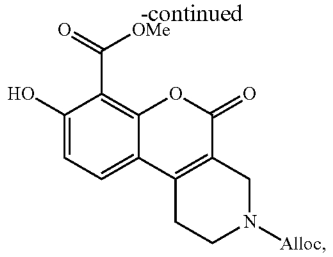

and

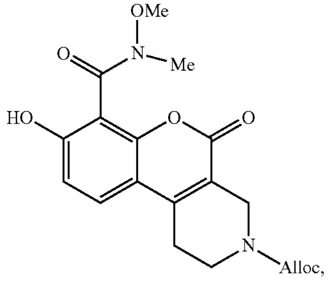

wherein Alloc is an allyloxycarbonyl moiety.

The syntheses of the compounds disclosed herein are addressed in more detail in the examples.

Also disclosed herein are pharmaceutically-acceptable salts and prodrugs of the disclosed compounds. Pharmaceutically-acceptable salts include salts of the disclosed compounds that are prepared with acids or bases, depending on the particular substituents found on the compounds. Under conditions where the compounds disclosed herein are sufficiently basic or acidic to form stable nontoxic acid or base salts, administration of the compounds as salts can be appropriate. Examples of pharmaceutically-acceptable base addition salts include sodium, potassium, calcium, ammonium, or magnesium salt. Examples of physiologically-acceptable acid addition salts include hydrochloric, hydrobromic, nitric, phosphoric, carbonic, sulphuric, and organic acids like acetic, propionic, benzoic, succinic, fumaric, mandelic, oxalic, citric, tartaric, malonic, ascorbic, alpha-ketoglutaric, alpha-glycophosphoric, maleic, tosyl acid, methanesulfonic, and the like. Thus, disclosed herein are the hydrochloride, nitrate, phosphate, carbonate, bicarbonate, sulfate, acetate, propionate, benzoate, succinate, fumarate, mandelate, oxalate, citrate, tartarate, malonate, ascorbate, alpha-ketoglutarate, alpha-glycophosphate, maleate, tosylate, and mesylate salts. Pharmaceutically acceptable salts of a compound can be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Methods of Use

Further provided are methods of treating or preventing a disease or pathology in a subject, comprising administering to the subject an effective amount of a compound or composition as disclosed. The disease can be associated with the transcription factor, XBP-1 activity. The disease can also be associated with the endoplasmic reticulum-resident, IRE-1 RNase activity. In some embodiments, the disease can be associated with upregulation of the IRE-1/XBP-1 pathway.

The disclosed compounds and compositions can electively inhibit IRE-1 RNase activity. For example, the compounds can inhibit IRE-1 RNase activity with 50% inhibitory concentration ($IC_{50}$) values of less than about 150 nM, less than 100 nM, less than 75 nM, less than 50 nM, less than 40 nM, less than 30 nM, less than 25 nM, less than 20 nM, less than 15 nM, or less than 10 nM. In some embodiments, the disclosed compounds and compositions can selectively inhibit the expression of XBP-1. In some embodiments, the disclosed compounds and compositions can selectively inhibit Akt signaling. In some embodiments, the disclosed compounds and compositions do not target critical cellular mechanisms involved in protein transport. For example, the disclosed compounds and compositions do not target secretory protein transport. In some embodiments, the disclosed compounds and compositions suppress disease progression, for e.g., leukemia without imposing systemic toxicity.

Further provided herein are methods of treating or preventing a disease, for example cancer in a subject, comprising administering to the subject an effective amount of a composition comprising a B cell receptor signaling inhibitor and any of the compounds disclosed herein. Representative examples of suitable B cell receptor signaling inhibitor include, but are not limited to, ibrutinib (a BTK inhibitor in clinical trials), fostamatinib, MK2206, CAL-101, and combinations thereof. Also provided are methods of treating or preventing a disease, for example cancer in a subject, comprising administering an effective amount of a composition comprising an immunotherapeutic agent and any of the compounds disclosed herein. Representative examples of suitable immunotherapeutic agents include, but are not limited to, Infliximab, Basiliximab, Daclizumab, Trastuzumab, Rituximab, Ibritumomab tiutexan, Tositumomab, Gemtuzumab ozogamicin, Alemtuzumab, or combinations thereof. Further provided are methods of treating or preventing a disease, for example cancer in a subject, comprising administering an effective amount of a composition comprising a chemotherapeutic agent and any of the compounds disclosed herein. Representative examples of suitable chemotherapeutic agents include, but are not limited to, 5-fluorouracil, aziathioprine, cyclophosphamide, antimetabolites (such as fludarabine), anti-neoplastics (such as etoposide, doxorubicin, methotrexate, vincristine), prednisone, carboplatin, cis-platinum, the taxanes such as taxol, or combinations thereof.

Methods of killing a tumor cell are also provided herein. The methods comprise contacting a tumor cell with an effective amount of a compound or composition as disclosed herein. The methods can further include administering a second compound or composition (e.g., an anticancer agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation. Methods of treating inflammation in a subject are further provided herein, the methods comprising administering to the subject an effective amount of a compound or composition as described herein. Optionally, the methods can further include administering a second compound or composition (e.g., an anti-inflammatory agent).

The disclosed subject matter also concerns methods for treating a subject having an oncological disorder or condition. In one embodiment, an effective amount of one or more compounds or compositions disclosed herein is administered to a subject having an oncological disorder and who is in need of treatment thereof. The disclosed methods can optionally include identifying a subject who is or can be in need of treatment of an oncological disorder. The subject can be a human or other mammal, such as a primate (monkey, chimpanzee, ape, etc.), dog, cat, cow, pig, or horse, or other animals having an oncological disorder. Means for administering and formulating compounds for administration to a subject are known in the art, examples of which are described herein. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include B cell cancers such as leukemia (acute lymphoblastic, acute myeloid, chronic lymphocytic, chronic myeloid, and other), lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lung cancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

The disclosed subject matter also concerns methods for treating a subject diagnosed with an inflammatory disease. Representative examples of inflammatory diseases that can be treated by the compounds disclosed include, but are not limited to, rheumatic arthritis, inflammatory bowel disease, ankylosing spondylitis, psoriasis, atherosclerosis, lupus, and multiple sclerosis.

Further provided herein are methods of treating or preventing a disease, for example a digestive disorder or disease in a subject. For example, the method can comprise administering to the subject an effective amount of a composition comprising any of the compounds disclosed herein. Examples of digestive disorders and diseases that can be treated or prevented include, but are not limited to, colitis, atypical colitis, chemical colitis, collagenous colitis, distal colitis, diversion colitis, fulminant colitis, indeterminate colitis, infectious colitis, ischemic colitis, lymphocytic colitis, microscopic colitis, Crohn's disease, gastroenteritis, Hirschsprung's disease, inflammatory digestive diseases, inflammatory bowel disease (IBD), Morbus Crohn, non-chronic or chronic digestive diseases, non-chronic or chronic inflammatory digestive diseases, regional enteritis and ulcerative colitis.

Also disclosed herein are methods of treating a subject diagnosed with a neurodegenerative disease associated with protein aggregation. In some examples the method comprises administering to the subject an effective amount of a composition comprising any of the compounds disclosed herein. As used herein "a neurodegenerative disease associated with protein aggregation" also referred to as "protein aggregation disorders", "protein conformation disorders", or "proteinopathies" include diseases or disorders characterized by the formation of detrimental intracellular protein aggregates (e.g., inclusions in the cytosol or nucleus) or extracellular protein aggregates (e.g., plaques). "Detrimental protein aggregation" is the undesirable and harmful accumulation, oligomerization, fibrillization or aggregation, of two or more, hetero- or homomeric, proteins or peptides. A detrimental protein aggregate may be deposited in bodies, inclusions or plaques, the characteristics of which are often indicative of disease and contain disease-specific proteins. For example, superoxide dismutase-1 aggregates are associated with ALS, poly-Q aggregates are associated with Huntington's disease, and α-synuclein-containing Lewy bodies are associated with Parkinson's disease. Non-limiting classes of Protein Aggregation Disorders or Proteopathies include Protein Conformational Disorders, Alpha-Synucleinopathies, Polyglutamine Diseases, Serpinopathies, Tauopathies or other related disorders. Non-limiting examples of Protein Aggregation Disorders include Amyotrophic Lateral Sclerosis (ALS), Huntington's Disease (HD), Parkinson's Disease (PD), Spinal Muscular Atrophy (SMA), Alzheimer's Disease (AD), diffuse Lewy body dementia (DLBD), multiple system atrophy (MSA), dystrophia myotonica, dentatorubro-pallidoluysian atrophy (DRPLA), Friedreich's ataxia, fragile X syndrome, fragile XE mental retardation, Machado-Joseph Disease (MJD or SCA3), spinobulbar muscular atrophy (also known as Kennedy's Disease), spinocerebellar ataxia type 1 (SCA1) gene, spinocerebellar ataxia type 2 (SCA2), spinocerebellar ataxia type 6 (SCA6), spinocerebellar ataxia type 7 (SCA7), spinocerebellar ataxia type 17 (SCA17), chronic liver diseases, familial encephalopathy with neuroserpin inclusion bodies (FENIB), Pick's disease, corticobasal degeneration (CBD), progressive supranuclear palsy (PSP), amyotrophic lateral sclerosis/parkinsonism dementia complex, Cataract, serpinopathies, haemolytic anemia, cystic fibrosis, Wilson's Disease, neurofibromatosis type 2, demyelinating peripheral neuropathies, retinitis pigmentosa, Marfan syndrome, emphysema, idiopathic pulmonary fibrosis, Argyophilic grain dementia, corticobasal degeneration, diffuse neurofibrillary tangles with calcification, frontotemporal dementia/parkinsonism linked to chromosome 17, Hallervorden-Spatz disease, Nieman-Pick disease type C, or subacute sclerosing panencephalitis.

Also disclosed herein are methods of inhibiting a neurodegenerative disease associated with protein aggregation. In some examples the method comprises administering to the subject an effective amount of a composition comprising any of the compounds disclosed herein.

Examples of disorders in which such inhibitory methods can be useful include, aberrant protein aggregation associated with a neurodegenerative disease, apoptosis of motor neuron cells, Amyotrophic Lateral Sclerosis (ALS), Huntington's Disease (HD), Parkinson's Disease (PD), diffuse Lewy body dementia (DLBD), multiple system atrophy (MSA), dystrophia myotonica, dentatorubro-pallidoluysian atrophy (DRPLA), Friedreich's ataxia, fragile X syndrome, fragile XE mental retardation, Machado-Joseph Disease (MJD or SCA3), spinobulbar muscular atrophy (also known as Kennedy's Disease), spinocerebellar ataxia type 1 (SCA1) gene, spinocerebellar ataxia type 2 (SCA2), spinocerebellar ataxia type 6 (SCA6), spinocerebellar ataxia type 7 (SCA7), spinocerebellar ataxia type 17 (SCA17), chronic liver diseases, familial encephalopathy with neuroserpin inclusion bodies (FENIB), Pick's disease, corticobasal degeneration (CBD), progressive supranuclear palsy (PSP), amyotrophic lateral sclerosis/parkinsonism dementia complex, Cataract, serpinopathies, haemolytic anemia, cystic fibrosis, Wilson's Disease, neurofibromatosis type 2, demyelinating peripheral neuropathies, retinitis pigmentosa, Marfan syndrome, emphysema, idiopathic pulmonary fibrosis, Argyophilic grain dementia, corticobasal degeneration, diffuse neurofibrillary tangles with calcification, frontotemporal dementia/parkinsonism linked to chromosome 17, Hallervorden-Spatz disease, Nieman-Pick disease type C, or subacute sclerosing panencephalitis.

The amount of the compositions to be administered can be readily determined by the attending physician based on a variety of factors including, but not limited to, age of the patient, weight of the patient, disease or disorder to be imaged or treated, and presence of a pre-existing condition, and dosage form to be administered (e.g., immediate release versus modified release dosage form).

Also disclosed herein are methods of diagnosing chronic lymphocytic leukemia (CLL). The method can comprise, for example, comparing protein expression of a sample suspected of being chronic lymphocytic leukemia to a control sample. The protein expression of the sample can, for example, comprise determining a protein expression of at least one protein (e.g., XBP-1, Derlin-1, Derlin-2, BiP, GRP94, PDI, phospho-eIF2α, or AKT). The control, for example, can comprise age-matched B-cells from an individual confirmed not to have chronic lymphocytic leukemia. In some examples, decreased protein expression of AKT or increased expression of XBP-1, Derlin-1, Derlin-2, BiP, GRP94, PDI or phospho-eIF2α compared to the control can be indicative of chronic lymphocytic leukemia.

In some examples, the method of diagnosing CLL can comprise comparing induced protein expression of a sample suspected of being CLL to a control sample. For example, the method can comprise determining a first protein expression of at least one protein, such as IRE-1, XBP-1, Derlin-1, Derlin-2, or C/EBP-homologous protein. In some examples, the sample suspected of being CLL and the control sample can be subjected to LPS or $F(ab')_2$ Ig fragments. The method can further comprise determining a second protein expression of at least one protein, such as IRE-1, XBP-1, Derlin-1, Derlin-2, or C/EBP-homologous protein. In some examples, the method further comprises comparing the second protein expression to the first protein expression, thereby determining the induced protein expression. In some examples, increased expression of IRE-1, XBP-1, Derlin-1, Derlin-2, IRF4, or Blimp-1, or decreased expression of C/EBP-homologous protein can be indicative of chronic lymphocytic leukemia.

In some examples, the method of diagnosing CLL can comprise comparing mRNA levels in immunoprecipitated nucleic acids in a sample suspected of being chronic lymphocytic leukemia to a control sample. For example, a first mRNA immunoprecipitate can be determined, such as, for example, by subjecting the sample suspected of being chronic lymphocytic leukemia and the control sample to anti-XBP-1 antibody. The method can further comprise, for example, subjecting the sample suspected of being chronic lymphocytic leukemia and the control sample to LPS. In some examples, a second mRNA immunoprecipitate can be determining, for example, by subjecting the sample suspected of being chronic lymphocytic leukemia and the control sample to anti-XBP-1 antibody. In some examples, the method can further comprise comparing the second mRNA immunoprecipitate to the first immunoprecipitate, thereby determining the induced protein expression. An elevated level of mRNA of total XBP-1, spliced XBP-1, Derlin-1, Derlin-2, Derlin-3, BiP, PDI, TCL1, or GRP94 can, for example, be indicative of chronic lymphocytic leukemia.

In some examples, the method of diagnosing CLL can comprise comparing Ig secretion levels in B cells. For example, an immunoglobulin expression in a sample suspected of being chronic lymphocytic leukemia and in a control sample can be determined. The immunoglobulin can, for example, comprise mIgM, secretory IgM, or combinations thereof. The control sample can, for example, comprise age-matched B-cells from an individual confirmed not to have chronic lymphocytic leukemia. Increased immunoglobulin expression can, for example, be indicative of chronic lymphocytic leukemia.

In some examples, the sample suspected of being chronic lymphocytic leukemia and the control sample can be cultured in LPS for 2 days. In some examples, the F(ab')2 fragments can be goat anti-mouse IgM antibodies or anti-XBP-1. In some examples, the F(ab')2 fragments can phosphorylate at least one of ERK or AKT.

Also disclosed herein are methods of treating chronic lymphocytic leukemia. The method can comprise, for example, administering an IRE-1 inhibitor to a patient having chronic lymphocytic leukemia, wherein the IRE-1 inhibitor can be, for example, STF-083010 or A-I06. In some examples, the STF-083010 or A-I06 can be administered at about 50 μM, at 50 μM, or at 100 μM. In some examples, the STF-083010 or A-I06 can be administered such that STF-083010 or A-I06 contacts the leukemic cells for 24 hours. In some examples, the method of treating CLL can further comprise administering fludarabine, geldanamycin, herbimycin A, chlorambucil, or combinations thereof.

Animals

Disclosed is an animal that is deficient in the expression of the endogenous X-box binding protein 1 (XBP1) gene, including methods for making such animal, comprising, for example, knockout technology. Preferably, the animal is a mammal. Such include, but is not limited to, the hereinbefore described mouse, guinea pig, rat, rabbit, pig, or goat. Preferably, the animal is a non-human mammal such as mouse, guinea pig, rat, or rabbit which is deficient in expression of an endogenous XBP1 gene.

As used herein the terms “disruption,” “functional inactivation,” “alteration” and “defect” connote a partial or complete reduction in the expression and/or function of the XBP1 polypeptide encoded by the endogenous gene of a single type of cell, selected cells or all of the cells of a XBP1 knockout animal. Thus, the expression or function of the XBP-1 gene product can be completely or partially disrupted or reduced (e.g., by 50%, 75%, 80%, 90%, 95% or more, e.g., 100%) in a selected group of cells (e.g., a tissue or organ) or in the entire animal. As used herein the term “a functionally disrupted XBP1 gene” includes a modified XBP1 gene that either fails to express any polypeptide product or that expresses a truncated protein having less than the entire amino acid polypeptide chain of a wild-type protein and is non-functional (partially or completely non-functional).

The term “knockout animal” refers to an animal comprising a partial or complete reduction of the expression of at least a portion of a polypeptide encoded by an endogenous gene (such as XBP1) in a single cell, selected cells, or all of the cells of said animal. The animal can be “heterozygous,” wherein one allele of the endogenous gene has been disrupted. Alternatively, the animal can be “homozygous” wherein both alleles of the endogenous gene have been disrupted.

Disruption of the XBP1 gene can be accomplished by a variety of methods known to those of skill in the art. For example, gene targeting using homologous recombination, mutagenesis (e.g., point mutation), RNA interference and antisense technology can be used to disrupt a XBP1 gene.

More specifically, disclosed is a knockout mammal, e.g. mouse, whose genome comprises either a homozygous or heterozygous disruption of its XBP1 gene. A knockout mammal whose genome comprises a homozygous disruption is characterized by somatic and germ cells that contain two nonfunctional (disrupted) alleles of the XBP1 gene, while a knockout mammal whose genome comprises a heterologous disruption is characterized by somatic and germ cells that contain one wild-type allele and one non-functional allele of the XBP1 gene.

The type of gene disruption can be global (i.e., wherein every cell of an animal is deficient in the gene) or tissue-specific (i.e., wherein disruption of the gene is limited to one or more tissues). In addition, disruption can be achieved at specific time points (i.e., time-specific knockout) using art known techniques. Preferably, the disclosed animals are XBP1 knockouts that are deficient in the endogenous XBP1 gene. Particularly preferable are animals that comprise homozygous disruption of the XBP1 gene. Such animals are characterized by the genotype $XBP1^{-/-}$. As hereinbefore described, the $XBP1^{-/-}$ genotype can be manifested globally or in a tissue-specific manner using art known knockout techniques.

As used herein, the term “genotype” refers to the genetic makeup of an animal. A particular genotype refers to one or more specific genes, e.g., XBP1. More specifically the term genotype refers to the status of the animal’s XBP1 alleles, which can either be intact and functional (e.g., wild-type or +/+); or disrupted (e.g., knockout) in a manner that confers either a heterozygous (e.g., +/−), or homozygous (e.g., −/−) knockout genotype.

Most preferably, the animal is a mouse which comprises a germline disruption of the gene encoding XBP1. The mice can be heterozygous (characterized by the genotype $XBP1^{+/-}$) or homozygous (characterized by the genotype $XBP1^{-/-}$) for the disrupted XBP1 allele.

Also disclosed are organs, tissues, cells, cell-lines, or sub-cellular fractions derived from XBP1 knockout animals. Preferably, such components are derived from animals which are homozygous for the XBP1 knockout genotype ($XBP1^{-/-}$). Examples of organs include, but are not limited to, spleen, thymus, liver, pancreas, heart, lung, kidney, bladder, brain, or blood. Examples of tissues include, but are not limited to, muscle tissue, connective tissue, nerve tissue, or epithelial tissue. Examples of cells include, but are not limited to, gamete cells (i.e., eggs, sperm), splenocytes, thymus cells, blood cells, epithelial cells, hepatic cells, pancreatic cells, cardiomyocytes, or nerve cells. Also included are stem cells of embryonic or adult lineage. Examples of cell-lines include, but are not limited to, primary cells, transformed cells, as well as immortalized cells.

The gene disruption, as used herein, can comprise one or more mutations in either the regulatory sequence or in coding sequence of XBP1. Possible outcomes can include, for example, an untranslated gene product (no protein) or an incompletely translated gene product (mutant protein). "Mutation" as used herein can thus result in total or partial loss of XBP1 gene function.

Also disclosed are methods of producing a non-human animal that lacks a functional XBP1 gene, or a homolog thereof. In one embodiment there is provided a method for obtaining a XBP1 knockout mammal comprising crossing a transgenic mammal having a XBP1 gene or an exon thereof flanked with recognition sites for a site specific recombination enzyme with a transgenic animal expressing a constitutively active or inducible recombinase. Such methods are known in the art, and a representative example is provided below.

Briefly, the standard methodology for producing a knockout embryo requires introducing a targeting construct, which is designed to integrate by homologous recombination with the endogenous nucleic acid sequence of the targeted gene, into a suitable embryonic stem cell (ES). The ES cells are then cultured under conditions that allow for homologous recombination (i.e., of the recombinant nucleic acid sequence of the targeting construct and the genomic nucleic acid sequence of the host cell chromosome). Genetically engineered stem cells that are identified as comprising a knockout genotype that comprises the recombinant allele are introduced into an animal, or parent thereof, at an embryonic stage using standard techniques that are well known in the art (e.g., by microinjecting the genetically engineered embryonic stem (ES) cell into a blastocyst). The resulting chimeric blastocyst is then placed within the uterus of a pseudopregnant foster mother for the development into viable pups. The resulting viable pups include potentially chimeric founder animals whose somatic and germline tissue comprise a mixture of cells derived from the genetically-engineered ES cells and the recipient blastocyst. The contribution of the genetically altered stem cell to the germline of the resulting chimeric mice allows the altered ES cell genome, which comprises the disrupted target gene, to be transmitted to the progeny of these founder animals, thereby facilitating the production of "knockout animals" whose genomes comprise a gene that has been genetically engineered to comprise a particular defect in a target gene.

One of skill in the art will easily recognize that the XBP1 gene can be disrupted in a number of different ways, any one of which can be used to produce the disclosed XBP1 knockout animals. For example, a knockout mouse can be produced by the method of gene targeting. As used herein the term "gene targeting" refers to a type of homologous recombination that occurs as a consequence of the introduction of a targeting construct (e.g., vector) into a cell (e.g., an ES cell) that is designed to locate and recombine with a corresponding portion of the nucleic acid sequence of the genomic locus targeted for alteration (e.g., disruption) thereby introducing an exogenous recombinant nucleic acid sequence capable of conferring a planned alteration to the endogenous gene. Thus, homologous recombination is a process (e.g., method) by which a particular DNA sequence can by replaced by an exogenous genetically engineered sequence. More specifically, regions of the targeting vector that have been genetically engineered to be homologous or complementary to the endogenous nucleotide sequence of the gene that is targeted for transgenic disruption line up or recombine with each other such that the nucleotide sequence of the targeting vector is incorporated into (e.g., integrates with) the corresponding position of the endogenous gene.

Also disclosed are DNA sequences for creating the disclosed knockout animals and vectors derived therefrom. In one embodiment, there is provided a DNA knockout construct comprising a selectable marker sequence flanked by DNA sequences homologous to the XBP1 gene of an animal, wherein when said construct is introduced into said animal at an embryonic stage, said selectable marker sequence disrupts the XBP1 gene in said mouse. Additionally disclosed is a vector construct designed to disrupt the function of a wild-type (endogenous) XBP1 gene. In general terms, an effective targeting vector comprises a recombinant sequence that is effective for homologous recombination with an endogenous XBP1 gene. For example, a replacement targeting vector comprising a genomic nucleotide sequence that is homologous to the target sequence operably linked to a second nucleotide sequence that encodes a selectable marker gene exemplifies an effective targeting vector. Integration of the targeting sequence into the chromosomal DNA of the host cell (e.g., embryonic stem cell) as a result of homologous recombination introduces an intentional disruption, defect or alteration (e.g., insertion, deletion or substitution) into the targeted sequence of the endogenous gene, e.g., the XBP1 gene. In some cases, all or part of the nucleotide sequence of a non-human gene that encodes the XBP1 polypeptide is replaced, thereby making a transgenic XBP1 knockout.

One of skill in the art will recognize that any XBP1 genomic nucleotide sequence of appropriate length and composition to facilitate homologous recombination at a specific site that has been preselected for disruption can be employed to construct a XXX targeting vector. For example, a wild-type XBP1 gene can be mutated and/or disrupted by inserting a recombinant nucleic acid sequence (e.g., a targeting construct or vector) into all or a portion of the XBP1 gene locus. For example, a targeting construct can be designed to recombine with a particular portion within the enhancer, promoter, coding region, start codon, noncoding sequence, introns or exons of the XBP1 gene. Alternatively, a targeting construct can comprise a recombinant nucleic acid that is designed to introduce a stop codon after an exon of the XBP1 gene.

Suitable targeting constructs can be prepared using standard molecular biology techniques known to those of skill in the art. For example, techniques useful for the preparation of suitable vectors are described by Maniatis, et al., Molecular Cloning: A Laboratory Manual, Cold Spring Harbor Laboratory, Cold Spring Harbor, N.Y.; which disclosures are hereby incorporated by reference. Appropriate vectors include a replacement vector such as the insertion vector described by Capecchi, M., 1989, Science, 244:1288-92, which disclosure is hereby incorporated by reference; or a vector based on a promoter trap strategy or a polyadenylation trap, or "tag-and-exchange" strategy described by Bradley, et al., 1992, Biotechnology (NY), 10:534-539; and Askew, G. et al., 1993, Mol. Cell. Biol., 13:4115-4124, which disclosures are also incorporated herein by reference.

One of skill in the art will readily recognize that a large number of appropriate vectors known in the art can be used as the basis of a suitable targeting vector. In practice, any vector that is capable of accommodating the recombinant nucleic acid sequence required to direct homologous recombination and to disrupt the target gene can be used. For example, pBR322, pACY164, pKK223-3, pUC8, pKG, pUC19, pLG339, pR290, pKC101 or other plasmid vectors can be used. Alternatively, a viral vector such as the lambda gt11 vector system can provide the backbone (e.g. cassette) for the targeting construct.

In a preferred embodiment, the knockout construct of the instant invention comprises a recognition site which is LoxP and utilizes a Cre recombinase. The recombinase can be placed under the transcriptional control of a constitutively active promoter or a tissue-specific promoter. Deletion of the XBP1 gene in a tissue-specific or time-specific manner can be achieved using art known techniques. To date, the loxP/Cre system is considered to be the most reliable experimental setup for spatio-temporally controlled site-specific somatic gene deletion in vivo. The deletion of the gene(s) of interest (e.g., XBP1) can be induced either by systemic injection or local application of an inducing agent. Other spatio-temporally controlled site-specific somatic gene deletion systems can be used to generate tissue-specific knockout mice of the instant invention. Examples for such alternative methods for engineering the conditional knockout animals include the Flp-FRT and the phiC31-att site-specific recombinase systems. As the loxP/Cre-system, these systems fulfill the requirements of having the gene(s) of interest flanked with recognition sites for the site specific recombination enzyme and of providing the recombination enzyme by crossing the conditional knockout animal with a transgenic animal expressing a constitutively active or inducible recombinase in the tissue of interest.

In preferred embodiments, the disclosed knockout animal is B-cell specific. For example, in some embodiments, Cre recombinase is under the control of a B-cell specific promoter, such as CD19, resulting in B-cell specific deletion of XBP1.

In some embodiments, the XBP1 knockout animal is further crossed with an Eμ-TCL1 transgenic model of CLL to produce a $XBP1^{-/-}$/Eμ-TCL1 animal.

Compositions, Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib. In other aspect, the disclosed compounds are coadministered with other HDAC inhibitors like ACY-1215, Tubacin, Tubastatin A, ST-3-06, OR ST-2-92.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

Kits

The disclosed subject matter also concerns a packaged dosage formulation comprising in one or more containers at least one inhibitor compound or composition disclosed herein, e.g., any compound of Formulas I through VII. A packaged dosage formulation can optionally comprise in one or more containers a pharmaceutically acceptable carrier or diluent. A packaged dosage formulation can also optionally comprise, in addition to an inhibitor compound or composition disclosed herein, other inhibitors.

Depending upon the disorder or disease condition to be treated, a suitable dose(s) can be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound and/or agent can be continuous or at distinct intervals, as can be determined by a person of ordinary skill in the art.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions.

Example 1

Background

Chronic lymphocytic leukemia (CLL) represents 30% of adult leukemia and is an incurable B cell malignancy. Malignant CLL cells use a limited repertoire of immunoglobulin heavy and light chain genes to manufacture their B cell receptors (BCR) (Hamblin et al., *Blood,* 94(6), 1848-1854 (1999); Murray et al., *Blood,* 111(3), 1524-1533 (2008); Widhopf et al., *Blood,* 111(6), 3137-3144 (2008)), and are very responsive to in vitro anti-IgM stimulation (Chen et al., *Blood,* 100(13), 4609-4614 (2002); Lanham et al., *Blood,* 101(3), 1087-1093 (2003)). Thus, antigen stimulation has been proposed to drive malignant progression of CLL.

The functions of the endoplasmic reticulum (ER) and its associated molecules in CLL have not attracted extensive investigative efforts because CLL cells do not exhibit a readily prominent ER structure like professional secretory cells. Exposure to Toll-like receptor ligands can activate CLL cells, which can allow rapid proliferation (Decker et al., *Blood,* 95(3), 999-1006 (2000); Chiron et al., *Blood,* 112(6), 2205-2213 (2008); Muzio et al., *Leuk Lymphoma,* 50(10), 1573-1580 (2009)), a cellular process that can be accompanied by robust production and folding of membrane receptors and secretory proteins in the ER.

The ER may play an important role in malignant progression of CLL. Electron microscopy examinations of human CLL cells showed ER expansions and immunoglobulin staining in the ER (Newell et al., *Blood,* 61(3), 511-519, (1983); Carew et al., *Blood,* 107(1), 222-231 (2006); Rubartelli et al., *Blood,* 62(2), 495-504 (1983)). Treatments that target ER-Golgi protein transport or inhibit BiP (HSP70 in the ER) and GRP94 (HSP90 in the ER) can sensitize CLL cells to drug-induced apoptosis (Carew et al., *Blood,* 107(1), 222-231 (2006); Jones et al., *Blood,* 103(5), 1855-1861 (2004); Rosati et al., *Blood,* 116(15), 2713-2723 (2010)).

The IRE-1/XBP-1 pathway is activated in response to stress conditions like proteotoxicity or hypoxia in the ER, but it also can play a role in maintaining basal cellular functions (Rutkowski and Hegde, *J Cell Biol,* 189(5), 783-794 (2010); Walter and Ron, *Science,* 334(6059), 1081-1086 (2011)). IRE-1 is an ER-resident transmembrane protein that contains a stress sensor domain in the lumen of the ER, and a serine/threonine kinase domain linked to an RNase domain in the cytoplasm. Upon stress conditions, IRE-1 oligomerizes via its luminal domains in the ER, bringing together the cytoplasmic kinase domains which can undergo autophosphorylation and upregulate IRE-1's RNase activity. The IRE-1 RNase can then splice 26 nucleotides from the mature XBP-1 mRNA, which can allow the spliced XBP-1 mRNA to encode the functional 54-kDa transcription factor XBP-1 (Shen et al., *Cell,* 107(7), 893-903 (2001); Yoshida et al., *Cell,* 107(7), 881-891 (2001); Calfon et al., *Nature,* 415 (6867), 92-96 (2002)). XBP-1 can regulate a panel of genes (Acosta-Alvear et al., *Mol Cell,* 27(1), 53-66 (2007)) and can crosstalk with other B-cell transcription factors, such as IRF4 and Blimp-1 (Hu et al., *Embo J,* 28(11), 1624-1636 (2009)). Overexpression of XBP-1 in B cells can cause monoclonal gammopathy of undetermined significance, a precursor condition for multiple myeloma (Carrasco et al., *Cancer Cell,* 11(4), 349-360 (2007)).

The roles of the ER stress response in the Eμ-TCL1 CLL mouse model were investigated, in which the TCL1 gene is under the control of the immunoglobulin heavy chain promoter/enhancer driving TCL1 overexpression in B cells (Bichi et al., *Proc Natl Acad Sci USA,* 99(10), 6955-6960 (2002)). TCL1 is expressed in ~90% human CLL patients (Herling et al., *Leukemia,* 20(2), 280-285 (2006)), and its overexpression can be associated with strong BCR signaling (Herling et al., *Blood,* 114(21), 4675-4686 (2009); Holler et al., *Blood,* 113(12), 2791-2794 (2009); Suljagic et al., *Blood,* 116(23), 4894-4905 (2010)), which can allow malignant CLL cells to undergo high-rate proliferation. Eμ-TCL1 mice initially developed a pre-leukemic state with CD5+IgM+ B cell characteristics in the blood, spleens, lymph nodes and bone marrow, and slowly progress to the full-blown monoclonal CLL stage with clinical features of aggressive human CLL (Bichi et al., *Proc Nat Acad Sci USA,* 99(10), 6955-6960 (2002); Yan et al., *Proc Natl Acad Sci USA,* 103(31), 11713-11718 (2006)). Just like human patients with aggressive CLL, Eμ-TCL1 mice initially responded to fludarabine (a purine analog that inhibits DNA synthesis), but quickly develop resistance and eventually die from leukemia (Johnson et al., *Blood,* 108(4), 1334-1338 (2006)). These features prompted the use of Eμ-TCL1 CLL cells to study the contribution of the ER stress response to malignant progression of CLL.

Methods and Materials

Mice

Eμ-TCL1 and μS−/− (Jackson Laboratories) mice were maintained at a local animal facility abiding by animal care guidelines.

Immunofluorescent Staining and Flow Cytometric Analysis of Mouse Peripheral Blood Mononuclear Cells (PBMCs).

PBMCs were non-lethally obtained from mice following the submandibular bleed and RBC lysis (Qiagen). Nonspecific staining was first blocked for 30 min at 4° C. with 300 μl FBS per $1.0\times10^6$ cells. Cell surface staining was accomplished by 30-min incubation at 4° C. with 1 μl per $1.0\times10^6$ cells of the following anti-mouse antibodies: B220-Alexa488, CD19-APC-Cy7 (BD Pharmingen), IgM-Alexa568 (Invitrogen), CD5-APC (eBioscience) and CD138-PE (BD Pharmingen). Viability staining was accomplished using DAPI exclusion (10 μg/ml; 200 μl/$1\times10^6$ cells) during acquisition. Apoptotic cells were detected by Annexin V-PE staining (BD Pharmingen). Acquisition of B-cell and CLL cell populations was performed on a LSRII cytometer (BD Biosciences) harboring a custom configuration for the H. Lee Moffitt Cancer Center & Research Institute, having multiple laser beams and detectors for excitation of various fluorophores and wide emission spectrum detection. Mid-range Spherotech FL1 fluorescent rainbow beads (BD Biosciences) were used to maintain consistent gains for all parameters across time points. Analysis of cytometry data was achieved using FlowJo software version 7.6.1 (Tree Star Inc.).

Antibodies and Reagents

Polyclonal antibodies against Igα, Igβ, Derlin-1, Derlin-2, BiP, class I MHC, and PDI were generated in rabbits. Antibodies to TCL1 (Cell Signaling), IRE-1 (Cell Signaling), XBP-1 (Santa Cruz), Blimp-1 (Santa Cruz), IRF4 (Cell Signaling), Pax5 (Santa Cruz), Syk (Cell Signaling), phospho-Syk (Tyr525/526) (Cell Signaling), AKT (Cell Signaling), phospho-AKT (Ser473) (Invitrogen), ERK1/2 (Cell Signaling), phospho-ERK1/2 (Thr202/Tyr204) (Cell Signaling), GRP94 (Stressgen), calreticulin (Stressgen), calnexin (Stressgen), phospho-eIF2α (Ser51) (Cell Signaling), eIF2α (Cell Signaling), HSP70 (Stressgen), p97 (Fitzgerald), CHOP (Cell Signaling), actin (Sigma), AID (Cell Signaling), phospho-Igα (Tyr182) (Cell Signaling), μ (SouthernBiotech) and κ (SouthernBiotech) were obtained commercially. LPS and fludarabine were procured from Sigma. Tunicamycin and thapsigargin were purchased from Enzo Life Sciences.

Cell Culture

B lymphocytes, μS−/− B cells and Eμ-TCL1 CLL cells were purified from mouse spleens by negative selection using anti-CD43 magnetic beads (Miltenyi Biotech). Primary human CLL cells were obtained from consented patients at the Moffitt Cancer Center following IRB guidelines. These cells as well as the three human CLL cell lines, MEC1, MEC2 and WaC3, and one mouse multiple myeloma cell line, 5TGM1 were all cultured in the RPMI 1640 media (Gibco) supplemented with 10% heat-inactivated fetal bovine serum (FBS), 2 mM L-glutamine, 100 U/ml penicillin G sodium, 100 μg/ml streptomycin sulfate, 1 mM sodium pyruvate, 0.1 mM non-essential amino acids, and 0.1 mM β-mercaptoethanol (β-ME).

Protein Isolation and Immunoblotting

Cells were lysed in RIPA buffer (10 mM Tris-HCl, pH 7.4; 150 mM NaCl; 1% NP-40; 0.5% sodium deoxycholate;

0.1% SDS; 1 mM EDTA) supplemented with protease inhibitor cocktail (Roche). The protein concentrations of the supernatants were determined by BCA assay (Pierce). Samples were boiled in SDS-PAGE sample buffer (62.5 mM Tris-HCl, pH 6.8; 2% SDS; 10% glycerol; 0.1% bromophenol blue) with R-ME and separated by SDS-PAGE. Proteins were transferred to nitrocellulose membranes, blocked in 5% milk (wt/vol in PBS), and immunoblotted with the indicated antibodies and appropriate horseradish peroxidase-conjugated secondary antibodies. Following multiple washes in PBS, the blots were developed using Western Lighting Chemiluminescence Reagent (Perkin-Elmer).

Reverse Transcription and Polymerase Chain Reaction (PCR)

Total RNA was isolated using TRIzol reagent (Invitrogen). Complementary DNA was synthesized from RNA using Superscript II reverse transcriptase (Invitrogen). The following sets of primers were used together with Platinum Taq DNA polymerase (Invitrogen) in PCR to detect the expression of human XBP-1 (GAG TTA AGA CAG CGC TTG GG (SEQ ID NO:1) and ACT GGG TCC AAG TTG TCC AG (SEQ ID NO:2)); human GAPDH (GGA TGA TGT TCT GGA GAG CC (SEQ ID NO: 10) and CAT CAC CAT CTT CCA GGA GC (SEQ ID NO:31)); human actin (CTG AGC GTG GCT ACT CCT TC (SEQ ID NO:3) and GGC ATA CAG GTC CTT CCT GA (SEQ ID NO:4)); mouse XBP-1 (GAT CCT GAC GAG GTT CCA GA (SEQ ID NO:5) and ACA GGG TCC AAC TTG TCC AG (SEQ ID NO:6)); and mouse actin (AGC CAT GTA CGT AGC CAT CC (SEQ ID NO:7) and CTC TCA GCT GTG GTG GTG AA (SEQ ID NO:8)).

BCR Activation and Phosphorylation Assay.

Wild-type mouse B cells and Eμ-TCL1 CLL cells were suspended in RPMI serum-free media supplemented with 25 mM Hepes, stimulated with $F(ab')_2$ fragments of the goat anti-mouse IgM antibody (20 μg/ml) (SouthernBiotech) for 2 min, and lysed immediately by adding ice-cold lysis buffer (50 mM Tris-HCl, pH 8.0; 150 mM NaCl; 1% Triton X-100; 1 mM EDTA) supplemented with protease inhibitor cocktail (Roche), 4 mM sodium pyrophosphate, 2 mM sodium vanadate and 10 mM sodium fluoride. The lysates were analyzed by SDS-PAGE.

Phosphorylated Proteins of Interest were Detected by Immunoblots Using Phospho-Specific Antibodies.

Pulse chase experiments, immunoprecipitation, protein deglycosylation and SDS-PAGE B cells or CLL cells were starved in methionine- and cysteine-free media containing dialyzed serum for 1 h, then pulse-labeled with 250 μCi/ml [$^{35}$S]-methionine and [$^{35}$S]-cysteine (Perkin-Elmer) for 15 min. After labeling, cells were incubated in chase medium containing unlabeled methionine (2.5 mM) and cysteine (0.5 mM). At the end of each chase interval, cells were lysed in RIPA buffer containing protease inhibitors. Pre-cleared lysates were incubated with a primary antibody and Protein G-agarose beads (Sigma). Bead-bound proteins were eluted using glycoprotein denaturing buffer (0.5% SDS, 1% β-ME) or reducing Laemmli SDS-PAGE sample buffer. Enzymatic deglycosylation of proteins was achieved by denaturation of the immunoprecipitates in glycoprotein denaturing buffer at 95° C. for 5 min, followed by addition of sodium citrate (pH 5.5) to a final concentration of 50 mM, and incubated with Endo H (New England Biolabs) at 37° C. for 2 h. Alternatively, sodium phosphate (pH 7.5) and NP-40 were added to the denatured cell lysates to a final concentration of 50 mM and 1%, respectively, and the mixture was incubated with PNGase F (New England Biolabs) at 37° C. for 2 h. Protein samples were then analyzed by SDS-PAGE followed by fluorography.

Chemical Synthesis and Characterization of the IRE-1 Inhibitors

STF-083010 and B-A05 were synthesized in-house from commercially available reagents. STF-083010 stability studies were performed using analytical reverse-phase high pressure liquid chromatography (RP-HPLC) with a $C_{18}$ column (4 mm×150 mm) and a 10-90% linear gradient of acetonitrile in water (containing 0.1% formic acid) as eluent over 20 minutes (1 ml/min flow rate). Compounds were detected at λ=254 nm. Crystalline STF-083010 was analyzed on a standard Bruker X8 Apex2 CCD-based X-ray diffractometer, and the solid-state structure was solved and refined with the Bruker SHELXTL (version 6.12) software package. Diffraction data (excluding structure factors) for STF-083010 have been deposited with the Cambridge Crystallographic Data Centre as supplementary CCDC publication number 850879.

Cell Proliferation Assays.

Eμ-TCL1, MEC1, MEC2, WaC3, or primary human CLL cells were grown in 96-well cell culture plates overnight and then treated with fresh phenol red-free culture medium containing STF-083010 (50 μM), A-I06 (50 μM), A-I07 (50 μM) or fludarabine (30 μM). Every 24th hour, cells were spun down and proliferative capabilities were assessed by XTT assays (Roche) according to the manufacturer's instructions. Briefly, 50 μl XTT labeling reagent was combined with 100 μl electron-coupling reagent, and the mixture was applied to each well of the 96-well plates. The test was based on cleavage of the yellow tetrazolium salt XTT by mitochondrial dehydrogenases of the metabolic active cells to form the orange formazan compound, which can be spectrophotometrically quantified at 492 nm using a BioTek microplate reader.

In Vivo Treatment of Mouse CLL with A-I06

Older Eμ-TCL1 mice (age >8 months) with high CLL burden in the peripheral blood were identified by examining the percentage of CLL cells in PBMCs. These mice then received intraperitoneal injections with A-I06 (60 mg/kg) dissolved in Cremophor© ELP (vehicle, Sigma). The progression of CLL was monitored by flow cytofluorometry.

Real-Time Quantitative Polymerase Chain Reaction (PCR)

Figure 6A:
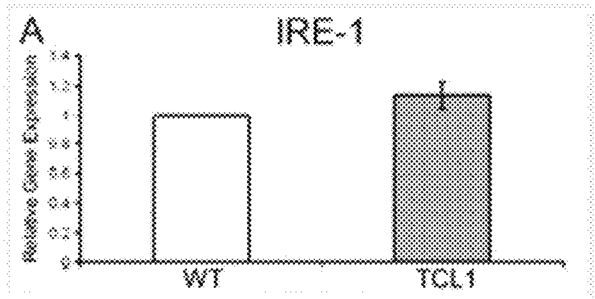
FIG. 6A: relative gene expression levels of IRE-1 in CD5−/B220+ wild-type B cells and CD5+/B220+ Eμ-TCL1 CLL cells that were stimulated with LPS for 1 day and lysed for purification of total RNA and synthesis of cDNA.
Figure 6C:
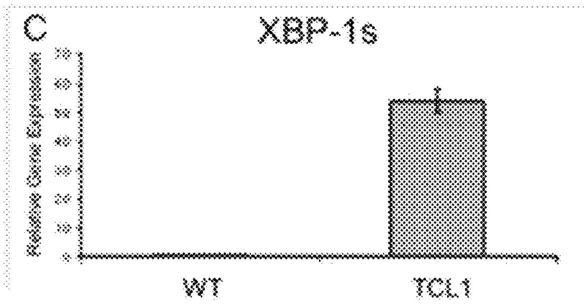
FIG. 6C: relative gene expression levels of XBP-1s in CD5−/B220+ wild-type B cells and CD5+/B220+ Eμ-TCL1 CLL cells that were stimulated with LPS for 1 day and lysed for purification of total RNA and synthesis of cDNA.
Figure 6B:
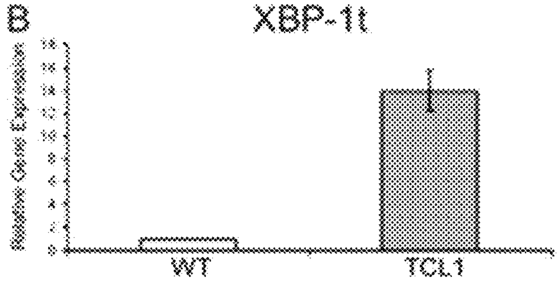
FIG. 6B: relative gene expression levels of XBP-1t in CD5−/B220+ wild-type B cells and CD5+/B220+ Eμ-TCL1 CLL cells that were stimulated with LPS for 1 day and lysed for purification of total RNA and synthesis of cDNA.
Figure 6D:
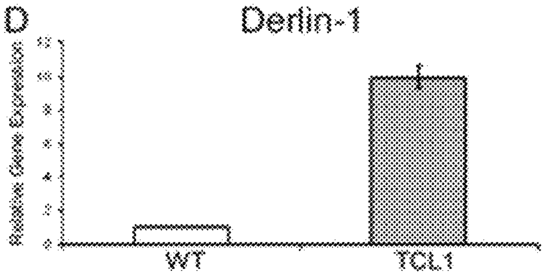
FIG. 6D: relative gene expression levels of Derlin-1 in CD5−/B220+ wild-type B cells and CD5+/B220+ Eμ-TCL1 CLL cells that were stimulated with LPS for 1 day and lysed for purification of total RNA and synthesis of cDNA.
Figure 6E:
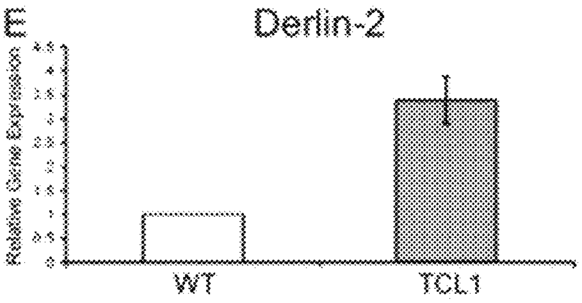
FIG. 6E: relative gene expression levels of Derlin-2 in CD5−/B220+ wild-type B cells and CD5+/B220+ Eμ-TCL1 CLL cells that were stimulated with LPS for 1 day and lysed for purification of total RNA and synthesis of cDNA.
Figure 6F:
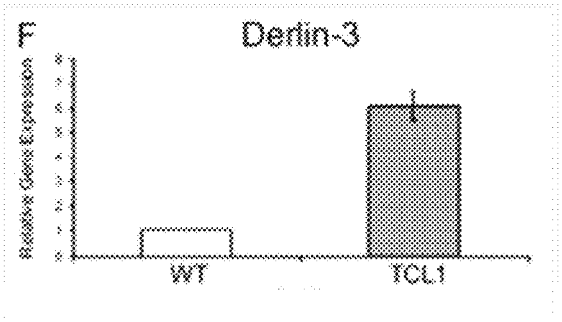
FIG. 6F: relative gene expression levels of Derlin-3 in CD5−/B220+ wild-type B cells and CD5+/B220+ Eμ-TCL1 CLL cells that were stimulated with LPS for 1 day and lysed for purification of total RNA and synthesis of cDNA.
Figure 6H:
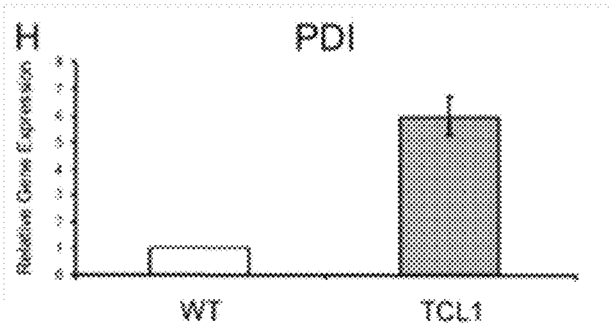
FIG. 6H: relative gene expression levels of PDI in CD5−/B220+ wild-type B cells and CD5+/B220+ Eμ-TCL1 CLL cells that were stimulated with LPS for 1 day and lysed for purification of total RNA and synthesis of cDNA.

Total RNA was prepared from wild-type mouse B cells, Eμ-TCL1 mouse CLL cells, or human WaC3 cells using Trizol reagent (Invitrogen), and DNAse treated using RQ1 DNAse (Promega) according to the manufacturer's protocols. The resulting cDNA derived from the purified RNA (using Invitrogen Superscript II reverse transcriptase) was utilized as a template for quantitative PCR using SYBR Green mastermix (Qiagen) performed on the ABI PRISM 7900HT real-time cycler. Primers used for quantitative PCR are documented in FIG. 6K, along with the data. The levels of mRNA from each specific gene were quantified using a calibration curve based on dilutions of concentrated cDNA, and normalized to that from GAPDH.

Synthesis of STF-083010

A 25 mL round bottom flask containing a mixture of A-I06 (2.81 g, 13.5 mmol) and A-I07 (2.00 g, 12.3 mmol) was treated with tetraethyl orthosilicate (2.81 g, 13.5 mmol) and fitted with a small distillation head and receiving flask. The reaction was heated to 150° C. for 6 hours while ethanol was collected in the receiving flask. After cooling to room temperature, the solid formed in the reaction flask was filtered and washed with 100 ml of diethyl ether. Purification by recrystallization (from a 1:3 mixture of ethyl acetate: dichloromethane) afforded pure STF-083010 as green crystals (2.21 g, 57%): $^1$H NMR (400 MHz, $CDCl_3$) δ 12.65 (s, 1H), 9.99 (s, 1H), 8.20 (d, J=8.5 Hz, 1H), 8.00 (d, J=9.1 Hz, 1H), 7.82 (d, J=4.5 Hz, 1H), 7.80 (d, J=8.8 Hz, 1H), 7.72 (d, J=5.0 Hz, 1H), 7.65 (t, J=7.7 Hz, 1H), 7.46 (t, J=7.5 Hz, 1H), 7.16 (d, J=8.8 Hz, 1H), 7.15 (t, J=4.5 Hz, 1H)); $^{13}$C NMR (101 MHz, $CDCl_3$) δ 167.0, 165.9, 140.3, 139.4, 134.3, 134.2, 133.5, 129.9, 129.7, 128.3, 128.1, 125.1, 119.9, 119.4 108.2; HRMS (ESI-TOF) m/z $[M+H]^+$ calculated for $C_{15}H_{12}NO_3S_2$ 318.0259, found 318.0263.

Synthesis of B-A05

A solution of STF-083010 (1.15 g, 3.62 mmol) was dissolved in 90 ml of methanol and cooled to 0° C. under an atmosphere of argon. Solid $NaBH_4$ (410 mg, 10.845 mmol) was added portionwise and the reaction allowed to stir for 2 hours at the same temperature. The solvent was removed under reduced pressure and the residue taken up in ethyl acetate (100 ml) and washed with sat. aq. $NaHCO_3$ (100 ml). The organic layer was separated and dried with $MgSO_4$, then filtered and concentrated under reduced pressure. The resulting solid was dissolved in 10 ml of dichloromethane and hexane was added until a white precipitate formed. The solid was filtered and washed with hexane. Drying the solid under vacuum afforded pure B-A05 white powder (1.10 g, 95%): $^1$H NMR (400 MHz, $CD_3OD$) δ 7.87 (d, J=8.6 Hz, 1H), 7.75 (dd, J=5.0, 1.3 Hz, 1H), 7.71 (d, J=8.2 Hz, 1H), 7.66 (d, J=8.8 Hz, 1H), 7.63 (dd, J=3.7, 1.3 Hz, 1H), 7.41 (ddd, J=8.5, 6.8, 1.3 Hz, 1H), 7.26 (ddd, J=8.0, 6.8, 1.1 Hz, 1H), 7.12 (dd, J=5.0, 3.8 Hz, 1H), 7.06 (d, J=8.6 Hz, 1H), 4.58 (s, 2H); $^{13}$C NMR (101 MHz, $CD_3OD$) δ 153.6, 141.4, 133.7, 131.8, 131.6, 129.7, 128.9, 128.2, 127.1, 126.5, 122.6, 122.5, 117.3, 113.2, 37.5; HRMS (ESI-TOF) m/z $[M-H]^+$ calculated for $C_{15}H_{12}NO_3S_2$ 318.0259, found 318.0268.

Results

Prolonged TCL1 Expression can Cause a Reduced Expression Level of AKT.

Figure 1:
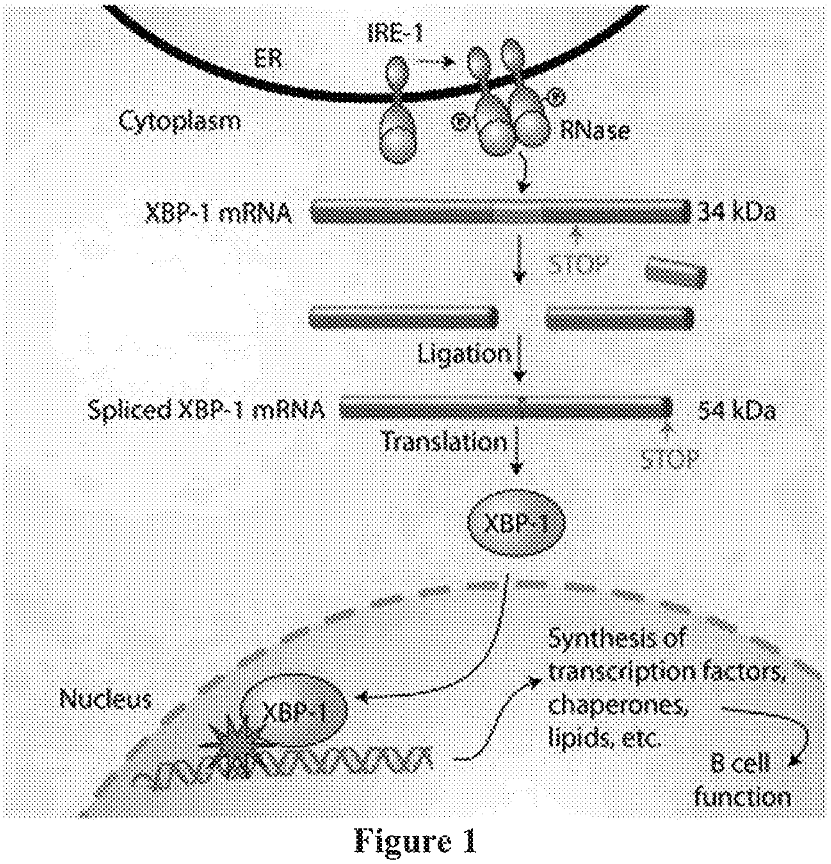
FIG. 1 displays the activation of the IRE-1/XBP-1 pathway in B cells.
Figure 2A:
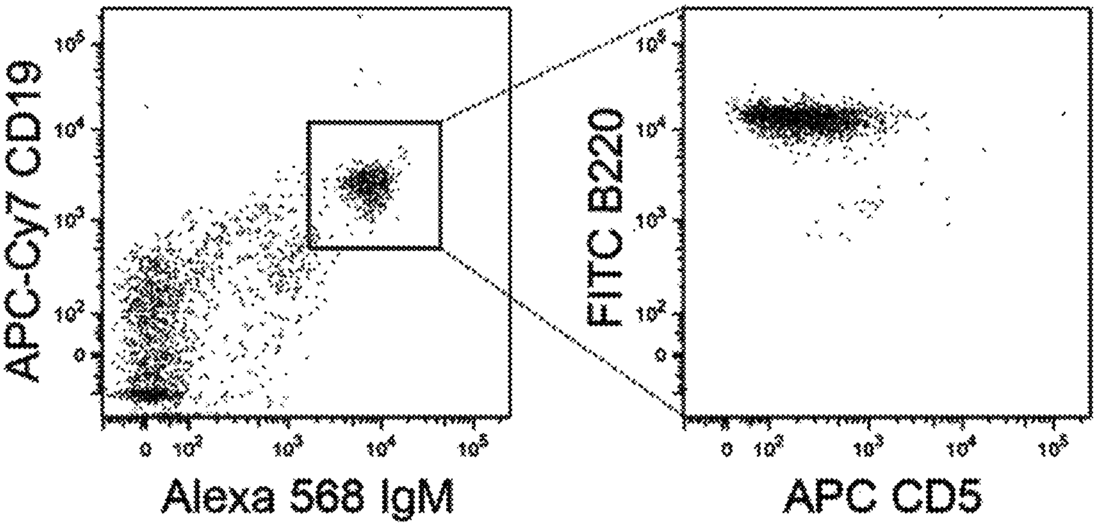
FIG. 2A: PBMCs isolated from 8-month old wild-type mice.
Figure 2B:
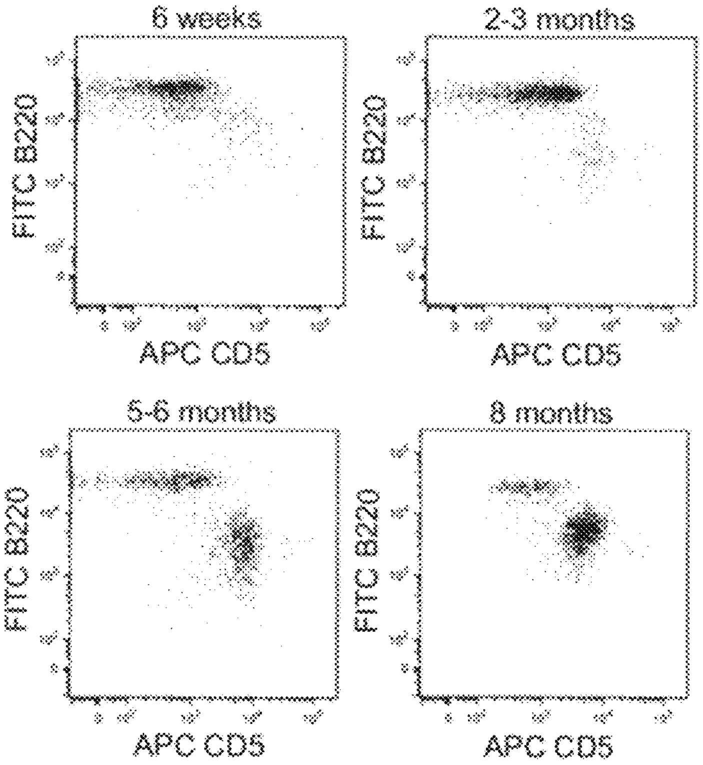
FIG. 2B: PBMCs isolated from Eμ-TCL1 mice of different age groups.
Figure 2C:
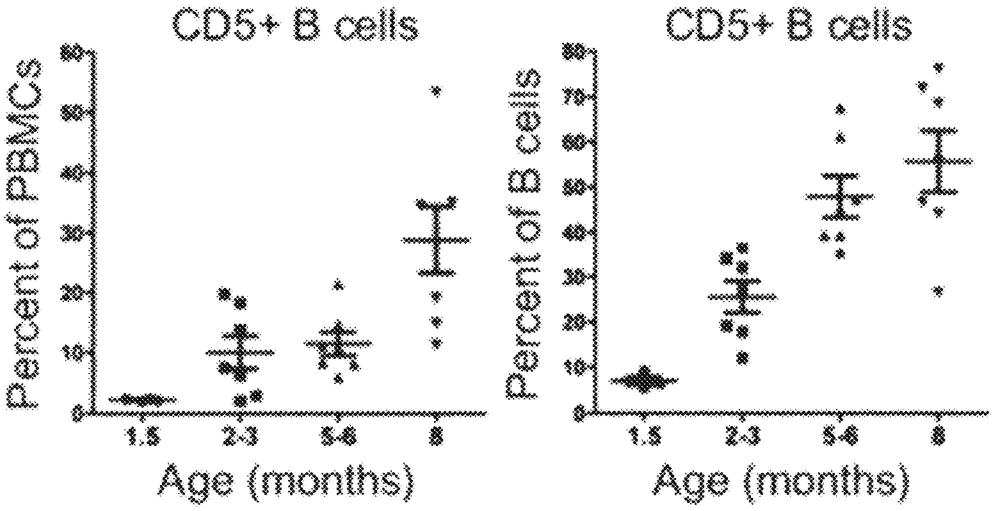
FIG. 2C: CD5+/B220+ CLL plotted against PBMCs or CD19+/IgM+ B cells.
Figure 2D:
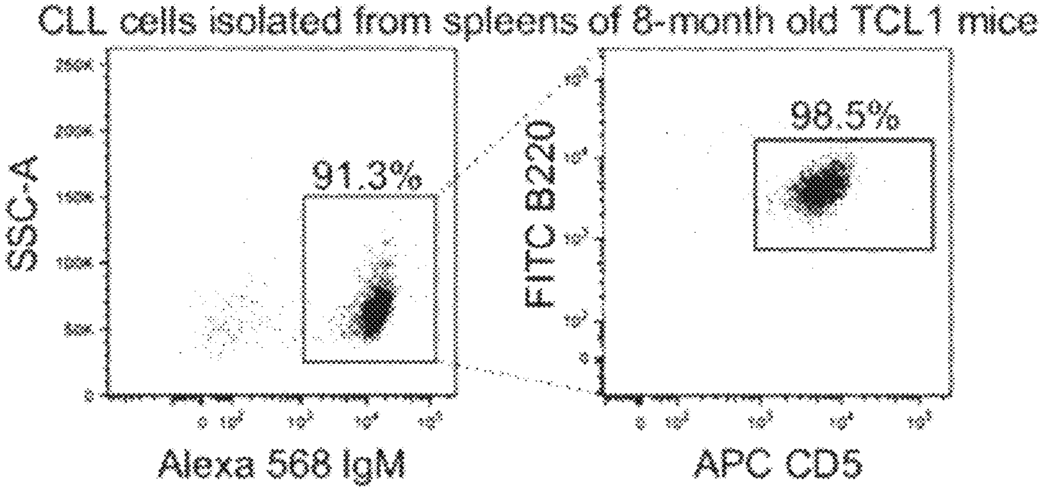
FIG. 2D: IgM+ cells purified from spleens of Eμ-TCL1 mice analyzed for the presence of CD5+/B220+ CLL cells.
Figure 2E:
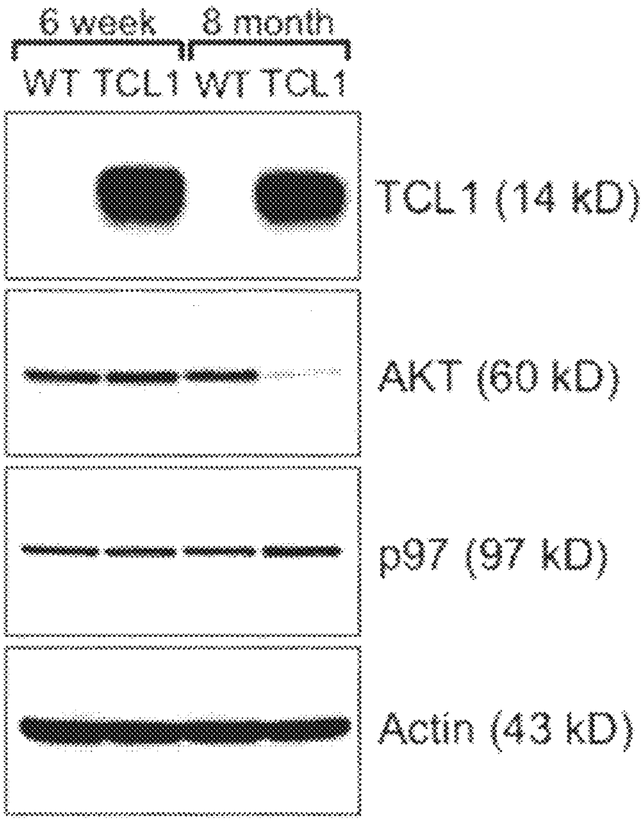
FIG. 2E: Lysates from CD5−/B220+ B cells of 6-week old wild-type (WT) and Eμ-TCL1 mice (lanes 1 and 2), from CD5−/B220+ B cells of 8-month old wild-type mice (lane 3) and from CD5+/B220+ CLL cells of 8-month old Eμ-TCL1 mice (lane 4) were immunoblotted for TCL1, AKT, p97 and actin.
Figure 3A:
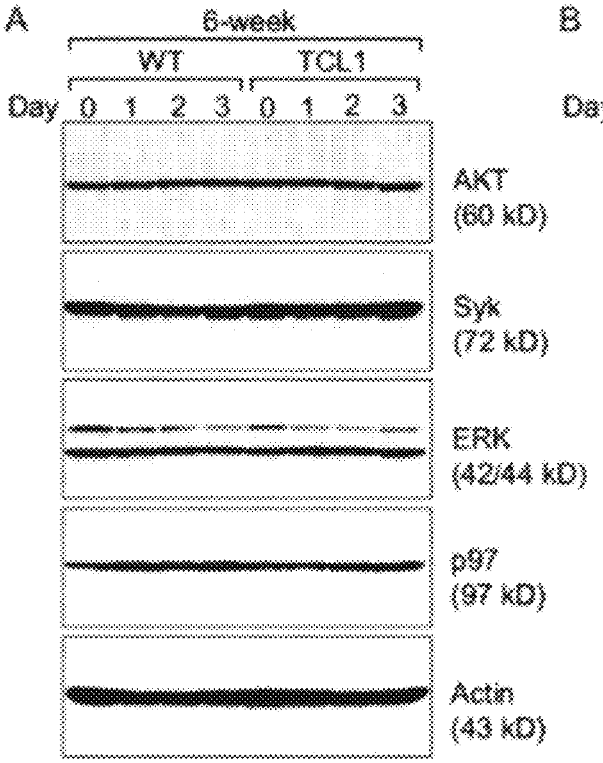
FIG. 3A: CD5−/B220+ B cells purified from 6-week old wild-type and Eμ-TCL1 mice were stimulated with LPS for a course of 3 days, and lysed for analysis by immunoblots for indicated proteins.
Figure 3B:
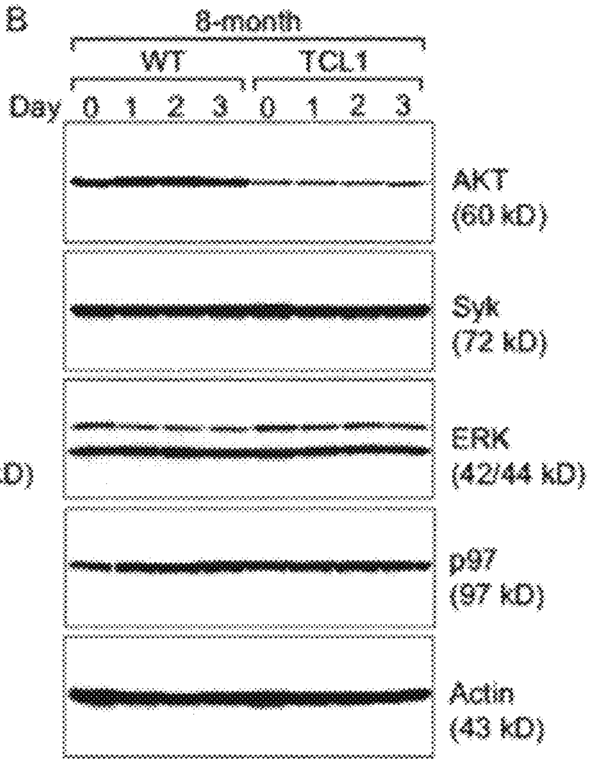
FIG. 3B: CD5−/B220+ B cells purified from 8-month old wild-type mice and CD5+/B220+ CLL cells from 8-month old Eμ-TCL1 mice were stimulated by LPS for 3 days and lysed for analysis by immunoblots for indicated proteins.

To monitor malignant progression of CLL in Eμ-TCL1 mice, mice of different ages (ranging from 6-week to 8-month old) were immunostained for purified peripheral blood mononuclear cells (PBMCs) using fluorescent antibodies against mouse CD19, IgM, B220, and CD5. B220+/CD5+ CLL cells were analyzed on gated CD19+/IgM+ B cell populations of Eμ-TCL1 mice (FIG. 2A), which confirmed that increased numbers of CLL cells can be positively correlated to the age of Eμ-TCL1 mice when compared to PBMCs or peripheral B cells (FIG. 2B-FIG. 2C) (Bichi et al., *Proc Nat Acad Sci USA,* 99(10), 6955-6960 (2002)). To purify CLL cells, 8-month Eμ-TCL1 mice with clear CLL presentation were sacrificed, and CLL cells purified from spleens by staining splenocytes with CD43 MicroBeads and performing negative selection using MACS columns. A cell population containing ~90% CD5+ CLL cells was consistently obtained from spleens of 8-month old Eμ-TCL1 mice (FIG. 2D). The same purification was also performed using 6-week old Eμ-TCL1 mice, and a precancerous B cell population containing consistently <1% CD5+ cells was obtained. By immunoblots, both precancerous Eμ-TCL1 B cells and CLL cells were found to express TCL1 proteins, encoded from the Eμ-TCL1 transgene. Although TCL1 is believed to function via AKT to promote CLL formation (Laine et al., *Mol Cell,* 6(2), 395-407 (2000); Pekarsky et al., *Proc Natl Acad Sci USA,* 97(7), 3028-3033 (2000); Teitell, *Nat Rev Cancer,* 5(8), 640-648 (2005)), prolonged TCL1 expression can lead to a decreased expression of AKT (FIG. 2E), suggesting that TCL1 may also contribute to malignant progression of CLL by other mechanisms. Control experiments showed no changes in the expression of the Syk or ERK kinase (FIG. 3A-FIG. 3B).

Prolonged TCL1 Expression can Lead to Upregulated Levels of the ER Stress Response Molecules.

Figure 4A:
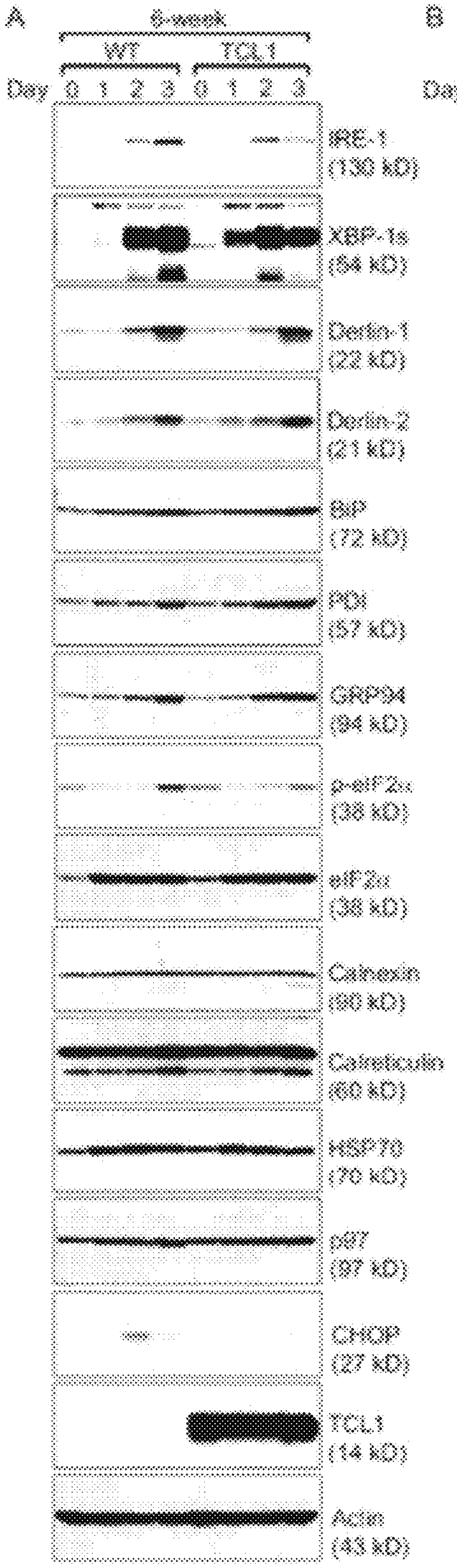
FIG. 4A: CD5−/B220+ B cells purified from 6-week old wild-type and Eμ-TCL1 mice were stimulated with LPS for a course of 3 days, and lysed for analysis by immunoblots for indicated proteins.
Figure 4B:
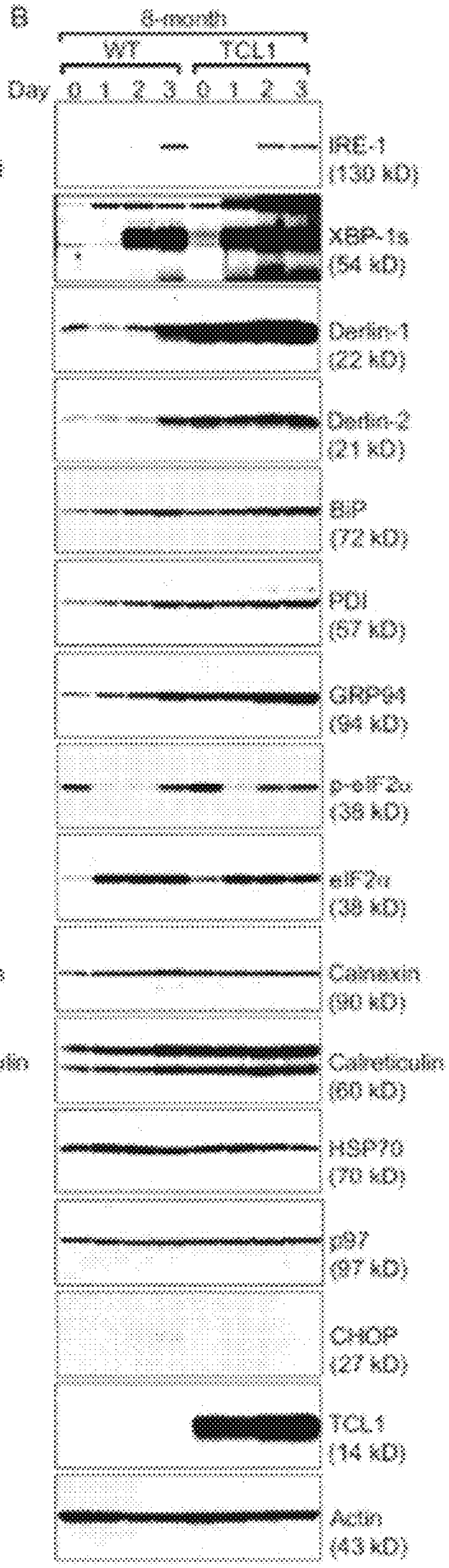
FIG. 4B: CD5−/B220+ B cells purified from 8-month old wild-type mice and CD5+/B220+ CLL cells from 8-month old Eμ-TCL1 mice were stimulated by LPS for 3 days and lysed for analysis by immunoblots for indicated proteins.
Figure 5A:
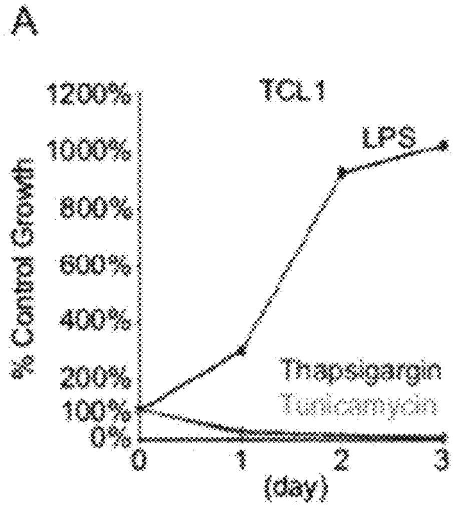
FIG. 5A: Eμ-TCL1 CLL cells were cultured in the presence of LPS (20 μg/ml), thapsigargin (Tg, 2.5 μM) or tunicamycin (Tu, 5 μg/ml) for 3 days. At the end of each day, cells were subjected to XTT assays.
Figure 5B:
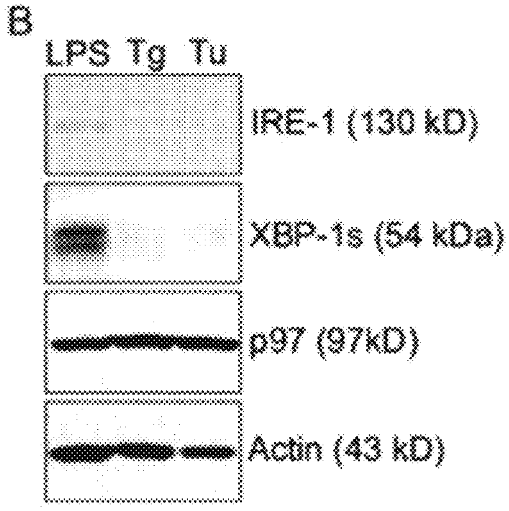
FIG. 5B: Eμ-TCL1 CLL cells were cultured in the presence of LPS, Tg or Tu for 18 h, and lysed for analysis by immunoblots using indicated antibodies.

Due to the lack of suitable protein antigen to stimulate polyclonal Eμ-TCL1 CLL cells in vitro, the expression of ER stress response molecules was examined in $CD5^-$ precancerous and $CD5^+$ cancerous Eμ-TCL1 B cells stimulated with lipopolysaccharides (LPS) for a course of 3 days. The expression of IRE-1, XBP-1, Derlin proteins, BiP, GRP94, protein disulfide isomerase (PDI, which catalyzes disulfide formation), eukaryotic initiation factor 2α (eIF2α, whose phosphorylation inhibits protein synthesis to relieve ER stress), calnexin and calreticulin were investigated, all of which are ER stress response molecules. The expression pattern of most ER proteins in precancerous Eμ-TCL1 B cells from 6-week old mice was found to be comparable to that of B cells purified from age-matched wild-type mice. One exception was the early onset of XBP-1 protein expression in precancerous Eμ-TCL1 B cells as a response to LPS stimulation (FIG. 4A). Eμ-TCL1 CLL cells from 8-month old mice were then compared with normal B cells from age-matched wild-type mice. Even before LPS stimulation, Eμ-TCL1 CLL cells already expressed XBP-1, Derlin-1, Derlin-2, BiP, GRP94, PDI, phosphorylated IRE-1 and phospho-eIF2α at significantly higher levels than their wild-type counterparts (FIG. 4B). Stimulation with LPS allowed detection of differences in the expression of IRE-1, XBP-1, Derlin-1 and Derlin-2 (FIG. 4B). Little change in the expression of eIF2α, calnexin and calreticulin was observed even when Eμ-TCL1 CLL cells were stimulated with LPS. Notably, substantially no difference was detected in the expression of p97 (a.k.a. AAA-ATPase) and HSP70 in the cytoplasm (FIG. 4B). While some wild-type B cells expressed the C/EBP-homologous protein (CHOP, which mediates apoptosis during ER stress) after being cultured in LPS for 2 days, Eμ-TCL1 B cells and Eμ-TCL1 CLL cells did not express CHOP (FIG. 4A-FIG. 4B). All these data support that Eμ-TCL1 CLL cells can respond to LPS by upregulating the ER stress response to sustain robust proliferation. Different from LPS, pharmacological ER stress inducers like thapsigargin (Tg) and tunicamycin (Tu) do not promote Eμ-TCL1 CLL cell growth or elicit activation of the IRE-1/XBP-1 pathway of the ER stress response (FIG. 5A-B).

To establish a link between TCL1 and activation of the ER stress response, it was hypothesized that TCL1 may associate with XBP-1 to upregulate the expression of chaperones at the transcriptional level. TCL1 was found in the immunoprecipitates retrieved from lysates of LPS-stimulated Eμ-TCL1 CLL cells using an anti-XBP-1 antibody (FIG. 4C), which may be specific to CLL. The mRNA levels of total XBP-1, spliced XBP-1, Derlin-1, Derlin-2, Derlin-3, BiP, PDI, and GRP94 were all elevated in LPS-stimulated Eμ-TCL1 CLL cells when compared with those in LPS-stimulated wild-type B cells (FIG. 6A-FIG. 6I).

Figure 4C:
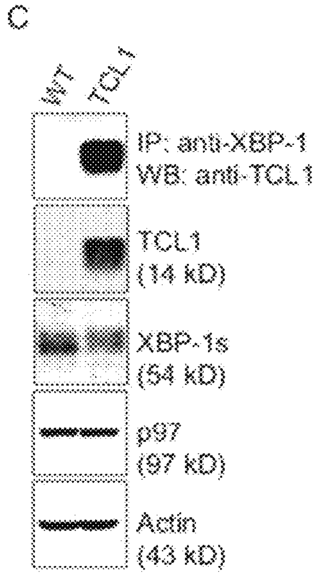
FIG. 4C: Association of TCL1 with XBP-1. CD5−/B220+ B cells purified from 8-month old wild-type mice and CD5+/B220+ CLL cells from 8-month old Eμ-TCL1 mice were stimulated by LPS for 3 days and lysed for analysis by immunoblots for TCL1, XBP-1, p97 and actin.
Figure 4D:
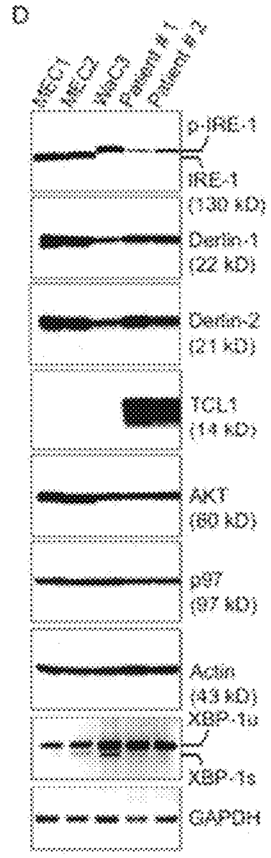
FIG. 4D: Human CLL cell lines (MEC1, MEC2 and WaC3) and freshly purified primary human CLL cells from two clinical patients (patient 1 and 2) were analyzed by immunoblots for the expression of indicated proteins.

To establish relevance, IRE-1, XBP-1, Derlin-1 and Derlin-2 were found expressed in human CLL cell lines (MEC1, MEC2 and WaC3) and primary CLL cells freshly isolated from two patients (FIG. 4D), with constitutively phosphorylated IRE-1 observed in WaC3 and the two primary human CLL cells (FIG. 4D). TCL1 is expressed in most primary human CLL cells, consistent with reported observations (Herling et al., *Leukemia,* 20(2), 280-285 (2006)), as discussed below.

Overexpression of TCL1 can Result in Dysregulated Expression of B Cell Transcription Factors and Activation-Induced Cytidine Deaminase (AID).

Figures 7A, 7B:
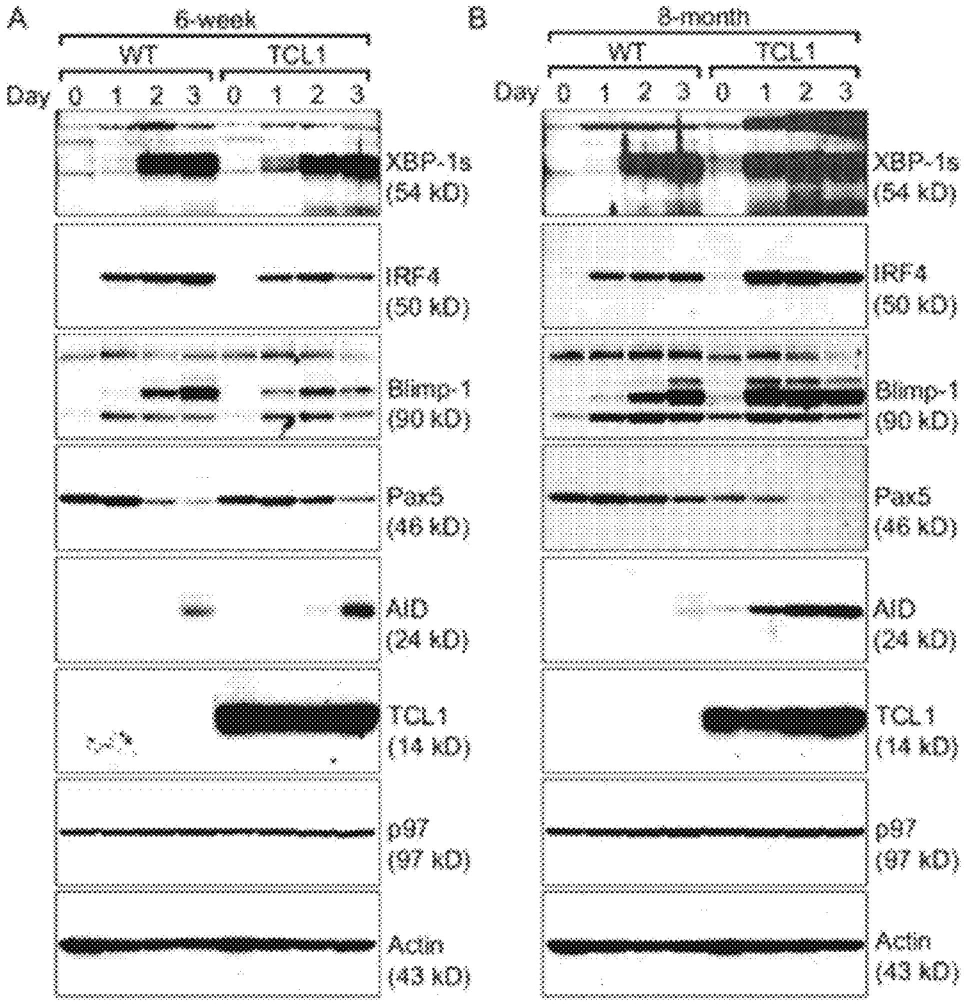
FIG. 7A: CD5−/B220+ B cells purified from 6-week old wild-type and Eμ-TCL1 mice were stimulated with LPS for a course of 3 days, and lysed for analysis by immunoblots for indicated proteins.
FIG. 7B: CD5−/B220+ B cells purified from 8-month old wild-type mice and CD5+/B220+ CLL cells from 8-month old Eμ-TCL1 mice were stimulated by LPS for 3 days and lysed for analysis by immunoblots for indicated proteins.
Figure 8:
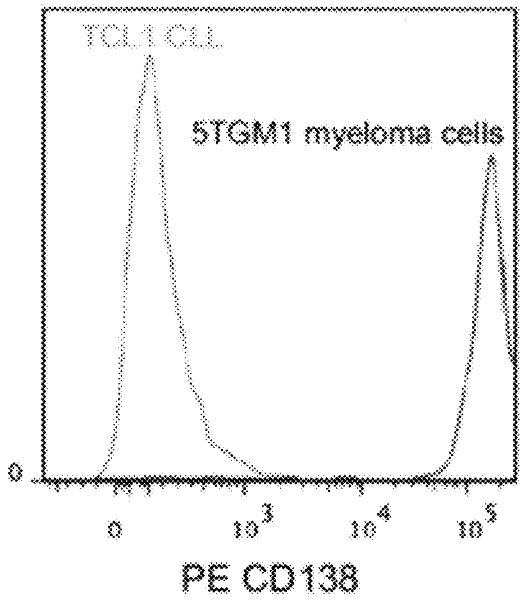
FIG. 8 displays that Eμ-TCL1 CLL cells does not express CD138, a surface marker for multiple myeloma cells. Eμ-TCL1 CLL cells and mouse 5TGM1 multiple myeloma cells were stained with CD138-PE and analyzed by flow cytofluorometry.

TCL1 is a transcriptional regulator, and its overexpression can cause an earlier and elevated expression of XBP-1 (FIG. 3A-FIG. 3B and FIG. 7A-FIG. 7B). Since TCL1 can associate with the XBP-1 transcription factor (FIG. 4C), other transcription factors for B cells were examined to determine how they respond to TCL1 overexpression, as the expression of transcription factors in B cells are tightly regulated (Hu et al., *Embo J,* 28(11), 1624-1636 (2009)). In precancerous Eμ-TCL1 B cells stimulated with LPS, IRF4 and Blimp-1 were expressed at decreased levels, and correspondingly, there was a persistent expression of the transcription suppressor Pax5 (FIG. 7A). Such data suggests that a dysregulated B cell differentiation can exist in precancerous Eμ-TCL1 B cells. In contrast, Eμ-TCL1 CLL cells already express Pax5 at a decreased level (FIG. 7B). Upon stimulation by LPS, the levels of Pax5 were further reduced, possibly causing IRF4 and Blimp-1 to be expressed at increased levels (FIG. 7B). To further link dysregulation of transcription factors to malignant progression of CLL, an increase in the expression of AID was seen (FIG. 7B), which is directly regulated by IRF4 (Klein et al., *Nat Immunol,* 7(7), 773-782 (2006)). Despite elevated levels of XBP-1, IRF4, Blimp-1 and AID, Eμ-TCL1 CLL cells do not acquire the CD138+ immunophenotype like mouse 5TGM1 multiple myeloma cells (FIG. 8).

TCL1 Overexpression can Contribute to a Constitutively Active BCR, Possibly Due to Increased Expression of IgM and Altered N-Linked Glycosylation of Igα and Igβ.

Figure 9A:
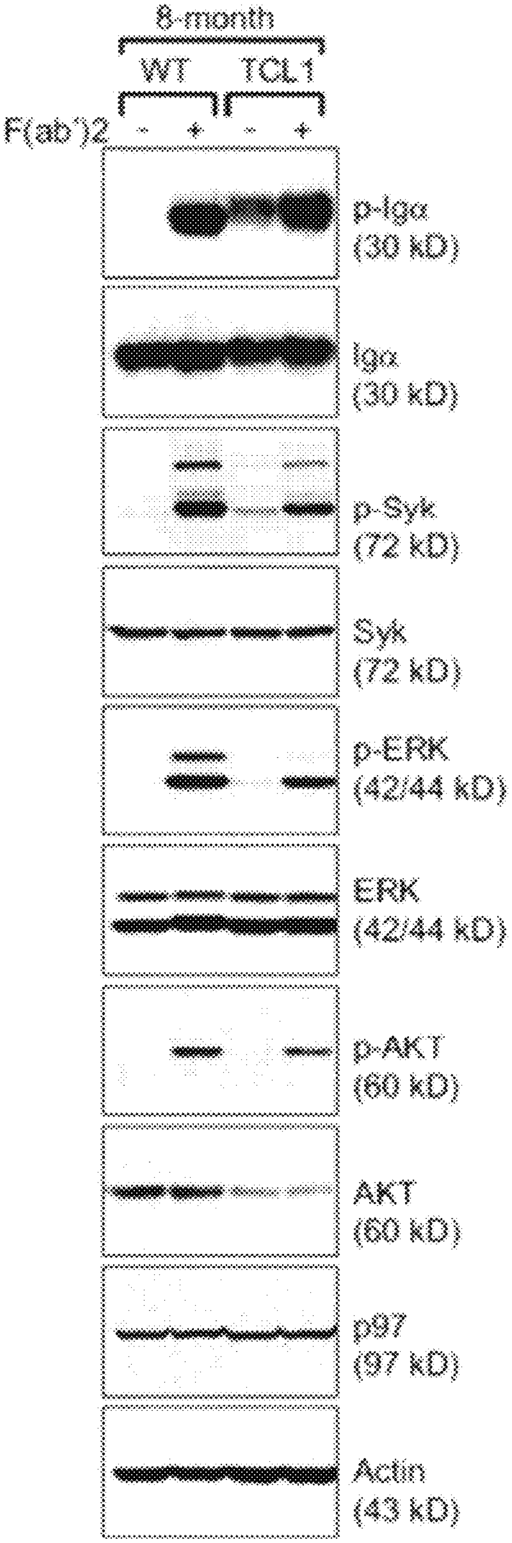
FIG. 9A: Wild-type B cells and CLL cells isolated from 8-month old wild-type and Eμ-TCL1 mice were cultured in the presence of LPS for three days. Their BCR is subsequently activated by F(ab')2 fragments of the goat anti-mouse IgM antibody for 2 min.

The malignant features of CLL cells are manifest in their robust, constitutive BCR signaling (Zenz et al., *Nat Rev Cancer,* 10(1), 37-50 (2010)). A functional BCR comprises a membrane-bound IgM (mIgM) and a membrane-bound disulfide-linked Igα and Igβ heterodimer. Both mIgM and Igα/Igβ are manufactured and assembled in the ER, and transported through the secretory pathway via the Golgi apparatus en route to the cell surface. Because the expression of XBP-1 can play an important role in maintaining normal BCR signaling (Hu et al., *Embo J,* 28(11), 1624-1636 (2009)), $F(ab')_2$ fragments from goat anti-mouse IgM antibodies were used to crosslink and activate the BCR of LPS-stimulated Eμ-TCL1 CLL cells, within which XBP-1 is overexpressed (FIG. 4B and FIG. 7B). As opposed to the wild-type B cells, the BCR of LPS-stimulated Eμ-TCL1 CLL cells was already conducting signal transduction before stimulation with $F(ab')_2$ fragments, as constitutive phosphorylation of Igα and the Syk kinase was observed (FIG. 9A). Upon stimulation with $F(ab')_2$ fragments, BCR signal transduction in Eμ-TCL1 CLL cells can be further strengthened to allow phosphorylation of two downstream kinases, ERK and AKT (FIG. 9A). Notably, $F(ab')_2$-mediated BCR signal transduction in Eμ-TCL1 CLL cells is slightly weaker than that in wild-type B cells (FIG. 9A), possibly due to less unengaged BCR available for crosslinking.

Figure 9B:
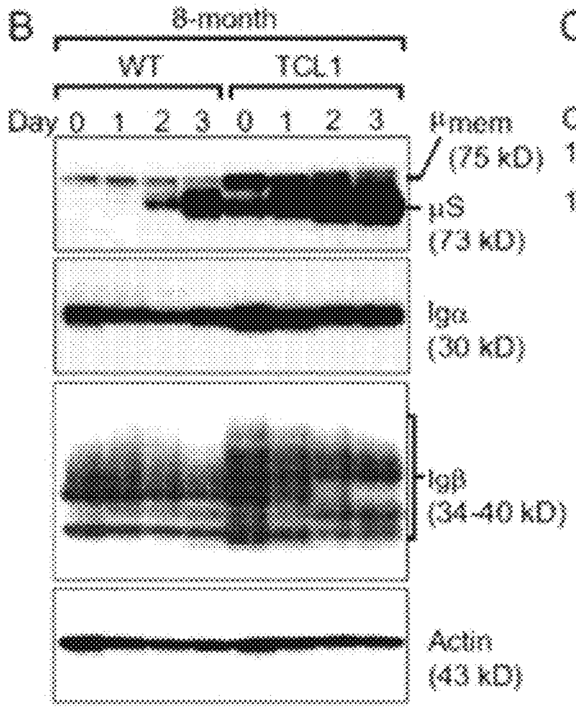
FIG. 9B: Wild-type B cells and CLL cells isolated from 8-month old wild-type and Eμ-TCL1 mice were stimulated with LPS for indicated days and lysed for analysis by immunoblots using antibodies to immunoglobulin μ heavy chain, Igα, Igβ and actin.
Figure 9C:
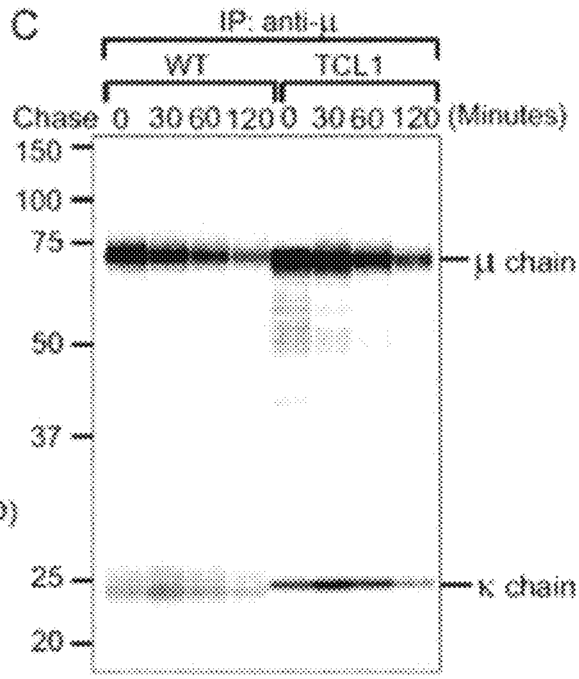
FIG. 9C: Wild-type B cells and Eμ-TCL1 CLL cells purified from 8-month old mice were radiolabeled for 15 min, chased for indicated time and lysed. Intracellular IgM was immunoprecipitated from the lysates using an anti-μ antibody, and analyzed on a SDS-PAGE gel. Data are representative of three independent experiments.
Figure 9D:
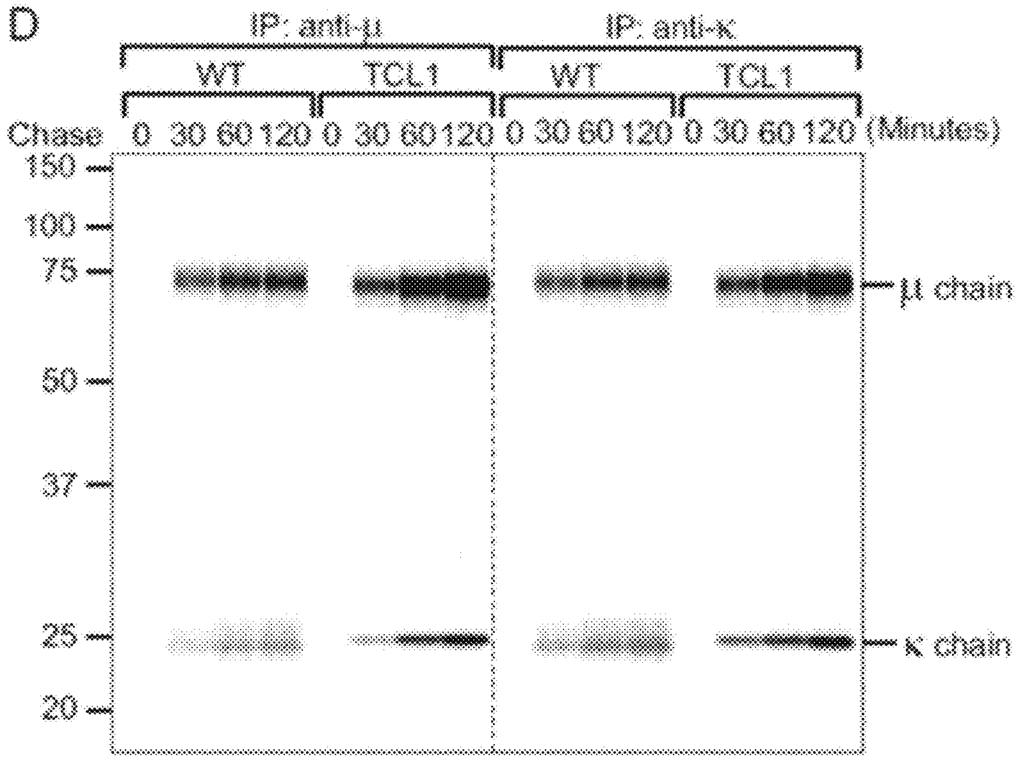
FIG. 9D: Extracellular sIgM was immunoprecipitated from culture media using an anti-μ or an anti-κ antibody and analyzed by SDS-PAGE. Data are representative of three independent experiments.

To provide an explanation for constitutive activation of the BCR, altered levels of ER stress response proteins were investigated for their contribution to the synthesis, assembly and trafficking of the BCR and other integral membrane and secretory proteins in Eμ-TCL1 CLL cells. Eμ-TCL1 CLL cells express more mIgM (FIG. 9B). In addition, Eμ-TCL1 CLL cells also synthesize and secrete more secretory IgM (sIgM) (FIG. 9B-FIG. 9D), as demonstrated by pulse chase experiments in which radiolabeled Eμ-TCL1 CLL cells, chased with cold media to allow IgM to be secreted, were retrieved radiolabeled IgM from cell lysates and culture media using an anti-μ or an anti-κ antibody (FIG. 9C-FIG. 9D). The κ light chains recovered from Eμ-TCL1 CLL cells exhibit as a sharper band in the SDS-PAGE gel, suggesting that these CLL cells have undergone clonal selection to use a limited repertoire of κ chains for IgM assembly.

Figure 9E:
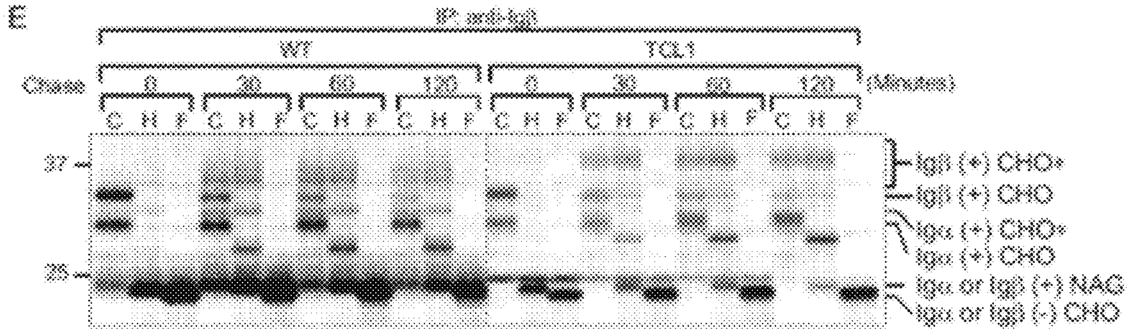
FIG. 9E: Immunoprecipitations using an anti-Ig antibody and protein G-conjugated agarose beads to retrieve the Igα/Igβ heterodimers.
Figure 9F:
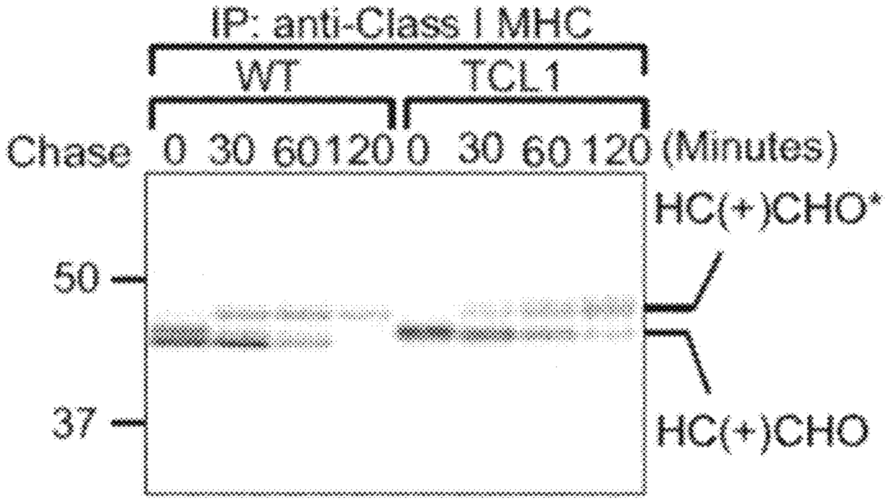
FIG. 9F: Immunoprecipitations using an antibody against the class I MHC heavy chain (HC).

Pulse chase experiments were performed to examine the expression and surface display of the Igα/Igβ heterodimer. Since Igβ can be the limiting step for the heterodimer assembly in the ER (McGehee et al., *J Immunol,* 183(6), 3690-3699 (2009)), the heterodimer was retrieved from Eμ-TCL1 CLL cell lysates using an anti-Ig antibody. To reveal glycosylation status of Igα and Igβ, the immunoprecipitated samples were treated with endoglycosidase (endo)-H to remove mannose glycans or with PNGase F to remove the entire N-linked glycans. It was found that both Igα and Igβ in Eμ-TCL1 CLL cells can be modified by different glycans when compared with those in wild-type B cells (FIG. 9E). In Eμ-TCL1 CLL cells, Igβ acquires more complex glycans in the Golgi apparatus (thus moving slower in the SDS-PAGE gel), but its assembled partner Igα only receives incomplete glycan modifications and thus still remains endo-H-sensitive (FIG. 9E). Without being bound to any specific theory, it is hypothesized that such distinct glycan modifications on Igα and Igβ may contribute to a hyper-responsive BCR in CLL cells. Such altered glycan modifications seem restricted to the BCR as it does not occur to the heavy chain (HC) of class I MHC molecules (FIG. 9F). Protein transportation in the secretory pathway is unaltered, as evidenced by normal secretion of sIgM and normal surface display of Igα, Igβ and class I MHC molecules (FIG. 9C-FIG. 9F).

A-I06, an Inhibitor to the RNAase Activity of IRE-1, can Downregulate the Expression of XBP-1 and Mimics XBP-1-Deficient Phenotypes in B Cells.

Figure 10A:
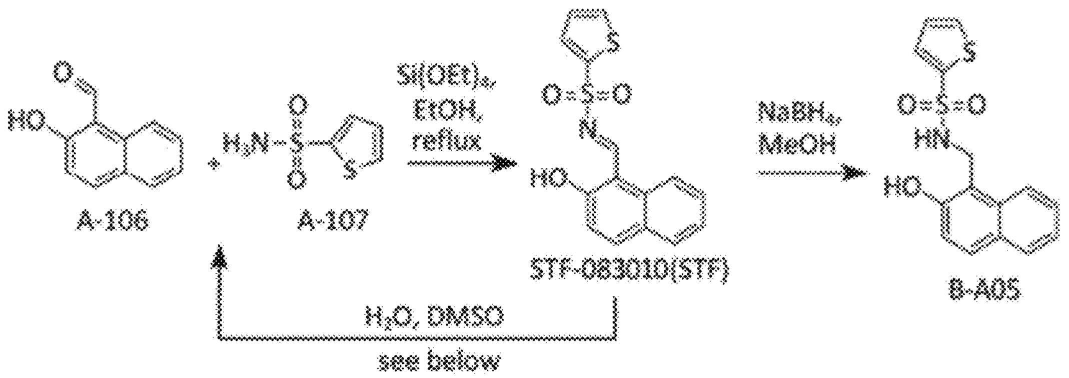
FIG. 10A: Structures and chemical synthesis of A-I06, A-I07, STF-083010, and B-A05, including the X-ray structure of STF-083010 with hydrogens omitted for clarity.

An inhibitor of IRE-1 RNase activity, STF-083010, was recently identified from a commercial screening library (Papandreou et al., *Blood,* 117(4), 1311-1314 (2011)). It shows promising effects in inhibiting proliferation of multiple myeloma without observed systemic toxicity in mice. The chemical synthesis of STF-083010 was carried out and confirmed its structure using small-molecule X-ray diffraction (FIG. 10A).

Figure 10B:
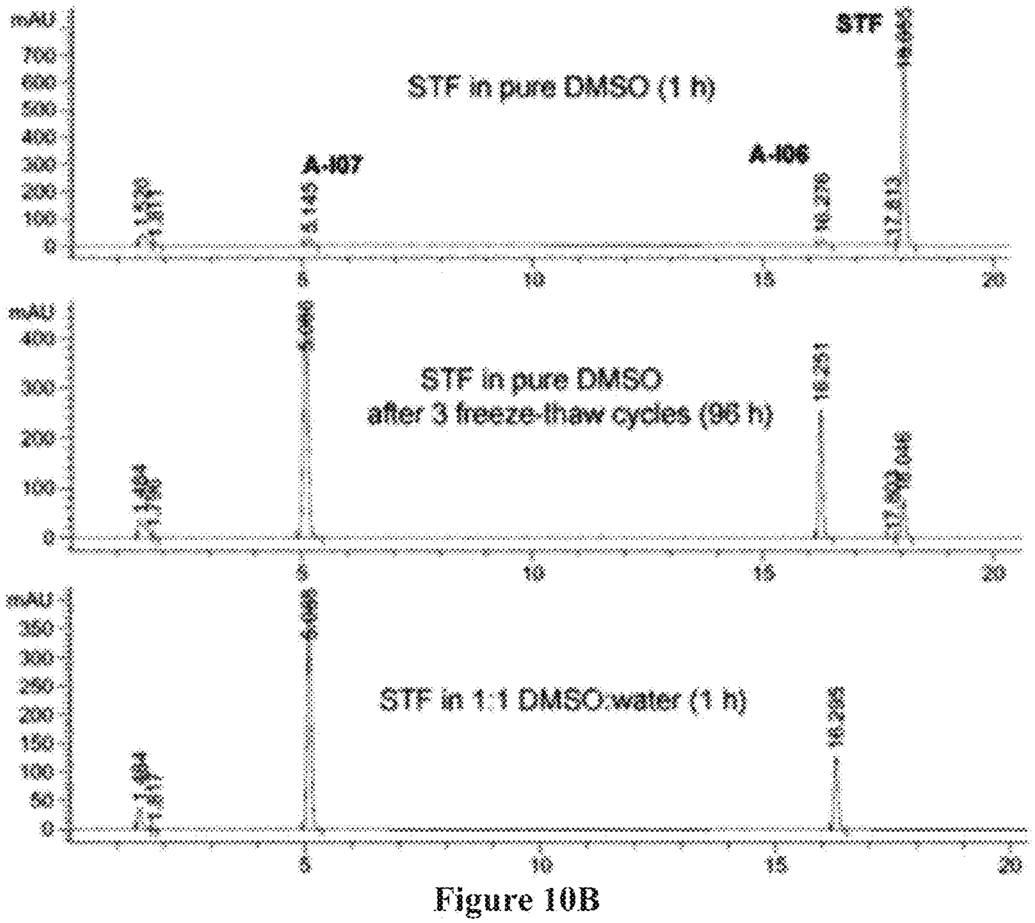
FIG. 10B: Assessment of STF-083010 aqueous stability using RP-HPLC.
Figure 10C:
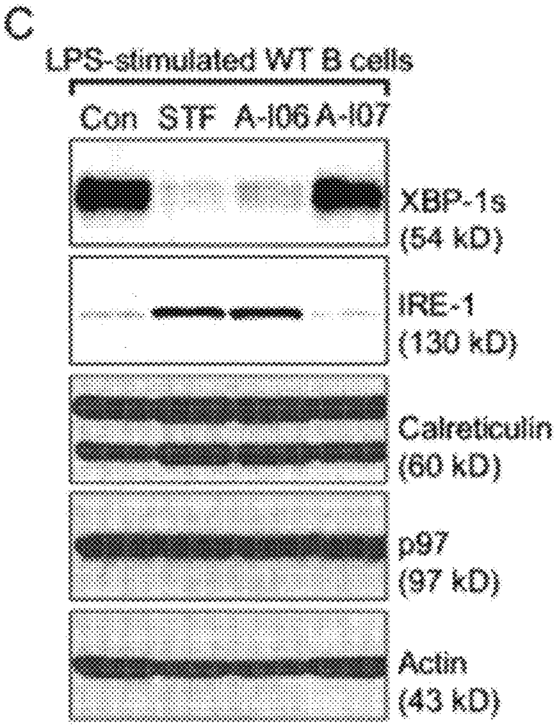
FIG. 10C: Wild-type B cells were stimulated with LPS (20 μg/ml) for 48 h to allow the expression of XBP-1, and subsequently treated with DMSO (control), STF-083010 (50 μM), A-I06 (50 μM), or A-I07 (50 μM) for 24 h. Cells were lysed and analyzed for the expression of XBP-1, IRE-1, calreticulin, p97 and actin by immunoblots using specific antibodies.
Figure 10D:
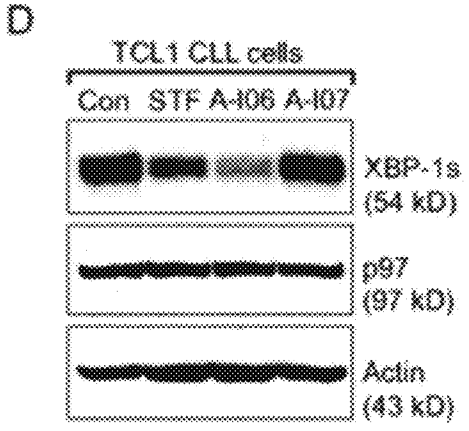
FIG. 10D: CLL cells isolated from 8-month old Eμ-TCL1 mice were cultured in the presence of LPS. Simultaneously, these cells were treated with DMSO (control), STF-083010 (50 μM), A-I06 (50 μM), or A-I07 (50 μM) for 48 h. Cells were lysed and analyzed for the expression of XBP-1, p97 and actin by immunoblots using specific antibodies.
Figure 10E:
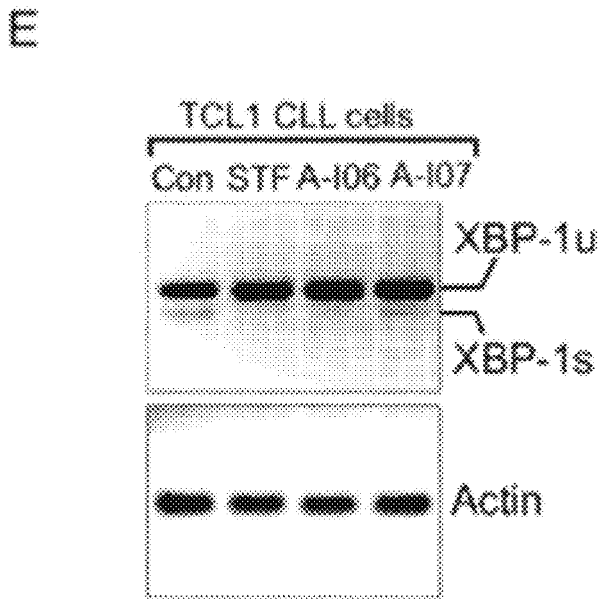
FIG. 10E: CLL cells isolated from 8-month old Eμ-TCL1 mice were cultured in the presence of LPS. Simultaneously, these cells were treated with DMSO (control), STF-083010 (50 μM), A-I06 (50 μM), or A-I07 (50 μM) for 48 h. Cells were lysed in TRIzol reagent to extract RNA. Unspliced and spliced forms of mouse XBP-1 mRNA, and mouse actin mRNA were detected by reverse transcription followed by PCR using specific primers.
Figure 10F:
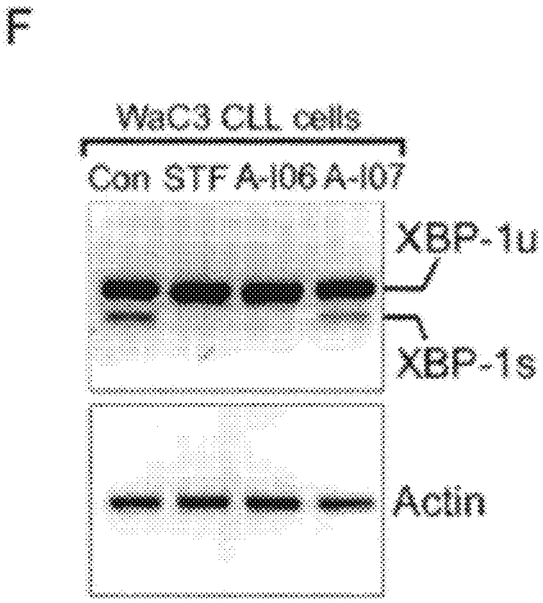
FIG. 10F: WaC3 cells were treated with DMSO (control), STF-083010 (50 μM), A-I06 (50 μM), or A-I07 (50 μM) for 72 h, and subsequently lysed for RNA extraction. Unspliced and spliced forms of human XBP-1 mRNA and human actin mRNA were detected by reverse transcription followed by PCR using specific primers.
Figure 10G:
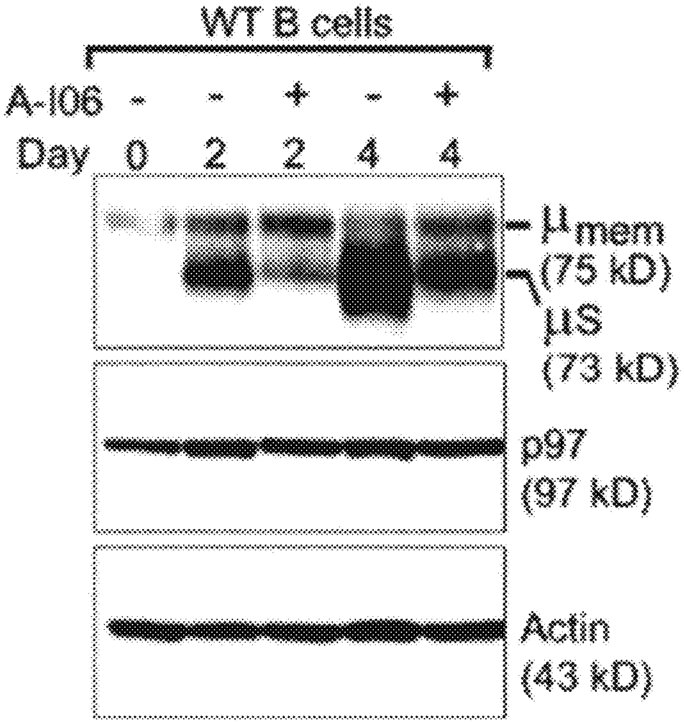
FIG. 10G: Wild-type B cells were cultured in the presence of LPS and A-I06 (50 μM) for indicated times and lysed for analysis by immunoblots using antibodies against μ heavy chain, p97 and actin.
Figure 11A:
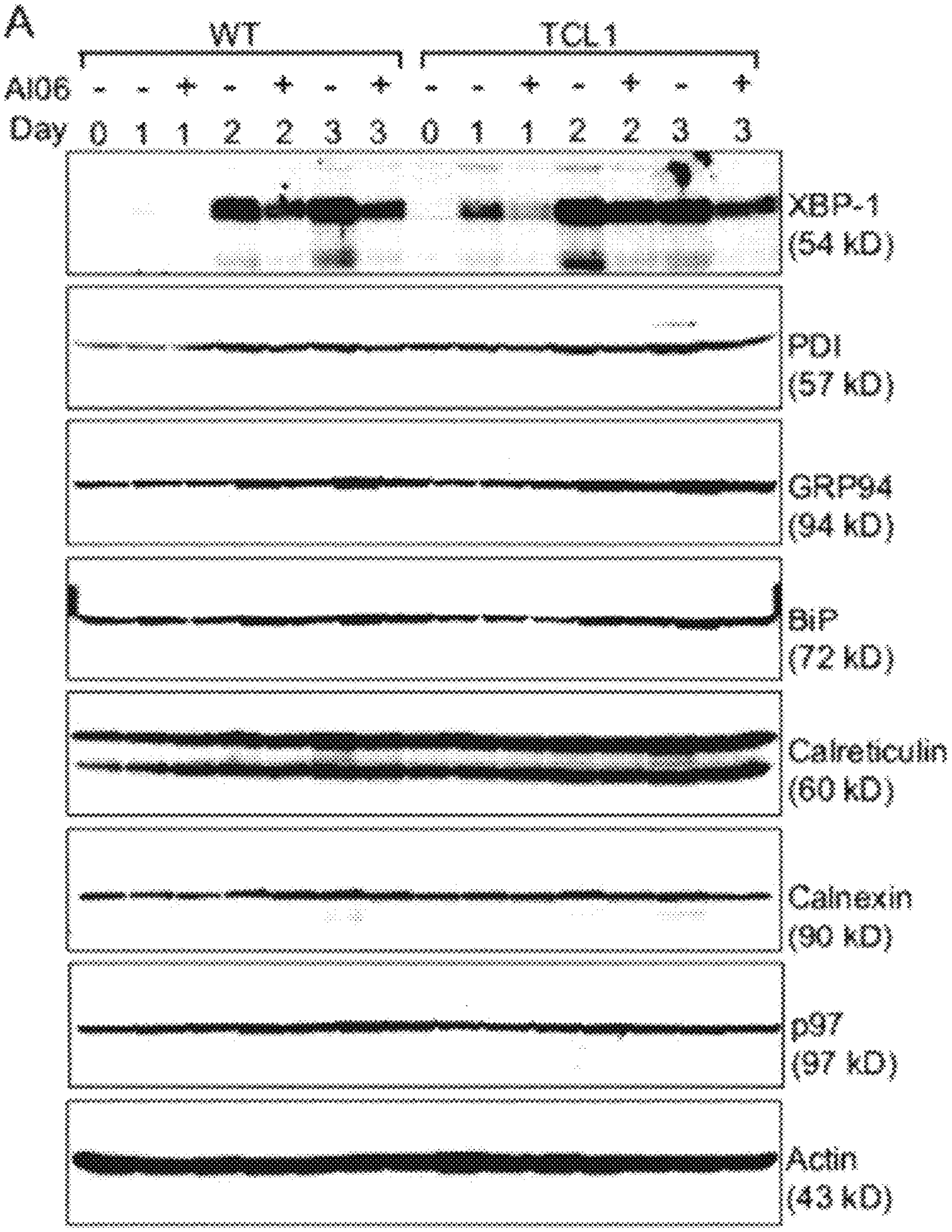
FIG. 11A: Wild-type and Eμ-TCL1 B cells were stimulated with LPS for 3 days in the absence or presence of A-I06 (50 μM). Each day, cells were lysed for analysis by immunoblots using indicated antibodies.
Figure 11B:
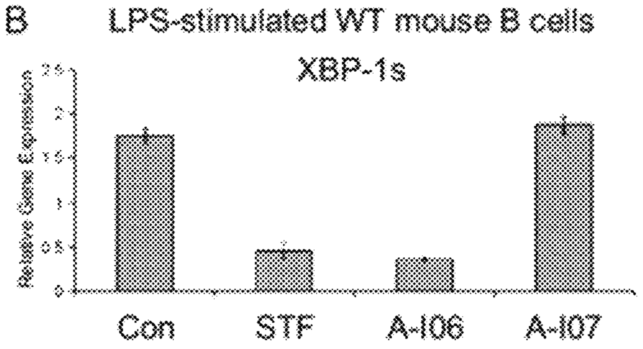
FIG. 11B: Wild-type B cells were stimulated with LPS (20 μg/ml) for 48 h and subsequently treated with DMSO (control), STF-083010 (50 μM), A-I06 (50 μM), or A-I07 (50 μM) for 24 h. Cells were lysed for purification of RNA and synthesis of cDNA. The mRNA expression levels of XBP-1 were measured by real-time quantitative PCR, performed in triplicate in each experiment (n=3).
Figure 11G:
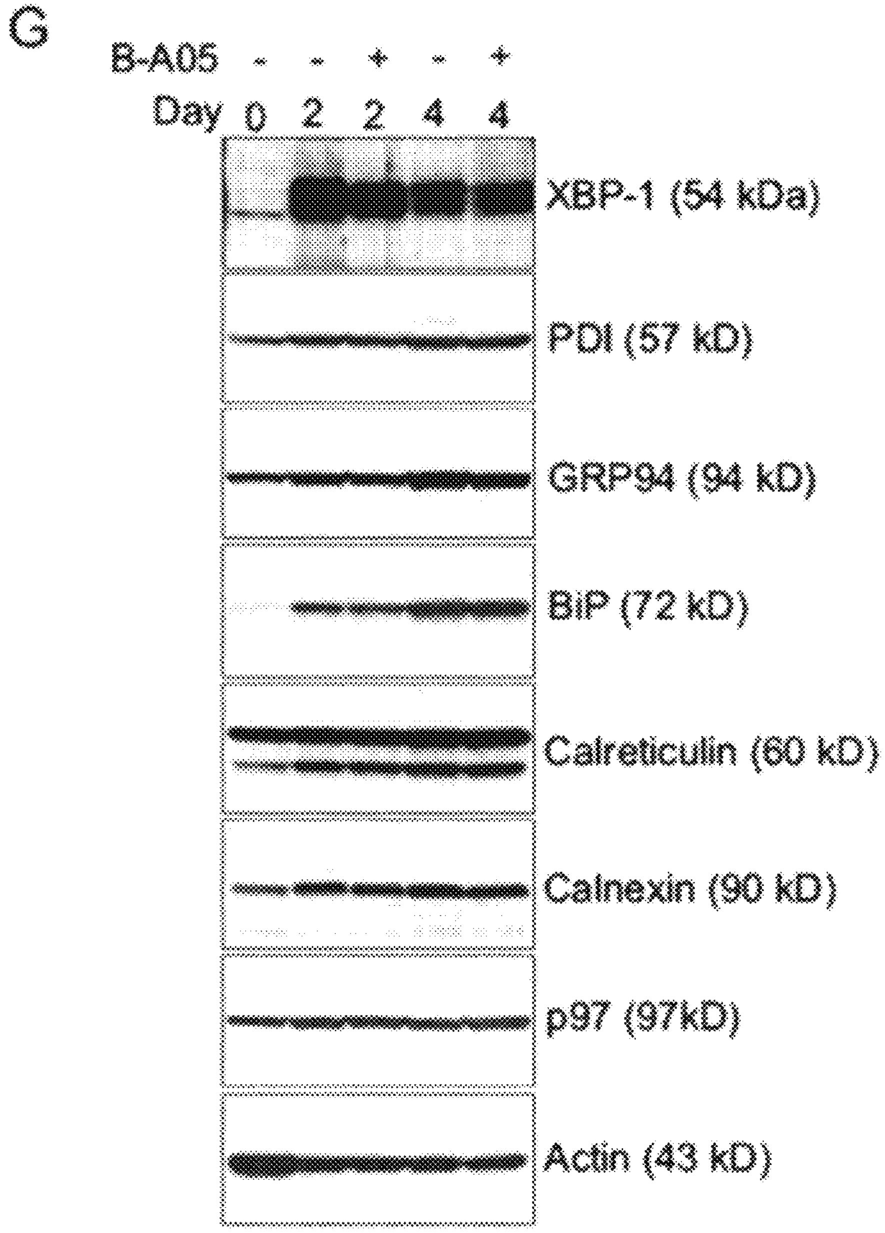
FIG. 11G: Wild-type B cells were unstimulated or stimulated with LPS for 2 or 4 days in the absence or presence of B-A05 (50 μM). On the indicated day, cells were lysed for analysis by immunoblots for indicated proteins.

While stable in crystalline form, stock solutions of STF-083010 in dimethyl sulfoxide (DMSO) readily hydrolyzed into precursors A-I06 and A-I07 after repeated freeze-thaw cycles. The instability of STF-083010 in aqueous conditions was confirmed by its complete decomposition upon brief exposure to 1:1 DMSO:water mixture (FIG. 10B). LPS-stimulated wild-type mouse B cells, LPS-stimulated mouse Eμ-TCL1 CLL cells and human WaC3 CLL cells were treated with STF-083010, A-I06 or A-I07 using various regimens, and it was found that STF-083010 and A-I06 can suppress the expression of XBP-1 (FIG. 10C-FIG. 10D and FIG. 10A), as a result of inhibiting the splicing of XBP-1 mRNA by IRE-1 (FIG. 10E-FIG. 10F and FIG. 10B, FIG. 10D-FIG. 10E). Chemical inhibition of XBP-1 by these IRE-1 inhibitors phenocopies XBP-1 deficiency introduced to B cells by gene deletion, as the expression of IRE-1 is upregulated at both protein and mRNA levels (FIG. 10C and FIG. 11C), and the synthesis of sIgM, but not mIgM, was inhibited by A-I06 (FIG. 10G) (Hu et al. *Embo J,* 28(11), 1624-1636 (2009)). A non-hydrolysable version of STF-083010, B-A05, was prepared to test the possibility that a stabilized analog may also block IRE-1 RNase activity. In contrast to A-I06, B-A05 did not significantly alter XBP-1 expression (FIG. 11G). These data establish the utility of A-I06 as a specific inhibitor of the IRE-1/XBP-1 pathway and suggest that A-I06 is responsible for the presumed activity of STF-083010. It appears that the compounds can decompose to form A-I06, which can physically interact with the aldehyde group of 4m8C with lysine 907 of IRE-1.

Figure 12A:
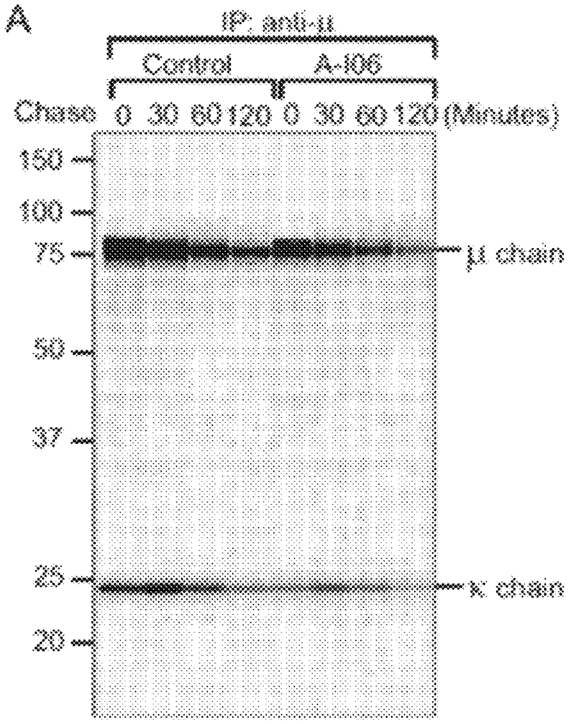
FIG. 12A: Wild-type B cells were stimulated with LPS for 2 days and subsequently treated with A-I06 (50 μM) for additional 1 day. Untreated control and A-I06-treated cells were radiolabeled for 15 min, chased for indicated time and lysed. Intracellular and extracellular IgM were immunoprecipitated from lysates using an anti-μ antibody. Immunoprecipitates were analyzed on a SDS-PAGE gel.
Figure 12B:
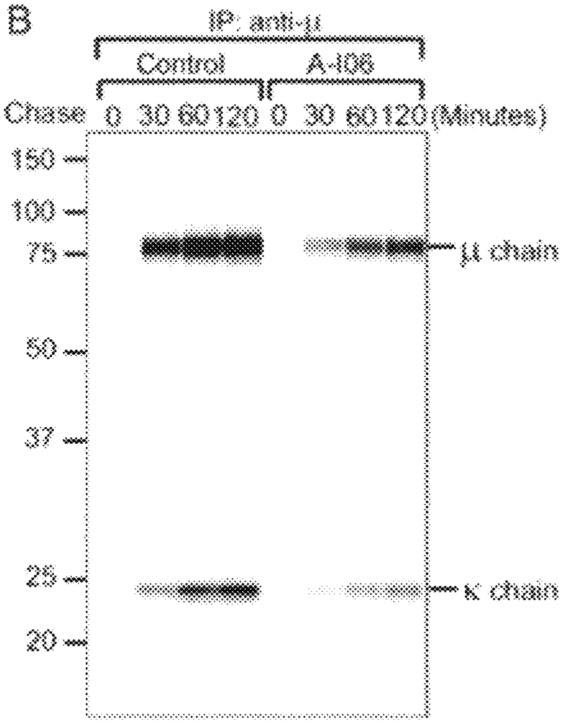
FIG. 12B: Wild-type B cells were stimulated with LPS for 2 days and subsequently treated with A-I06 (50 μM) for additional 1 day. Untreated control and A-I06-treated cells were radiolabeled for 15 min, chased for indicated time and lysed. Intracellular and extracellular IgM were immunoprecipitated from culture media using an anti-μ antibody. Immunoprecipitates were analyzed on a SDS-PAGE gel.
Figure 12C:
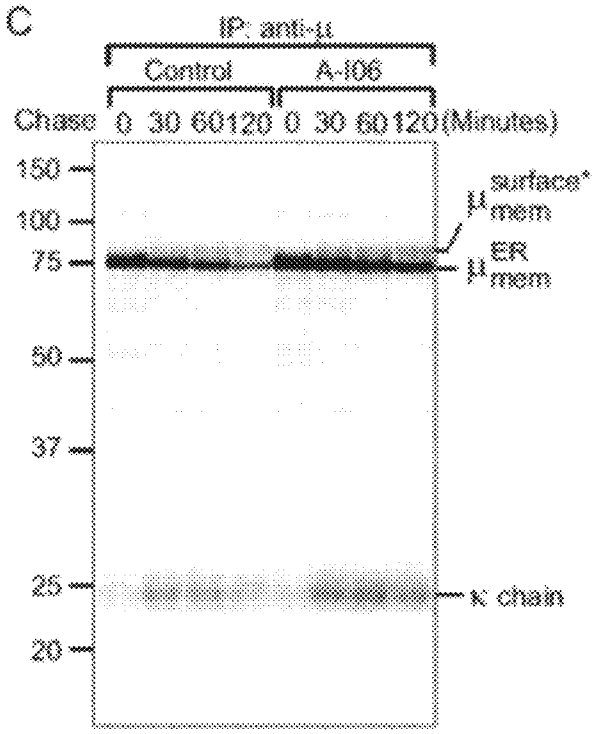
FIG. 12C: To reveal the effect of A-I06 on mIgM, B cells purified from μS−/− mouse spleens were stimulated with LPS for 2 days and subsequently treated with A-I06 (50 μM) for an additional day. Untreated control and A-I06-treated cells were radiolabeled for 15 min, chased for indicated time and lysed. Intracellular mIgM was immunoprecipitated from lysates using an anti-μ antibody. Immunoprecipitates were analyzed on a SDS-PAGE gel. Asterisk marks complex-type glycan modifications.
Figure 12D:
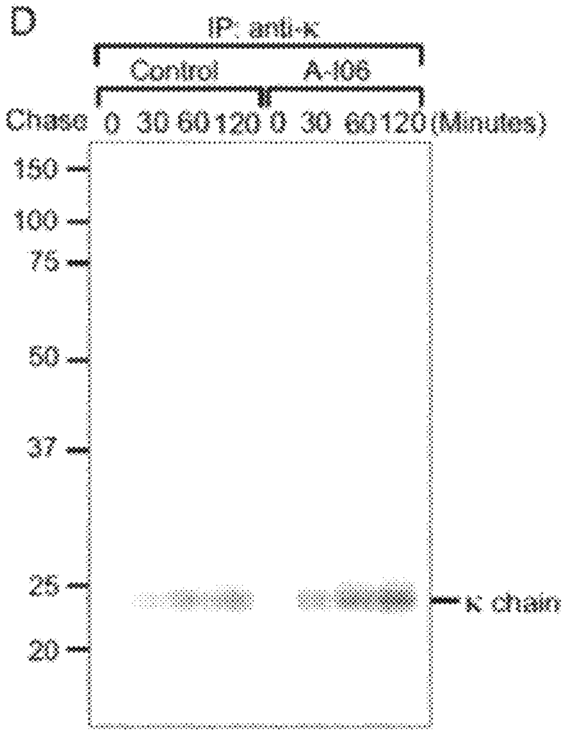
FIG. 12D: To reveal the effect of A-I06 on mIgM, B cells purified from μS−/− mouse spleens were stimulated with LPS for 2 days and subsequently treated with A-I06 (50 μM) for an additional day. Untreated control and A-I06-treated cells were radiolabeled for 15 min, chased for indicated time and lysed. Secreted free κ chains were immunoprecipitated from culture media using an anti-κ antibody. Immunoprecipitates were analyzed on a SDS-PAGE gel. Asterisk marks complex-type glycan modifications.
Figure 12E:
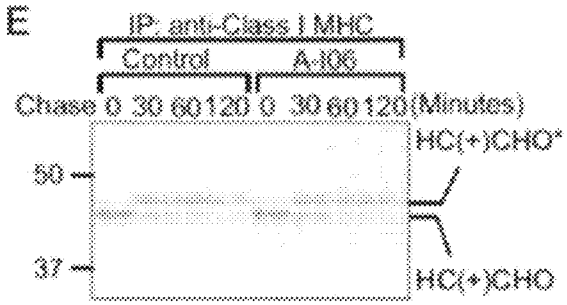
FIG. 12E: Similar wild-type B cell lysates as those in A were immunoprecipitated using an anti-class I MHC HC antibody and analyzed by SDS-PAGE. CHO and CHO* represent high mannose-type glycans and complex-type glycans, respectively.
Figure 12F:
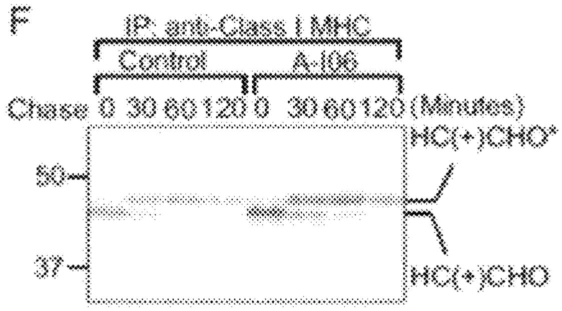
FIG. 12F: Similar μS−/− B cell lysates as those in C were immunoprecipitated using an anti-class I MHC HC antibody and analyzed by SDS-PAGE.

As genetic ablation of XBP-1 does not affect secretion of sIgM and surface display of mIgM in B cells (Hu et al., *Embo J,* 28(11), 1624-1636 (2009)), A-I06 was tested to determine if it exerted similar effects in B cells. To investigate the secretion of sIgM, B cells were stimulated with LPS for two days to allow the expression of sIgM, then the B cells were treated for additional 24 h with A-I06 to inhibit the expression of XBP-1, followed by pulse chase experiments and IgM immunoprecipitation from cell lysates and culture media using an anti-μ antibody. A-I06-treated B cells synthesize less sIgM, which can all be secreted into culture media (FIG. 12A-FIG. 12B). Because mIgM and sIgM differ only in a short transmembrane domain, it is difficult to resolve them in the SDS-PAGE gel. To investigate the surface display of mIgM, the characteristics of μS−/− B cells were used, which have been genetically manipulated to allow expression of only membrane-bound μ heavy chain (Boes et al., *J Immunol,* 160(10), 4776-4787 (1998)). In similar pulse chase experiments, the surface display of mIgM was found to not be affected by treatment with A-I06, as evidenced by successful acquisition of complex glycans on the μ heavy chain (FIG. 12C). The A-I06-treated μS−/− B cells also produced comparable amounts of membrane-bound μ chains and κ light chains, and the latter can be secreted into culture media (FIG. 12C-FIG. 12D). Wild-type and μS−/− B cells also synthesize and present class I MHC molecules to their surface when treated with A-I06 (FIG. 12E-FIG. 12F).

Downregulated Expression of XBP-1 Using A-I06 can Lead to Apoptosis of CLL Cells in Culture and in Mice.

Figure 13A:
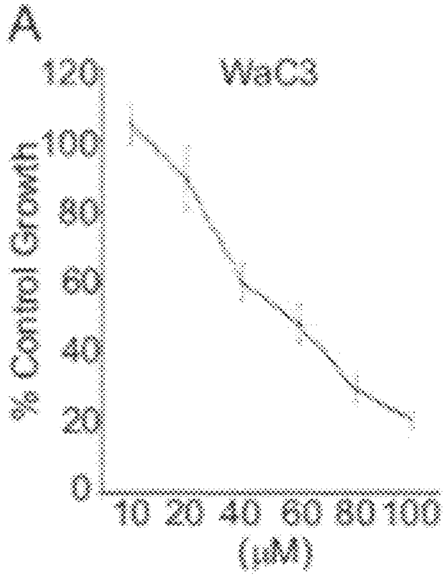
FIG. 13A displays the fifty percent growth inhibition concentration ($GI_{50}$) of A-I06. WaC3 cells were untreated or treated with 10 μM, 20 μM, 40 μM, 60 μM, 80 μM or 100 μM A-I06 for 48 h, and subjected to XTT assays.
Figure 13B:
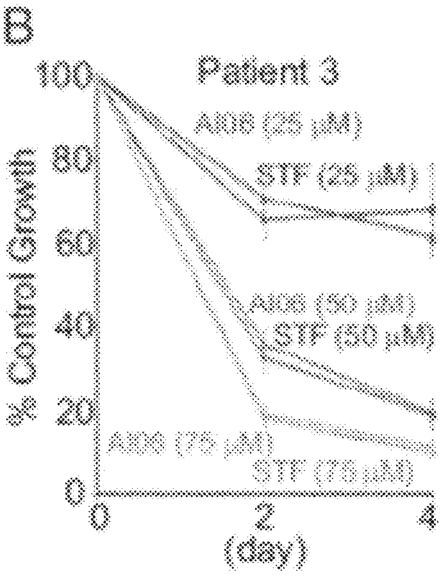
FIG. 13B displays the fifty percent growth inhibition concentration ($GI_{50}$) of A-I06. Primary human CLL cells (from patient 3) were untreated or treated with 25 μM, 50 μM or 75 μM STF-083010 or A-I06 for 2 or 4 days, and subjected to XTT assays.
Figure 14A:
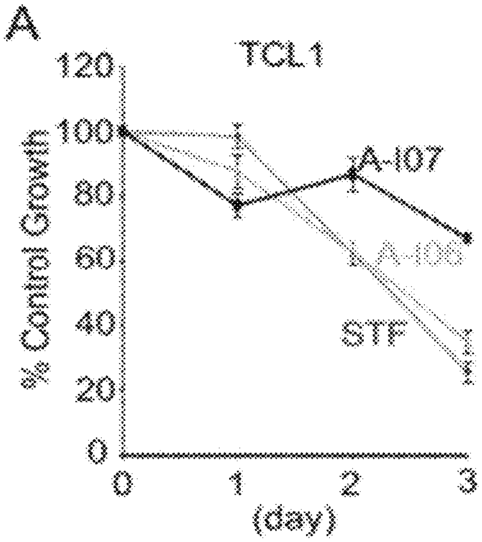
FIG. 14A displays the XTT assays at the end of each day for Eμ-TCL1 CLL cells, that were untreated or treated with STF-083010 (50 μM), A-I06 (50 μM), or A-I07 (50 μM) for a course of 3 or 4 days.
Figure 14B:
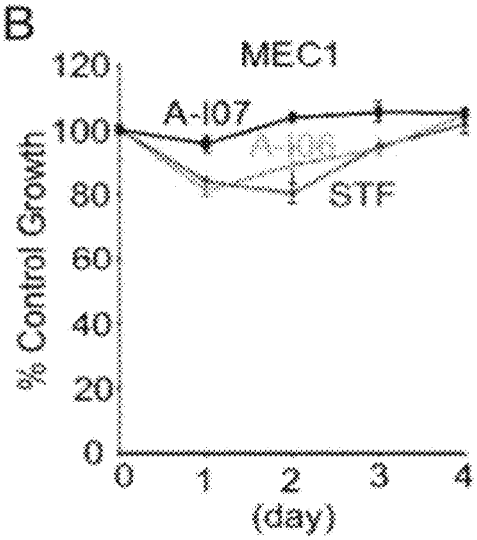
FIG. 14B displays the XTT assays at the end of each day for MEC1 cells that were untreated or treated with STF-083010 (50 μM), A-I06 (50 μM), or A-I07 (50 μM) for a course of 3 or 4 days.
Figure 14C:
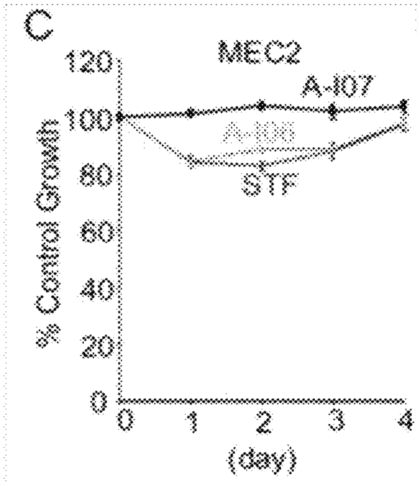
FIG. 14C displays the XTT assays at the end of each day for MEC2 cells that were untreated or treated with STF-083010 (50 μM), A-I06 (50 μM), or A-I07 (50 μM) for a course of 3 or 4 days.
Figure 14D:
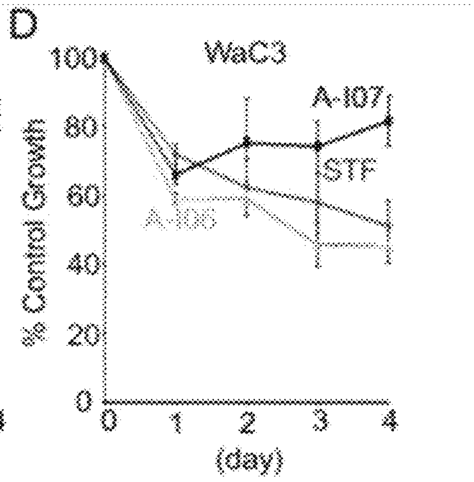
FIG. 14D displays the XTT assays at the end of each day for WaC3 cells that were untreated or treated with STF-083010 (50 μM), A-I06 (50 μM), or A-I07 (50 μM) for a course of 3 or 4 days.
Figure 14E:
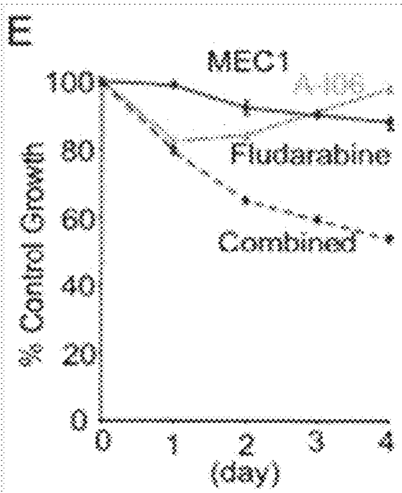
FIG. 14E: MEC1 cells that were untreated or treated with A-I06 (50 μM), fludarabine (30 μM), or the combination of both for a course of 4 days.
Figure 14F:
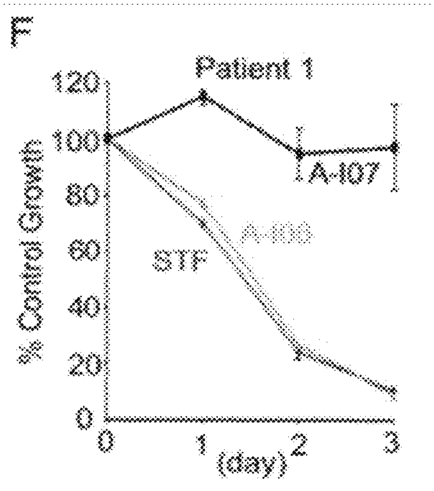
FIG. 14F: Primary human CLL cells isolated from patient 1 that were untreated or treated with STF-083010 (50 μM), A-I06 (50 μM), or A-I07 (50 μM) for a course of 3 days.
Figure 14G:
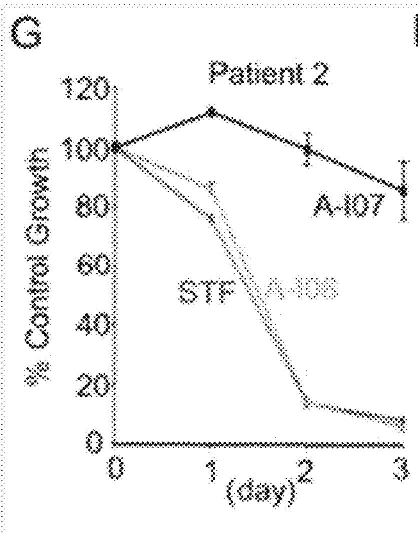
FIG. 14G: Primary human CLL cells isolated from patient 2 that were untreated or treated with STF-083010 (50 μM), A-I06 (50 μM), or A-I07 (50 μM) for a course of 3 days.
Figure 15:
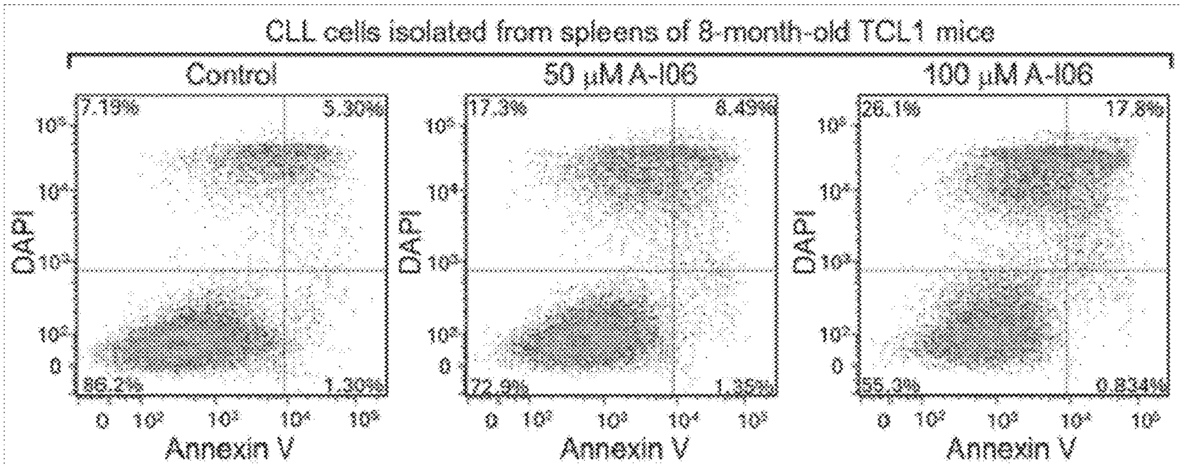
FIG. 15 displays the flow cytofluorometry results for purified CD5+/B220+ Eμ-TCL1 CLL cells were untreated or treated with A-I06 (50 μM or 100 μM) for 24 h and subsequently stained with Annexin V-PE and DAPI.

A $GI_{50}$ (50% growth inhibition concentration) of ~50 μM was determined for human WaC3 CLL cells treated with A-I06 (FIG. 13A). At 50 μM concentration, A-I06 and STF-083010 exert similar growth inhibitory effects in human CLL cells (FIG. 13B). When Eμ-TCL1 CLL cells were treated with STF-083010 or A-I06, a ~70% growth inhibition was observed after 3 days (FIG. 14A). Increased apoptosis was detected in Eμ-TCL1 CLL cells exposed to 50 μM or 100 μM A-I06 for 24 h (FIG. 15). Next, human MEC1, MEC2 and WaC3 CLL cell lines were treated with these compounds. MEC1 and MEC2 cells respond to STF-083010 or A-I06 with ~20% growth inhibition in the first 48 h; however, these cells eventually overcome the inhibitory effect of each compound (FIG. 14B-FIG. 14C). In contrast, WaC3 cells respond to treatments with STF-083010 or A-I06 with gradually decreased growth (FIG. 14D). This can be explained by the fact that WaC3 cells have already acquired a constitutively phosphorylated IRE-1 (FIG. 4D). MEC1 cells were further treated with A-I06 in combination with fludarabine, an FDA-approved purine analog for clinical CLL treatments. A-I06 synergizes with fludarabine to elicit a better growth inhibition effect on MEC1 cells (FIG. 14E). Because primary human CLL cells expressed activated IRE-1 (FIG. 4D and FIG. 16A), the cells were treated with STF-083010, A-I06 or A-I07. STF-083010 and A-I06 exert a significant cytotoxic effect on primary human CLL cells by inducing apoptosis (FIG. 14F-FIG. 14G and FIG. 16B-FIG. 16J). Geldanamycin, herbimycin A, and chlorambucil are also useful with STF-083010, A-I06 or A-I07.

Figure 14H:
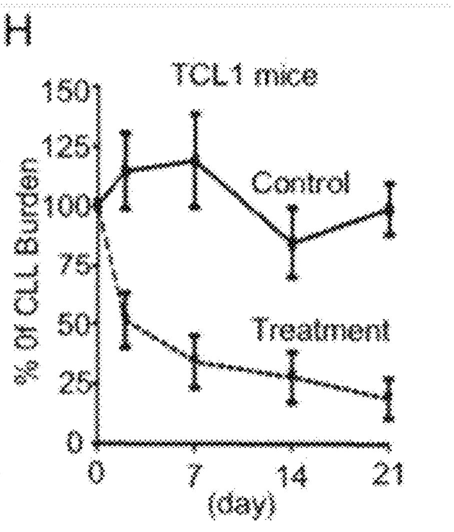
FIG. 14H: Eμ-TCL1 mice with high percentage of CLL cells in the peripheral blood were identified and injected intraperitoneally with vehicle (n=9) or A-I06 (60 mg/kg) (n=5) on Day 0, Day 1, Day 12 and Day 13. The percentage of CLL cells in PBMCs for each mouse was determined by flow cytofluorometry on Day 2, Day 7, Day 14 and Day 21, and compared with its CLL burden data on Day 0 (100%).
Figure 14I:
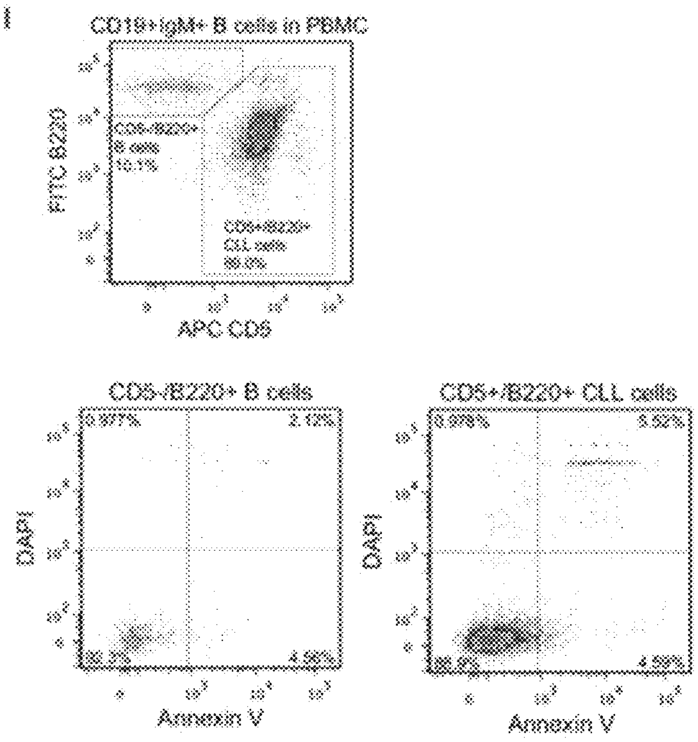
FIG. 14I: PBMCs isolated from Eμ-TCL1 CLL mice injected with vehicle for 24 h were stained with CD19-APC-Cy7, IgM-Alexa568, CD5-APC, B220-Alexa488, Annexin V-PE and DAPI. CD5−/B220+ B cells and CD5+/B220+ CLL cells were analyzed on gated CD19+/IgM+ B cell populations (left panel). CD5−/B220+ B cells and CD5+/B220+ CLL cells were further gated, and analyzed for the presence of Annexin V+ and DAPI+ populations (middle and right panels).
Figure 14J:
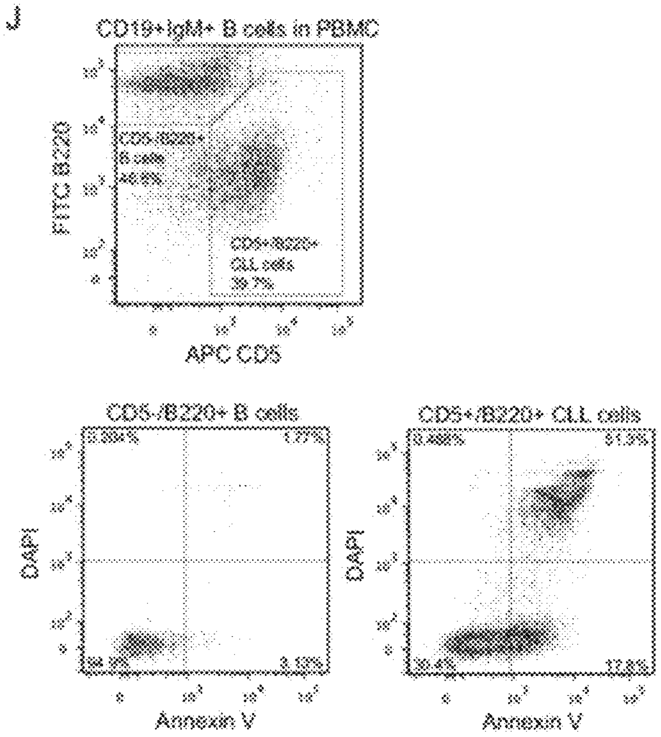
FIG. 14J: PBMCs isolated from A-I06-injected Eμ-TCL1 CLL mice were stained with CD19-APC-Cy7, IgM-Alexa568, CD5-APC, B220-Alexa488, Annexin V-PE and DAPI. CD5-/B220+ B cells and CD5+/B220+ CLL cells were analyzed on gated CD19+/IgM+ B cell populations (left panel). CD5−/B220+ B cells and CD5+/B220+ CLL cells were further gated, and analyzed for the presence of Annexin V+ and DAPI+ populations (middle and right panels).

To test whether the IRE-1 inhibitor can inhibit CLL cell growth in mice, we injected CLL-bearing Eμ-TCL1 mice with A-I06, and observed reduced CLL burden during the course of treatment (FIG. 14H). The reduction in CLL burden can be explained by the increase of Annexin V+ apoptotic CD5+/B220+ CLL cells in A-I06-treated Eμ-TCL1 mice (FIG. 14I-FIG. 14J, right panels). Treatment with A-I06 does not induce CD5−/B220+ B cells to undergo apoptosis in Eμ-TCL1 CLL mice (FIG. 14I-FIG. 14J, middle panels).

Discussion

Figure 16A:
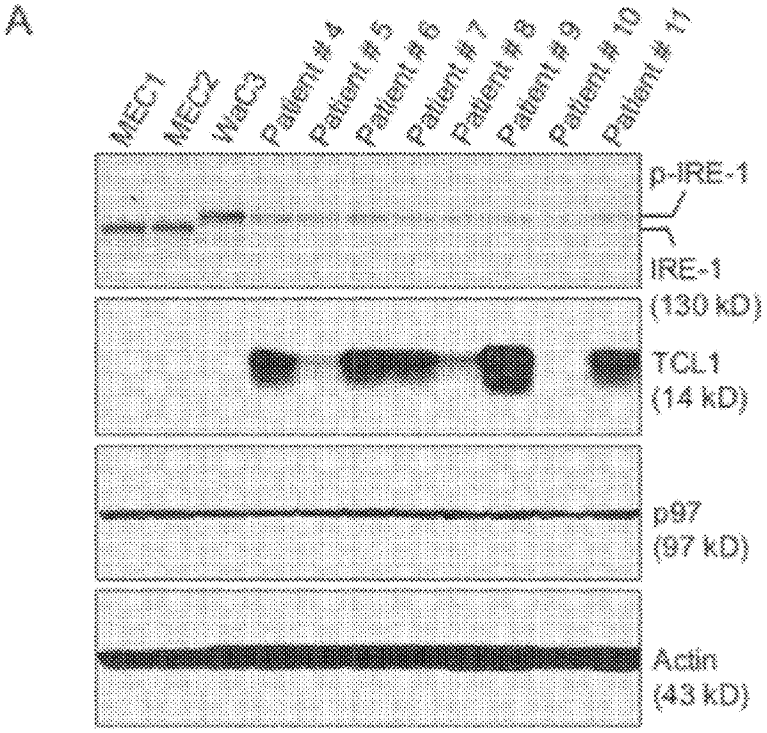
FIG. 16A: MEC1, MEC2, WaC3 and primary human CLL cells from eight clinical patients (patients 4-11) were analyzed by immunoblots for the expression of indicated proteins. Results are representative of three independent experiments.
Figure 16B:
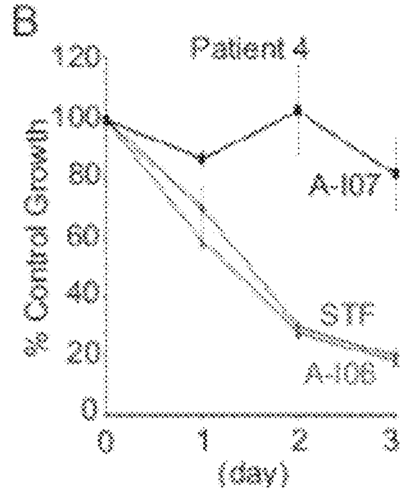
FIG. 16B: Primary human CLL cells isolated from patient 4 were untreated or treated with STF-083010 (50 μM), A-I06 (50 μM), or A-I07 (50 μM) for a course of 3 days, and subjected to XTT assays.
Figure 16C:
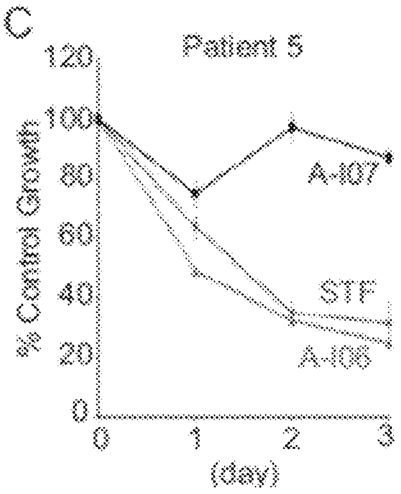
FIG. 16C: Primary human CLL cells isolated from patient 5 were untreated or treated with STF-083010 (50 μM), A-I06 (50 μM), or A-I07 (50 μM) for a course of 3 days, and subjected to XTT assays.
Figure 16D:
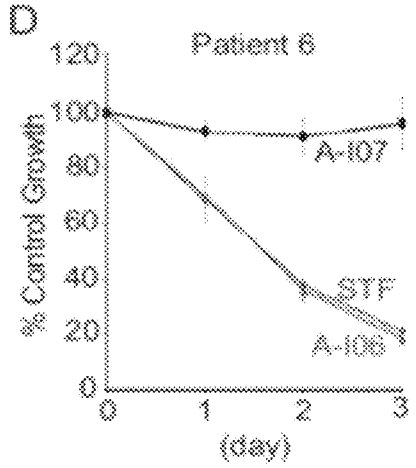
FIG. 16D: Primary human CLL cells isolated from patient 6 were untreated or treated with STF-083010 (50 μM), A-I06 (50 μM), or A-I07 (50 μM) for a course of 3 days, and subjected to XTT assays.
Figure 16E:
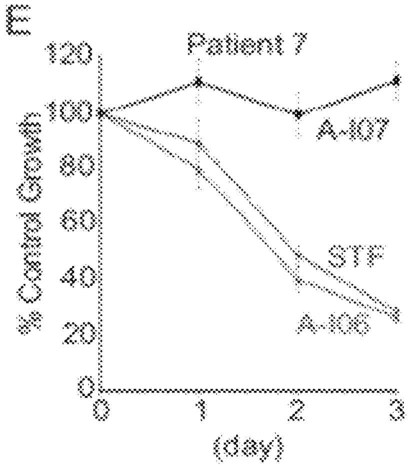
FIG. 16E: Primary human CLL cells isolated from patient 7 were untreated or treated with STF-083010 (50 μM), A-I06 (50 μM), or A-I07 (50 μM) for a course of 3 days, and subjected to XTT assays.
Figure 16F:
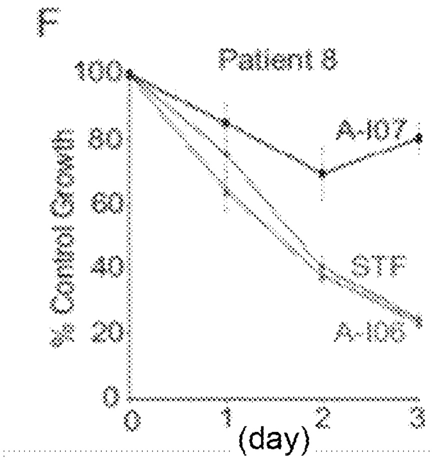
FIG. 16F: Primary human CLL cells isolated from patient 8 were untreated or treated with STF-083010 (50 μM), A-I06 (50 μM), or A-I07 (50 μM) for a course of 3 days, and subjected to XTT assays.
Figure 16G:
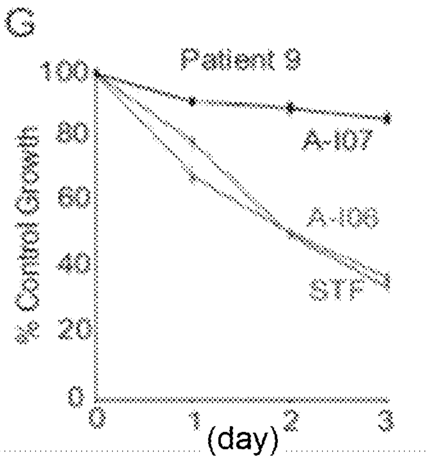
FIG. 16G: Primary human CLL cells isolated from patient 9 were untreated or treated with STF-083010 (50 μM), A-I06 (50 μM), or A-I07 (50 μM) for a course of 3 days, and subjected to XTT assays.
Figures 16H, 16I:
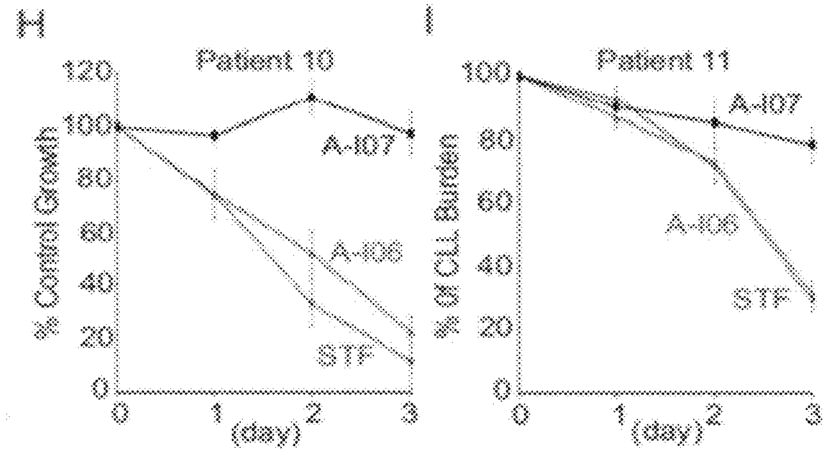
FIG. 16H: Primary human CLL cells isolated from patient 10 were untreated or treated with STF-083010 (50 μM), A-I06 (50 μM), or A-I07 (50 μM) for a course of 3 days, and subjected to XTT assays.
FIG. 16I: Primary human CLL cells isolated from patient 11 were untreated or treated with STF-083010 (50 μM), A-I06 (50 μM), or A-I07 (50 μM) for a course of 3 days, and subjected to XTT assays.
Figure 16J:
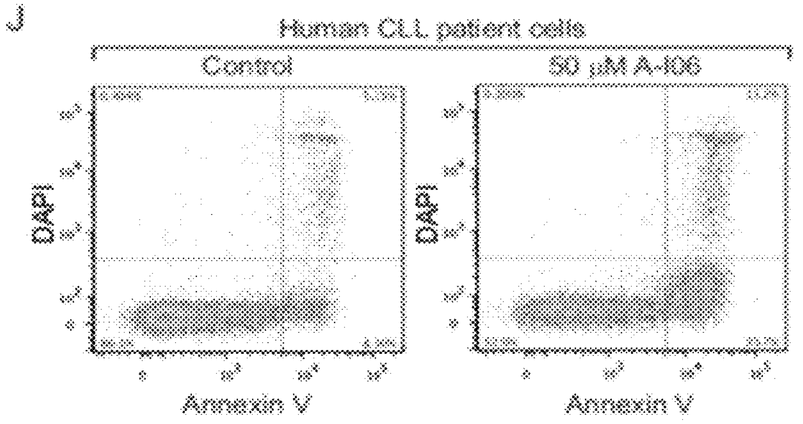
FIG. 16J: Primary human patient CLL cells were untreated or treated with A-I06 (50 μM) for 48 h, subsequently stained with Annexin V-PE and DAPI, and analyzed by flow cytofluorometry for the presence of Annexin V+ and DAPI+ populations.
Figure 17:
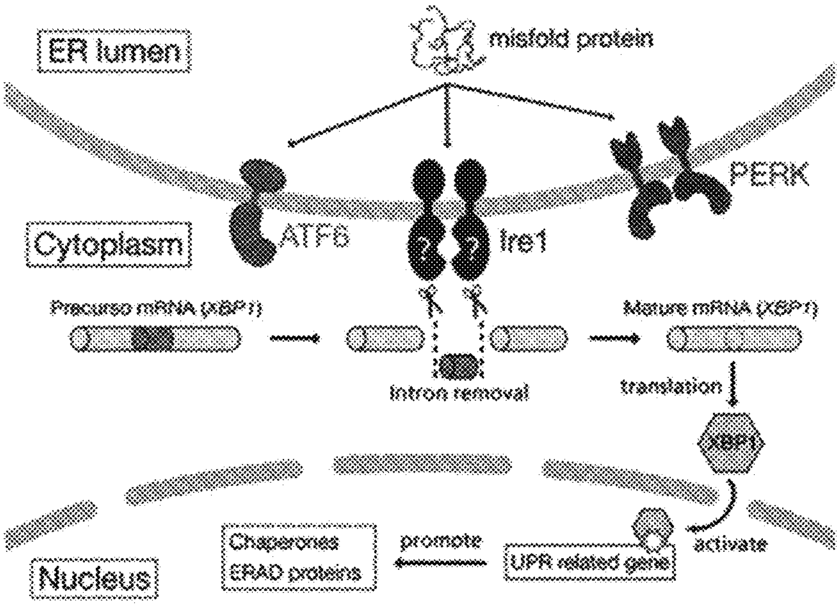
FIG. 17 displays an XBP-1 cell cycle.

TCL1 is an oncoprotein that can contribute to the occurrence of T cell prolymphocytic leukemia, as a result of chromosomal translocations and inversions at 14q31.2 (Virgilio et al., *Proc Nat Acad Sci USA,* 91(26), 12530-12534 (1994)). Although such a chromosomal defect is not found in CLL, TCL1 expresses in ~90% human CLL patients (Herling et al., *Leukemia,* 20(2), 280-285 (2006)) (FIG. 4D and FIG. 16A). TCL1 overexpression alone can drive the formation of mouse CLL (Bichi et al., *Proc Nat Acad Sci USA,* 99(10), 6955-6960 (2002)). Abnormal epigenetic regulations may account for abnormal expression of TCL1 (Pekarsky et al., *Cancer Res,* 66(24), 11590-11593 (2006)). The oncogenic effect of TCL1 may be a result of AKT activation. TCL1 can physically bind to AKT, enhance AKT's kinase activity and promote transport of AKT to the nucleus, contributing to cell survival and rapid proliferation (Laine et al., *Mol Cell,* 6(2), 395-407 (2000); Pekarsky et al., *Proc Natl Acad Sci USA,* 97(7), 3028-3033 (2000)). Data now reveals that TCL1 can contribute to activation of the ER stress response at the transcriptional level (FIG. 4B and FIG. 6A-FIG. 6I), possibly through its association with the transcription factor, XBP-1 (FIG. 4C). The dysregulated expression of XBP-1 may disrupt normal crosstalk between transcription factors (FIG. 7A-FIG. 7B), and promote constitutively active BCR signal transduction (FIG. 9A). All of these data help to explain why a TCL1-overexpressed B cell can turn into CLL.

The functional roles of the ER stress response proteins in CLL have been largely overlooked because CLL cells do not develop a prominent ER structure like the plasma cell cancer, multiple myeloma. However, the ER stress response was found to play a role in the growth of mouse and human CLL. Because CLL cells are genetically heterogeneous, they are difficult to treat. However, they may all share the ER stress response as their survival mechanism, which can be targeted for therapy. Geldanamycin and herbimycin A were used as inhibitors for GRP94 to induce apoptosis in CLL cells, and synergized with fludarabine and chlorambucil in killing CLL cells (Jones et al., *Blood,* 103(5), 1855-1861 (2004)). Downregulation of BiP by siRNA can also induce apoptosis in CLL (Rosati et al., *Blood,* 116(15), 2713-2723 (2010)). Although there is no precedent study on the expression of Derlin proteins in CLL cells (FIG. 4B and FIG. 4D), Derlin-1 is overexpressed in many solid malignancies and is a potential molecular target for therapeutic intervention (Ran et al., *Clin Cancer Res,* 14(20), 6538-6545 (2008)). The results suggest that the IRE-1/XBP-1 pathway can be a target for CLL treatment (FIG. 14A-J). The A-I06 inhibitor can induce apoptosis of mouse and human CLL cells in vitro (FIG. 15 and FIG. 16J) and selectively target CD5+ CLL cells in Eμ-TCL1 mice (FIG. 14H-FIG. 14J).

TCL1 can drive malignant progression of CLL via dysregulated expression of transcription factors and AID (FIG. 7B). IRF4 alone can transform cells in vitro (Iida et al., *Nature genetics,* 17(2), 226-230 (1997)). Although IRF4 is expressed in CLL, its contribution in patient survival outcome is unclear. Recent studies suggest a genetic variant of IRF4 common in CLL patients may be associated with malignant progression of CLL (Di Bernardo et al., *Nature genetics,* 40(10), 1204-1210 (2008); Allan et al., *Leukemia,*

24(4), 877-881 (2010)). IRF4 can upregulate the expression of Blimp-1 by binding to the promoter region and fourth intron of the Blimp-1 gene, and can directly regulate the expression of AID (Klein et al., *Nat Immunol,* 7(7), 773-782 (2006); Sciammas et al., *Immunity,* 25(2), 225-236 (2006); Shaffer et al., *Nature,* 454(7201), 226-231 (2008)). AID can perform somatic hypermutation and class switch recombination in immunoglobulin genes. Such processes, if not confined to immunoglobulin genes, can contribute to the formation of cancer (Okazaki et al., *J Exp Med,* 197(9), 1173-1181 (2003)). Increased expression of AID can be found in malignant CLL cases (Albesiano et al., *Blood,* 102(9), 3333-3339 (2003); McCarthy et al., *Blood,* 101(12), 4903-4908 (2003)).

TCL1 expression can be associated with active BCR signal transduction (Herling et al., *Blood,* 114(21), 4675-4686 (2009); Holler et al., *Blood,* 113(12), 2791-2794 (2009); Suljagic et al., *Blood,* 116(23), 4894-4905 (2010)), which allows malignant CLL cells to sustain robust proliferation (Zenz et al., *Nat Rev Cancer,* 10(1), 37-50 (2010)). Targeting the BCR signaling pathway has been proposed as a therapeutic intervention for CLL (Pleyer et al., *Nat Rev Clin Oncol,* 6(7), 405-418 (2009)). In normal B cells, a functional BCR is composed of a mIgM and its associated disulfide-linked Igα/Igβ heterodimer. Both Igα and Igβ contain the immunoreceptor tyrosine-based activation motifs, whose phosphorylation leads to a series of downstream signaling cascades. CLL cells employ similar BCR signaling pathways (Zenz et al., *Nat Rev Cancer,* 10(1), 37-50 (2010)). TCL1 overexpression can allow CLL cells to express a distinct BCR. Increased expression of mIgM and altered glycosylated Igα and Igβ (FIGS. 9B and E) may altogether contribute to the constitutively active BCR signal transduction in malignant CLL cells (FIG. 9A).

Clinically, about 90% of CLL cases express TCL1 (Herling M et al., *Leukemia,* 20(2), 280-285 (2006)). When the expression of TCL1 in CLL cells from 10 human patients was examine, it was found that TCL1 was not expressed in the CLL cells from patient 10 (FIG. 4D and FIG. 16A). In addition, TCL1 is also not expressed in MEC1, MEC2, and WaC3 cells, which exhibit the ER stress response (FIG. 4D). While the role of TCL1 in activation of the ER stress response has been established using Eμ-TCL1 mice, the robust ER stress response found also in TCL1-null human CLL cells suggests that such activation can be achieved via other mechanisms. Interestingly, MEC1, MEC2, and WaC3 cells are all EBV-positive (Stacchini A et al., *Leuk Res,* 23(2), 127-136 (1999); Wendel-Hansen V et al., *Leukemia,* 8(3), 476-484 (1994)). EBV can activate the ER stress response in B cells (Lee D Y, Sugden B; *Blood,* 111(4), 2280-2289 (2008)).

Example 2

Chemical Synthesis General Notes

Unless stated otherwise, reactions were performed in flame-dried glassware under a positive pressure of argon or nitrogen gas using dry solvents. Commercial grade reagents and solvents were used without further purification except where noted. Diethyl ether, toluene, dimethylformamide dichloromethane, and tetrahydrofuran were purified by a Glass Contour column-based solvent purification system. Other anhydrous solvents were purchased directly from chemical suppliers. Thin-layer chromatography (TLC) was performed using silica gel 60 F254 pre-coated plates (0.25 mm). Flash chromatography was performed using silica gel (60 μm particle size). The purity of all compounds was judged by TLC analysis (single spot/two solvent systems) using a UV lamp, CAM (ceric ammonium molybdate), ninhydrin, or basic $KMnO_4$ stain(s) for detection purposes. NMR spectra were recorded on a 400 MHz spectrometer. $^1H$ and $^{13}C$ NMR chemical shifts are reported as 6 using residual solvent as an internal standard. Analytical (4×150 mm column, 1 mL/min flow rate) RP-HPLC was performed on a $C_{18}$ column with acetonitrile/water (0.1% formic acid) as eluent.

Synthesis of B-B07 (methyl 3-(5-formyl-6-hydroxynaphthalen-2-yl)benzoate)

A mixture of 6-bromo-2-hydroxy-1-naphthaldehyde (50 mg, 200 μmol), (3-methoxycarbonyl)phenylboronic acid (45 mg, 250 μmol), and sodium carbonate (84 mg, 804 μmol) in 2 mL of 1:1 DMF:$H_2O$ was treated with tetrakis(triphenylphosphine)palladium(0) (12 mg, 10 μmol) and stirred at 100° C. for 30 min. The reaction was cooled to room temperature, diluted with sat. aq. $NH_4Cl$, and extracted with $CHCl_3$. The organic layers were dried over $Na_2SO_4$, concentrated, and the crude residue purified by flash chromatography over silica gel (40% EtOAc/hexanes eluent) to give B-B07 as a pale yellow solid (12 mg, 19%). $^1H$ NMR (400 MHz, $CDCl_3$) δ 13.17 (s, 1H), 10.85 (s, 1H), 8.44 (d, J=8.8 Hz, 1H), 8.38 (t, J=1.6 Hz, 1H), 8.07 (s, 1H), 8.05 (d, J=4.6 Hz, 2H), 7.93-7.87 (m, 2H), 7.57 (t, J=8.0 Hz, 1H), 7.20 (d, J=9.1 Hz, 1H), 3.98 (s, 3H); $^{13}C$ NMR (101 MHz, $CDCl_3$) δ 193.4, 167.1, 165.2, 140.5, 139.5, 136.3, 132.4, 131.6, 131.0, 129.3, 128.8, 128.5, 128.3, 128.3, 127.6, 120.0, 119.6, 111.4, 52.5; HRMS (ESI-TOF) (m/z) $[M+H]^+$ calcd for $C_{19}HO_4$ 307.09703, found 307.09696.

Synthesis of B-H10 (allyl (2-(8-formyl-7-hydroxy-2-oxo-2H-chromen-4-yl)ethyl)carbamate)

A solution of β-alanine (3.00 g, 33.7 mmol) in 50 mL of dioxane:$H_2O$ (1:1) was treated with $Na_2CO_3$ (7.15 g, 33.7 mmol) and allyloxychloroformate (3.58 mL, 67.4 mmol). The reaction was stirred for 2 days at room temperature, quenched with 1 M aq. KHSO4, and extracted with EtOAc. The combined organic layers were dried over $Na_2SO_4$ and evaporated to afford (N-Alloc)-β-alanine as a white solid (4.70 g, 97%).

A solution of (N-Alloc)-β-alanine (4.13 g, 23.87 mmol) in 100 mL of DCM at 0° C. was treated with 2,2-Dimethyl-1,3-dioxane-4,6-dione (4.47 g, 31.03 mmol), 4-dimethylaminopyridine (2.92 g, 23.9 mmol), and diisopropylcarbodiimide (3.70 mL, 23.9 mmol). The reaction was stirred from 0° C. to room temperature over 4 h, then washed with 10% aq. $KHSO_4$ followed by brine. The organic layer was dried over $Na_2SO_4$ and concentrated. The resulting colorless liquid was dissolved in a 10:1 methanol:toluene mixture and stirred at reflux for 15 h. After cooling, the reaction was concentrated under reduced pressure. Purification by flash column chromatography over silica gel (25%-60% EtOAc/hexanes eluent) afforded methyl 5-(((allyloxy)carbonyl)amino)-3-oxopentanoate as a colorless oil (5.02 g, 91%). $^1H$ NMR (400 MHz, $CDCl_3$) δ 5.97-5.82 (m, 1H), 5.37-5.12 (m, 3H), 4.53 (d, J=5.6 Hz, 2H), 3.73 (s, 3H), 3.50-3.37 (m, 4H), 2.80 (t, J=5.7 Hz, 2H); $^{13}C$ NMR (101 MHz, $CDCl_3$) δ 202.2, 167.3, 156.2, 132.8, 132.8, 117.6, 117.5, 65.4, 52.4, 52.4, 48.9, 42.8, 35.3; HRMS (ESI-TOF) (m/z) $[M+H]^+$ calcd for $C_{10}H_{16}NO_5$ 230.10285, found 230.10297.

A solution of 5-(((allyloxy)carbonyl)amino)-3-oxopentanoate (2.31 g, 10.06 mmol) in 50 mL of methanesulfonic acid at 0° C. was treated with resorcinol (1.11 g, 10.06 mmol) and stirred for 3.5 h. The mixture was poured into ice cold water and the resulting yellow mixture was filtered. The filtrate was extracted with EtOAc and combined with the solids. The combined organic layer was concentrated and purified by flash chromatography over silica gel (0-20% MeOH/$CHCl_3$ eluent) to afford allyl (2-(7-hydroxy-2-oxo-2H-chromen-4-yl)ethyl)carbamate as a yellow solid (2.56 g, 88%). $^1$H NMR (400 MHz, DMSO-$d_6$) δ 10.55 (s, 1H), 7.68 (d, J=8.8 Hz, 1H), 7.40 (m, 1H), 6.80 (dd, J=8.7, 2.3 Hz, 1H), 6.71 (d, J=2.3 Hz, 1H), 6.07 (s, 1H), 5.99-5.78 (m, 1H), 5.24 (m, 1H), 5.15 (m, 1H), 4.45 (m, 2H), 3.29 (m, 2H), 2.87 (t, J=6.7 Hz, 2H); $^{13}$C NMR (101 MHz, DMSO-$d_6$) δ 161.1, 160.3, 156.0, 155.2, 154.2, 133.8, 133.7, 126.3, 116.9, 113.0, 111.3, 110.5, 110.4, 102.5, 102.4, 64.3, 31.5, 23.4; HRMS (ESI-TOF) (m/z) $[M+H]^+$ calcd for $C_{16}H_{16}NO_5$ 302.10285, found 302.10305.

A solution of allyl (2-(7-hydroxy-2-oxo-2H-chromen-4-yl)ethyl)carbamate (0.37 g, 1.28 mmol) in 15 mL of glacial acetic acid was treated with hexamethylenetetramine (0.27 g, 1.92 mmol) and stirred at room temperature for 5.5 h. The reaction mixture was concentrated and the resulting slurry was dissolved in a 1:1 mixture of 1 M aq. HCl and EtOAc and stirred at 60° C. for 45 min. The organic layer was separated and the aqueous layer was extracted with EtOAc. The organic layers were concentrated and purified by flash column chromatography over silica gel (35%-100% EtOAc/hexanes eluent) to give B-H10 (allyl (2-(8-formyl-7-hydroxy-2-oxo-2H-chromen-4-yl)ethyl)carbamate) as a colorless oil (32 mg, 10%). $^1$H NMR (400 MHz, $CDCl_3$) δ 12.24 (s, 1H), 10.60 (s, 1H), 7.92 (d, J=9.1 Hz, 1H), 6.93 (d, J=9.0 Hz, 1H), 6.19 (s, 1H), 5.90 (m, 1H), 5.39-5.15 (m, 2H), 5.03 (bs, 1H), 4.58 (m, 2H), 3.49 (m, 2H), 2.99 (t, J=7.2 Hz, 2H); $^{13}$C NMR (101 MHz, $CDCl_3$) δ 193.5, 193.4, 165.5, 159.2, 156.6, 156.5, 153.4, 133.1, 132.6, 118.2, 114.8, 112.2, 112.1, 111.1, 109.0, 66.0, 40.1, 32.8; HRMS (ESI-TOF) (m/z) $[M+H]^+$ calcd for $C_{16}H_{16}NO_6$ 318.09777, found 318.09746.

Synthesis of B-H09 (allyl 7-formyl-8-hydroxy-5-oxo-4,5-dihydro-1H-chromeno[3,4-c]pyridine-3 (2H)-carboxylate)

A solution of the allyl (2-(7-hydroxy-2-oxo-2H-chromen-4-yl)ethyl)carbamate intermediate above (0.50 g, 1.73 mmol) in 50 mL of acetonitrile at room temperature was treated with pyridine (0.07 mL, 0.86 mmol) and acetic anhydride (0.82 mL, 8.64 mmol). After stirring for 6 h, the reaction mixture was concentrated and partitioned between EtOAc and brine. The organic layer was dried over $Na_2SO_4$ and concentrated. The resulting residue was dissolved in 4 mL of trifluoroacetic acid, treated with hexamethylenetetramine (0.61 g, 4.32 mmol), and refluxed for 20 h. The reaction mixture was concentrated under reduced pressure and the resulting mixture was dissolved in a 1:1 mixture of EtOAc and 1 M aq. HCl and stirred at 60° C. for 1.5 h. The organic layer was separated and the aqueous layer was extracted with EtOAc. The organic layers were concentrated and purified by flash column chromatography over silica gel (20%-35% EtOAc/hexanes eluent) to give B-H09 (allyl 7-formyl-8-hydroxy-5-oxo-4,5-dihydro-1H-chromeno[3,4-c]pyridine-3(2H)-carboxylate) as a yellow solid (235 mg, 41%). $^1$H NMR (400 MHz, $CDCl_3$) δ 12.15 (s, 1H), 10.61 (s, 1H), 7.68 (d, J=8.4 Hz, 1H), 6.92 (d, J=9.0 Hz, 1H), 5.94 (m, 1H), 5.33 (m, 1H), 5.24 (m, 1H), 4.64 (d, J=5.7 Hz, 2H), 4.47 (m, 2H), 3.81 (t, J=5.8 Hz, 2H), 2.86 (m, 2H); $^{13}$C NMR (101 MHz, $CDCl_3$) δ 193.3, 164.9, 158.4, 155.2, 154.7, 146.4, 132.7, 131.8, 118.3, 117.2, 114.8, 111.2, 108.7, 66.7, 41.9, 39.2, 24.9; HRMS (ESI-TOF) (m/z) $[M+H]^+$ calcd for $C_{17}H_{16}NO_6$ 330.09721, found 330.09624.

Synthesis of B-I08 (allyl 7-formyl-8-hydroxy-5-oxo-4,5-dihydro-1H-chromeno[3,4-c]pyridine-3 (2H)-carboxylate)

A solution of B-H09 in (150 mg, 455 μmol) in 4 mL of benzene was treated with 1,3-propanediol (99 μL, 1.4 mmol) and p-toluenesulfonic acid monohydrate (4.3 mg, 23 μmol) and stirred at reflux (85° C.) for 2 h. The reaction was quenched with 2 drops of triethylamine, diluted with EtOAc, and washed with brine. The organic layer was dried over $Na_2SO_4$ and concentrated. Purification by flash column chromatography over silica gel (30%-50% EtOAc/hexanes eluent) afforded B-I08 (allyl 7-formyl-8-hydroxy-5-oxo-4,5-dihydro-1H-chromeno[3,4-c]pyridine-3(2H)-carboxylate) as a yellow solid (157 mg, 89%). $^1$H NMR (400 MHz, $CDCl_3$) δ 8.82 (s, 1H), 7.36 (d, J=8.2 Hz, 1H), 6.79 (d, J=8.8 Hz, 1H), 6.28 (s, 1H), 5.91 (m, 1H), 5.30 (m, 1H), 5.20 (m, 1H), 4.61 (d, J=5.6 Hz, 2H), 4.39 (s, 2H), 4.28 (dd, J=11.6, J=4.6 Hz, 2H), 4.09 (m, 2H), 3.74 (t, J=5.8 Hz, 2H), 2.79 (m, 2H), 2.26 (m, 1H), 1.53 (m, 1H); $^{13}$C NMR (101 MHz, $CDCl_3$) δ 159.5, 159.3, 155.2, 150.5, 146.6, 132.8, 125.3, 118.0, 116.3, 114.5, 111.8, 109.9, 98.1, 67.9, 66.5, 41.8, 39.3, 25.8, 24.7; HRMS (ESI-TOF) (m/z) $[M+H]^+$ calcd for $C_{20}H_{22}NO_7$ 388.13908, found 388.13810.

Synthesis of B-I09 (7-(1,3-dioxan-2-yl)-8-hydroxy-3,4-dihydro-1H-chromeno[3,4-c]pyridin-5(2H)-one)

A solution of B-I08 (70 mg, 180 μmol) in 4 mL of DCM at room temperature was treated with phenylsilane (67 mg, 540 μmol) and tetrakis(triphenylphosphine)palladium(0) (10 mg, 9.0 μmol) and stirred at room temperature 25 min. The reaction was concentrated and the residue purified by flash chromatography over silica gel (0%-10% MeOH/$CHCl_3$ eluent) to afford B-I09 (7-(1,3-dioxan-2-yl)-8-hydroxy-3,4-dihydro-1H-chromeno[3,4-c]pyridin-5(2H)-one) as a yellow solid (54 mg, 98%). $^1$H NMR (400 MHz, $CDCl_3$) δ 7.35 (d, J=8.8 Hz, 1H), 6.78 (d, J=8.8 Hz, 1H), 6.28 (s, 1H), 4.24 (m, 2H), 4.06 (m, 2H), 3.75 (m, 2H), 3.11 (t, J=5.8 Hz, 2H), 2.70 (m, 2H), 2.36-2.11 (m, 1H), 1.92 (bs, 1H), 1.50 (m, 1H); $^{13}$C NMR (101 MHz, $CDCl_3$) δ 160.2, 159.0, 150.6, 146.8, 135.0, 125.1, 119.0, 114.3, 112.5, 109.9, 98.3, 68.0, 43.4, 42.0, 25.9, 25.3; HRMS (ESI-TOF) (m/z) $[M+H]^+$ calcd for $C_{16}H_{18}NO_5$ 304.11795, found 304.11782.

Synthesis of Biotinylated Derivatives B-I06 and B-I07

A solution of B-I09 (46 mg, 150 μmol) in 3 mL of DCM:MeCN (1:1) was treated with triethylamine (43 μL, 300 μmol) and biotinamidohexanoyl-6-aminohexanoic acid N-hydroxysuccinimide ester (76 mg, 170 μmol) and the reaction was stirred at room temperature for 20 h. The mixture was concentrated under reduced pressure and purified by flash column chromatography over silica gel (30%-50% EtOAc/hexanes eluent) to give N-(6-(7-(1,3-dioxan-2-yl)-8-hydroxy-5-oxo-1H-chromeno[3,4-c]pyridin-3(2H,4H,5H)-yl)-6-oxohexyl)-5-((3aS,4S,6aR)-2-oxohexahydro-1H-thieno[3,4-d]imidazol-4-yl)pentanamide as a yellow solid (96 mg, 96%). $^1$H NMR (400 MHz, $CDCl_3$) δ 8.83 (m, 1H), 7.35 (m, 1H), 6.79 (m, 1H), 6.74-6.40 (m, 2H), 6.26 (s, 1H), 5.81 (bs, 1H), 4.44 (m, 2H), 4.33 (bs, 1H), 4.23 (m, 3H), 4.06 (m, 2H), 3.80 (m, 1.5H), 3.68 (m, 0.5H), 3.17 (m, 2H), 3.06 (m, 1H), 2.84 (m, 1H), 2.76 (m, 1H), 2.66 (m, 1H), 2.54

(m, 1H), 2.37 (m, 2H), 2.24 (m, 1H), 2.11 (m, 2H), 1.73-1.42 (m, 9H), 1.41-1.22 (m, 4H); $^{13}C$ NMR (101 MHz, $CDCl_3$) δ 173.7, 173.5, 173.5, 172.2, 171.9, 169.6, 168.7, 164.3, 164.3, 159.7, 159.6, 159.4, 159.3, 150.6, 147.7, 145.8, 125.5, 125.3, 116.8, 115.7, 114.8, 114.5, 111.7, 111.6, 109.9, 98.1, 68.0, 61.9, 61.8, 60.3, 55.9, 43.2, 41.4, 40.7, 40.2, 39.2, 39.1, 39.1, 37.3, 36.1, 36.0, 33.6, 33.1, 30.9, 29.2, 28.9, 28.3, 28.3, 28.1, 26.6, 25.9, 25.9, 25.8, 25.7, 24.7, 24.6, 24.3; HRMS (ESI-TOF) (m/z) $[M+H]^+$ calcd for $C_{32}H_{43}N_4O_8S$ 643.27961, found 643.27695.

A solution of the above intermediate (40 mg, 72 μmol) in 1.5 mL of acetone was treated with 4N aq. HCl and stirred for 4 h at room temperature. The reaction was concentrated and the crude product was purified by semipreparative RP-HPLC ($C_{18}$ 9.4×250 mm column, 20-100% $MeCN/H_2O$ linear gradient, 20 min) to afford B-I06 as a white solid (19 mg, 52%). $^1H$ NMR (400 MHz, $CDCl_3$) δ 12.16 (m, 1H), 10.61 (m, 1H), 7.69 (m, 1H), 6.93 (m, 1H), 6.51 (m, 0.5H), 6.33 (m, 1.5H), 5.58 (m, 1H), 4.52 (m, 2H), 4.44 (s, 1H), 4.32 (m, 1H), 3.91 (t, J=5.6 Hz, 1H), 3.79 (t, J=5.4 Hz, 1H), 3.25 (m, 2H), 3.13 (m, 1H), 2.89 (m, 3H), 2.72 (m, 1H), 2.45 (t, J=7.1 Hz, 2H), 2.20 (t, J=7.2 Hz, 2H), 1.91 (bs, 1H), 1.69 (m, 6H), 1.53 (m, 1.5H), 1.41 (m, 3.5H); $^{13}C$ NMR (101 MHz, $CDCl_3$) δ 193.2, 173.4, 172.3, 165.1, 164.0, 158.7, 154.7, 147.6, 132.0, 116.9, 115.0, 114.8, 111.2, 108.7, 61.9, 60.3, 55.8, 43.2, 40.7, 39.2, 37.2, 36.1, 33.6, 29.3, 28.3, 28.1, 26.6, 25.8, 24.9, 24.5; HRMS (ESI-TOF) (m/z) $[M+H]^+$ calcd for $C_{29}H_{37}N_4O_7S$ 585.23775, found 585.23708.

Negative control compound B-I07 was obtained by dissolving B-I06 (25 mg, 42 μmol) in 2 mL of MeOH and adding sodium borohydride (1.6 mg, 42 μmol). After stirring 3 h, the reaction was quenched with 1 M aq. HCl and extracted with chloroform. The organic layer was concentrated and the crude product was purified by semipreparative RP-HPLC ($C_{18}$ 9.4×250 mm column, 40-90% $MeCN/H_2O$ linear gradient, 20 min) to afford B-I07 as a white solid (7 mg, 28%); $^1H$ NMR (400 MHz, DMOS-$d_6$) δ 8.44 (bs, 1H), 7.75 (m, 1H), 7.34 (m, 1H), 6.56 (d, J=8.6 Hz, 1H), 6.42 (m, 1H), 6.35 (m, 1H), 4.75 (s, 2H), 4.27 (d, J=6.2 Hz, 3H), 4.08 (m, 1H), 3.69 (m, 2H), 3.08 (m, 0.3H), 2.99 (m, 1.7H), 2.89 (m, 1H), 2.77 (m, 2H), 2.56 (m, 1H), 2.36 (m, 2H), 2.01 (t, J=7.3 Hz, 2H), 1.67-1.11 (m, 14H); $^{13}C$ NMR (101 MHz, DMSO) δ 172.2, 171.5, 163.1, 149.3, 122.8, 114.9, 113.9, 113.6, 112.6, 109.4, 109.3, 105.0, 61.5, 59.6, 56.6, 55.9, 38.7, 35.7, 32.8, 29.5, 28.7, 28.5, 26.6, 25.8, 24.9, 24.7; HRMS (ESI-TOF) (m/z) $[M+H]^+$ calcd for $C_{29}H_{39}N_4O_7S$ 587.25395, found 587.25300.

B-I09 Degradation Studies

A 20 mM stock solution of B-I09 in DMSO was diluted to 0.5 mM in FRET assay buffer (20 mM HEPES, pH 7.5, 50 mM KOAc, 0.5 mM $MgCl_2$, 3 mM DTT, 0.4% PEG) or cell culture media (RPMI supplemented with 10% fetal bovine serum). The FRET assay buffer and cell culture media solutions were incubated at room temperature and 37° C., respectively. At various time points, a 50 μL aliquot of each solution was added to 50 μL of methanol and the mixture analyzed by analytical reverse-phase HPLC ($C_{18}$ 4 mm×150 mm column, 1 mL/min flow rate) with acetonitrile/water (0.1% formic acid) as eluent. Absorbance was read at 320 nm and the degradation product (aldehyde) was identified by LCMS and co-injection with pure synthetic sample. Degradation studies were carried out in duplicate and data points reported as the mean of two values.

Chemical Synthesis of Ibrutinib

Ibrutinib was prepared from commercially available 4-aminopyrazolo-(3,4-d)pyrimidine (Sigma-Aldrich Co.) using a modification to the known synthetic route (Pan Z et al. *Chem Med Chem* 2, 58-61 (2007)). Although the originally reported yield of ibrutunib is 5% (over 5 steps), the protocol below was found to be more convenient for the synthesis of larger quantities as it requires only 2 column purifications, avoids the use of costly polymer-bound triphenylphosphine, and affords the final product in 11% overall yield and >95% purity (RP-HPLC).

A solution of commercially available 4-aminopyrazolo-(3,4-d)pyrimidine (3.36 g, 24.9 mmol) in 70 mL of DMF was treated with N-iodosuccinamide (8.39 g, 37.3 mmol) and stirred at 80° C. for 20 h. The reaction mixture was cooled to room temperature and added into 70 mL of ice cold water. A brown precipitate formed, which was filtered and washed with ice cold ethanol. The resulting solid was dried under reduced pressure to give 3-iodo-1H-pyrazolo[3,4-d]pyrimidin-4-amine (4.50 g, 69%), which was used directly in the next reaction.

A solution of the above iodide (1.80 g, 6.89 mmol) in 30 mL of toluene:ethanol:water (3:1:1) was treated with potassium phosphate (2.93 g, 13.8 mmol), 4-phenoxybenzene boronic acid (2.95 g, 13.8 mmol), and tetrakis(triphenylphosphine)palladium(0) (0.79 g, 1.02 mmol) and irradiated at 120° C. for 1 h using a microwave reactor. The resulting mixture was partitioned between EtOAc and water. The aqueous layer was extracted with EtOAc and concentrated. The crude solid was washed repeatedly with $Et_2O$ to remove impurities, as judged by TLC. The remaining yellow solid was dried under reduced pressure to afford a 3-(4-phenoxyphenyl)-1H-pyrazolo[3,4-d]pyrimidin-4-amine (1.06 g, 50%); $^1H$ NMR (400 MHz, DMSO-$d_6$) δ 13.57 (s, 1H), 8.22 (s, 1H), 7.67 (m, 2H), 7.44 (m, 2H), 7.16 (m, 5H); HRMS (ESI-TOF) (m/z) $[M+H]^+$ calcd for $C_{17}H_{14}N_5O$ 304.11864, found 304.11929.

A solution of 3-(4-phenoxyphenyl)-1H-pyrazolo[3,4-d]pyrimidin-4-amine (1.00 g, 3.29 mmol) in 60 mL of THE was treated with triphenylphosphine (2.59 g, 9.89 mmol), (S)-3-hydroxy-N-Boc-piperidine (1.99 g, 9.89 mmol), and diisopropylazodicarboxylate (1.95 mL, 9.89 mmol) and stirred for 24 h at room temperature. The reaction was concentrated and partially purified by chromatography over silica gel (25-70% EtOAc:Hexane, then 5% $MeOH:CHCl_3$ eluent). The resulting semi-crude product (contaminated with triphenylphosphonium oxide) was directly treated with 4 M HCl in dioxane and stirred for 4 h at room temperature. The mixture was concentrated and the crude material washed repeatedly with $Et_2O$ to afford (R)-3-(4-phenoxyphenyl)-1-(piperidin-3-yl)-1H-pyrazolo[3,4-d]pyrimidin-4-amine as a white solid. (0.67 g, 52%); $^1H$ NMR (400 MHz, DMSO-$d_6$) δ 9.38 (m, 1H), 9.25 (m, 1H), 8.47 (s, 1H), 7.66 (m, 2H), 7.45 (m, 2H), 7.24-7.09 (m, 5H), 5.16 (m, 1H), 3.58-3.37 (m, 2H), 3.31 (d, J=12.4 Hz, 1H), 3.01 (m, 1H), 2.14 (m, 2H), 1.94 (m, 2H). $^1H$ NMR (400 MHz, DMSO-$d_6$) δ 9.46-9.29 (m, 1H), 9.25 (s, 1H), 8.47 (s, 1H), 7.73-7.60 (m, 2H), 7.49-7.41 (m, 2H), 7.24-7.09 (m, 5H), 5.23-5.08 (m, 1H), 3.58-3.37 (m, 3H), 3.31 (d, J=12.4 Hz, 1H), 3.09-2.93 (m, 1H), 2.23-2.06 (m, 2H), 2.05-1.84 (m, 2H); HRMS (ESI-TOF) (m/z) $[M+H]^+$ calcd for $C_{22}H_{23}N_6O$ 387.19279, found 387.19248.

The above amine (106 mg, 275 μmol) in 2 mL of DCM at 0° C. was treated with triethylamine (0.15 mL, 1.10 mmol) and acryloyl chloride (29 μL, 360 μmol). The reaction was stirred for 4 h and washed with 5% aq. citric acid and brine. The organic layer was dried over anhydrous $Na_2SO_4$ and concentrated. Purification by column chromatography over silica gel (2-10% $MeOH/CHCl_3$ eluent) afforded ibrutinib as a white solid (76 mg, 62%). $^1H$ NMR (400 MHz, DMSO-$d_6$) δ 8.25 (s, 1H), 7.66 (m, 2H), 7.44 (m, 2H), 7.15 (m, 5H), 6.87 (dd, J=16.5, 10.5 Hz, 0.5H), 6.72 (dd, J=16.5, 10.5 Hz, 0.5H), 6.10 (dd, J=28.3, 17.3 Hz, 1H), 5.71 (d, J=12.2 Hz, 0.5H), 5.59 (d, J=10.1 Hz, 0.5H), 4.70 (m, 1H), 4.55 (d, J=12.5 Hz, 1H), 4.21 (m, 1H), 4.06 (m, 0.5H), 3.70 (m, 0.5H), 3.20 (m, 1H), 3.00 (m, 0.5H), 2.27 (m, 1H), 2.11 (m, 1H), 1.92 (m, 1H), 1.58 (m, 1H); HRMS (ESI-TOF) (m/z) $[M+H]^+$ calcd for $C_{25}H_{25}N_6O_2$ 441.20335, found 441.20321.

Mice

Eμ-TCL1 transgenic mice are arguably the best CLL mouse model to date (Bertilaccio, M. T., et al. *Leukemia* 27, 534-540 (2013); Bichi, R., et al. *Proc Nat Acad Sci USA* 99, 6955-6960 (2002)). The Eμ-TCL1 mouse model is clinically relevant because TCL1 expression is found in 90% of human CLL cases (Kriss, C. L., et al. *Blood* 120, 1027-1038 (2012); Herling, M., et al. *Leukemia* 20, 280-285 (2006)). Eμ-TCL1 mice develop leukemia with all clinical features of aggressive human CLL (Bichi, R., et al. *Proc Nat Acad Sci USA* 99, 6955-6960 (2002); Yan, X. J., et al. *Proc Natl Acad Sci USA* 103, 11713-11718 (2006)) and have been used repeatedly for preclinical drug tests (Johnson, A. J., et al. *Blood* 108, 1334-1338 (2006); Suljagic, M., et al. *Blood* 116, 4894-4905 (2010); Ponader, S., et al. *Blood* 119, 1182-1189 (2012); Lapalombella, R., et al. *Blood* 120, 4621-4634 (2012); Hertlein, E., et al. *Blood* 116, 45-53 (2010); Hamblin, T. J. *Leuk Res* 34, 135-136 (2010); Lucas, D. M., et al. *Blood* 113, 4656-4666 (2009); Zanesi, N., et al. *Cancer Res* 66, 915-920 (2006)).

The XBP-1-deficient CLL mouse model (XBP-$1^{KO}$/Eμ-TCL1) was generated by crossing CD19Cre/XBP-$1^{flox/flox}$ mice (Hu, C. C., Dougan, S. K., McGehee, A. M., Love, J. C. & Ploegh, H. L. *Embo J* 28, 1624-1636 (2009)) with Eμ-TCL1 mice (Bichi, R., et al. *Proc Natl Acad Sci USA* 99, 6955-6960 (2002)). These colonies together with μS−/− mice (Boes, M., et al. *J Immunol* 160, 4776-4787 (1998)) were maintained at an animal facility strictly following the guidelines provided by the University of South Florida and the H. Lee Moffitt Cancer Center Committees on Animal Care.

Immunofluorescent Staining and Flow Cytometric Analysis of Mouse Splenocytes and Purified B-CLL Cells.

Splenocytes were obtained from mice by mashing the spleens through cell strainers followed by RBC lysis (Qiagen). Mouse B cells, μS−/− B cells and Eμ-TCL1 CLL cells were purified from mouse spleens by negative selection using Pan-B magnetic beads (Miltenyi Biotech). After non-specific blocking for 30 minutes using FBS, cell surface staining was achieved by incubating cells at 4° C. for 30 minutes with the following anti-mouse antibodies: CD3 (145-2C11; Biolegend), IgM (e-Bioscience), B220 (RA3-6B2; BD Pharmingen), CD5 (53-7.3; eBioscience), CD1d (1B1; Biolegend), CD20 (A1SB12; e-Bioscience), CD21 (7E9; Biolegend), CD22 (OX-97; Biolegend), CD23 (B3B4; Biolegend), CD24 (M1/69; Biolegend), CD25 (PC61; Biolegend), CD38 (90; Biolegend), CD43 (eBioR2/60; e-Bioscience), CD49b (DX5; Biolegend), CD138 (281-2; BD Pharmingen), CD184 (2B11; e-Bioscience), MHC II (M5/114; Biolegend), S1P1 (713412; R&D), GL7 (GL7; Biolegend) and IgD (11-26c.2a; Biolegend). Viability staining was accomplished using DAPI exclusion during acquisition. Acquisition of B-cell and CLL cell populations was performed on a LSRII cytometer (BD Biosciences) harboring a custom configuration for the H. Lee Moffitt Cancer Center & Research Institute. Mid-range Spherotech FL1 fluorescent rainbow beads (BD Biosciences) were used to maintain consistent gains for all parameters across different time points. Cytometry data was analyzed using FlowJo software version 7.6.1 (Tree Star Inc.).

Antibodies and Reagents

Antibodies to TCL1 (Cell Signaling), IRE-1 (Cell Signaling), XBP-1 (Santa Cruz), Syk (Cell Signaling), phospho-Syk (Tyr525/526) (Cell Signaling), phospho-BTK (Cell Signaling), cleaved caspase 3 (Cell Signaling), PARP (Cell Signaling), cleaved PARP (Cell Signaling), p97 (Fitzgerald), actin (Sigma), μ (SouthernBiotech) and κ (SouthernBiotech) were obtained commercially. Polyclonal antibodies against Igβ, class I MHC and class II MHC molecules were generated in rabbits. LPS was procured from Sigma.

Cell Culture

Primary human CLL cells were obtained from consented patients following the IRB guidelines. Primary mouse B cells, mouse Eμ-TCL1 CLL cells, primary human CLL cells, human CLL cell lines (MEC1, MEC2 and WaC3), multiple myeloma (MM) cell lines (mouse 5TGM1, human RPMI-8226, human U266, and human NCI-H929), and human mantle cell lymphoma (MCL) cell lines (Mino, Jeko and HBL2) were all cultured in the RPMI 1640 media (Gibco) supplemented with 10% heat-inactivated fetal bovine serum (FBS), 2 mM L-glutamine, 100 U/ml penicillin G sodium, 100 μg/ml streptomycin sulfate, 1 mM sodium pyruvate, 0.1 mM non-essential amino acids, and 0.1 mM β-mercapto-ethanol (O-ME). Human MCL cell line Z138 was cultured in the IMDM media (Gibco) with the same supplemental nutrients.

Protein Isolation and Immunoblotting

Cells were lysed using RIPA buffer (10 mM Tris-HCl, pH 7.4; 150 mM NaCl; 1% NP-40; 0.5% sodium deoxycholate; 0.1% SDS; 1 mM EDTA) supplemented with protease inhibitors (Roche). Protein concentrations were determined by BCA assays (Pierce). Samples were boiled in SDS-PAGE sample buffer (62.5 mM Tris-HCl, pH 6.8; 2% SDS; 10% glycerol; 0.1% bromophenol blue) with R-ME and analyzed by SDS-PAGE. Proteins were transferred to nitrocellulose membranes, blocked in 5% non-fat milk (wt/vol in PBS), and immunoblotted with indicated primary antibodies and appropriate horseradish peroxidase-conjugated secondary antibodies. Immunoblots were developed using Western Lighting Chemiluminescence Reagent (Perkin-Elmer).

BCR Activation and Phosphorylation Assay

XBP-$1^{WT}$/Eμ-TCL1 B cells, XBP-$1^{KO}$/Eμ-TCL1 B cells, B-I09-treated wild-type B cells or B-I09-treated Eμ-TCL1 B cells were suspended in RPMI serum-free media supplemented with 25 mM Hepes, stimulated with $F(ab')^2$ fragments of the goat anti-mouse IgM antibody (20 μg/ml) (SouthernBiotech) for 2 min, and lysed immediately by adding ice-cold lysis buffer (50 mM Tris-HCl, pH 8.0; 150 mM NaCl; 1% Triton X-100; 1 mM EDTA) supplemented with protease inhibitor cocktail (Roche), 4 mM sodium pyrophosphate, 2 mM sodium vanadate and 10 mM sodium fluoride. The lysates were analyzed by SDS-PAGE. Phosphorylated proteins of interest were detected by immunoblots using phospho-specific antibodies.

Pulse Chase Experiments, Immunoprecipitation, Protein Deglycosylation and SDS-PAGE Eμ-TCL1 CLL cells and primary mouse B cells were starved in methionine- and cysteine-free media containing dialyzed serum for 1 h, then pulse-labeled with 250 μCi/ml $[^{35}S]$-methionine and $[^{3}S]$-cysteine (Perkin-Elmer) for 15 minutes. After labeling, cells were incubated in chase medium containing unlabeled methionine (2.5 mM) and cysteine (0.5 mM). At the end of each chase interval, cells were lysed in RIPA buffer containing protease inhibitors. Pre-cleared lysates were incubated with a primary antibody and Protein G-agarose beads (Sigma). Bead-bound proteins were eluted using glycoprotein denaturing buffer (0.5% SDS, 1% β-ME) or reducing Laemmli SDS-PAGE sample buffer. Enzymatic deglycosylation of proteins was achieved by denaturation of the immunoprecipitates in glycoprotein denaturing buffer at 95° C. for 10 min, followed by addition of sodium citrate (pH 5.5) to a final concentration of 50 mM, and incubated with Endo H (New England Biolabs) at 37° C. for 2 h. Alternatively, sodium phosphate (pH 7.5) and NP-40 were added to the denatured cell lysates to a final concentration of 50 mM and 1%, respectively, and the mixture was incubated with PNGase F (New England Biolabs) at 37° C. for 2 h. Protein samples were then analyzed by SDS-PAGE followed by fluorography.

Reverse Transcription and Polymerase Chain Reaction (PCR)

Total RNA was isolated using TRIzol reagent (Invitrogen). Complementary DNA was synthesized from RNA using Superscript II reverse transcriptase (Invitrogen). The following sets of primers were used together with Platinum Taq DNA polymerase (Invitrogen) in PCR to detect the expression of human XBP-1 (GAGTTAAGACAGCGCTTGGG (SEQ ID NO:1) and ACTGGGTCCAAGTTGTCCAG (SEQ ID NO:2)); human actin (CTGAGCGTGGCTACTCCTTC (SEQ ID NO:3) and GGCATACAGGTCCTTCCTGA (SEQ ID NO:4)); mouse XBP-1 (GATCCTGACGAGGTTCCAGA (SEQ ID NO:5) and ACAGGGTCCAACTTGTCCAG (SEQ ID NO:6)); and mouse actin (AGCCATGTACGTAGCCATCC (SEQ ID NO:7) and CTCTCAGCTGTGGTGGTGAA (SEQ ID NO:8)).

Recombinant Human IRE-1 Expression and Purification

Expression of 59.2 kD polyhistidine-tagged puritin-hIRE-1 fusion protein was carried out in SF21 cells using the Bac to Bac expression system (Invitrogen) according to manufacturer specifications. An 8×-His-puritin sequence was fused to the N-terminal end of the cytoplasmic kinase/RNase domain of human IRE-1 (aa. 547-977) in the pFastbacDual-PBL expression vector and included a PreScission protease cleavage site in the linker. Frozen insect cell paste (1 g) was suspended in 8 mL lysis buffer (50 mM Tris/HCl pH 8.0, 300 mM NaCl, 5 mM BME, 10 mM imidazole) containing one protease inhibitor tablet and lysed using sonication. After removal of the cell debris via centrifugation, the supernatant was applied to a Ni(NTA) column (5 mL). After washing untagged protein by flushing with 10 column volumes of lysis buffer, the target protein was eluted using a linear imidazole gradient (15 column volumes, 10-300 mM). Fractions were analyzed via SDS-PAGE. Pooled protein-containing fractions were concentrated and rebuffered into 50 mM Tris, pH 8.0, 150 mM NaCl, 1 mM DTT via ultrafiltration. Typically, 1 L of insect cell culture yielded 3 mg of recombinant 8×-His-puritin-hIRE-1 following Ni(NTA) column purification.

In Vitro FRET-Suppression Assay

The endoribonuclease activity of recombinant hIRE-1 was assayed by incubation of 50 μL of 10 nM hIRE-1 and 50 μL of various concentrations (0.01-1 μM) of fluorescently tagged XBP-1 RNA stem loop (5'-Cy5-CAGUCCGCAGCACUG-BHQ-3' (SEQ ID NO:9 underlined portion), obtained from Sigma-Aldrich Co.) in assay buffer (20 mM HEPES, pH 7.5, 50 mM KOAc, 0.5 mM $MgCl_2$, 3 mM DTT, 0.4% PEG, and 5% DMSO) for up to 2 hours at room temperature in a black 96-well plate. Fluorescence was read at various time points using a Biotek Synergy H1 plate reader with excitation and emission at 620 nm and 680 nm, respectively. The $K_m$ of purified recombinant hIRE-1 was determined to be 45 nM using the Michaelis-Menten kinetic model. Inhibition of RNA cleavage by small molecules was determined by pre-incubation of 40 μL of 15 nM hIRE-1 with various concentrations of compounds (40 μL) in assay buffer for 30 min at room temperature. A 150 nM solution of fluorescent XBP-1 RNA (40 μL) was then added to each well and the reaction allowed to proceed for 2 hours before reading fluorescence as described above. Final concentrations of hIRE-1 and XBP-1 RNA were 5 nM and 50 nM, respectively. All fluorescence readings were corrected using background values from wells containing only 120 μL of 50 nM XBP-1 RNA. Dose-response experiments were carried out a minimum of 3 times on different days and $IC_{50}$ values calculated from the mean inhibition value at each concentration.

Chemical Inhibitors

A-I06 (2-hydroxynaphthaldehyde) and 4μ8C (7-hydroxy-4-methyl-2-oxo-2H-chromene-8-carbaldehyde) are commercially available and were obtained from Sigma-Aldrich Co. and Matrix Scientific, respectively. All other IRE-1 inhibitors and the BTK inhibitor ibrutinib were chemically synthesized in-house. Ibrutinib was prepared from commercially available 4-aminopyrazolo-(3,4-d)pyrimidine (Sigma-Aldrich Co.) using a modification to the known synthetic route Pharmacokinetics In vivo pharmacokinetics studies were carried out at Agilux Laboratories, Inc. (Worchester, MA) using male CD-1 mice (Charles River Laboratories, Wilmington, MA). B-I09 was administered intraperitoneally at 50 mg/kg as a solution in DMSO to a group of 3 male CD-1 mice. Compound blood was collected via tail snip into calibrated microvette tubes containing $K_2EDTA$ at 0.25, 0.5, 1, 2, 4, 8, and 24 h post dosing. Blood samples were stored on wet ice until processed to plasma by centrifugation within 1 hour of collection. All plasma samples were transferred to 96 well plates and stored at −80° C. until analyzed for B-I09 concentration via LC/MS/MS using a C18 RP-HPLC column (2.1×50 mm) and an acetonitrile:water (with 0.1% formic acid) mobile phase elution gradient. B-I09 was quantified by analysis with API 5500 TurboIonSpray positive ion MS detection. A non-compartmental model was applied to calculate pharmacokinetic parameters using WinNonlin 4.2 software.

Compound Synergism

The activity levels of compounds alone and in combination were determined by a high-throughput CellTiter-Blue (Promega Corp.) cell viability assay. Cell viability measurement is based on the ability of living cells to convert resazurin dye into the fluorescent resofurin. Cells ($3\times10^3$) were plated in each well of 384-well plates using a Precision XS liquid handling station (Bio-Tek Instruments, Inc., Winooski, VT). A liquid handling station was then used to serially dilute all drugs in media, and 5 μL were added to four replicate wells and an additional four control wells received a diluent control without drug. At the end of the incubation period with drugs, 5 μL of CellTiter-Blue reagent were added to each well. The fluorescence of the product of viable cells' bioreduction, resorufin, (579 nm excitation/584 nm emission), was measured with a Synergy 4 microplate reader (Bio-Tek Instruments, Inc). The fluorescence data were transferred to Microsoft Excel to calculate the percent viability. $IC_{50}$ values were determined using a sigmoidal equilibrium model regression and XLfit version 5.2 (ID Business Solutions Ltd.). The $IC_{50}$ values obtained from single-drug cell viability assays were used to design subsequent drug combination experiments.

For drug combination experiments, the cell viability assays were performed as described above, and the results were analyzed for synergistic, additive, or antagonistic effects using the combination index (CI) method developed by Chou and Talalay (Chou, T. C. *Pharmacol Rev* 58, 621-681 (2006)). For the application of this method, the drug concentration dilutions were used at fixed dose molar ratios based on the $IC_{50}$ levels of each drug obtained from preliminary experiments. The dose-effect curve for each drug alone was determined based on experimental observations using the median-effect principle and then compared to the effect achieved with a combination of the two drugs to derive a CI value. This method involves plotting dose-effect curves, for each agent and their combination, using the median-effect equation: fa/fu=(D/Dm)m, where D is the dose of the drug, Dm is the dose required for a 50% effect (equivalent to $IC_{50}$), fa and fu are the affected and unaffected fractions, respectively (fa=1-fu), and m is the exponent signifying the sigmoidicity of the dose-effect curve. XLfit software was used to calculate the values of Dm and m. The CI used for the analysis of the drug combinations was determined by the isobologram equation for mutually non-exclusive drugs that have different modes of action: CI=(D)1/(Dx)1+(D)2/(Dx)2+(D)1(D)2/(Dx)1(Dx)2, where (Dx)1 and (Dx)2 in the denominators are the doses (or concentrations) for D1 (drug 1) and D2 (drug 2) alone that gives x % inhibition, whereas (D)1 and (D)2 in the numerators are the doses of drug 1 and drug 2 in combination that also inhibited x % (i.e., isoeffective). CI<1, CI=1, and CI>1 indicate synergism, additive effects, and antagonism, respectively.

Cell Proliferation XTT Assays

Appropriate numbers of cells were suspended in phenol red-free culture media, seeded in 96-well cell culture plates, and treated with indicated IRE-1 inhibitors (20 μM, unless indicated otherwise), PCI-32765 (ibrutinib; 10 μM) or the combination. Every 24 hours after the treatment, cells were spun down and proliferation was assessed by XTT assays (Roche) according to the manufacturer's instructions. Briefly, 50 μl XTT labeling reagent, 1 μl electron-coupling reagent and 100 μl phenol red-free culture media were combined and applied to each well of the 96-well plates. Cells were then incubated for 4 h in a $CO_2$ incubator to allow for the yellow tetrazolium salt XTT to be cleaved by mitochondrial dehydrogenases of metabolic active cells to form the orange formazan dye, which can be quantified at 492 nm using a BioTek Synergy H1 MicroPlate Reader.

Statistics

Mouse survival was evaluated using the Kaplan-Meier analysis. A P value of less than 0.05 was considered significant.

Results

XBP-$1^{KO}$/Eμ-TCL1 Mice Develop Leukemia Significantly Slower than XBP-$1^{WT}$/Eμ-TCL1 Mice.

Figure 18A:
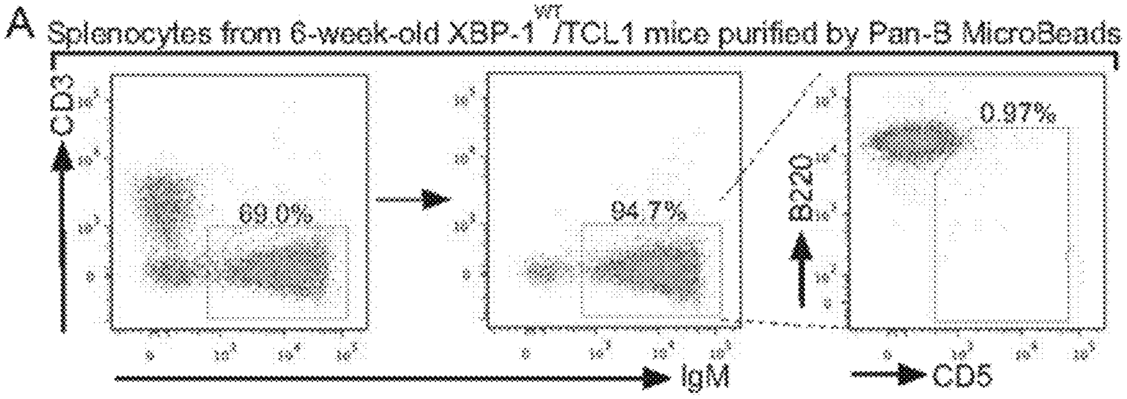
FIG. 18A: B or CLL cell purification from spleens of XBP-$1^{WT}$/TCL1 and XBP-$1^{KO}$/TCL1 mice. Splenocytes (left panel) from 6-week-old XBP-$1^{WT}$/TCL1 mice were purified using Pan B Cell Isolation MicroBeads (middle panel) and stained with CD3-APC-Cy7, IgM-PE-Cy7, B220-FITC and CD5-APC monoclonal antibodies. CD3+/IgM− T cells and the majority of CD3−/IgM− non-B/non-T cells were removed successfully. Gated CD3−/IgM+ B cells were analyzed for the expression of B220 and CD5 (right panel).
Figure 19A:
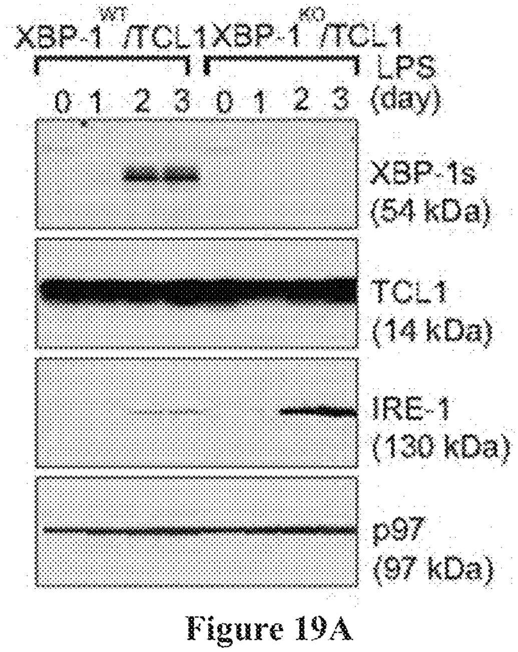
FIG. 19A: CD5−/B220+ B cells purified from 6-week old XBP-$1^{WT}$/Eμ-TCL1 and XBP-$1^{KO}$/Eμ-TCL1 mice were stimulated with LPS for a course of 3 days, and lysed for analysis of indicated proteins by immunoblots.
Figure 19B:
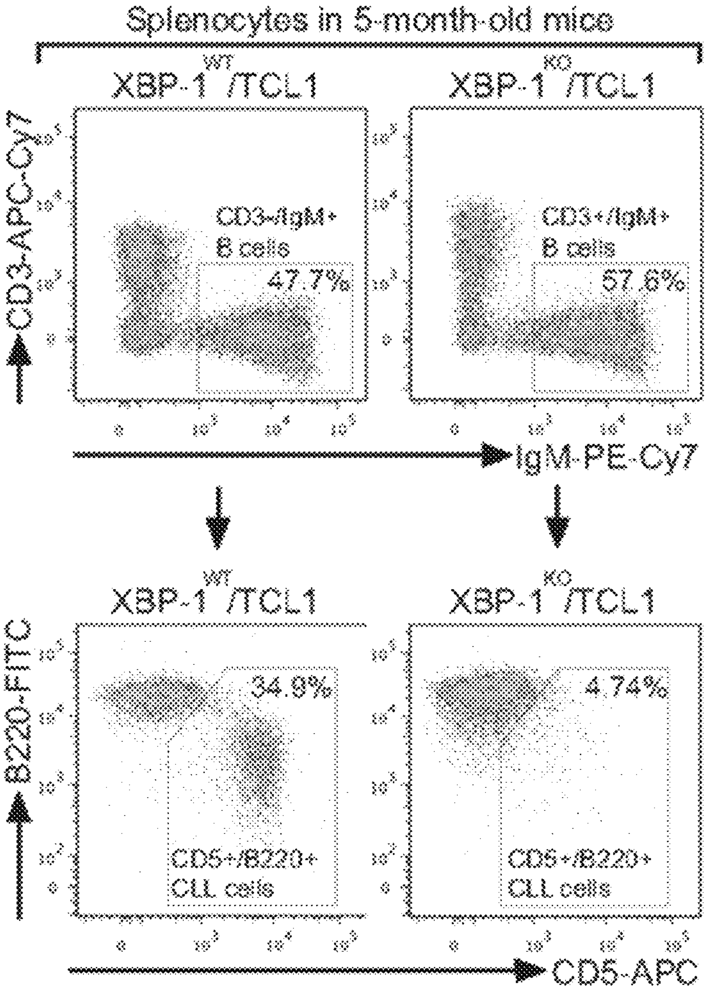
FIG. 19B: Splenocytes isolated from XBP-$1^{WT}$/Eμ-TCL1 and XBP-$1^{KO}$/Eμ-TCL1 mice at the age of 5 months were stained with CD3-APC-Cy7, IgM-PE-Cy7, B220-FITC, CD5-APC and DAPI. Gated live CD3−/IgM+ B cell populations were analyzed for the expression of B220 and CD5.
Figure 19C:
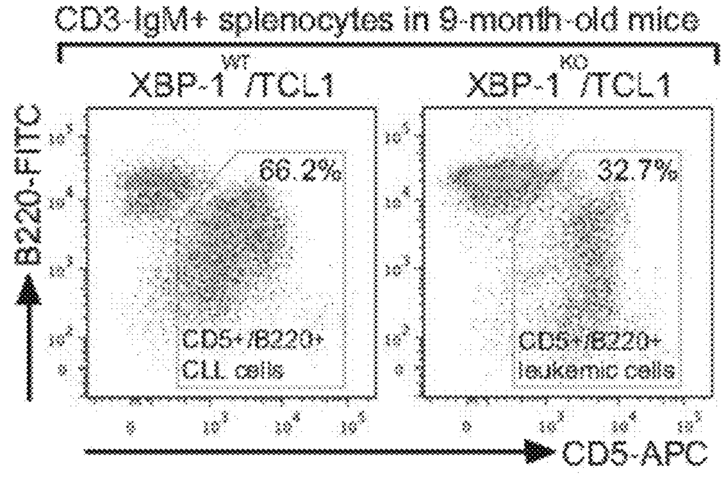
FIG. 19C: Splenocytes isolated from XBP-$1^{WT}$/Eμ-TCL1 and XBP-$1^{KO}$/Eμ-TCL1 mice at the age of 9 months were stained with CD3-APC-Cy7, IgM-PE-Cy7, B220-FITC, CD5-APC and DAPI. Gated live CD3−/IgM+ B cell populations were analyzed for the expression of B220 and CD5.
Figure 19D:
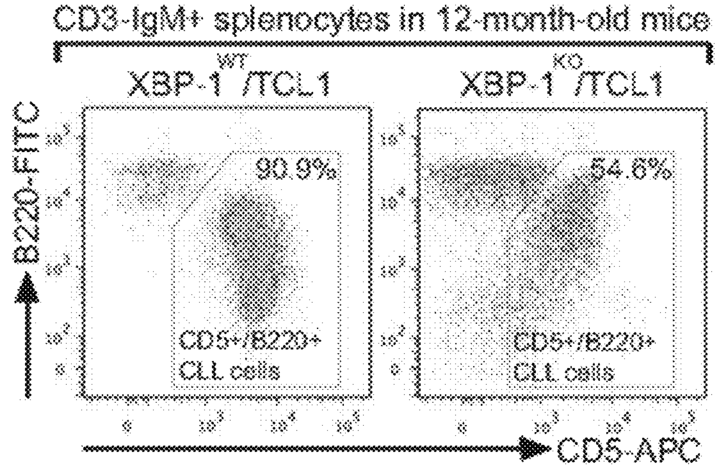
FIG. 19D: Splenocytes isolated from XBP-$1^{WT}$/Eμ-TCL1 and XBP-$1^{KO}$/Eμ-TCL1 mice at the age of 12 months were stained with CD3-APC-Cy7, IgM-PE-Cy7, B220-FITC, CD5-APC and DAPI. Gated live CD3−/IgM+ B cell populations were analyzed for the expression of B220 and CD5.
Figure 19E:
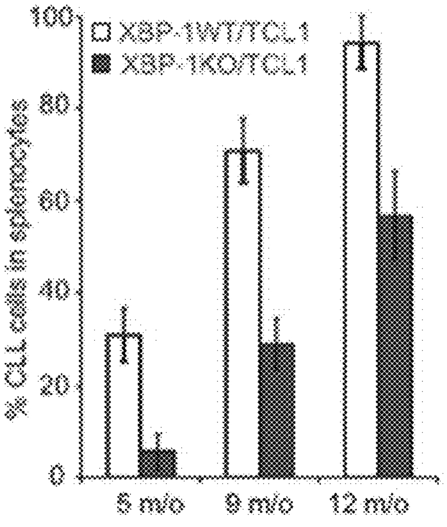
FIG. 19E: The percentages of CD5+/B220+ CLL cells in splenocytes of XBP-$1^{WT}$/Eμ-TCL1 and XBP-$1^{KO}$/Eμ-TCL1 mice at the age of 5, 9 and 12 months were plotted as mean±SEM (n=5 in each age group).
Figure 19F:
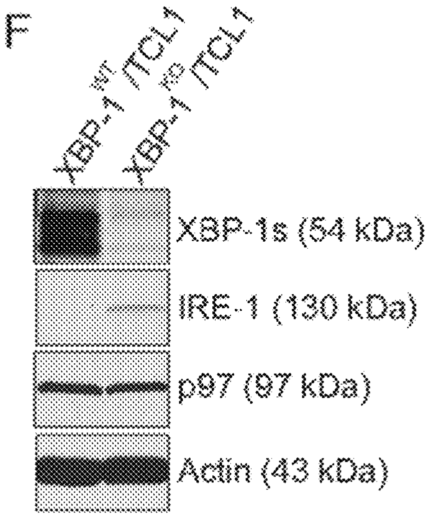
FIG. 19F: CD5+/B220+ CLL cells purified from spleens of XBP-$1^{WT}$/Eμ-TCL1 and XBP-$1^{KO}$/Eμ-TCL1 mice were lysed to analyze for the expression of indicated proteins.
Figure 19G:
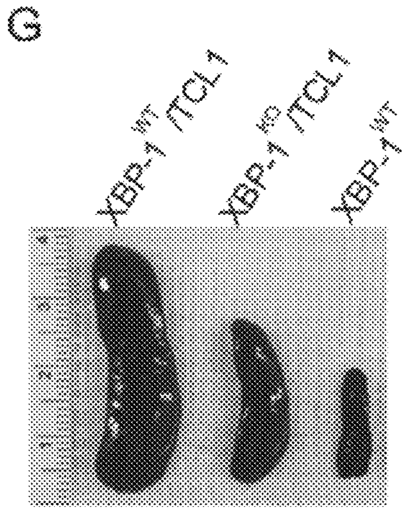
FIG. 19G: A picture of spleens from 12-month-old age-matched XBP-$1^{WT}$/Eμ-TCL1 and XBP-$1^{KO}$/Eμ-TCL1 littermates and a wild-type mouse.
Figure 19H:
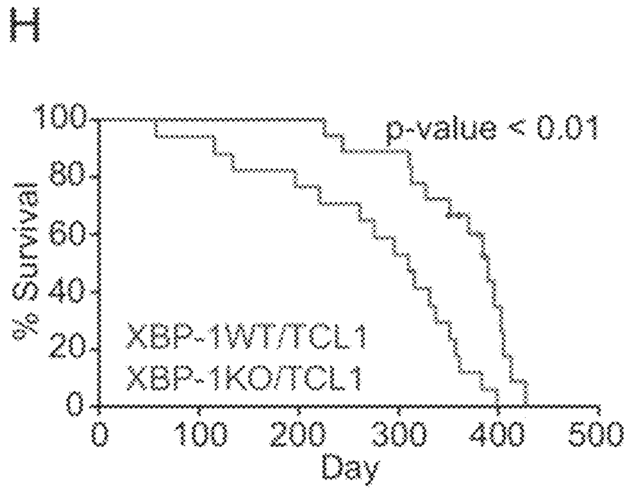
FIG. 19H: The Kaplan-Meier analysis of overall survival of XBP-1KO/E□-TCL1 mice (n=18). Four mice from the XBP-1KO/Eμ-TCL1 group were censored (circled) and removed for other studies.

To investigate how the loss of XBP-1 can counter malignant progression of leukemia, B cell-specific XBP-$1^{KO}$ mice (CD19Cre/XBP-$1^{f/f}$; the expression of Cre recombinase is under the control of the CD19 promoter) were crossed with Eμ-TCL1 mice to create a B cell-specific XBP-1-deficient CLL mouse model, XBP-$1^{KO}$/Eμ-TCL1. To show that B cells produced by this new mouse model do not produce the 54-kDa spliced XBP-1 protein (XBP-1s), B cells were isolated from spleens of 6-week-old XBP-$1^{KO}$/Eμ-TCL1 and XBP-$1^{WT}$/Eμ-TCL1 mice (FIG. 18A), stimulated with LPS, and confirmed no expression of XBP-1s in XBP-$1^{KO}$/Eμ-TCL1 B cells (FIG. 19A). When XBP-1s is missing, the elevated expression of IRE-1 is observed in XBP-$1^{KO}$/Eμ-TCL1 B cells (FIG. 19A), consistent with previous XBP-1 knockout and inhibition data in wild-type B cells (Kriss, C. L., et al. *Blood* 120, 1027-1038 (2012); Hu, C. C., Dougan, S. K., McGehee, A. M., Love, J. C. & Ploegh, *Embo J* 28, 1624-1636 (2009)). Leukemic progression was monitored in 5-, 9- and 12-month-old XBP-$1^{KO}$/Eμ-TCL1 mice by analyzing CD5+/B220+ CLL cells on gated CD3−/IgM+ B cell populations in the spleens (FIG. 19B), and it was found that XBP-$1^{KO}$/Eμ-TCL1 mice developed leukemia significantly slower than their age-matched XBP-$1^{WT}$/Eμ-TCL1 littermates (FIG. 19B-FIG. 19E). It was also confirmed that indeed XBP-1s is expressed by CD3−/IgM+/CD5+/B220+ CLL cells isolated from the spleens of 12-month-old XBP-$1^{WT}$/Eμ-TCL1 mice but not age-matched XBP-$1^{KO}$/Eμ-TCL1 littermates (FIG. 19F). As a result, spleens isolated from XBP-$1^{KO}$/Eμ-TCL1 mice are significantly smaller than those from their control littermates (FIG. 19G).

XBP-1-Deficient Eμ-TCL1 CLL Cells Exhibit Compromised BCR Signaling.

Figure 18B:
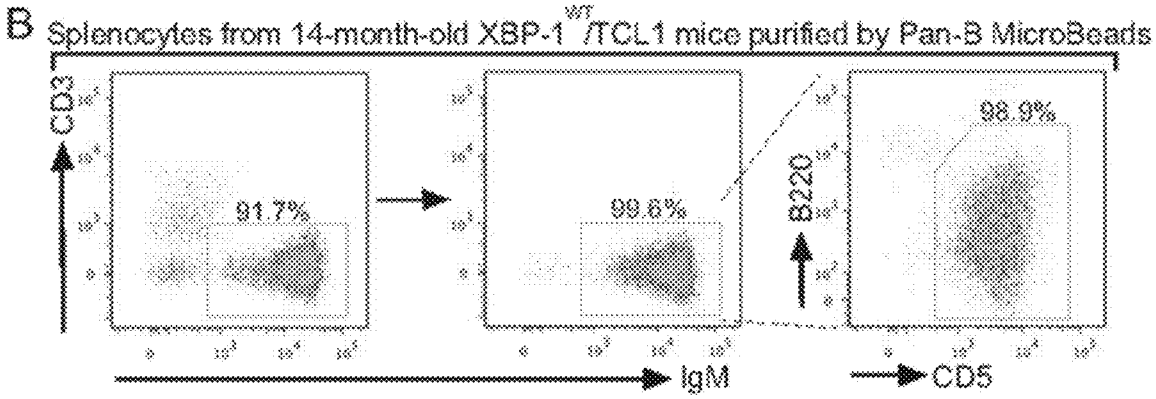
FIG. 18B: B or CLL cell purification from spleens of XBP-$1^{WT}$/TCL1 and XBP-$1^{KO}$/TCL1 mice. Splenocytes (left panel) from 14-month-old XBP-$1^{WT}$/Eμ-TCL1 mice were purified using Pan B Cell MicroBeads (middle panel), and stained with monoclonal antibodies as described in FIG. 18A. Gated CD3−/IgM+ B cell populations were analyzed for the expression of B220 and CD5 (right panel).
Figure 18C:
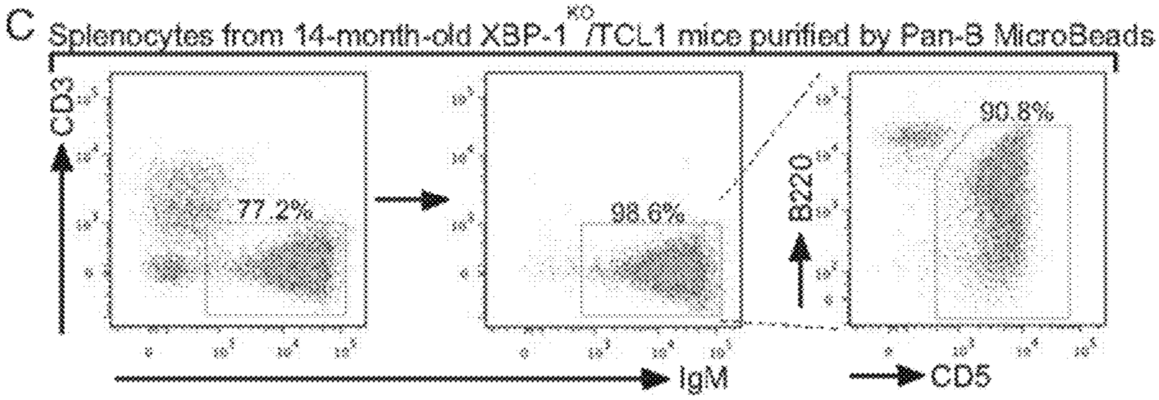
FIG. 18C: B or CLL cell purification from spleens of XBP-$1^{WT}$/TCL1 and XBP-$1^{KO}$/TCL1 mice. Splenocytes (left panel) from 14-month-old XBP-$1^{KO}$/Eμ-TCL1 mice were purified using Pan B Cell MicroBeads (middle panel), and stained with monoclonal antibodies as described in FIG. 18A, Gated CD3−/IgM+ B cell populations were analyzed for the expression of B220 and CD5 (right panel).
Figure 20A:
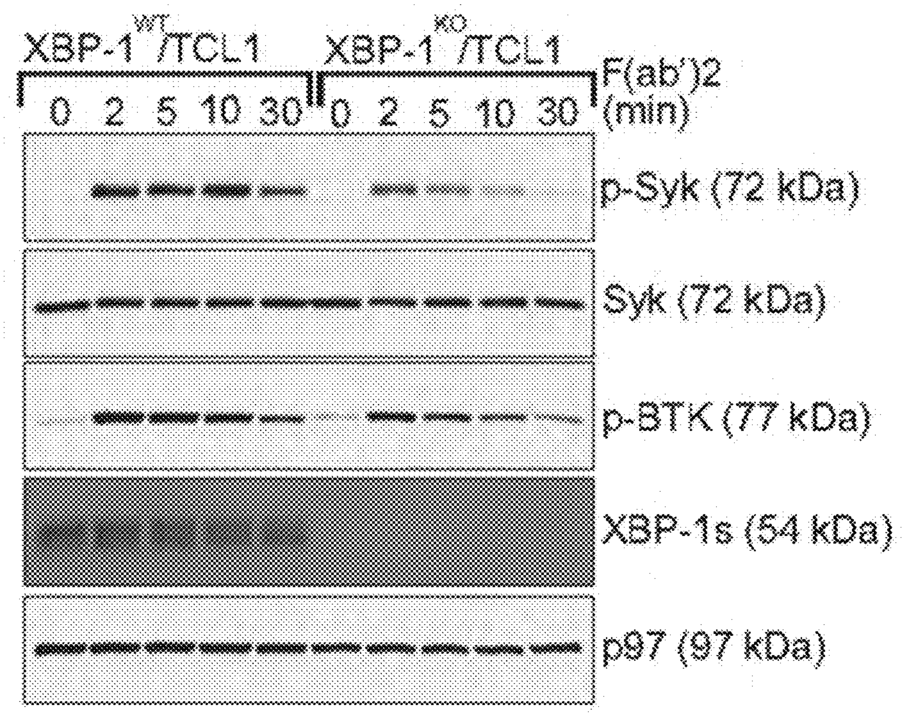
FIG. 20A: XBP-$1^{KO}$/Eμ-TCL1 B cells respond ineffectively to activation via the BCR. XBP-$1^{WT}$/Eμ-TCL1 and XBP-$1^{KO}$/Eμ-TCL1 B cells were treated with LPS for 3 days, stimulated with F(ab')2 anti-mouse IgM to crosslink the BCR for indicated times and lysed for analysis of indicated proteins by immunoblots.
Figure 20B:
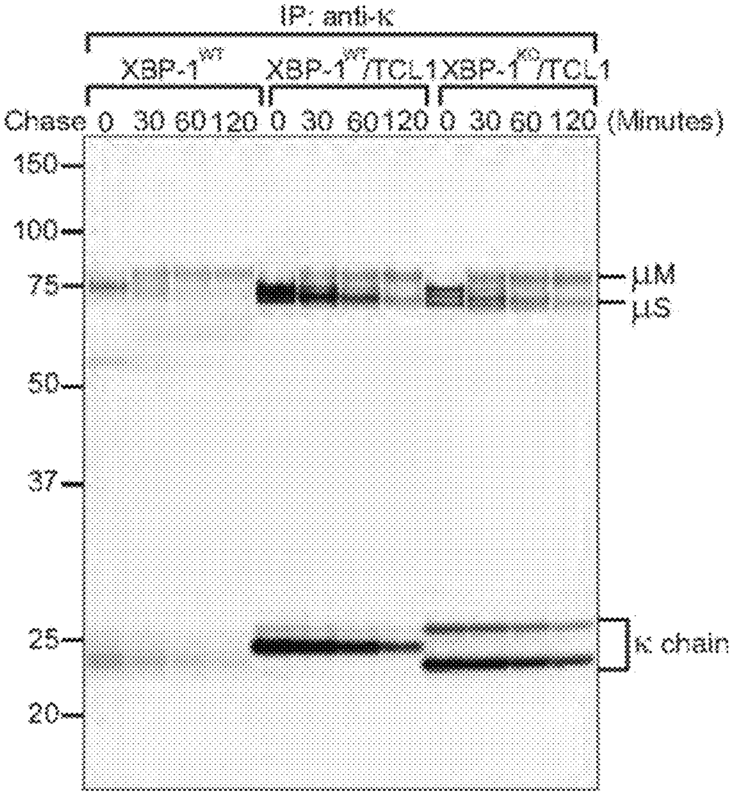
FIG. 20B: Wild-type B cells and CLL cells were isolated from 12-month-old wild-type, XBP-$1^{WT}$/Eμ-TCL1 and XBP-$1^{KO}$/Eμ-TCL1 mice. Purified cells were radiolabeled for 15 min, chased for indicated time and lysed. Intracellular and extracellular IgM were immunoprecipitated from lysates using an anti-K antibody. Immunoprecipitates were analyzed on an SDS-PAGE gel.
Figure 20C:
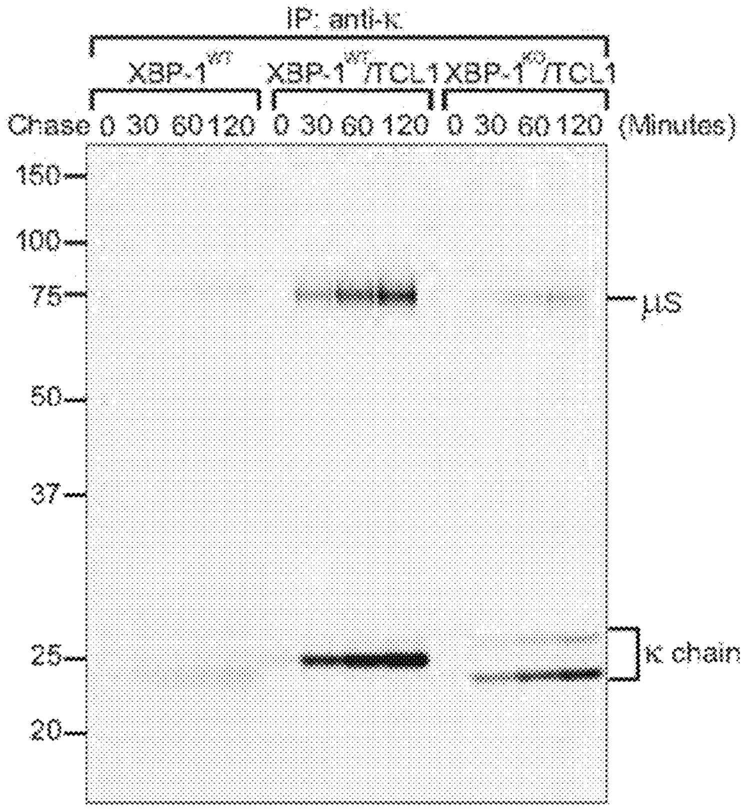
FIG. 20C: Wild-type B cells and CLL cells were isolated from 12-month-old wild-type, XBP-$1^{WT}$/Eμ-TCL1 and XBP-$1^{KO}$/Eμ-TCL1 mice. Purified cells were radiolabeled for 15 min, chased for indicated time and lysed. Intracellular and extracellular IgM were immunoprecipitated from culture media using an anti-K antibody. Immunoprecipitates were analyzed on an SDS-PAGE gel.
Figure 20D:
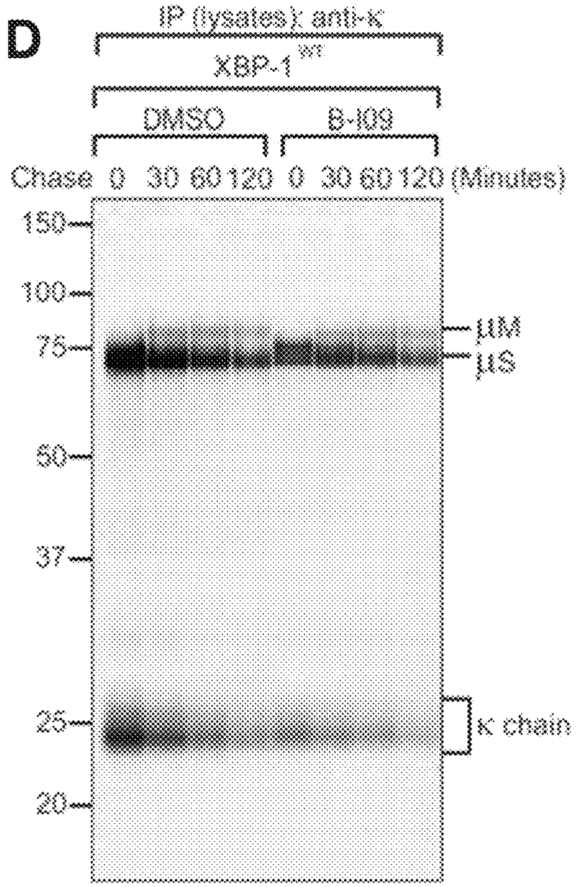
FIG. 20D: Wild-type B cells were stimulated with LPS for 2 days and subsequently treated with DMSO (control) or B-I09 (20 μM) for additional 1 day. DMSO- or B-I09-treated wild-type B cells were radiolabeled for 15 min, chased for indicated times and lysed. Intracellular membrane-bound μ chain (μM), secretory μ chain (μM) and κ light chain was immunoprecipitated from lysates using an anti-κ antibody.
Figure 20E:
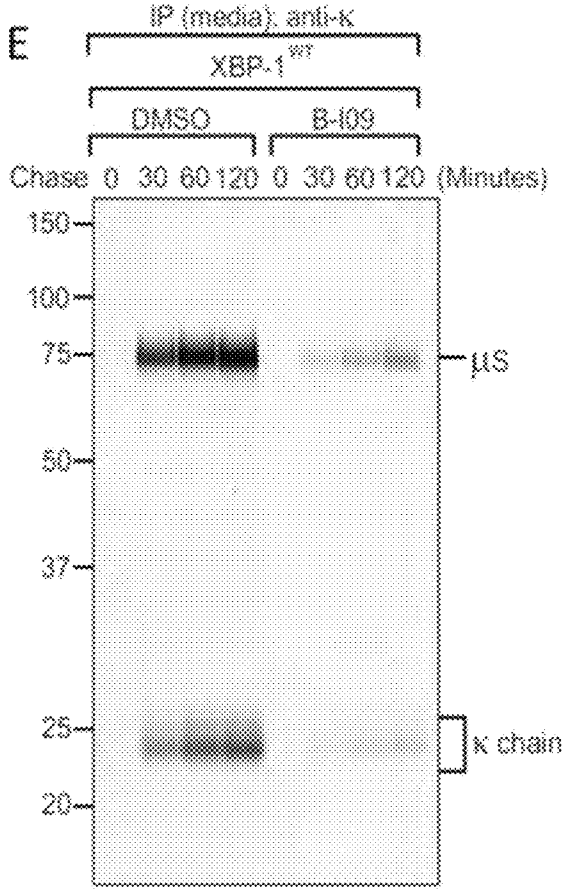
FIG. 20E: Secreted μ and κ chains were also immunoprecipitated from culture media using an anti-κ antibody. Immunoprecipitates were analyzed by SDS-PAGE.
Figure 20F:
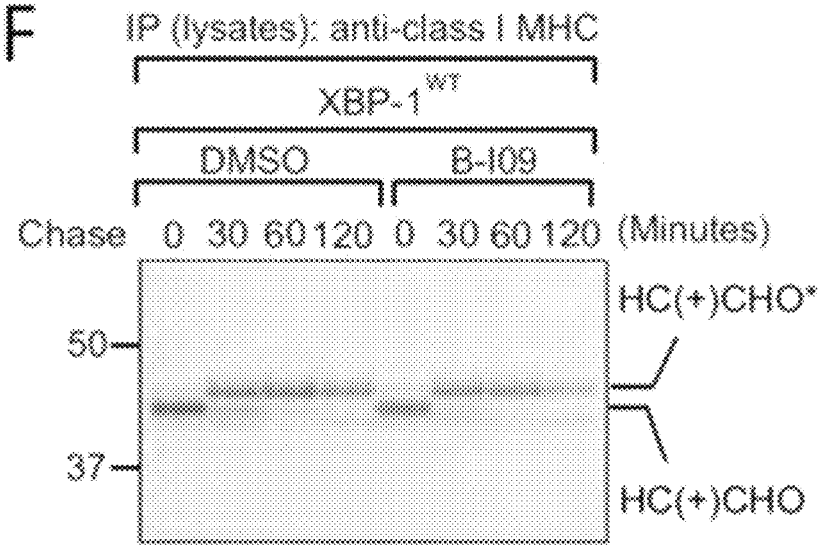
FIG. 20F: Similar lysates as those in FIG. 20D were immunoprecipitated using an antibody against the class I MHC heavy chain (HC), and immunoprecipitates were analyzed by SDS-PAGE. CHO and CHO* denote high mannose-type glycans and complex-type glycans, respectively.
Figure 20G:
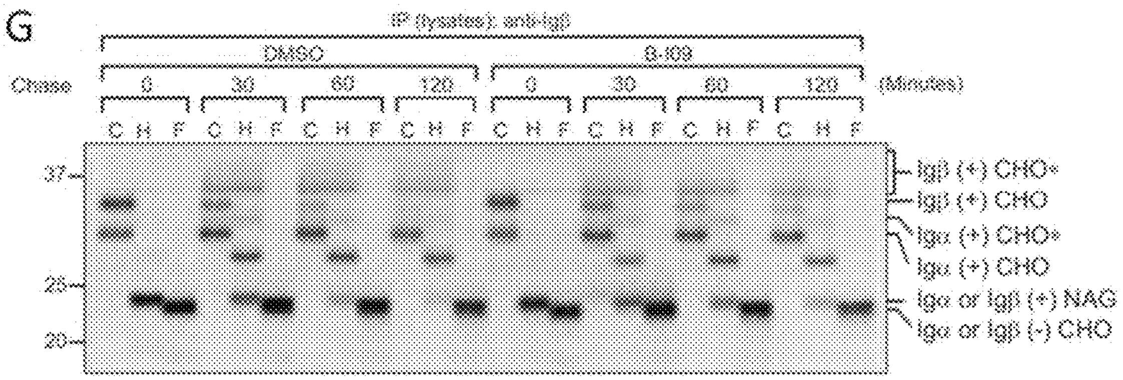
FIG. 20G: From similar lysates as those in FIG. 20A, Igα/Igβ heterodimers were immunoprecipitated using an anti-Ig antibody. Immunoprecipitated Igα/Igβ heterodimers were eluted from the beads and treated with endo-H or PNGase F before analyzed by SDS-PAGE. CHO, CHO*, NAG indicate high mannose-type glycans, complex-type glycan and N-acetylglucosamines, respectively.
Figure 21A:
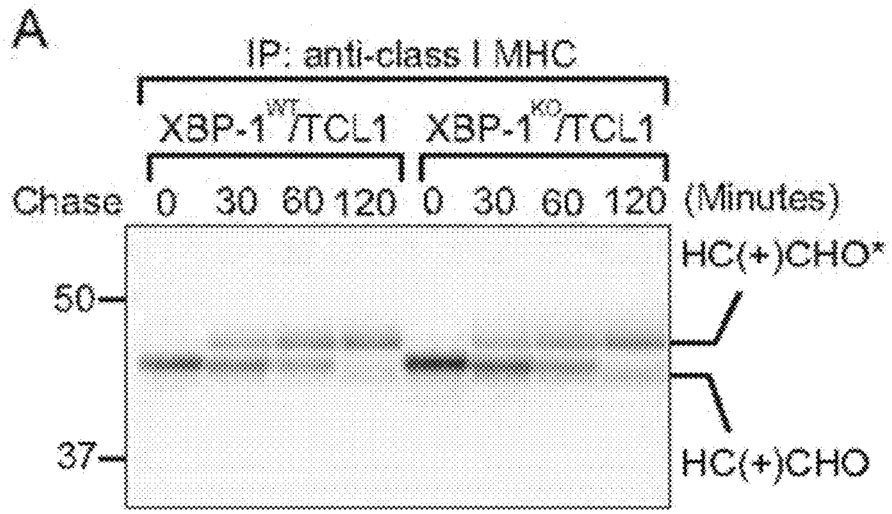
FIG. 21A: CLL cells isolated 12-month-old XBP-$1^{WT}$/Eμ-TCL1 and XBP-$1^{KO}$/Eμ-TCL1 mice were labeled with [$^{3}$S]-methionine and [$^{3}$S]-cysteine for 15 min, chased for the indicated times, and lysed. Lysates were immunoprecipitated using antibodies against the class I MHC molecules. Immunoprecipitates were analyzed by SDS-PAGE. HC denotes the class I MHC heavy chain; CHO, high mannose-type glycans; and CHO*, complex-type glycans.
Figure 21B:
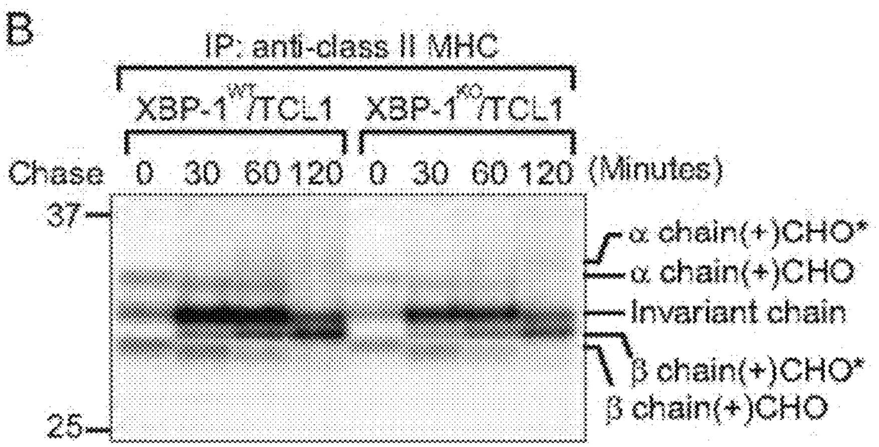
FIG. 21B: CLL cells isolated 12-month-old XBP-$1^{WT}$/Eμ-TCL1 and XBP-$1^{KO}$/Eμ-TCL1 mice were labeled with [$^{3}$S]-methionine and [$^{3}$S]-cysteine for 15 min, chased for the indicated times, and lysed. Lysates were immunoprecipitated using antibodies against the class II MHC molecules. Immunoprecipitates were analyzed by SDS-PAGE. HC denotes the class I MHC heavy chain; CHO, high mannose-type glycans; and CHO*, complex-type glycans.

Constitutive BCR activation is a survival signal for CLL cells (Zenz, T., Mertens, D., Kuppers, R., Dohner, H. & Stilgenbauer, S. *Nat Rev Cancer* 10, 37-50 (2010); Woyach, J. A., Johnson, A. J. & Byrd, J. C. *Blood* 120, 1175-1184 (2012)). To understand how the loss of XBP-1 can contribute to the slower progression of leukemia in Eμ-TCL1 mice, CLL cells were purified from XBP-$1^{WT}$/Eμ-TCL1 and XBP-$1^{KO}$/Eμ-TCL1 littermates (FIG. 18B-FIG. 18C), cultured in LPS for 3 days, then the BCR was activated using F(ab')2 anti-mouse IgM, and the cells were lysed. Cell lysates were immunoblotted for phospho-Syk and phospho-BTK because Syk and BTK are BCR signaling molecules for CLL survival (Zenz, T., Mertens, D., Kuppers, R., Dohner, H. & Stilgenbauer, S. *Nat Rev Cancer* 10, 37-50 (2010); Woyach, J. A., Johnson, A. J. & Byrd, J. C. *Blood* 120, 1175-1184 (2012)). Compared to XBP-$1^{WT}$/Eμ-TCL1 CLL cells, XBP-$1^{KO}$/Eμ-TCL1 CLL cells are defective in Syk and BTK phosphorylation upon activation of the BCR (FIG. 20A). Different from naïve normal B cells, XBP-$1^{WT}$/Eμ-TCL1 CLL cells can synthesize the secretory forms of IgM and release them into culture media in the absence of any stimulation (FIG. 20B-FIG. 20C). The lack of XBP-1 leads to dramatically decreased synthesis of secretory μ heavy chains, resulting in decreased secretion of IgM into culture media. Both XBP-$1^{WT}$/Eμ-TCL1 and XBP-$1^{KO}$/Eμ-TCL1 CLL cells produce comparable amounts of membrane-bound μ heavy chains (FIG. 20B). The μ heavy chains can be assembled with κ light chains in the ER to form membrane-bound IgM (mIgM), which can be delivered to the cell surface (FIG. 20B). While CLL cells isolated from XBP-$1^{WT}$/Eμ-TCL1 mice acquire monoclonality, as evidenced by the use of a unique κ light chain, XBP-1-deficient CLL cells undergo slower clonal selection (FIG. 20B-FIG. 20C). The synthesis, assembly and transport of the class I and class II MHC molecules are similar when comparing XBP-$1^{WT}$/Eμ-TCL1 and XBP-$1^{KO}$/Eμ-TCL1 CLL cells (FIG. 21A-FIG. 21B).

XBP-1 Deficiency Leads to Increased Surface Expression of S1P1, but not Other Critical B-Cell Markers in Eμ-TCL1 CLL Cells.

Figure 22A:
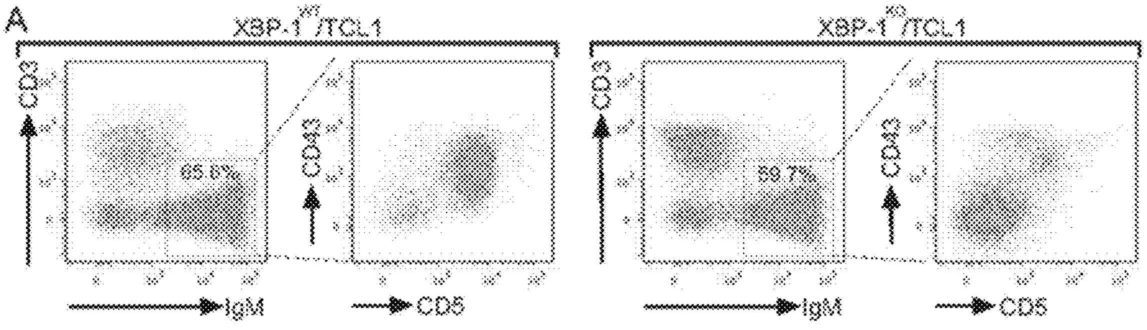
FIG. 22A: Splenocytes isolated from approximately 9-month-old XBP-$1^{WT}$/Eμ-TCL1 and XBP-$1^{KO}$/Eμ-TCL1 mice were stained with monoclonal antibodies against CD3, IgM, CD5 and CD43. The expression of CD43 on the surface of CD5− B cells and CD5+ CLL cells were analyzed on gated CD3−/IgM+ B cell populations of the spleens.
Figure 22B:
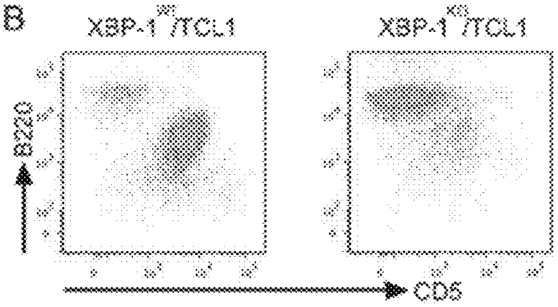
FIG. 22B: Splenocytes isolated from approximately 9-month-old XBP-$1^{WT}$/Eμ-TCL1 and XBP-$1^{KO}$/Eμ-TCL1 mice were stained with monoclonal antibodies against CD3, IgM, CD5 and an additional marker, B220. The expression of the indicated marker on the surface of CD5− B cells and CD5+ CLL cells were analyzed on gated CD3−/IgM+ B cell populations of the spleens.
Figure 22C:
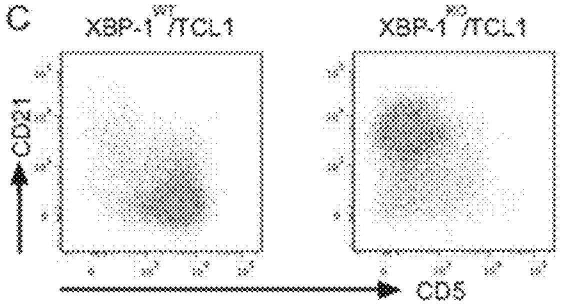
FIG. 22C: Splenocytes isolated from approximately 9-month-old XBP-$1^{WT}$/Eμ-TCL1 and XBP-$1^{KO}$/Eμ-TCL1 mice were stained with monoclonal antibodies against CD3, IgM, CD5 and an additional marker, CD21. The expression of the indicated marker on the surface of CD5− B cells and CD5+ CLL cells were analyzed on gated CD3−/IgM+ B cell populations of the spleens.
Figure 22D:
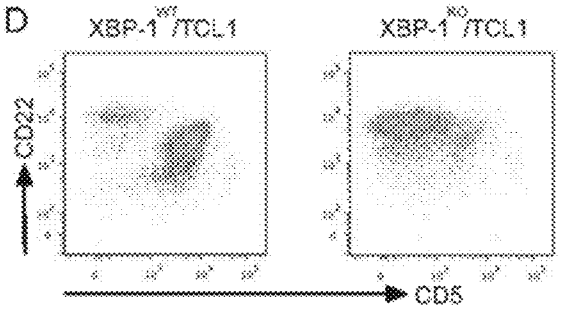
FIG. 22D: Splenocytes isolated from approximately 9-month-old XBP-$1^{WT}$/Eμ-TCL1 and XBP-$1^{KO}$/Eμ-TCL1 mice were stained with monoclonal antibodies against CD3, IgM, CD5 and an additional marker, CD22. The expression of the indicated marker on the surface of CD5− B cells and CD5+ CLL cells were analyzed on gated CD3−/IgM+ B cell populations of the spleens.
Figure 22E:
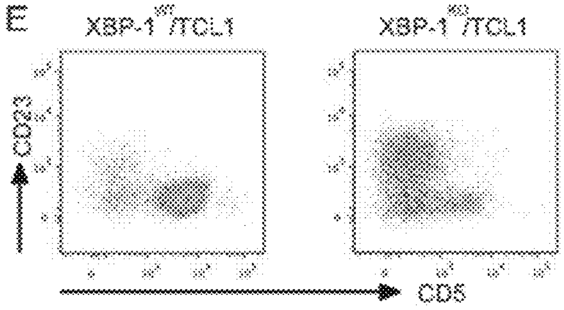
FIG. 22E: Splenocytes isolated from approximately 9-month-old XBP-$1^{WT}$/Eμ-TCL1 and XBP-$1^{KO}$/Eμ-TCL1 mice were stained with monoclonal antibodies against CD3, IgM, CD5 and an additional marker, CD23. The expression of the indicated marker on the surface of CD5− B cells and CD5+ CLL cells were analyzed on gated CD3−/IgM+ B cell populations of the spleens.
Figure 22F:
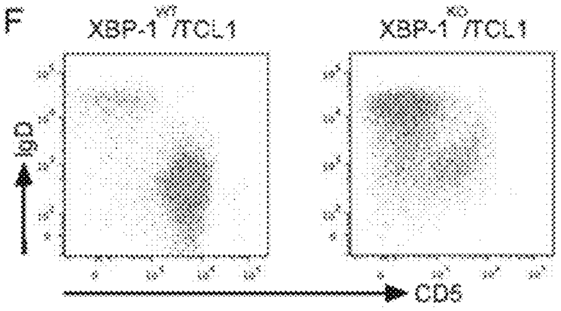
FIG. 22F: Splenocytes isolated from approximately 9-month-old XBP-$1^{WT}$/Eμ-TCL1 and XBP-$1^{KO}$/Eμ-TCL1 mice were stained with monoclonal antibodies against CD3, IgM, CD5 and an additional marker, IgD. The expression of the indicated marker on the surface of CD5− B cells and CD5+ CLL cells were analyzed on gated CD3−/IgM+ B cell populations of the spleens.
Figure 22G:
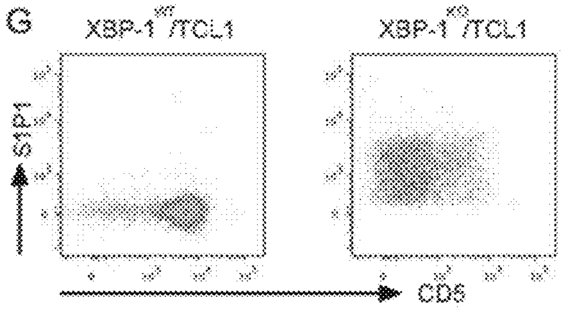
FIG. 22G: Splenocytes isolated from approximately 9-month-old XBP-$1^{WT}$/Eμ-TCL1 and XBP-$1^{KO}$/Eμ-TCL1 mice were stained with monoclonal antibodies against CD3, IgM, CD5 and an additional marker, S1P1. The expression of the indicated marker on the surface of CD5− B cells and CD5+ CLL cells were analyzed on gated CD3−/IgM+ B cell populations of the spleens.
Figure 22H:
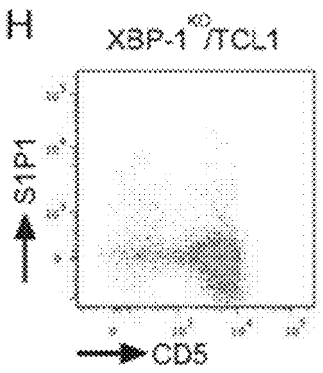
FIG. 22H: Splenocytes isolated from a 14-month-old XBP-$1^{KO}$/Eμ-TCL1 mouse were stained with monoclonal antibodies against CD3, IgM, CD5 and S1P1, and similarly analyzed.
Figure 23A:
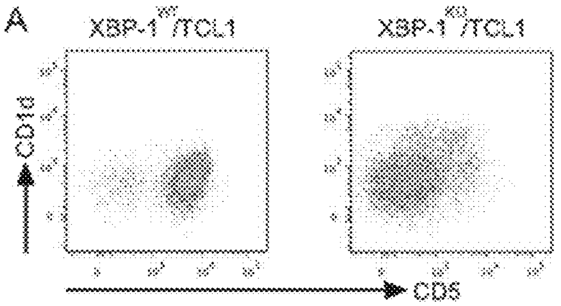
FIG. 23A displays splenocytes isolated from approximately 9-month-old XBP-$1^{WT}$/Ep TCL1 and XBP-$1^{KO}$/Eμ-TCL1 mice were stained with monoclonal antibodies against CD3, IgM, CD5 together with the following B cell surface marker: CD1d. The expression of each specific marker on the surface of CD5− B cells and CD5+ CLL cells were analyzed on gated CD3−/IgM+ B cell populations in the mouse spleens.
Figure 23B:
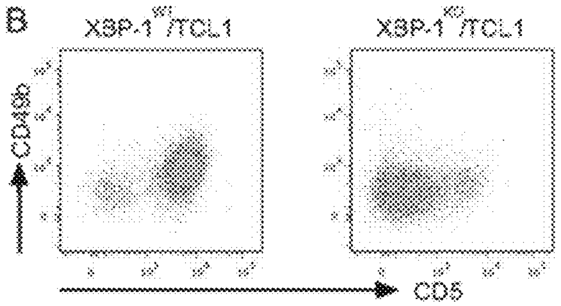
FIG. 23B displays splenocytes isolated from approximately 9-month-old XBP-$1^{WT}$/Eμ-TCL1 and XBP-$1^{KO}$/Eμ-TCL1 mice were stained with monoclonal antibodies against CD3, IgM, CD5 together with the following B cell surface marker: CD49b. The expression of each specific marker on the surface of CD5− B cells and CD5+ CLL cells were analyzed on gated CD3−/IgM+ B cell populations in the mouse spleens.
Figure 23C:
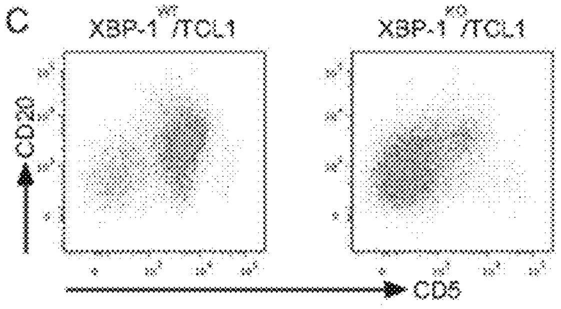
FIG. 23C displays splenocytes isolated from approximately 9-month-old XBP-$1^{WT}$/Eμ-TCL1 and XBP-$1^{KO}$/Eμ-TCL1 mice were stained with monoclonal antibodies against CD3, IgM, CD5 together with the following B cell surface marker: CD20. The expression of each specific marker on the surface of CD5− B cells and CD5+ CLL cells were analyzed on gated CD3−/IgM+ B cell populations in the mouse spleens.
Figure 23D:
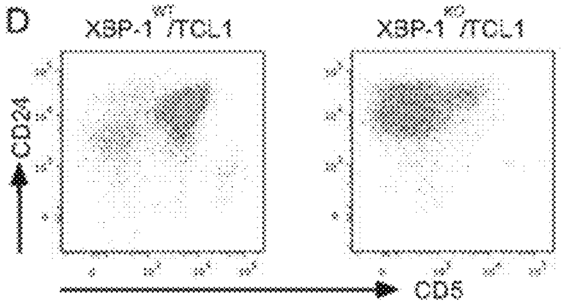
FIG. 23D displays splenocytes isolated from approximately 9-month-old XBP-$1^{WT}$/Ep TCL1 and XBP-$1^{KO}$/Eμ-TCL1 mice were stained with monoclonal antibodies against CD3, IgM, CD5 together with the following B cell surface marker: CD24. The expression of each specific marker on the surface of CD5− B cells and CD5+ CLL cells were analyzed on gated CD3−/IgM+ B cell populations in the mouse spleens.
Figure 23E:
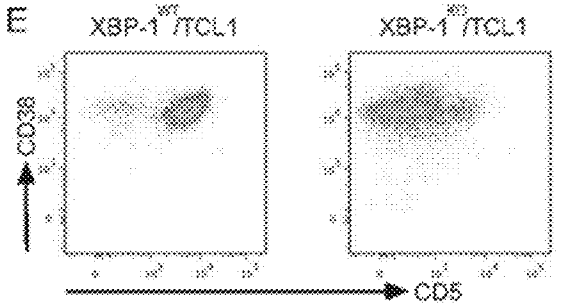
FIG. 23E displays splenocytes isolated from approximately 9-month-old XBP-$1^{WT}$/Ep TCL1 and XBP-$1^{KO}$/Eμ-TCL1 mice were stained with monoclonal antibodies against CD3, IgM, CD5 together with the following B cell surface marker: CD38. The expression of each specific marker on the surface of CD5− B cells and CD5+ CLL cells were analyzed on gated CD3−/IgM+ B cell populations in the mouse spleens.
Figure 23F:
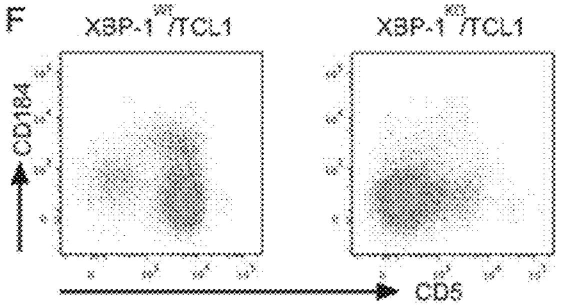
FIG. 23F displays splenocytes isolated from approximately 9-month-old XBP-$1^{WT}$/Eμ-TCL1 and XBP-$1^{KO}$/Eμ-TCL1 mice were stained with monoclonal antibodies against CD3, IgM, CD5 together with the following B cell surface marker: CD184. The expression of each specific marker on the surface of CD5− B cells and CD5+ CLL cells were analyzed on gated CD3−/IgM+ B cell populations in the mouse spleens.
Figure 23G:
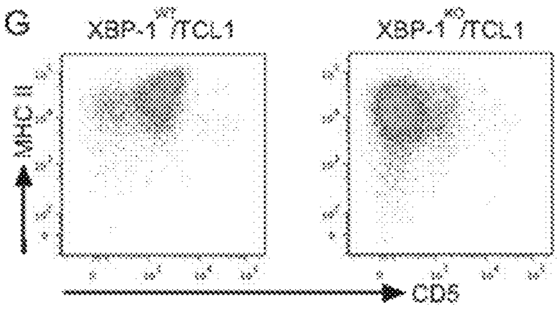
FIG. 23G displays splenocytes isolated from approximately 9-month-old XBP-$1^{WT}$/Ep TCL1 and XBP-$1^{KO}$/Eμ-TCL1 mice were stained with monoclonal antibodies against CD3, IgM, CD5 together with the following B cell surface marker: class II MHC. The expression of each specific marker on the surface of CD5− B cells and CD5+ CLL cells were analyzed on gated CD3−/IgM+ B cell populations in the mouse spleens.
Figure 23H:
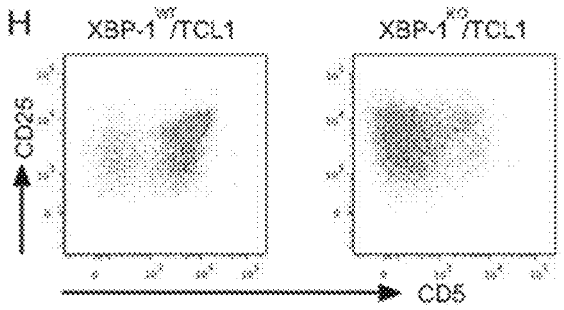
FIG. 23H displays splenocytes isolated from approximately 9-month-old XBP-$1^{WT}$/Ep TCL1 and XBP-$1^{KO}$/Eμ-TCL1 mice were stained with monoclonal antibodies against CD3, IgM, CD5 together with the following B cell surface marker: CD25. The expression of each specific marker on the surface of CD5− B cells and CD5+ CLL cells were analyzed on gated CD3−/IgM+ B cell populations in the mouse spleens.
Figure 23I:
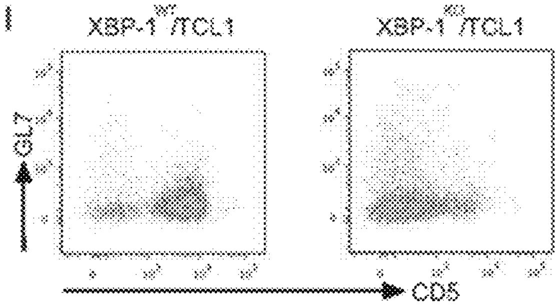
FIG. 23I displays splenocytes isolated from approximately 9-month-old XBP-$1^{WT}$/Ep TCL1 and XBP-$1^{KO}$/Eμ-TCL1 mice were stained with monoclonal antibodies against CD3, IgM, CD5 together with the following B cell surface marker: GL7. The expression of each specific marker on the surface of CD5− B cells and CD5+ CLL cells were analyzed on gated CD3−/IgM+ B cell populations in the mouse spleens.
Figure 23J:
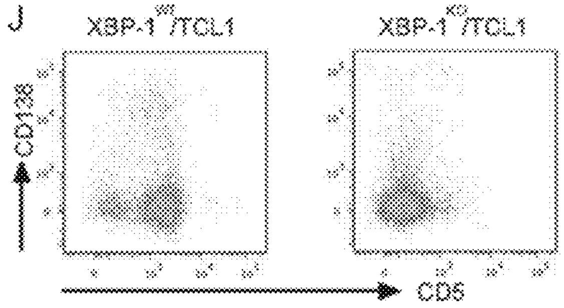
FIG. 23J displays splenocytes isolated from approximately 9-month-old XBP-$1^{WT}$/Ep TCL1 and XBP-$1^{KO}$/Eμ-TCL1 mice were stained with monoclonal antibodies against CD3, IgM, CD5 together with the following B cell surface marker: CD138. The expression of each specific marker on the surface of CD5− B cells and CD5+ CLL cells were analyzed on gated CD3−/IgM+ B cell populations in the mouse spleens.

In addition to the BCR, CLL cells express critical surface proteins that contribute to their survival. To determine how XBP-1 deficiency contributes to the surface expression of B-cell markers on Eμ-TCL1 CLL cells, age-matched XBP-$1^{WT}$/Eμ-TCL1 and XBP-$1^{KO}$/Eμ-TCL1 mice, in the spleens of which still contain CD5− precancerous B cells and CD5+ CLL cells, were investigated. When Eμ-TCL1 CD5− B cells turn into CD5+ CLL cells, increased surface expression of CD43, and decreased expression of B220, CD21, CD22, CD23 and IgD (FIG. 22A-FIG. 22H) was observed. There is little change in the surface expression of CD1d, CD49b, CD20, CD24, CD38, CD184, MHC class II molecules, CD25, and GL7. In contrast to multiple myeloma cells, these CLL cells do not express CD138 (FIG. 23A-FIG. 23J). Notably, S1P1 is expressed at the elevated levels on the surface of the XBP-$1^{KO}$/Eμ-TCL1 B cells (FIG. 22G). Although XBP-$1^{KO}$/Eμ-TCL1 B cells eventually express similar levels of S1P1 when they turn into CD5+ CLL cells (FIG. 22H), the initial increased expression of S1P1 as a result of XBP-1 deficiency can contribute to opposing homing signals and facilitate the egress of CLL cells from spleens and lymph nodes, leading to delayed leukemic progression (Capitani, N., et al. *Blood* 120, 4391-4399 (2012)).

A Potent IRE-1 Inhibitor, B-H09, Derived from Chemical Synthesis of 4μ8C Analogs Interacts with IRE-1 in B Cells.

In an effort to develop IRE-1 RNase inhibitors with improved potency and cellular efficacy, the expression and purification of recombinant human IRE-1 for use in an in vitro fluorescence resonance energy transfer (FRET)-suppression assay carried out (Wiseman, R. L., et al. *Mol Cell* 38, 291-304 (2010)). The cytoplasmic kinase/RNase domain (aa. 547-977) of IRE-1 was expressed as a puritin-His-tagged IRE-1 fusion protein in SF21 insect cells and purified by Ni-NTA affinity chromatography (FIG. 24A). The activity of the recombinant IRE-1 was evaluated using a synthetic mRNA stem-loop corresponding to the XBP-1 substrate sequence. This stem-loop incorporates a Cy5 fluorophore on its 5' end and the black hole quencher (BHQ) on its 3' end, resulting in fluorescence only upon site-specific cleavage by IRE-1 (FIG. 24B). IRE-1 exhibits functional RNase activity with a $K_m$ value of 45 nM (FIG. 24C).

First, salicylaldehyde-based compounds A-I06 and 4μ8C, which are known to potently inhibit XBP-1 mRNA splicing by IRE-1 (Kriss, C. L., et al. *Blood* 120, 1027-1038 (2012); Cross, B. C., et al. *Proc Natl Acad Sci USA* 109, E869-878 (2012)), were assayed. The $IC_{50}$ value of each compound was calculated by the fluorescence readout which is inversely correlated with the capability of a compound to inhibit IRE-1 from cleaving the XBP-1 stem-loop substrate. The coumarin derivative 4μ8C exhibited an $IC_{50}$ of 155 nM in the FRET suppression assay, while A-I06 displayed weaker activity in vitro. The chemical synthesis of a library of A-I06 and 4μ8C analogs, of which B-H09 stands out as the most potent inhibitor with an $IC_{50}$ of 111 nM (FIG. 24D-FIG. 24E), was then conducted. The aldehyde moiety of each of these inhibitors is believed to be critical for inhibition of RNase function, allowing the formation of an unusual but highly specific Schiff base with lysine 907 in the RNase domain of IRE-1 (Cross, B. C., et al. *Proc Natl Acad Sci USA* 109, E869-878 (2012); Tomasio, S. M., Harding, H. P., Ron, D., Cross, B. C. & Bond, P. J. *Mol Biosyst* 9, 2408-2416 (2013)). Indeed, protection of the aldehyde group of B-H09 as an acid-labile 1,3-dioxane acetal (as in B-I08) resulted in a 16-fold drop in inhibitory activity.

Next, a biotin-tagged derivative, B-I06, was prepared in order to carry out direct binding experiments with endogenously expressed IRE-1 in B cells. In a FRET-suppression assay, it was confirmed that B-I06 essentially retains the potency of its parent compound in vitro ($IC_{50}$=136 nM), while the reduced (primary alcohol) derivative B-I07 was found to be inactive. As confirmation that B-H09 interacts with IRE-1, it was shown that B-I06 but not the negative control B-I07, can pull down IRE-1 from mouse B cell lysates via the use of a monoclonal anti-biotin antibody immobilized to protein G-conjugated agarose beads (FIG. 24F).

IRE-1 Inhibitors with Masked Aldehyde Moieties Exert Stronger Effects in Suppressing XBP-1s and Leukemic Cell Growth.

A-I06 induces cell death in multiple myeloma and CLL cells without imposing toxicity to normal B cells or to mice (Kriss, C. L., et al. *Blood* 120, 1027-1038 (2012); Papandreou, I., et al. *Blood* 117, 1311-1314 (2011)). Consistent with the $IC_{50}$ values derived from in vitro FRET-suppression assay, B-H09 is significantly more effective than A-I06 in inhibiting the splicing of XBP-1 mRNA in human WaC3 CLL cells as determined by RT-PCR (FIG. 24G). At the protein level, B-H09 effectively blocks the expression of XBP-1s in lipopolysaccharide (LPS)-stimulated B cells, while A-I06 requires a higher concentration to achieve complete inhibition (FIG. 24H). The dose-dependent efficacy of B-H09 in suppressing XBP-1s expression in LPS-stimulated B cells was also assessed, and an approximate $IC_{50}$ value of 5.1 μM was determined by immunoblots followed by quantitation using densitometry (FIG. 24I). To establish growth inhibitory effects, Eμ-TCL1 CLL cells were with these inhibitors (20 μM) and it was found that B-H09 is more potent than A-I06 and the closely related coumarin derivative 4μ8C in inhibiting mouse CLL cell growth (FIG. 24J). To optimize the cellular efficacy of B-H09, it was tested whether the 1,3-dioxane group in B-I08 can serve as a putative prodrug moiety, thus avoiding potential interactions of the aldehyde with serum proteins in culture media prior to cell entry. The aqueous solubility of B-I08 was also enhanced through removal of allyloxycarbonyl group to afford B-I09. Although B-I08 and B-I09 exhibited weaker activity in the FRET-suppression assay, both were highly effective in inhibiting splicing of XBP-1 mRNA in human WaC3 cells and the expression of XBP-1s in LPS-stimulated B cells (FIG. 24E, FIG. 24G and FIG. 24H). The water soluble 1,3-dioxane derivative B-I09 is more effective than B-H09 and 4μ8C in suppressing the growth of mouse Eμ-TCL1 CLL cells (FIG. 24J). B-I09 is the most potent inhibitor of the growth of CLL cells freshly isolated from human patients (FIG. 24J-FIG. 24L). LC-MS was used to confirm that the 1,3-dioxane protecting group of B-I09 remains completely intact after 48-h exposure to the FRET-suppression assay buffer (pH 7.4), and remains greater than 50% intact after incubation in cell culture media at 37° C. for 24 h (FIG. 25A-FIG. 25E). These results suggest that the 1,3-dioxane moiety improves cellular uptake, and can decompose to reveal the bioactive aldehyde once inside the cell. This decomposed compound, C-B06, has an $IC_{50}$ of 248 nM, and can inhibit splicing of XBP-1 mRNA and expression of XBP-1s in human MEC1 and MEC2 CLL cell lines (FIG. 25C-FIG. 25E).

Protein Trafficking Pathways are Unaffected by Inhibiting the IRE-1/XBP-1 Pathway Using B-I09.

Figure 19I:
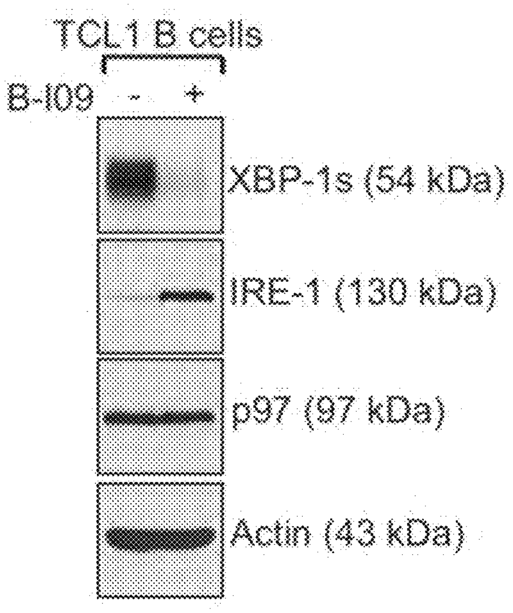
FIG. 19I: B-I09 treatment leads to the upregulated expression of IRE-1. Eμ-TCL1 B cells were cultured in LPS for 2 days, subsequently treated with B-I09 (20 μM) for an additional day, and lysed for analysis of the expression of XBP-1s, IRE-1, p97 and actin by immunoblots.

Secretory protein transport in mammalian cells posits an intricate process, as it involves coordination between chaperones, glycosyltransferases, GTPases and vesicular transport systems (Ellgaard, L. & Helenius, A. *Nat Rev Mol Cell Biol* 4, 181-191 (2003)). Minor defects in post-translational modifications, folding, or assembly of a membrane protein can stall transport and lead to proteolysis. Thus, whether B-I09 can impose adverse effects on this process was tested. To investigate the trafficking of mIgM to the cell surface, μS−/− B cells, which have been genetically manipulated to allow for the expression of only membrane-bound μ heavy chain, were used (Boes, M., et al. *J Immunol* 160, 4776-4787 (1998)). B cells were stimulated with LPS for two days to allow the expression of XBP-1s, after which these B cells were treated for additional 24 h with B-I09 to inhibit the expression of XBP-1s, pulse chase experiments were performed, and IgM was immunoprecipitated from cell lysates and culture media using an anti-κ antibody. The surface display of mIgM is clearly not affected by treatment with B-I09, as evidenced by successful acquisition of complex glycans on membrane-bound μ heavy chains (FIG. 26A). The B-I09-treated μS−/− B cells also produce comparable amounts of membrane-bound μ chains and κ light chains, and the latter can be secreted into culture media (FIG. 26B). In addition, B-I09-treated μS−/− and wild-type B cells synthesize, assemble and present class I MHC molecules, Igα and Igβ to their surface normally (FIG. 26C-FIG. 26D, FIG. 27C-FIG. 27D). Similar to genetic XBP-1-deficient CLL cells, B-I09-treated B cells are ineffective in synthesizing secretory μ chains (FIG. 27A-FIG. 27B, FIG. 20B-FIG. 20C). These data show that B-I09 phenocopies genetic XBP-1 knockout and does not indiscriminately target other critical cellular mechanisms, such as those involved in protein transport. Similar to genetic XBP-1-deficient CLL cells, B-I09-treated B cells are ineffective in synthesizing secretory μ chains (4 B-4E). B-I09 also phenocopies genetic XBP-1 knockout by upregulating the expression levels of IRE-1 (FIG. 19A, FIG. 19F, and FIG. 19I).

Inhibition of the IRE-1/XBP-1 Pathway Compromises BCR Signaling and Synergizes with Ibrutinib to Induce Apoptosis in B Cell Cancer.

Genetic XBP-1 deficiency is known to compromise BCR signaling (Hu, C. C., Dougan, S. K., McGehee, A. M., Love, J. C. & Ploegh *Embo J* 28, 1624-1636 (2009)) (FIG. 20A), which is crucial for the survival of CLL (Zenz, T., Mertens, D., Kuppers, R., Dohner, H. & Stilgenbauer, S. *Nat Rev Cancer* 10, 37-50 (2010); Woyach, J. A., Johnson, A. J. & Byrd, J. C. *Blood* 120, 1175-1184 (2012)). To examine whether B-I09 can phenocopy genetic XBP-1 knockout in compromising BCR signaling, B cells were cultured from wild-type and Eμ-TCL1 mice in LPS and B-I09 for 48 h. These cells were subsequently stimulated with F(ab')2 anti-mouse IgM and analyzed for the phosphorylation of BTK, a central BCR signaling molecule serving as a promising target for the treatment of CLL (Ponader, S., et al. *Blood* 119, 1182-1189 (2012)). Similar to XBP-1-deficient B cells, B-I09-treated wild-type and Eμ-TCL1 B cells exhibit compromised BCR signaling, as evidenced by reduced phosphorylation of BTK (FIG. 28A).

In recent clinical studies, the treatment of human CLL with ibrutinib (a specific inhibitor of BTK) has led to significantly improved prognosis (Burger, J. A. & Buggy, J. J. *Leuk Lymphoma* (2013); Advani, R. H., et al. *J Clin Oncol* 31, 88-94 (2013); Byrd, J. C., et al. *The New England Journal of Medicine* 369, 32-42 (2013)). Since inhibition of the IRE-1/XBP-1 pathway results in reduced phosphorylation of BTK, whether B-I09 can aggrandize the effect of ibrutinib was tested. Ibrutinib was synthesized using an optimized protocol to reduce cost and guarantee steady supply. When mouse Eμ-TCL1 CLL cells were treated with B-I09 in combination with ibrutinib, enhanced growth inhibition, possibly because such a combination can effectively block phosphorylation of AKT upon BCR activation on LPS-stimulated Eμ-TCL1 B cells (FIG. 28L-FIG. 28M) was shown. Of note, TCL1 drives leukemia via activation of AKT.

When ibrutinib was combined with B-I09 (dual serial dilution) to treat human MEC1, MEC2 and WaC3 CLL cell lines for 48 h, $GI_{50}$ (50% growth inhibition) concentrations for ibrutinib (between 10-20 μM) and B-I09 (between 30-40 μM) were determined, and strong synergistic effect in suppressing human CLL cell growth (FIG. 28B-FIG. 28D; Table 1) was observed. When treating these human CLL cell lines with 10 μM ibrutinib, 20 μM B-I09, or a combination of the two for a course of 4 days, >80% growth inhibition occurs within the first two days of combined treatment (FIG. 28E-FIG. 28G). Although MEC1 and MEC2 cells become resistant to treatment with ibrutinib or B-I09 alone, both cell lines are highly sensitive to the combined treatment (FIG. 28E-FIG. 28F). WaC3 cells are sensitive to ibrutinib, B-I09 and the combination (FIG. 28G). The expression of XBP-1s was confirmed to be suppressed by B-I09 in all three human CLL cell lines (FIG. 28H, FIG. 28G), and that the growth inhibition is a result of apoptosis, as evidenced by proteolytic cleavage of procaspase-3 and PARP in B-I09-treated human CLL cells (FIG. 28I).

TABLE 1

Synergism of B-I09 and ibrutinib. The indicated human cell lines were plated in 384-well plates and then treated concurrently with B-I09 and ibrutinib for 48 h. Cell viability was measured by a CellTiter-Blue assay (Promega), and results were used to calculate the Chou and Talalay combination index (CI) value at effect levels of 0.75, 0.9 and 0.95 as well as the mean value for all three effect levels. CI values represent the mean +/− the standard error of the mean (SEM) for 2 or 3 independent replicate experiments. CI values can be characterized for additivity, synergy or antagonism as described by Chou (Ref. 35).

| | | CI at effect levels | | | CI | | | |
|---|---|---|---|---|---|---|---|---|
| Line | Cancer type | 0.75 | 0.9 | 0.95 | Mean | SEM | Rank | n |
| MEC1 | B-Chronic Lymphocytic Leukemia | 0.561 | 0.660 | 0.761 | 0.661 | 0.582 | +++ | 2 |
| MEC2 | B-Chronic Lymphocytic Leukemia | 0.333 | 0.276 | 0.247 | 0.285 | 0.139 | ++++ | 2 |
| WaC3 | B-Chronic Lymphocytic Leukemia | 0.335 | 0.246 | 0.202 | 0.261 | 0.016 | ++++ | 2 |
| U266 | Multiple Myeloma | 0.802 | 0.780 | 0.797 | 0.793 | 0.249 | ++ | 2 |
| RPMI-8226 | Multiple Myeloma | 0.803 | 0.655 | 0.575 | 0.677 | 0.119 | +++ | 2 |
| NCI-H929 | Multiple Myeloma | 0.508 | 0.425 | 0.378 | 0.437 | 0.163 | +++ | 2 |
| HBL2 | Mantle Cell Lymphoma | 0.558 | 0.568 | 0.518 | 0.581 | 0.038 | +++ | 2 |
| Jeko | Mantle Cell Lymphoma | 0.941 | 0.874 | 0.842 | 0.886 | 0.092 | + | 2 |
| Mino | Mantle Cell Lymphoma | 0.906 | 0.797 | 0.734 | 0.813 | 0.145 | ++ | 2 |
| Z138 | Mantle Cell Lymphoma | 0.849 | 0.719 | 0.649 | 0.739 | 0.090 | ++ | 3 |

A combination index of <0.3 is represented as ++++ ranking and indicates strong synergism by this method. Other CI symbols and descriptions of combination effects are as follows: 0.3-0.7, +++, synergism; 0.7-0.85, ++, moderate synergism; 0.85-0.90, +, slight synergism; 0.90-1.10, and ±, nearly additive.

The IRE-1/XBP-1 pathway is important for the survival of multiple myeloma (MM), malignancies derived from plasma cells (Papandreou, I., et al. *Blood* 117, 1311-1314 (2011); Mimura, N., et al. *Blood* 119, 5772-5781 (2012)).

Several MM cell lines (mouse 5TGM1, human RPMI-8226, human U266, and human NCI-H929) were examined, and it was shown that B-I09 can effectively suppress the expression of XBP-1s (FIG. 29A). The combination of B-I09 with ibrutinib exerts a synergistic cytotoxic effect against all four MM cell lines (FIG. 28J and FIG. 29B-FIG. 29E). Mantle cell lymphoma (MCL) is an incurable non-Hodgkin's lymphoma derived from mature B cells in the mantle zone. Since the role of the IRE-1/XBP-1 pathway in MCL is completely unknown, four human MCL cell lines (HBL2, Jeko, Mino, and Z138) were examined for the expression of XBP-1s, and it was discovered that XBP-1s is constitutively expressed by all four human MCL cell lines (FIG. 30A). Treatment with B-I09 for 24 h effectively inhibits the expression of XBP-1s in these MCL cells (FIG. 30A). The combination of B-I09 with ibrutinib similarly exerts synergistic cytotoxicity against all four human MCL cell lines (FIG. 28K and FIG. 30B-FIG. 30E). The synergistic cytotoxicity is a result of apoptosis in both human MM and MCL cells (FIG. 31A-FIG. 31B).

B-I09 Suppresses Leukemic Progression without Imposing Systemic Toxicity in Mice.

To determine the appropriate dosing of B-I09 in vivo, mice were intraperitoneally injected with B-I09 (50 mg/kg). B-I09 has a half-life of ~1.5 h and reaches its peak concentration of ~39 μM in mouse plasma serum 15 min after administration (FIG. 32A). Tumor-bearing Eμ-TCL1 mice in which CLL cells comprise the majority of the lymphocytes in the peripheral blood (FIG. 33) were selected. The mice were then treated with 50 mg/kg B-I09 on the first five days of each week for three weeks. Clear CLL regression in the peripheral blood was observed (FIG. 32B). After treatment with B-I09 for three weeks, the numbers of lymphocytes in the peripheral blood dropped close to the normal range of 500-5000 cells/μL (FIG. 32C). Immunoblots showed that B-I09 inhibits the expression of XBP-1s in CLL cells collected from the peripheral blood of B-I09-injected Eμ-TCL1 mice (FIG. 32D). Since CLL cells proliferate in secondary lymphoid organs and are protected from cell death through interactions with microenvironments, whether B-I09 has an effect on CLL cells residing in the spleen was evaluated. When comparing mice injected with DMSO or B-I09 (50 mg/kg) for three weeks, a significant increase in apoptotic CD5+ CLL cells in the spleens of B-I09-injected mice (FIG. 32E-FIG. 32F) was shown. Injection of B-I09 has no apparent adverse effects or toxicity to mice, as evidenced by no significant weight loss or apparent histological changes to vital organs, such as liver, lungs, kidney and heart, after three weeks of treatment (FIG. 32G-FIG. 32H).

Discussion

Overexpression of XBP-1s in mouse B cells leads to monoclonal gammopathy of undetermined significance (MGUS) (Carrasco, D. R., et al *Cancer Cell* 11, 349-360 (2007)), a precursor syndrome of MM. Inhibitors that block the splicing of XBP-1 mRNA by IRE-1 were discovered through screening chemical libraries (Volkmann, K., et al. *J Biol Chem* 286, 12743-12755 (2011); Papandreou, I., et al. *Blood* 117, 1311-1314 (2011); Cross, B. C., et al. *Proc Natl Acad Sci USA* 109, E869-878 (2012)). While the inhibitor STF-083010 (or A-I06) shows promising results in the treatment of MM and CLL (Kriss, C. L., et al. *Blood* 120, 1027-1038 (2012); Papandreou, I., et al. *Blood* 117, 1311-1314 (2011)), it is shown that B-cell-specific deletion of the XBP-1 gene can decelerate leukemic progression in mice. These data provide the strongest validation of the IRE-1/XBP-1 pathway as a target for therapeutic intervention in B cell cancer (FIG. 19A-FIG. 19I). By chemical synthesis, a 'prodrug' inhibitor was developed, B-I09, which is highly effective in suppressing the expression of XBP-1s and leukemic cell growth (FIG. 24A-FIG. 24L and FIG. 32A-FIG. 32G).

The expression of XBP-1s is for the survival of B-cell leukemia and lymphoma (FIG. 24J-FIG. 24L, FIG. 28A-FIG. 28M, FIG. 29A-FIG. 29E, FIG. 30A-FIG. 30E, FIG. 31A-31B, FIG. 32A-FIG. 32H). Notably, CLL cells freshly purified from spleens of Eμ-TCL1 mice produce significantly increased amounts of secretory IgM relative to B cells isolated from spleens of wild-type mice (FIG. 20B-FIG. 20C). Deletion of the XBP-1 gene from Eμ-TCL1 CLL cells specifically inhibits synthesis of secretory IgM but not membrane-bound IgM or class I and class II MHC molecules (FIG. 20B-FIG. 20C and FIG. 21A-FIG. 21B). Eμ-TCL1 CLL cells thus require the expression of XBP-1s to support the production of secretory IgM.

Deletion or inhibition of the IRE-1/XBP-1 pathway can compromise BCR signaling (FIG. 20A and FIG. 28A). Because the survival of mature B-cell cancer relies on activation of the BCR (Zenz, T., Mertens, D., Kuppers, R., Dohner, H. & Stilgenbauer, S. *Nat Rev Cancer* 10, 37-50 (2010); Gururajan, M., *Jennings, C. D.* & Bondada, S. *J Immunol* 176, 5715-5719 (2006)), this makes targeting the IRE-1/XBP-1 pathway even more attractive for the therapy of B cell leukemia and lymphoma. Targeting BCR signaling in CLL and MCL using ibrutinib is considered to be one of the most exciting breakthroughs in B-cell cancer therapy (Burger, J. A. & Buggy, J. J. *Leuk Lymphoma* (2013); Advani, R. H., et al. *J Clin Oncol* 31, 88-94 (2013); Byrd, J. C., et al. *The New England Journal of Medicine* 369, 32-42 (2013); Wang, M. L., et al. *The New England Journal of Medicine* 369, 507-516 (2013)). The pharmacological synergism between B-I09 and ibrutinib in inducing apoptosis of human CLL, MCL and MM cells suggests a promising treatment strategy for B-cell cancer (FIG. 28A-FIG. 28M, FIG. 29A-FIG. 29E, FIG. 30A-FIG. 30E, and FIG. 31A-FIG. 31B).

Example 3: Synthesis of Novel Tricyclic Chromenone-Based Inhibitors of IRE-1 RNase Activity Unless stated otherwise, reactions were performed in flame-dried glassware under a positive pressure of argon or nitrogen gas using dry solvents. Commercial grade reagents and solvents were used without further purification except where noted. Diethyl ether, toluene, dimethylformamide dichloromethane, and tetrahydrofuran were purified by a Glass Contour column-based solvent purification system. Other anhydrous solvents were purchased directly from chemical suppliers. Thin-layer chromatography (TLC) was performed using silica gel 60 F254 pre-coated plates (0.25 mm). Flash chromatography was performed using silica gel (60 μm particle size). The purity of all compounds was judged by TLC analysis (single spot/two solvent systems) using a UV lamp, CAM (ceric ammonium molybdate), ninhydrin, or basic $KMnO_4$ stain(s) for detection purposes. 1D and 2D NMR spectra were recorded on a Varian 400 MHz spectrometer. Proton chemical shifts are reported as δ values relative to residual signals from deuterated solvents ($CDCl_3$, $CD_3OD$, or DMSO-$d_6$). The purity of all assayed compounds was determined by RP-HPLC using an analytical $C_{18}$ column with MeCN/water (0.1% formic acid) as eluent (4×150 mm column, 1 mL/min flow rate). All final compounds were determined to be between 95 and 98% pure. Compounds 2, 5, 8, 10-12, and 14-were purchased from commercial sources. Compounds 1 and 9 were synthesized as described previously.

Antibodies against IRE-1 (Cell Signaling), PARP (Cell Signaling), XBP-1s (Santa Cruz), p97 (Fitzgerald), and actin (Sigma), were obtained commercially.

Primary B cells were purified from wild-type mouse spleens by negative selection using anti-CD43 magnetic beads (Miltenyi Biotech). These cells as well as the human mantle cell lymphoma (MCL) cell lines Mino and Jeko were cultured in RPMI 1640 media (Gibco) supplemented with 10% heat-inactivated fetal bovine serum (FBS), 2 mM L-glutamine, 100 U/ml penicillin G sodium, 100 μg/ml streptomycin sulfate, 1 mM sodium pyruvate, 0.1 mM non-essential amino acids, and 0.1 mM β-mercaptoethanol (β-ME).

Synthesis of b-Ketoester Derivatives, 18a-d

A solution of the appropriate (N-Alloc) amino acid 17 (23.9 mmol) in 100 mL of dichloromethane (DCM) at 0° C. was treated with 2,2-dimethyl-1,3-dioxane-4,6-dione (4.47 g, 31.0 mmol), 4-dimethylaminopyridine (2.92 g, 23.9 mmol), and diisopropylcarbodiimide (3.70 mL, 23.9 mmol). The reaction was stirred from 0° C. to room temperature over 4 h, then washed with 10% aq. $KHSO_4$ followed by brine. The organic layer was dried over $Na_2SO_4$ and concentrated. The resulting colorless liquid was dissolved in 50 mL of a 10:1 MeOH:toluene mixture and stirred at reflux for 15 h. After cooling, the reaction was concentrated under reduced pressure. Purification by flash column chromatography over silica gel (25%-60% EtOAc/hexanes) afforded 18a, 18b, and 18d as colorless oils. Alkylidene pyrrolidine 18c was obtained as a white solid.

Methyl 5-(((allyloxy)carbonyl)amino)-3-oxobutanoate (18a)

Obtained in 64% yield from 17a. $^1$H NMR (400 MHz, $CDCl_3$) δ 5.88 (ddt, J=16.2, 10.7, 5.6 Hz, 1H), 5.49 (s, 1H), 5.29 (d, J=17.2 Hz, 1H), 5.20 (d, J=10.5 Hz, 1H), 4.56 (d, J=5.5 Hz, 2H), 4.18 (d, J=5.1 Hz, 2H), 3.72 (s, 3H), 3.50 (s, 2H); $^{13}$C NMR (101 MHz, $CDCl_3$) δ 198.2. 167.0, 156.1, 132.5, 117.9, 66.0, 52.6, 50.8, 46.2; HRMS (ESI-TOF) m/z $[M+H]^+$ calcd for $C_9H_{14}NO_5$ 216.0867, found 216.0862.

Methyl 5-(((allyloxy)carbonyl)amino)-3-oxopentanoate (18b)

Obtained in 94% yield from 17b. $^1$H NMR (400 MHz, $CDCl_3$) δ 5.97-5.82 (m, 1H), 5.37-5.12 (m, 3H), 4.53 (d, J=5.6 Hz, 2H), 3.73 (s, 3H), 3.50-3.37 (m, 4H), 2.80 (t, J=5.7 Hz, 2H); $^{13}$C NMR (101 MHz, $CDCl_3$) δ 202.2, 167.3, 156.2, 132.8, 132.8, 117.6, 117.5, 65.4, 52.4, 52.4, 48.9, 42.8, 35.3; HRMS (ESI-TOF) (m/z) $[M+H]^+$ calcd for $C_{10}H_{16}NO_5$ 230.10285, found 230.10297.

Allyl 2-(2-methoxy-2-oxoethylidene)pyrrolidine-1-carboxylate (18c)

Obtained in 56% yield from 17c. $^1$H NMR (400 MHz, $CDCl_3$) δ 6.52 (s, 1H), 5.94 (ddt, J=17.2, 10.5, 5.7 Hz, 1H), 5.33 (d, J=17.2 Hz, 1H), 5.25 (d, J=10.4 Hz, 1H), 4.66 (d, J=5.7 Hz, 2H), 3.73 (t, J=7.2 Hz, 2H), 3.65 (s, 3H), 3.17 (t, J=7.7 Hz, 2H), 1.91 (p, J=7.5 Hz, 2H); 13C NMR (101 MHz, $CDCl_3$) δ 169.2, 157.3, 152.6, 131.9, 118.5, 96.4, 66.6, 50.8, 49.5, 31.6, 21.1; HRMS (ESI-TOF) m/z $[M+H]^+$ calcd for $C_{11}H_{16}NO_4$ 226.1074, found 226.1068.

Methyl 7-(((allyloxy)carbonyl)amino)-3-oxoheptanoate (18d)

Obtained in 65% yield from 17d. $^1$H NMR (400 MHz, $CDCl_3$) δ 5.89 (ddt, J=16.2, 10.7, 5.4 Hz, 1H), 5.28 (dd, J=17.2, 1.5 Hz, 1H), 5.19 (dd, J=10.4, 1.1 Hz, 1H), 4.82 (s, 1H), 4.53 (d, J=5.5 Hz, 2H), 3.72 (s, 3H), 3.43 (s, 2H), 3.16 (dd, J=12.9, 6.5 Hz, 2H), 2.56 (t, J=7.1 Hz, 2H), 1.68-1.57 (m, 2H), 1.56-1.43 (m, 2H); 13C NMR (101 MHz, $CDCl_3$) δ 202.4, 167.6, 156.3, 132.9, 117.6, 65.4, 52.4, 49.0, 42.4, 40.5, 29.1, 20.2; HRMS (ESI-TOF) m/z $[M+H]^+$ calcd for $C_{12}H_{20}NO_5$ 258.1336, found 258.1326.

Synthesis of Coumarin Derivatives, 19a-d

A solution of the appropriate b-keto ester 18 (10.1 mmol) in 50 mL of methanesulfonic acid at 0° C. was treated with resorcinol (1.11 g, 10.1 mmol) and stirred for 3.5 h. The mixture was poured into ice cold water and the resulting yellow mixture was filtered. The filtrate was extracted with EtOAc and combined with the solids. The combined organic layer was concentrated and purified by flash chromatography over silica gel (0-20% MeOH/$CHCl_3$) to afford the pure coumarin derivatives 19a-d.

Allyl (2-(7-hydroxy-2-oxo-2H-chromen-4-yl) methyl)carbamate (19a)

Obtained in 36% yield from 18a. $^1$H NMR (400 MHz, DMSO-$d_6$) δ 10.60 (s, 1H), 7.88 (t, J=5.9 Hz, 1H), 7.64 (d, J=8.7 Hz, 1H), 6.78 (d, J=8.7 Hz, 1H), 6.73 (d, J=2.3 Hz, 1H), 5.99 (s, 1H), 5.92 (ddt, J=17.0, 10.6, 5.4 Hz, 1H), 5.29 (dd, J=17.2, 1.6 Hz, 1H), 5.18 (d, J=10.5 Hz, 1H), 4.52 (d, J=5.3 Hz, 2H), 4.37 (d, J=5.8 Hz, 2H); $^{13}$C NMR (101 MHz, DMSO-$d_6$) δ 161.7, 160.8, 156.6, 155.4, 154.2, 134.0, 126.2, 117.6, 113.4, 110.3, 107.9, 102.8, 65.2, 41.0; HRMS (ESI-TOF) m/z $[M+H]^+$ calcd for $C_1H_{14}NO_5$ 276.0867, found 276.0863.

Allyl (2-(7-hydroxy-2-oxo-2H-chromen-4-yl)ethyl) carbamate (19b)

Obtained in 88% yield from 18b. $^1$H NMR (400 MHz, DMSO-$d_6$) δ 10.55 (s, 1H), 7.68 (d, J=8.8 Hz, 1H), 7.40 (m, 1H), 6.80 (dd, J=8.7, 2.3 Hz, 1H), 6.71 (d, J=2.3 Hz, 1H), 6.07 (s, 1H), 5.99-5.78 (m, 1H), 5.24 (m, 1H), 5.15 (m, 1H), 4.45 (m, 2H), 3.29 (m, 2H), 2.87 (t, J=6.7 Hz, 2H); $^{13}$C NMR (101 MHz, DMSO-$d_6$) β 161.1, 160.3, 156.0, 155.2, 154.2, 133.8, 133.7, 126.3, 116.9, 113.0, 111.3, 110.5, 110.4, 102.5, 102.4, 64.3, 31.5, 23.4; HRMS (ESI-TOF) (m/z) $[M+H]^+$ calcd for $C_{16}H_{16}NO_5$ 302.10285, found 302.10305.

Allyl (2-(7-hydroxy-2-oxo-2H-chromen-4-yl)propyl) carbamate (19c)

Obtained in 88% yield from 18c. $^1$H NMR (400 MHz, DMSO-$d_6$) δ 10.53 (s, 1H), 7.61 (d, J=8.8 Hz, 1H), 7.33 (t, J=5.5 Hz, 1H), 6.78 (d, J=8.7, 1H), 6.69 (d, J=2.4 Hz, 1H), 6.10 (s, 1H), 5.89 (ddt, J=17.0, 10.6, 5.4 Hz, 1H), 5.25 (dd, J=17.2, 1.6 Hz, 1H), 5.15 (d, J=10.4 Hz, 1H), 4.45 (d, J=5.3 Hz, 2H), 3.07 (q, J=6.6 Hz, 2H), 2.72 (t, J=7.6 Hz, 2H), 1.96-1.63 (m, 2H); $^{13}$C NMR (101 MHz, DMSO-$d_6$) δ 161.5, 160.8, 157.0, 156.4, 155.6, 134.3, 126.7, 117.3, 113.3, 111.6, 109.9, 102.9, 64.6, 40.2, 28.7, 28.6; HRMS (ESI-TOF) m/z $[M+H]^+$ calcd for $C_{16}H_{18}NO_5$ 304.1180, found 304.1172.

Allyl (2-(7-hydroxy-2-oxo-2H-chromen-4-yl)butyl) carbamate (19d)

Obtained in 84% yield from 18d. $^1H$ NMR (400 MHz, DMSO-$d_6$) δ 10.50 (s, 1H), 7.60 (d, J=8.8 Hz, 1H), 7.21 (t, J=5.7 Hz, 1H), 6.76 (d, J=8.7 Hz, 1H), 6.67 (d, J=2.4 Hz, 1H), 6.05 (s, 1H), 5.86 (ddt, J=17.2, 10.5, 5.3 Hz, 1H), 5.22 (dd, J=17.2, 1.7 Hz, 1H), 5.11 (dd, J=10.4, 1.6 Hz, 1H), 4.42 (d, J=5.3 Hz, 2H), 3.00 (d, J=6.1 Hz, 2H), 2.69 (t, J=7.4 Hz, 2H), 1.62-1.51 (m, 2H), 1.51-1.42 (m, 2H); $^{13}C$ NMR (101 MHz, DMSO-$d_6$) δ 161.5, 160.9, 157.5, 156.4, 155.5, 134.3, 126.8, 117.2, 113.3, 111.6, 109.7, 102.8, 64.5, 40.2, 31.0, 29.5, 25.8; HRMS (ESI-TOF) m/z $[M+H]^+$ calcd for $C_{17}H_{20}NO_5$ 318.1336, found 318.1339.

Duff Reaction of Coumarin Derivatives: Condition A

The appropriate coumarin derivative 19 (0.73 mmol) in 9 mL of AcOH was treated with HMTA (255 mg, 1.82 mmol) and stirred for 18 h at 95° C. The reaction mixture was concentrated and the resulting slurry was dissolved in 12 mL of a 1:1 1 M aq. HCl:EtOAc solution and stirred at 60° C. for 2 h. The organic layer was separated and the aqueous layer was extracted with EtOAc. The combined organic layers were washed with water, dried with $MgSO_4$, and concentrated. Purification by silica gel flash column chromatography (EtOAc/hexane) afforded the desired bicyclic formyl derivatives 20a-d.

Duff Reaction of Coumarin Derivatives: Condition B

The appropriate coumarin derivative 19 (0.73 mmol) in 3 mL of TFA was treated with HMTA (255 mg, 1.82 mmol) and stirred for 18 h at 75° C. The reaction mixture was concentrated and the resulting slurry was dissolved in 12 mL of a 1:1 1 M aq. HCl:EtOAc solution and stirred at 60° C. for 2 h. The organic layer was separated and the aqueous layer was extracted with EtOAc. The combined organic layers were washed with water, dried with $MgSO_4$, and concentrated. Purification by silica gel flash column chromatography (EtOAc/Hexane) afforded the desired bicyclic and tricyclic formyl derivatives.

Duff Reaction of Coumarin Derivatives: Condition C

The appropriate coumarin derivative 19 (0.47 mmol) in 15 mL of MeCN was treated with pyridine (18.5 mg, 0.23 mmol) and acetic anhydride (239 mg, 2.35 mmol). After stirring for 6 hours at room temperature, the reaction was diluted with brine and extracted with EtOAc. The organic layer was dried with $MgSO_4$ and concentrated. The resulting crude product was dissolved in 2 mL of TFA was treated with HMTA (164 mg, 1.17 mmol) and stirred for 18 h at 95° C. The reaction mixture was concentrated and the resulting slurry was dissolved in 12 mL of a 1:1 1 M aq. HCl:EtOAc solution and stirred at 60° C. for 2 h. The organic layer was separated and the aqueous layer was extracted with EtOAc. The combined organic layers were washed with water, dried with $MgSO_4$, and concentrated. Purification by silica gel flash column chromatography (EtOAc/Hexane) afforded the desired bicyclic and tricyclic formyl derivatives.

Allyl (2-(8-formyl-7-hydroxy-2-oxo-2H-chromen-4-yl)methyl)carbamate (20a)

Obtained in 4% yield (Methods A, B, and C) from 19a. $^1H$ NMR (400 MHz, $CDCl_3$) δ 12.24 (s, 1H), 10.60 (s, 1H), 7.73 (d, J=9.0 Hz, 1H), 6.91 (d, J=9.0 Hz, 1H), 6.32 (s, 1H), 5.94 (ddt, J=16.5, 11.1, 5.8 Hz, 1H), 5.34 (d, J=17.2 Hz, 1H), 5.27 (d, J=10.3 Hz, 1H), 5.19 (t, J=5.6 Hz, 1H), 4.64 (dt, J=5.7, 1.4 Hz, 2H), 4.54 (d, J=6.3 Hz, 2H); $^{13}C$ NMR (101 MHz, $CDCl_3$) δ 193.3, 165.4, 159.1, 156.3, 156.1, 152.1, 132.2, 131.8, 118.5, 114.7, 109.74, 109.71, 108.8, 66.4, 41.3; HRMS (ESI-TOF) m/z $[M+H]^+$ calcd for $C_{15}H_{14}NO_6$ 304.0816, found 304.0820.

Allyl (2-(8-formyl-7-hydroxy-2-oxo-2H-chromen-4-yl)ethyl)carbamate (20b)

Obtained in 10% yield (Method A) from 19b. $^1H$ NMR (400 MHz, $CDCl_3$) δ 12.24 (s, 1H), 10.60 (s, 1H), 7.92 (d, J=9.1 Hz, 1H), 6.93 (d, J=9.0 Hz, 1H), 6.19 (s, 1H), 5.90 (m, 1H), 5.39-5.15 (m, 2H), 5.03 (bs, 1H), 4.58 (m, 2H), 3.49 (m, 2H), 2.99 (t, J=7.2 Hz, 2H); $^{13}C$ NMR (101 MHz, $CDCl_3$) δ 193.5, 193.4, 165.5, 159.2, 156.6, 156.5, 153.4, 133.1, 132.6, 118.2, 114.8, 112.2, 112.1, 111.1, 109.0, 66.0, 40.1, 32.8; HRMS (ESI-TOF) (m/z) $[M+H]^+$ calcd for $C_{16}H_{16}NO_6$ 318.09777, found 318.09746.

Allyl (2-(8-formyl-7-hydroxy-2-oxo-2H-chromen-4-yl)propyl)carbamate (20c)

Obtained in 13% yield (Method A) from 19c. $^1H$ NMR (400 MHz, $CDCl_3$) δ 12.20 (s, 1H), 10.58 (s, 1H), 7.72 (d, J=9.0 Hz, 1H), 6.88 (d, J=9.0 Hz, 1H), 6.19 (s, 1H), 5.90 (ddt, J=16.8, 11.1, 5.6 Hz, 1H), 5.29 (dd, J=17.2, 1.5 Hz, 1H), 5.20 (dd, J=10.4, 1.2 Hz, 1H), 4.98 (t, J=5.2 Hz, 1H), 4.56 (d, J=5.4 Hz, 2H), 3.33 (q, J=6.5 Hz, 2H), 2.98-2.59 (m, 2H), 1.90 (tt, J=13.7, 6.9 Hz, 2H); $^{13}C$ NMR (101 MHz, $CDCl_3$) δ 193.4, 165.2, 159.3, 156.4, 156.3, 155.6, 132.7, 132.5, 117.9, 114.4, 111.0, 110.9, 108.8, 65.7, 40.4, 29.1, 28.5; HRMS (ESI-TOF) m/z $[M+H]^+$ calcd for $C_{17}H_{18}NO_6$ 332.1129, found 332.1128.

Allyl (2-(8-formyl-7-hydroxy-2-oxo-2H-chromen-4-yl)butyl)carbamate (20d)

Obtained in 15% yield (Method A) from 19d. $^1H$ NMR (400 MHz, $CDCl_3$) δ 12.22 (s, 1H), 10.60 (s, 1H), 7.74 (d, J=9.0 Hz, 1H), 6.89 (d, J=9.0 Hz, 1H), 6.17 (s, 1H), 5.90 (ddt, J=16.1, 10.8, 5.7 Hz, 1H), 5.29 (dd, J=17.2, 1.6 Hz, 1H), 5.20 (dd, J=10.4, 1.3 Hz, 1H), 4.80 (s, 1H), 4.55 (d, J=5.6 Hz, 2H) 3.26 (q, J=6.4 Hz, 2H), 2.93-2.56 (m, 2H), 1.78-1.56 (m, 4H); $^{13}C$ NMR (101 MHz, $CDCl_3$) δ 139.4, 165.2, 159.4, 156.38, 156.37, 156.1, 132.8, 132.7, 117.8, 114.4, 111.1, 111.0, 109.8, 65.6, 40.3, 31.5, 29.9, 25.2; HRMS (ESI-TOF) m/z $[M+H]^+$ calcd for $C_{18}H_{20}NO_6$ 346.1285, found 346.1288.

Allyl 7-formyl-8-hydroxy-5-oxo-4,5-dihydro-1H-chromeno[3,4-c]pyridine-3(2H)-carboxylate (21b)

Obtained in 22% (Method B) and 41% (Method C) yield from 19b. $^1H$ NMR (400 MHz, $CDCl_3$) δ 12.15 (s, 1H), 10.61 (s, 1H), 7.68 (d, J=8.4 Hz, 1H), 6.92 (d, J=9.0 Hz, 1H), 5.94 (m, 1H), 5.33 (m, 1H), 5.24 (m, 1H), 4.64 (d, J=5.7 Hz, 2H), 4.47 (m, 2H), 3.81 (t, J=5.8 Hz, 2H), 2.86 (m, 2H); $^{13}C$ NMR (101 MHz, $CDCl_3$) δ 193.3, 164.9, 158.4, 155.2, 154.7, 146.4, 132.7, 131.8, 118.3, 117.2, 114.8, 111.2, 108.7, 66.7, 41.9, 39.2, 24.9; HRMS (ESI-TOF) (m/z) $[M+H]^+$ calcd for $C_{17}H_{16}NO_6$ 330.09721, found 330.09624.

Allyl 8-formyl-9-hydroxy-6-oxo-2,3,5,6-tetrahydro-chromeno[3,4-c]azepine-4(1H)-carboxylate (21c)

Obtained 18% (Method B) and 17% (Method C) yield from 19c. $^1H$ NMR (400 MHz, $CDCl_3$) δ 12.17 (s, 1H), 10.61 (s, 1H), 7.79 (d, J=9.2 Hz, 1H), 6.90 (d, J=8.9 Hz, 1H), 5.87 (ddt, J=16.3, 10.8, 5.3 Hz, 1H), 5.28 (dd, J=17.2, 1.5 Hz, 1H), 5.16 (d, J=10.8 Hz, 1H), 4.65 (s, 2H), 4.55 (d, J=5.1 Hz, 2H), 3.98-3.57 (m, 2H), 3.08-2.96 (m, 2H), 2.13-2.00 (m, 2H); $^{13}$C NMR (101 MHz, $CDCl_3$) δ 193.4, 164.8, 159.3, 155.7, 155.0, 152.2, 132.54, 132.50, 122.0, 117.3, 114.4, 111.9, 108.6, 66.3, 47.8, 42.9, 27.6, 24.6; HRMS (ESI-TOF) m/z $[M+H]^+$ calcd for $C_{18}H_{18}NO_6$ 344.1129, found 344.1137.

Allyl 9-formyl-10-hydroxy-7-oxo-2,3,5,6-tetrahydro-1H-chromeno[3,4-d]azocine-4(7H)-carboxylate (21d)

Obtained in 3% (Method B) and 9% (Method C) yield from 19d. $^1$H NMR (400 MHz, $CDCl_3$) δ 12.18 (s, 1H), 10.61 (s, 1H), 7.78 (d, J=8.6 Hz, 1H), 6.91 (d, J=8.9 Hz, 1H), 5.95 (ddt, J=16.9, 10.8, 5.6 Hz, 1H), 5.32 (d, J=17.1 Hz, 1H), 5.21 (d, J=10.3 Hz, 1H), 4.66 (s, 2H), 4.64 (d, J=4.7 Hz, 2H), 3.62-3.49 (m, 2H), 3.07-2.96 (m, 2H), 1.92-1.80 (m, 2H), 1.80-1.69 (m, 2H); $^{13}$C NMR (101 MHz, $CDCl_3$) δ 139.3, 164.8, 159.1, 155.8, 155.5, 152.0, 132.9, 132.6, 119.5, 117.6, 114.5, 111.3, 108.7, 66.5, 46.2, 44.4, 26.1, 25.7, 25.1; HRMS (ESI-TOF) m/z $[M+H]^+$ calcd for $C_{19}H_{20}NO_6$ 358.1285, found 358.1290.

Allyl 8-hydroxy-7-(hydroxymethyl)-5-oxo-4,5-dihydro-1H-chromeno[3,4-c]pyridine-3(2H)-carboxylate (22)

Compound 21b (24 mg, 73 μmol) in 2 mL of MeOH at 0° C. was treated with sodium borohydride (3.0 mg, 73 μmol) and stirred for 40 min. The reaction was quenched with 1 M aq. HCl and extracted with EtOAc. The organic layers were dried over $Na_2SO_4$ and concentrated. Purification by flash column chromatography over silica gel (40%-50% EtOAc/hexane) afforded 22 as white foam (16 mg, 66%); $^1$H NMR (400 MHz, $CDCl_3$) δ 9.65 (bs, 1H), 7.35 (d, J=8.4 Hz, 1H), 6.85 (d, J=8.7 Hz, 1H), 5.94 (m, J=11.1, 5.6 Hz, 1H), 5.33 (m, 3H), 5.24 (m, 1H), 4.64 (m, 2H), 4.40 (s, 2H), 3.77 (t, J=5.7 Hz, 2H), 2.84 (m, 2H); $^{13}$C NMR (101 MHz, $CDCl_3$) δ 180.6, 160.4, 149.8, 147.8, 132.7, 123.5, 118.2, 114.7, 111.8, 111.1, 66.7, 59.0, 41.8, 39.3, 24.9; HRMS (ESI-TOF) (m/z) $[M+H]^+$ calcd for $C_{17}H_{18}NO_6$ 332.11342, found 332.11473.

Synthesis of allyl 8-hydroxy-7-chloro-5-oxo-4,5-dihydro-1H-chromeno[3,4-c]pyridine-3(2H)-carboxylate (23)

Compound 22 (17 mg, 51 mmol) in 2 mL of DCM at room temperature was treated with thionyl chloride (19 μL, 257 mmol) and stirred for 5.5 h. The reaction was diluted with DCM and washed with sat. aq. $NH_4Cl$, dried over $Na_2SO_4$, and concentrated under reduced pressure. The resulting white solid 23 was sufficiently pure by NMR and HPLC analysis for further use (12 mg, 67%). $^1$H NMR (400 MHz, $CDCl_3$) δ 9.42 (m, 0.5H), 7.69 (m, 0.5H), 7.38 (m, 1H), 6.89 (m, 1H), 5.95 (m, 1H), 5.30 (m, 3H), 4.91 (s, 1H), 4.65 (m, 2H), 4.44 (d, J=17.7 Hz, 2H), 3.79 (m, 2H), 2.85 (m, 2H); $^{13}$C NMR (101 MHz, $CDCl_3$) δ 160.3, 157.9, 151.5, 149.9, 132.7, 124.7, 123.6, 118.3, 114.5, 113.1, 112.7, 112.3, 111.9, 111.2, 66.8, 58.9, 42.0, 39.4, 34.3, 29.8, 24.8; HRMS (ESI-TOF) (m/z) $[M+H]^+$ calcd for $C_{17}H_{16}ClNO_5$ 350.07898, found 346.12850 (observed mass corresponds to the 7-methoxymethyl derivative, resulting from displacement of the chloride with methanol during LCMS).

Synthesis of allyl 7-(1,3-dioxan-2-yl)-8-hydroxy-5-oxo-4,5-dihydro-1H-chromeno[3,4-c]pyridine-3(2H)-carboxylate (24)

A solution of 21b in (150 mg, 455 mmol) in 4 mL of benzene was treated with 1,3-propanediol (99.0 mL, 1.40 mmol) and p-toluenesulfonic acid monohydrate (4.3 mg, 23 mmol) and stirred for 2 h. The reaction was quenched with 2 drops of $NEt_3$, diluted with EtOAc, and washed with brine. The organic layer was dried over $Na_2SO_4$ and concentrated. Purification by flash column chromatography over silica gel (30%-50% EtOAc/hexanes eluent) afforded 24 as a yellow solid (157 mg, 89%). $^1$H NMR (400 MHz, $CDCl_3$) δ 8.82 (s, 1H), 7.36 (d, J=8.2 Hz, 1H), 6.79 (d, J=8.8 Hz, 1H), 6.28 (s, 1H), 5.91 (m, 1H), 5.30 (m, 1H), 5.20 (m, 1H), 4.61 (d, J=5.6 Hz, 2H), 4.39 (s, 2H), 4.28 (dd, J=11.6, J=4.6 Hz, 2H), 4.09 (m, 2H), 3.74 (t, J=5.8 Hz, 2H), 2.79 (m, 2H), 2.26 (m, 1H), 1.53 (m, 1H); $^{13}$C NMR (101 MHz, $CDCl_3$) δ 159.5, 159.3, 155.2, 150.5, 146.6, 132.8, 125.3, 118.0, 116.3, 114.5, 111.8, 109.9, 98.1, 67.9, 66.5, 41.8, 39.3, 25.8, 24.7; HRMS (ESI-TOF) (m/z) $[M+H]^+$ calcd for $C_{20}H_{22}NO_7$ 388.13908, found 388.13810.

Synthesis of allyl 7-(1,3-dithian-2-yl)-8-hydroxy-5-oxo-4,5-dihydro-1H-chromeno[3,4-c]pyridine-3(2H)-carboxylate (25)

Compound 21b (39.0 mg, 118 mmol) and 1,3-propanedithiol (13.0 μL, 130 mmol) in 2.5 mL of DCM at room temperature was treated with $BF_3 \cdot OEt_2$ (6.0 μL, 47 mmol) and stirred for 17 h. The reaction was quenched with sat. aq. $NaHCO_3$ and the aqueous layer was extracted with EtOAc. The combined organic layers were dried over $Na_2SO_4$ and concentrated under reduced pressure. Purification by flash column chromatography over silica gel (25-50% EtOAc/hexane) afforded 25 as a white foam (39 mg, 79%). $^1$H NMR (400 MHz, $CDCl_3$) δ 7.55 (s, 1H), 7.43 (d, J=8.4 Hz, 1H), 6.91 (d, J=8.9 Hz, 1H), 6.26 (s, 1H), 5.95 (m, 1H), 5.33 (m, 1H), 5.24 (m, 1H), 4.64 (m, 2H), 4.47 (m, 2H), 3.78 (t, J=5.8 Hz, 2H), 3.17 (m, 2H), 2.91 (m, 4H), 2.24 (m, 1H), 1.94 (m, 1H); $^{13}$C NMR (101 MHz, $CDCl_3$) δ 159.5, 155.3, 149.8, 146.9, 132.8, 124.8, 118.1, 116.7, 114.9, 112.5, 111.1, 110.6, 77.5, 77.2, 76.8, 66.6, 42.0, 39.2, 37.4, 31.3, 24.9, 24.7, 23.0, 14.3, 14.3. HRMS (ESI-TOF) (m/z) $[M+H]^+$ calcd for $C_{20}H_{22}NO_5S_2$ 420.09399, found 420.09248.

Synthesis of allyl 7-formyl-8-methoxy-5-oxo-4,5-dihydro-1H-chromeno[3,4-c]pyridine-3(2H)-carboxylate (26)

A solution of 24 (20 mg, 52 mmol) in 1 mL DMF was treated with $K_2CO_3$ (36 mg, 258 mmol) followed by iodomethane (10 mL, 155 mmol). After stirring at rt for 18 h, the mixture was diluted with sat. aq. $NH_4Cl$, extracted with DCM, and concentrated to dryness. The residue was taken up in 500 mL of dioxane, treated with 2 mL of 4 M aq. HCl, and stirred at rt for 30 min. The mixture was diluted with water and extracted with DCM. The combined organic layers were dried over $Na_2SO_4$ and concentrated under reduced pressure. Purification by flash column chromatography over silica gel (0-10% MeOH/$CHCl_3$) afforded 26 as a white powder (12 mg, 67%). $^1$H NMR (400 MHz, $CDCl_3$) δ 10.68 (s, 1H), 7.71 (d, J=8.7 Hz, 1H), 6.98 (d, J=9.0 Hz, 1H), 5.95 (m, 1H), 5.33 (m, 1H), 5.24 (m, 1H), 4.65 (m, 2H), 4.48 (s, 2H), 4.01 (s, 3H), 3.82 (t, J=5.8 Hz, 2H), 2.87 (m, 2H); $^{13}C$ NMR (101 MHz, $CDCl_3$) δ 187.2, 162.6, 158.6, 157.2, 155.3, 145.7, 132.8, 132.7, 132.7, 129.7, 118.3, 118.2, 112.9, 112.7, 108.2, 66.7, 56.8, 42.0, 39.3, 29.9, 24.9; HRMS (ESI-TOF) (m/z) $[M+H]^+$ calcd for $C_{18}H_{18}NO_6$ 344.11341, found 344.11432.

Synthesis of allyl 7-formyl-8-benzyloxy-5-oxo-4,5-dihydro-1H-chromeno[3,4-c]pyridine-3(2H)-carboxylate (27)

A solution of 24 (20 mg, 52 mmol) in 1 mL DMF was treated with $K_2CO_3$ (36 mg, 260 mmol) followed by benzyl bromide (9.0 mL, 78 mmol). After stirring at rt for 18 h, the mixture was diluted with sat. aq. $NH_4Cl$, extracted with DCM, and concentrated to dryness. The residue was taken up in 500 mL of dioxane, treated with 2 mL of 4N aq. HCl, and stirred at rt 30 min. The mixture was diluted with water and extracted with DCM. The combined organic layers were dried over $Na_2SO_4$ and concentrated under reduced pressure. Purification by flash column chromatography over silica gel (0-10% MeOH/$CHCl_3$) afforded 27 as a white powder (18 mg, 72%). $^1H$ NMR (400 MHz, $CDCl_3$) δ 10.72 (d, J=5.4 Hz, 1H), 7.67 (d, J=8.6 Hz, 1H), 7.58-7.31 (m, 5H), 7.01 (d, J=9.0 Hz, 1H), 5.95 (m, 1H), 5.35 (m, 0.5H), 5.30 (m, 2.5H), 5.24 (m, 1H), 4.65 (m, 2H), 4.47 (s, 2H), 3.81 (t, J=5.8 Hz, 2H), 2.87 (m, 2H); $^{13}C$ NMR (101 MHz, $CDCl_3$) δ 187.1, 161.7, 158.7, 154.0, 145.6, 135.4, 132.7, 129.5, 128.9, 128.5, 127.0, 118.3, 113.2, 113.1, 109.6, 71.2, 66.7, 51.3, 42.0, 39.2, 29.8, 24.8; HRMS (ESI-TOF) (m/z) $[M+H]^+$ calcd for $C_{24}H_{22}NO_6$ 420.14471, found 420.14529.

Synthesis of 7-(1,3-dioxan-2-yl)-8-hydroxy-3,4-dihydro-1H-chromeno[3,4-c]pyridin-5(2H)-one (28)

A solution of 24 (70 mg, 180 mmol) in 4 mL of DCM at room temperature was treated with phenylsilane (67 mg, 540 mmol) and tetrakis(triphenylphosphine)palladium(0) (10 mg, 9.0 mmol), and stirred at room temperature for 25 min. The reaction was concentrated and the residue purified by flash chromatography over silica gel (0%-10% MeOH/$CHCl_3$) to afford 28 as a yellow solid (54 mg, 98%). $^1H$ NMR (400 MHz, $CDCl_3$) δ 7.35 (d, J=8.8 Hz, 1H), 6.78 (d, J=8.8 Hz, 1H), 6.28 (s, 1H), 4.24 (m, 2H), 4.06 (m, 2H), 3.75 (m, 2H), 3.11 (t, J=5.8 Hz, 2H), 2.70 (m, 2H), 2.36-2.11 (m, 1H), 1.92 (bs, 1H), 1.50 (m, 1H); $^{13}C$ NMR (101 MHz, $CDCl_3$) δ 160.2, 159.0, 150.6, 146.8, 135.0, 125.1, 119.0, 114.3, 112.5, 109.9, 98.3, 68.0, 43.4, 42.0, 25.9, 25.3; HRMS (ESI-TOF) (m/z) $[M+H]^+$ calcd for $C_{16}H_{18}NO_5$ 304.11795, found 304.11782.

Synthesis of 3-acetyl-8-hydroxy-5-oxo-2,3,4,5-tetrahydro-1H-chromeno[3,4-c]pyridine-7-carbaldehyde (29)

A solution of 28 (20 mg, 66 mmol) in 1 mL of DCM was treated with pyridine (11 mL, 130 mmol) and acetyl chloride (7.0 mL, 99 mmol), then stirred at room temperature for 20 min. After concentration under reduced pressure, the residue was taken up in 500 mL of dioxane, treated with 2 mL of 4 M aq. HCl, and stirred at room temperature for 30 min. The mixture was diluted with water and extracted with DCM. The combined organic layers were dried over $Na_2SO_4$ and concentrated under reduced pressure. Purification by flash column chromatography over silica gel (0-10% MeOH/$CHCl_3$) afforded 29 as a white powder (17 mg, 90%). $^1H$ NMR (400 MHz, DMSO-$d_6$) δ 11.84 (s, 1H), 10.46 (s, 1H), 7.90 (m (rotomer), 1H), 7.00 (d, J=8.9 Hz, 1H), 4.32 (m, 2H), 3.73 (t, J=5.7 Hz, 2H), 2.96 (m, 2H), 2.83 (m, 1H), 2.10 (m (rotomer), 3H); $^{13}C$ NMR (101 MHz, DMSO-$d_6$) δ 191.1, 191.0, 168.9, 163.2, 163.1, 158.2, 153.5, 147.0, 146.8, 132.2, 116.7, 116.5, 113.9, 111.1, 109.1, 104.6, 43.2, 41.4, 36.3, 25.0, 24.3, 21.8, 21.3; HRMS (ESI-TOF) (m/z) $[M+H]^+$ calcd $C_{15}H_{14}NO_5$ 288.08720, found 288.08654.

Synthesis of 8-hydroxy-3-methyl-5-oxo-2,3,4,5-tetrahydro-1H-chromeno[3,4-c]pyridine-7-carbaldehyde (30)

A solution of 28 (50.0 mg, 165 mM) in 2 mL of 1:1 dioxane:THF was treated with 37% aq. formaldehyde (27.0 mL, 330 mM), 10% Pd/C (40 mg), placed under $H_2$ atmosphere, and stirred at room temperature for 3 h. The reaction was filtered through celite with MeOH rinsing and concentrated to afford the crude methyl amine. The residue was taken up in 500 mL of dioxane, treated with 2 mL of 4 M aq. HCl, and stirred at room temperature for 30 min. The mixture was diluted with water and extracted with DCM. The combined organic layers were dried over $Na_2SO_4$ and concentrated under reduced pressure. Purification by flash column chromatography over silica gel (0-10% MeOH/$CHCl_3$) afforded 30 as a white powder (35 mg, 67%). $^1H$ NMR (400 MHz, $CDCl_3$) δ 12.15 (s, 1H), 10.61 (s, 1H), 7.66 (d, J=9.0 Hz, 1H), 6.92 (d, J=9.0 Hz, 1H), 3.59 (s, 2H), 3.03-2.97 (m, 2H), 2.97-2.90 (m, 2H), 2.64 (s, 3H); 13C NMR (101 MHz, $CDCl_3$) δ 193.2, 164.8, 158.4, 154.6, 145.5, 131.7, 117.3, 114.6, 111.0, 108.6, 51.6, 50.2, 45.0, 25.3; HRMS (ESI-TOF) m/z $[M+H]^+$ calcd for $C_{14}H_{14}NO_4$ 260.0917, found 260.0915.

Synthesis of 3-benzyl-8-hydroxy-5-oxo-2,3,4,5-tetrahydro-1H-chromeno[3,4-c]pyridine-7-carbaldehyde (31)

A solution of 28 (20 mg, 66 mmol) in 1.5 mL DMF at room temperature was treated with $NEt_3$ (10 mg, 99 mmol) and benzylbromide (12 mg, 73 mmol). After stirring 5 hours, the reaction was concentrated and treated with 4 mL of 4 M aq. HCl and stirred for 1 hour. The reaction was adjusted to pH 7 with 10% aq. $Na_2CO_3$, extracted with DCM, dried over $MgSO_4$, and concentrated. Purification by silica gel flash column chromatography (MeOH/$CHCl_3$) 31 as a white solid (15.4 mg, 70%). $^1H$ NMR (400 MHz, $CDCl_3$) δ 12.15 (s, 1H), 10.61 (s, 1H), 7.65 (d, J=9.0 Hz, 1H), 7.42-7.30 (m, 5H), 6.90 (d, J=9.0 Hz, 1H), 3.87 (s, 2H), 3.59 (s, 2H), 2.94 (s, 4H); $^{13}C$ NMR (101 MHz, $CDCl_3$) δ 193.3, 164.5, 158.8, 154.5, 146.2, 137.1, 131.7, 129.2, 128.5, 127.6, 119.0, 114.3, 111.5, 108.5, 62.3, 50.1, 48.0, 26.0; HRMS (ESI-TOF) m/z $[M+H]^+$ calcd for $C_{20}H_{18}NO_4$ 336.1230, found 336.1224.

Synthesis of 3-(4-Fluorobenzyl)-8-hydroxy-5-oxo-2,3,4,5-tetrahydro-1H-chromeno[3,4-c]pyridine-7-carbaldehyde (32)

A solution of 28 (20 mg, 66 mmol) in 1.5 mL DMF at room temperature was treated with $NEt_3$ (10 mg, 99 mmol) and 4-fluorobenzyl bromide (12 mg, 73 mmol). After stirring 5 h, the reaction was concentrated and treated with 4 mL of 4 M aq. HCl and stirred for 1 h. The reaction was adjusted to pH 7 with 10% aq. $Na_2CO_3$, extracted with DCM, dried over $MgSO_4$, and concentrated. Purification by silica gel flash column chromatography (MeOH/$CHCl_3$) gave 32 as a pale yellow solid (12 mg, 49%). $^1H$ NMR (400 MHz, $CDCl_3$) δ 12.15 (s, 1H), 10.62 (s, 1H), 7.66 (d, J=9.0 Hz, 1H), 7.36 (m, 2H), 7.06 (m, 2H), 6.86 (m, 1H), 3.70 (bs, 2H), 3.51 (m, 2H), 2.86 (m, 4H); $^{13}C$ NMR (101 MHz, $CDCl_3$) δ 193.4, 164.7, 158.8, 156.3, 154.7, 146.2, 143.8, 131.9, 131.0, 127.9, 125.4, 115.7, 115.5, 114.6, 114.0, 111.5, 108.7, 68.7, 68.0, 61.5, 50.4, 48.1, 31.2, 29.9, 26.0; HRMS (ESI-TOF) m/z $[M+H]^+$ calcd for $C_{20}H_{17}FNO_4$ 354.11416, found 354.11438.

Synthesis of 8-hydroxy-3-(2-methylallyl)-5-oxo-2,3,4,5-tetrahydro-1H-chromeno[3,4-c]pyridine-7-carbaldehyde (33)

A solution of 28 (20 mg, 67 mmol) in 1.5 mL DMF at room temperature was treated with $NEt_3$ (10 mg, 99 mmol) and 3-bromo-2-methylpropene (9.9 mg, 74 mmol). After stirring 5 h, the reaction was concentrated and treated with 4 mL of 4 M aq. HCl and stirred for 1 h. The reaction was adjusted to pH 7 with 10% aq. $Na_2CO_3$, extracted with DCM, dried over $MgSO_4$, and concentrated. Purification by silica gel flash column chromatography ($MeOH/CHCl_3$) gave 33 as a yellow solid (15 mg, 75%). $^1H$ NMR (400 MHz, $CDCl_3$) δ 12.14 (s, 1H), 10.61 (s, 1H), 7.66 (d, J=9.0 Hz, 1H), 6.90 (d, J=9.0 Hz, 1H), 5.01 (s, 2H), 3.52 (s, 2H), 3.22 (s, 2H), 2.94 (s, 2H), 2.87 (s, 2H), 1.81 (s, 3H); $^{13}C$ NMR (101 MHz, $CDCl_3$) δ 193.2, 164.6, 158.6, 154.6, 146.0, 140.5, 131.7, 115.3, 114.5, 111.3, 108.5, 105.0, 64.4, 50.2, 48.0, 25.6, 20.8; HRMS (ESI-TOF) m/z $[M+H]^+$ calcd for $C_{17}H_{18}NO_4$ 300.1230, found 300.1223.

Synthesis of 7-Formyl-8-hydroxy-5-oxo-4,5-dihydro-1H-chromeno[3,4-c]pyridine-3(2H)-carboximidamide (34)

A solution of 28 (20 mg, 66 mmol) in 1 mL of DCM was treated with $NEt_3$ (28 mL, 198 mmol) followed by 1,3-di-Boc-2-(trifluoromethylsulfonyl)guanidine (58 mg, 146 mmol) and stirred at room temperature for 18 h. The reaction was diluted with sat. aq. $NH_4Cl$ and extracted with DCM. The combined organic layers were dried over $Na_2SO_4$ and concentrated under reduced pressure. Purification by flash column chromatography over silica gel (40% EtOAc/hexanes) gave the guanidinylated intermediate as a glassy solid. The material was then treated with 2 mL of a 1:1 TFA:DCM solution and stirred at room temperature for 4 h. The reaction was concentrated to remove TFA and the resulting solid was washed with 3 portions of DCM. Drying of the solid under vacuum afforded 34 (12 mg, 63%), which was pure by NMR. $^1H$ NMR (400 MHz, DMSO-$d_6$) δ 11.93 (s, 1H), 10.46 (s, 1H), 7.94 (d, J=9.0 Hz, 1H), 7.64 (m, 3H), 7.02 (d, J=9.0 Hz, 1H), 4.31 (s, 2H), 3.71 (t, J=5.7 Hz, 2H), 2.99 (m, 2H); $^{13}C$ NMR (101 MHz, DMSO-$d_6$) δ 190.8, 163.5, 158.1, 156.3, 153.5, 146.7, 132.3, 115.3, 114.1, 110.9, 109.3, 104.7, 43.2, 41.0, 24.2; HRMS (ESI-TOF) m/z $[M+H]^+$ calcd for $C_{14}H_{14}N_3O_4$ 288.09843, found 288.09881.

Synthesis of allyl 7-formyl-8-(methoxymethoxy)-5-oxo-4,5-dihydro-1H-chromeno[3,4-c]pyridine-3(2H)-carboxylate (35)

Compound 21b (301 mg, 914 mmol) in 5 mL of DCM at 0° C. was treated with DIEA (790 mL, 4.57 mmol) and chloromethyl methyl ether (347 mL, 4.57 mmol). The reaction was stirred for 30 h, quenched with sat. aq. $NH_4Cl$, and the organic layer washed with sat. aq. $NH_4Cl$. The organic layer was dried over $Na_2SO_4$ and concentrated. Purification by flash column chromatography over silica gel (35%-70% EtOAc/hexanes) afforded 35 as a white solid (226 mg, 67%). $^1H$ NMR (400 MHz, $CDCl_3$) δ 10.68 (s, 1H), 7.67 (d, J=8.9 Hz, 1H), 7.20 (d, J=9.0 Hz, 1H), 5.95 (m, 1H), 5.35 (m, 2.5H), 5.30 (m, 0.5H), 5.24 (m, 1H), 4.64 (d, J=5.7 Hz, 2H), 4.48 (s, 2H), 3.81 (t, J=5.8 Hz, 2H), 3.53 (s, 3H), 2.87 (m, 2H); $^{13}C$ NMR (101 MHz, $CDCl_3$) δ 186.8, 160.2, 158.4, 155.0, 153.4, 145.7, 132.6, 129.4, 118.2, 117.9, 113.5, 113.3, 111.4, 94.9, 66.4, 56.8, 41.7, 39.1, 24.7; HRMS (ESI-TOF) (m/z) $[M+H]^+$ calcd for $C_{19}H_{20}NO_7$ 374.12343, found 374.12310.

Synthesis of allyl 7-acetyl-8-hydroxy-5-oxo-4,5-dihydro-1H-chromeno[3,4-c]pyridine-3(2H)-carboxylate (36)

Compound 35 (50.0 mg, 134 mmol) in 2 mL of THE at −78° C. under Ar was treated with 3 M MeMgBr in $Et_2O$ (134 mL, 402 mmol). After 3 h at −78° C., the reaction was carefully quenched then diluted with sat. aq. $NH_4Cl$, warmed to room temperature, and partitioned with EtOAc. The organic layer was dried over $Na_2SO_4$ and concentrated under reduced pressure to give the crude alcohol as an oil.

The above alcohol was dissolved in 3 mL of DCM and treated with Dess-Martin periodinane (123 mg, 291 mmol) and stirred at room temperature for 3 h. the reaction was quenched with 10% aq. $Na_2S_2O_3$ and washed with brine. The organic layer was dried over $Na_2SO_4$, concentrated, and the residue purified by flash column chromatography over silica gel (35-70% EtOAc/Hexane) to give the intermediate ketone as a gum (34 mg, 66%, 2 steps). $^1H$ NMR (400 MHz, $CDCl_3$) δ 7.50 (d, J=8.8 Hz, 1H), 7.13 (d, J=8.9 Hz, 1H), 5.95 (m, 1H), 5.34 (m, 1H), 5.30 (m, 1H), 5.25 (m, 2.5H), 5.21 (m, 0.5H), 4.64 (d, J=5.7 Hz, 2H), 4.45 (m, 2H), 3.80 (t, J=5.8 Hz, 2H), 3.48 (s, 3H), 2.86 (m, 2H), 2.61 (s, 3H); $^{13}C$ NMR (101 MHz, $CDCl_3$) δ 199.1, 158.9, 155.6, 149.3, 145.8, 133.5, 132.7, 125.0, 120.6, 118.2, 114.0, 111.2, 108.6, 94.8, 66.7, 56.7, 42.0, 39.3, 32.7, 29.8, 24.8; HRMS (ESI-TOF) (m/z) $[M+H]^+$ calcd for $C_{20}H_{22}NO_7$ 388.13908, found 388.13945.

The ketone above (9.0 mg, 23 μmol) in 1.5 mL of 33% TFA/DCM solution was stirred for 1.5 h at room temperature. The reaction was concentrated under reduced pressure and the resulting residue was purified by flash column chromatography over silica gel (30% EtOAc/Hexane) to afford 36 as a white foam (6.0 mg, 75%). $^1H$ NMR (400 MHz, $CDCl_3$) δ 13.54 (s, 1H), 7.63 (d, J=8.8 Hz, 1H), 6.95 (d, J=9.0 Hz, 1H), 5.96 (m, 1H), 5.33 (m, 2H), 5.24 (ddd, J=10.4, 2.5, 1.2 Hz, 1H), 4.65 (dt, J=5.7, 1.3 Hz, 2H), 4.47 (m, 2H), 3.81 (t, J=5.8 Hz, 2H), 2.98 (s, 3H), 2.87 (m, 2H); $^{13}C$ NMR (101 MHz, $CDCl_3$) δ 204.4, 166.3, 158.6, 155.3, 153.8, 132.8, 130.2, 118.2, 116.6, 115.7, 111.3, 109.5, 66.7, 41.8, 39.3, 34.2, 25.1; HRMS (ESI-TOF) (m/z) $[M+H]^+$ calcd for $C_{18}H_{18}NO_6$ 344.11286, found 344.11116.

Synthesis of allyl 7-(3-ethoxy-3-oxoprop-1-en-1-yl)-8-hydroxy-5-oxo-4,5-dihydro-1H-chromeno[3,4-c]pyridine-3(2H)-carboxylate (37)

Compound 35 (40.0 mg, 107 mmol) in 2 mL of DCM at room temperature was treated with triethylphosphonoacetate (48.0 mg, 139 mmol) and stirred for 20 h. the reaction was concentrated under reduced pressure. Purification by flash column chromatography over silica gel (20%-40% EtOAc/hexanes) afforded the intermediate ethyl enoate as a white solid (46 mg, 96%). $^1H$ NMR (400 MHz, $CDCl_3$) δ 8.11 (d, J=16.4 Hz, 1H), 7.46 (m, 1H), 7.16 (d, J=9.0 Hz, 1H), 7.05

(d, J=16.4 Hz, 1H), 5.96 (m, 1H), 5.34 (m, 2.5H), 5.30 (m, 0.5H), 5.23 (m, 1H), 4.64 (dt, J=5.6, 1.2 Hz, 2H), 4.46 (s, 2H), 4.28 (q, J=7.1 Hz, 2H), 3.79 (t, J=5.8 Hz, 2H), 3.50 (s, 3H), 2.85 (m, 2H), 1.35 (t, J=7.1 Hz, 3H); $^{13}$C NMR (101 MHz, $CDCl_3$) δ 167.8, 158.5, 151.8, 132.8, 132.7, 132.2, 132.1, 132.1, 132.0, 128.7, 128.5, 125.2, 124.4, 118.1, 113.8, 112.4, 110.9, 94.8, 66.6, 60.7, 56.8, 56.8, 42.0, 39.3, 24.9, 14.5; HRMS (ESI-TOF) (m/z) $[M+H]^+$ calcd for $C_{23}H_{26}NO_8$ 444.16529, found 444.16576.

The above ethyl enoate (20 mg, 45 mmol) in 2 mL MeOH:$CHCl_3$ (3:1) at room temperature was treated with 2 mL of 4N aq. HCl and stirred for 18 h. The reaction was extracted with EtOAc, dried over $Na_2SO_4$, and concentrated under reduced pressure. Purification by flash column chromatography over silica gel (40%-70% EtOAc/hexanes) afforded 37 as a white solid (15 mg, 83%). $^1$H NMR (400 MHz, DMSO-$d_6$) δ 11.57 (m, 1H), 8.01 (d, J=16.3 Hz, 1H), 7.62 (d, J=8.8 Hz, 1H), 6.99 (m, 2H), 5.96 (ddt, J=17.2, 10.6, 5.3 Hz, 1H), 5.31 (m, 1H), 5.22 (m, 1H), 4.59 (dt, J=5.3, 1.4 Hz, 2H), 4.34-4.12 (m, 4H), 3.68 (m, 2H), 2.87 (m, 2H), 1.27 (t, J=7.1 Hz, 3H); $^{13}$C NMR (101 MHz, DMSO-$d_6$) δ 167.0, 160.3, 158.7, 154.3, 151.7, 146.9, 133.3, 133.2, 126.7, 121.5, 117.4, 112.9, 111.3, 108.2, 65.6, 60.1, 41.3, 24.4, 14.3; HRMS (ESI-TOF) (m/z) $[M+H]^+$ calcd for $C_{21}H_{22}NO_7$ 400.13908, found 400.13992.

Synthesis of allyl 8-hydroxy-7-(2-(methylsulfonyl)vinyl)-5-oxo-4,5-dihydro-1H-chromeno[3,4-c]pyridine-3(2H)-carboxylate (38)

LiCl (8.0 mg, 20 mmol) and diethyl(methylsulfonylmethyl) phosphonate (54.0 g, 236 mmol) in 2.5 mL of acetonitrile at room temperature was treated with DBU (24.0 µL, 157 mmol) and stirred for 10 min. Compound 35 (43.0 mg, 131 mmol) in 2 mL of acetonitrile was cannulated into the mixture and stirred for 2 h. The reaction was quenched with sat. aq. $NH_4Cl$, and extracted with EtOAc. Purification by flash column chromatography over silica gel (0-5% MeOH/$CHCl_3$) afforded the intermediate vinyl sulfone as a white solid (41 mg, 79%). $^1$H NMR (400 MHz, $CDCl_3$) δ 8.09 (d, J=15.8 Hz, 1H), 7.68 (d, J=15.8 Hz, 1H), 7.56 (d, J=8.9 Hz, 1H), 7.20 (d, J=9.0 Hz, 1H), 5.95 (m, 1H), 5.34 (m, 2.5H), 5.30 m, 0.5H), 5.23 (m, 1H), 4.64 (m, 2H), 4.46 (s, 2H), 3.80 (t, J=5.8 Hz, 2H), 3.51 (s, 3H), 3.06 (s, 3H), 2.86 (m, 2H); $^{13}$C NMR (101 MHz, $CDCl_3$) δ 158.8, 158.6, 155.3, 152.2, 146.1, 132.7, 131.7, 131.5, 126.8, 118.2, 113.8, 110.9, 109.9, 95.1, 66.6, 57.0, 43.3, 41.9, 39.3, 24.9; HRMS (ESI-TOF) (m/z) $[M+H]^+$ calcd for $C_{21}H_{24}NO_8S$ 450.12172, found 450.12390.

The above vinyl sulfone (38 mg, 84 mmol) in 2.5 mL of acetonitrile:$CHCl_3$ (2:1) was treated with 2.5 mL of 4N aq. HCl and stirred for 20 h at rt. the reaction was concentrated under reduced pressure. The resulting white solid was washed with DCM/$Et_2O$ and the resulting solid dried to afford pure 38 (32 mg, 92%). $^1$H NMR (400 MHz, DMSO-$d_6$) δ 11.78 (s, 1H), 7.87 (d, J=15.7 Hz, 1H), 7.68 (d, J=8.8 Hz, 2H), 7.66 (d, J=15.7 Hz, 2H), 7.01 (d, J=8.9 Hz, 1H), 5.97 (m, 1H), 5.31 (m, 1H), 5.21 (m, 1H), 4.59 (dt, J=5.3, 1.5 Hz, 2H), 4.29 (s, 2H), 3.84 (s, 3H), 3.15 (s, 3H), 2.88 (s, 2H); $^{13}$C NMR (101 MHz, DMSO-$d_6$) δ 160.5, 158.6, 154.3, 151.8, 146.9, 133.3, 130.8, 130.1, 127.6, 117.4, 112.9, 111.3, 106.5, 65.6, 42.6, 41.3, 24.2; HRMS (ESI-TOF) (m/z) $[M+H]^+$ calcd for $C_{19}H_{20}NO_7S$ 406.09550, found 406.09500.

Synthesis of 3-((allyloxy)carbonyl)-8-(methoxymethoxy)-5-oxo-2,3,4,5-tetrahydro-1H-chromeno[3,4-c]pyridine-7-carboxylic acid (39)

Compound 35 (80.0 mg, 214 mmol) and 2-methyl-2-butene (272 mL, 2.57 mmol) in 3.5 mL of t-BuOH:$H_2O$:$CH_3CN$ (3:3:1) at 0° C. was treated with a solution of sodium chlorite (145 mg, 1.29 mmol) and sodium monophosphate (265 mg, 1.93 mmol) in water, dropwise. After 30 min the reaction was quenched with 5% aq. $Na_2S2O_3$. The pH of the solution was adjusted to 6 and extracted with EtOAc. The organic layer was dried over $Na_2SO_4$ and concentrated. Purification by flash column chromatography over silica gel (70%-100% EtOAc/hexanes) afforded 39 as a thick oil (64 mg, 77%). $^1$H NMR (400 MHz, $CDCl_3$) δ 7.57 (d, J=8.2 Hz, 1H), 7.19 (d, J=9.0 Hz, 1H), 6.07 (bs, 12H), 5.96 (m, 1H), 5.33 (m, 2.5H), 5.24 (m, 1H), 4.65 (m, 2H), 4.48 (s, 2H), 3.82 (t, J=5.7 Hz, 2H), 3.52 (s, 3H), 2.90 (m, 2H); 13C NMR (101 MHz, CDCl3) δ 166.5, 163.5, 162.5, 159.9, 156.9, 156.4, 155.4, 150.3, 149.7, 146.7, 132.7, 125.5, 118.3, 113.7, 113.5, 111.5, 111.1, 99.9, 95.0, 94.7, 91.8, 66.8, 56.9, 56.7, 41.9, 41.7, 39.3, 24.8; HRMS (ESI-TOF) (m/z) $[M+H]^+$ calcd for $C_{19}H_{20}NO_8$ 390.11835, found 390.11750.

3-((Allyloxy)carbonyl)-8-hydroxy-5-oxo-2,3,4,5-tetrahydro-1H-chromeno[3,4-c]pyridine-7-carboxylic acid (40)

Compound 39 (32 mg, 82 mmol) in 1 mL of MeOH was treated with 2 mL of 4N aq. HCl and stirred for 20 h at rt. The reaction was concentrated under reduced pressure. Purification by semi-preparative RP-HPLC ($C_{18}$ column, 0%-70% MeCN/$H_2O$ gradient over 20 min) and subsequent lyophilization afforded compound 40 as a white solid (12 mg, 56%). $^1$H NMR (400 MHz, CD3CN) δ 12.39-11.57 (m, 1H), 7.75 (d, J=9.0 Hz, 0.7H), 7.69 (rotamer: d, J=8.9 Hz, 0.3H), 6.95 (dd, J=9.0, 1.0 Hz, 0.7H), 6.85 (rotamer: d, J=8.9 Hz, 0.3H), 5.99 (m, 1H), 5.32 (m, 1H), 5.21 (m, 1H), 4.61 (m, 2H), 4.31 (s, 2H), 3.73 (m, 2H), 2.86 (m, 2H); $^{13}$C NMR (101 MHz, CD3CN) δ 171.4, 165.9, 159.7, 153.7, 148.9, 147.7, 134.3, 131.4, 130.4, 117.6, 116.1, 115.0, 112.9, 102.5, 66.8, 42.4, 42.3, 25.6; HRMS (ESI-TOF) (m/z) $[M+H]^+$ calcd for $C_{17}H_{16}NO_7$ 346.09213, found 346.09198.

Synthesis of 3-allyl 7-methyl 8-hydroxy-5-oxo-4,5-dihydro-1H-chromeno[3,4-c]pyridine-3,7(2H)-dicarboxylate (41)

Compound 39 (20 mg, 51 mmol) in 2 mL of acetone at room temperature was treated with potassium carbonate (10 mg, 77 mmol) and methyl iodide (5.0 µL, 77 mmol) and stirred for 24 h. The reaction was diluted with EtOAc, washed with brine, and dried over $Na_2SO_4$. Purification by flash column chromatography over silica gel (50%-70% EtOAc/hexanes) afforded the intermediate methyl ester as a thick oil (10 mg, 48%). $^1$H NMR (400 MHz, $CDCl_3$) δ 7.51 (d, J=8.2 Hz, 1H), 7.13 (d, J=9.0 Hz, 1H), 5.94 (m, 1H), 5.37-5.18 (m, 4H), 4.63 (m, 2H), 4.44 (s, 2H), 3.98 (s, 3H), 3.78 (t, J=5.8 Hz, 2H), 3.48 (m, 3H), 2.85 (m, 2H); $^{13}$C NMR (101 MHz, $CDCl_3$) δ 164.4, 163.5, 158.8, 156.3, 150.1, 145.6, 132.8, 125.6, 125.4, 118.2, 113.9, 113.4, 111.2, 94.8, 91.9, 66.7, 56.7, 53.2, 42.2, 39.3, 24.8; HRMS (ESI-TOF) (m/z) $[M+H]^+$ calcd for $C_{20}H_{22}NO_8$ 404.13399, found 404.13465.

The above ester (10 mg, 25 mmol) was treated with 1.5 mL of 33% TFA/DCM at room temperature and stirred for 1 h. The excess TFA was removed under reduced pressure to afford 41 as semi-solid (8.0 mg, 90%). $^1$H NMR (400 MHz, $CDCl_3$) δ 11.96 (bs, 1H), 7.63 (d, J=8.5 Hz, 1H), 7.01 (d, 8.9 Hz, 1H), 5.95 (m, 1H), 5.33 (m, 1H), 5.25 (m, 1H), 4.66 (m, 2H), 4.49 (s, 2H), 4.08 (s, 3H), 3.80 (m, 2H), 2.88 (m, 2H); $^{13}$C NMR (101 MHz, $CDCl_3$) δ 170.4, 165.3, 152.8, 152.6, 146.8, 132.5, 129.5, 118.5, 115.1, 111.9, 102.2, 101.0, 67.0, 53.5, 41.8, 39.5, 25.0; HRMS (ESI-TOF) (m/z) $[M+H]^+$ calcd for $C_{18}H_{18}NO_7$ 360.10778, found 360.10759.

Synthesis of allyl 8-hydroxy-7-(methoxy(methyl) carbamoyl)-5-oxo-4,5-dihydro-1H-chromeno[3,4-c] pyridine-3(2H)-carboxylate (42)

Compound 39 (91.0 mg, 276 mmol) and 2-methyl-2-butene (350 mL, 3.31 mmol) in 3.5 mL of $CH_3CN$:$H_2O$ (1:1) at 0° C. was treated with a solution of sodium chlorite (187 mg, 1.66 mmol) and sodium monophosphate (343 mg, 2.48 mmol) in water, dropwise. After 1 h stirring, the reaction was quenched with 5% aq. $Na_2S_2O_3$ solution in water. The pH of the solution was adjusted to 6 and extracted with EtOAc. The organic layer was dried over $Na_2SO_4$ and concentrated under reduced pressure.

The resulting thick oil was dissolved in 4 mL of DCM and treated with 4-N-methyl morpholine (60 mL, 540 mmol), N,O-dimethylhydroxylamine hydrochloride (27 mg, 280 mmol), and EDC (53 mg, 280 mmol). The reaction was stirred for 20 h at room temperature, diluted with DCM, and washed with 1 M aq. HCl. The organic layer was dried over $Na_2SO_4$ and concentrated under reduced pressure. Purification by flash column chromatography over silica gel (3-6% MeOH/$CHCl_3$) to give the intermediate Weinreb amide as a gum (61 mg, 51%, 2 steps) $^1$H NMR (400 MHz, $CDCl_3$) δ 7.50 (d, J=8.6 Hz, 1H), 7.14 (t, J=7.8 Hz, 1H), 5.94 (m, 1H), 5.28 (m, 4H), 4.63 (d, J=5.6 Hz, 2H), 4.42 (m, 2H), 3.96 (s, 0.5H), 3.73 (m, 2H), 3.48 (m, 5.5H), 3.43 (m, 2.5H), 3.14 (s, 0.5H), 2.87 (s, 2H); $^{13}$C NMR (101 MHz, $CDCl_3$) δ 164.3, 159.1, 155.8, 155.3, 149.5, 145.8, 132.8, 125.4, 124.7, 118.2, 115.0, 113.8, 111.1, 94.7, 66.6, 61.8, 61.2, 56.7, 42.1, 39.3, 35.8, 32.4, 24.8; HRMS (ESI-TOF) (m/z) $[M+H]^+$ calcd for $C_{21}H_{25}N_2O_8$ 433.16054, found 433.15886.

The above amide (15 mg, 35 mmol) was treated with 1.5 mL of 33% TFA/DCM at room temperature and stirred for 2 h. The excess TFA was removed under reduced pressure to afford pure 42 as a semi-solid (13 mg, 96%). $^1$H NMR (400 MHz, $CDCl_3$) δ 7.49 (bs, 1H), 6.96 (d, J=7.2 Hz, 1H), 6.88-6.35 (bs 1H), 5.94 (m, 1H), 5.33 (m, 1H), 5.24 (m, 1H), 4.65 (m, 2H), 4.45 (m, 2H), 3.80 (m, 2H), 3.75-3.50 (bs, 3H), 3.39 (s, 3H), 2.87 (m, 2H); $^{13}$C NMR (101 MHz, $CDCl_3$) δ 159.2, 158.9, 155.4, 150.0, 146.6, 132.6, 126.4, 118.3, 116.9, 114.2, 112.0, 108.8, 76.6, 76.5, 66.8, 61.8, 41.9, 39.4, 24.9; HRMS (ESI-TOF) (m/z) $[M+H]^+$ calcd for $C_{19}H_{21}N_2O_7$ 389.13433, found 389.13365.

Recombinant Human IRE-1 Expression and Purification.

Expression of 59.2 kD polyhistidine-tagged puritin-hIRE-1 fusion protein was carried out in SF21 cells using the Bac to Bac expression system (Invitrogen) according to manufacturer specifications. An 8×-His-puritin sequence was fused to the N-terminal end of the cytoplasmic kinase/RNase domain of human IRE-1 (aa. 547-977) in the pFastbacDual-PBL expression vector and included a PreScission protease cleavage site in the linker. Frozen insect cell paste (1 g) was suspended in 8 mL lysis buffer (50 mM Tris/HCl pH 8.0, 300 mM NaCl, 5 mM bME, 10 mM imidazole) containing one protease inhibitor tablet and lysed using sonication. After removal of the cell debris via centrifugation, the supernatant was applied to a Ni(NTA) column (5 mL). After washing untagged protein by flushing with 10 column volumes of lysis buffer, the target protein was eluted using a linear imidazole gradient (15 column volumes, 10-300 mM). Fractions were analyzed via SDS-PAGE. Pooled protein-containing fractions were concentrated and rebuffered into 50 mM Tris, pH 8.0, 150 mM NaCl, 1 mM DTT via ultrafiltration. Typically, 1 L of insect cell culture yielded 3 mg of recombinant 8×-His-puritin-hIRE-1 following Ni(NTA) column purification.

In Vitro IRE-1 RNase FRET-Suppression Assay.

The endoribonuclease activity of recombinant hIRE-1 was assayed by incubation of 50 mL of 10 nM hIRE-1 and 50 mL of various concentrations (0.01-1 mM) of fluorescently tagged XBP-1 RNA stem loop (5'-Cy5-CAGUCCGCAGCACUG-BHQ-3' (SEQ ID NO:9 underlined portion), obtained from Sigma-Aldrich Co.) in assay buffer (20 mM HEPES, pH 7.5, 50 mM KOAc, 0.5 mM $MgCl_2$, 3 mM DTT, 0.4% PEG, and 5% DMSO) for up to 2 hours at room temperature in a black 96-well plate. Fluorescence was read at various time points using a Biotek Synergy H1 plate reader with excitation and emission at 620 nm and 680 nm, respectively. The $K_m$ of purified recombinant hIRE-1 was determined to be 45 nM using the Michaelis-Menten kinetic model. Inhibition of RNA cleavage by small molecules was determined by pre-incubation of 40 mL of 15 nM hIRE-1 with various concentrations of compounds (40 mL) in assay buffer for 30 min at room temperature. A 150 nM solution of fluorescent XBP-1 RNA (40 mL) was then added to each well and the reaction allowed to proceed for 2 hours before reading fluorescence as described above. Final concentrations of hIRE-1 and XBP-1 RNA were 5 nM and 50 nM, respectively. All fluorescence readings were corrected using background values from wells containing only 120 mL of 50 nM XBP-1 RNA. Dose-response experiments were carried out a minimum of 4 times on different days and $IC_{50}$ values calculated from the mean inhibition value at each concentration.

Protein Isolation and Immunoblotting.

Cells were lysed using RIPA buffer (10 mM Tris-HCl, pH 7.4; 150 mM NaCl; 1% NP-40; 0.5% sodium deoxycholate; 0.1% SDS; 1 mM EDTA) supplemented with protease inhibitors (Roche). Protein concentrations were determined by BCA assays (Pierce). Samples were boiled in SDS-PAGE sample buffer (62.5 mM Tris-HCl, pH 6.8; 2% SDS; 10% glycerol; 0.1% bromophenol blue) with β-ME and analyzed by SDS-PAGE. Proteins were transferred to nitrocellulose membranes, blocked in 5% non-fat milk (wt/vol in PBS), and immunoblotted with indicated primary antibodies and appropriate horseradish peroxidase-conjugated secondary antibodies. Immunoblots were developed using Western Lighting Chemiluminescence Reagent (Perkin-Elmer).

Cell Proliferation XTT Assays.

Appropriate numbers of cells were suspended in phenol red-free culture media, seeded in 96-well cell culture plates, and treated with indicated IRE-1 inhibitors. After 48 h, cells were spun down and proliferation was assessed by XTT assays (Roche) according to the manufacturer's instructions. Briefly, 50 ml XTT labeling reagent, 1 ml electron-coupling reagent and 100 ml phenol red-free culture media were combined and applied to each well of the 96-well plates. Cells were then incubated for 4 h in a $CO_2$ incubator to allow for the yellow tetrazolium salt XTT to be cleaved by mitochondrial dehydrogenases of metabolic active cells to form the orange formazan dye, which can be quantified at 492 nm using a BioTek Synergy H1 MicroPlate Reader.

Results and Discussion

FRET-Suppression Assay of Potential IRE-1 Inhibitors.

To assess the in vitro activity of potential IRE-1 RNase inhibitors, the expression and purification of recombinant human IRE-1 for use in an in vitro FRET-suppression assay was evaluated. The cytoplasmic kinase/RNase domain (aa. 547-977) of human IRE-1 was expressed as a soluble puritin-His-tagged 59 kD fusion protein in SF21 cells and purified by Ni-NTA affinity chromatography. To confirm that hIRE-1 exhibited a functional RNase domain, its activity in vitro using a synthetic mRNA stem-loop corresponding to the XBP-1 substrate sequence was tested. This stem-loop incorporates a Cy5 fluorophore on its 5' end and the black hole quencher (BHQ) on its 3' end, resulting in fluorescence only upon site-specific cleavage by the protein. Protein (5 nM) was incubated in a 96-well plate at room temperature with different concentrations of the XPB-1 stem loop for up to 2 h, and fluorescence was measured upon excitation and emission at 620 and 680 nm, respectively. Recombinant hIRE-1 exhibited functional RNase activity a $K_m$ value of 45 nM.

A set of known IRE-1 inhibitors, synthetic analogs, and commercially available salicyladehyde derivatives were evaluated for anti-IRE-1 RNase activity by using the FRET-suppression assay (FIG. 34). Naphthaldehyde derivative 2 (A-I06) is believed to be the bioactive breakdown product of the known IRE-1 inhibitor 1 (STF-038010). In this study, 1 and 2 exhibit similar $IC_{50}$ values (9.94 and 9.73 mM, respectively), while decomposition product 8 and reduced derivative 9 showed no appreciable inhibition at 20 mM. The salicylaldehyde moiety alone was not sufficient for IRE-1 RNase inhibition, as evidenced by the weak activity (>20 mM $IC_{50}$) of compounds 10-13. Modification of the aldehyde or phenol functionalities also resulted in inactive compounds (14-16). Coumarin derivative 5, exhibited significantly enhanced potency against IRE-1 RNase function with an $IC_{50}$ value of 206 nM in the FRET-suppression assay.

Synthesis of Tricyclic Chromenones

Analogs 20a-d were synthesized in 4 steps from the appropriate amino acids (FIG. 35). Installation of the aldehyde moiety in each case relied on a Duff formylation carried out using hexamethylenetetramine (HMTA) in refluxing glacial acetic acid. Refluxing TFA using intermediate 19b as a starting material, formylation was attended by an annulation reaction involving the pendant carbamate nitrogen to give tetrahydrochromeno[3,4-c]pyridine 21b as the sole product. The structure and connectivity of this tricyclic scaffold was confirmed by HMBC NMR. The yield of 21b improved to 41% when the reaction was preceded by acetylation of the o-hydroxyl group.

A proposed mechanism for the formation of 21b involves electrophilic aromatic substitution at position 3 of the chromenone core (FIG. 36). The reaction of electron rich aromatics with HMTA in organic acid occasionally results in aminomethylation in addition to formylation via decomposition of intermediates such as B. In the case of 21b, this decomposition is likely precluded by attack of the carbamate nitrogen onto the electrophilic methylene group in C. The interrupted Duff reaction at position 3 presumably occurs prior to formylation at position 8, as the use of only 1 equivalent of HMTA in refluxing TFA afforded intermediate D as the major product from 19b. The concomitant annulation reaction was not observed in the case of substrate 19a under any of the conditions listed in FIG. 34. However, hexahydrochromeno[3,4-c]azepine 21c and hexahydrochromeno[3,4-c]azocine 21d were isolated as the sole products from 19c and 19d when TFA was used as the solvent.

Structure-Activity Relationships.

When evaluated in the FRET-suppression assay, bicyclic derivatives 19a-d, exhibited inhibitory activities in the 100-500 nM range (FIG. 37). The constrained tricyclic derivative III 21b consistently showed enhanced activity against IRE-1 RNase activity relative to the bicyclic compounds 20b and 5 in side-by-side experiments. Given the optimal in vitro potency and chemical yield of 21b, a family of analogs to assess the relationship between the hydroxyl group and the distal N-substituent (FIG. 38) was synthesized. A covalent irreversible inhibitor 23 was obtained by chlorination of the reduced derivative 22. Compounds 24 and 25 were prepared by acid-catalyzed protection of the aldehyde in 21b as the 1,3-dioxane or dithiane derivatives. Analogs 26 and 27 were prepared by O-alkylation of 24, followed by acidic hydrolysis of the dioxane. Compounds 29-34 were synthesized by reaction of intermediate 28 with various acylating or alkylating reagents, followed by acidolysis.

Alternative electrophilic groups at the 8 position of the chromenone core were evaluated. FIG. 39 depicts the synthesis of analogs 36-42 from compound 21b. Formation of the ketone in 36 via oxidation of the Grignard product required prior protection of the o-hydroxyl as methoxymethyl ether 35. Olefination of 35 and acetal hydrolysis afforded electrophilic analogs 37 and 38. Oxidized variants 40-42 were synthesized via Pinnick oxidation of 35.

All compounds were evaluated by FRET-suppression assay in side-by-side experiments using 21b as a control inhibitor (Table 2). Protection of the aldehyde group in 21b as the 1,3-dioxane or dithiane acetal (24 and 25) resulted in weaker IRE-1 inhibitory activity. Alkylation of the phenol oxygen (compounds 26, 27, and 35) resulted in a complete loss of potency below 20 mM. The N-acyl derivative 29 exhibited an $IC_{50}$ value of 312 nM while N-alkyl analogs 30-33 were found to be slightly more potent. N-benzyl analog 31 was almost 3-fold more active than the corresponding fluorinated derivative 32. Guanidinylation to give 34 resulted in a notable increase in potency ($IC_{50}$=47 nM) relative to the parent compound, though solubility decreased. Ketone 36, vinyl sulfone 38, and Weinreb amide 42 showed no significant IRE-1 RNase inhibitory activity below 20 mM. However, electrophilic compounds 37, 40, and 41 displayed moderate potency (1-5 mM) in vitro. Also of note, 1,3-dioxane derivative 24 exhibited an in vitro $IC_{50}$ of 3.1 mM, whereas the corresponding 1,3-dithiane analog 25 displayed more than 5-fold weaker activity. To confirm that the enhanced inhibitory activity of 24 is not simply a function of a labile aldehyde masking group, stability studies in assay buffer were carried out; no significant decomposition of the 1,3-dioxane moiety over 12 hours was observed.

TABLE 2

In vitro IRE-1 RNase inhibition by analogs of 21b.

| compound | $IC_{50}$ (nM) | 95% CI (nM) |
|---|---|---|
| 21b | 111 | (76-162) |
| 22 | >20000 | — |
| 23 | >20000 | — |
| 24 | 3051 | (2031-4584) |
| 25 | 16210 | (12900-20360) |
| 26 | >20000 | — |

TABLE 2-continued

In vitro IRE-1 RNase inhibition by analogs of 21b.

| compound | $IC_{50}$ (nM) | 95% CI (nM) |
|---|---|---|
| 27 | >20000 | — |
| 28 | 1230 | (704-2148) |
| 29 | 312 | (222-439) |
| 30 | 200 | (149-268) |
| 31 | 113 | (62-207) |
| 32 | 303 | (181-500) |
| 33 | 255 | (183-354) |
| 34 | 47 | (35-64) |
| 35 | >20000 | — |
| 36 | >20000 | — |
| 37 | 1718 | (1289-2288) |
| 38 | >20000 | — |
| 40 | 4109 | (3099-5448) |
| 41 | 5644 | (3902-8162) |
| 42 | >20000 | — |

Inhibition of XBP-1s Expression in Whole Cells.

In order to determine whether the inhibitors could block the expression of XBP-1s in whole cells, LPS-stimulated B cells from the spleens of wild-type mice were incubated with 20 mM of selected compounds for 24 hours, lysed the cells, and analyzed the lysates for the expression of XBP-1s by immunoblots. Compounds 29 and 30 potently suppress the expression of XBP-1s at 20 mM in wild-type mouse B cells (FIG. 40A). In addition, 5, 21b, and 24 exhibit strong inhibition of XBP-1s, as does treatment with 50 mM of 2. Despite their activity in the FRET-suppression assay, compounds 31-34 did not effectively inhibit XBP-1s expression in whole cells, presumably due to poor cell permeability and solubility. Compounds 37, 40, and 41, which featured alternative electrophilic functional groups, similarly showed little to no inhibitory effect on XBP-1s expression in B cells at 20 mM. An inverse correlation between pharmacological inhibition of XBP-1s and expression level of IRE-1 (FIG. 40A) was observed.

The IRE-1/XBP-1 pathway is known to be critical for the survival multiple myeloma, malignancies derives from plasma cells. However, the functional role of the ER stress response in leukemia or lymphoma derived from mature B cells has been largely overlooked because leukemia and lymphoma cells do not expand their ER like that of multiple myeloma cells. Chronic lymphocytic leukemia (CLL) growth and survival is highly dependent on the IRE-1/XBP-1 pathway and is inhibited by small molecules targeting IRE-1 RNase activity. Mantle cell lymphoma (MCL) is an incurable non-Hodgkin's lymphoma developed from mantle zone-resident B cells. Since the role of the IRE-1/XBP-1 pathway in MCL is unknown, the MCL cell lines, Mino and Jeko, were examined for the expression of XBP-1s. It was shown that XBP-1s is constitutively expressed by both. Inhibitors were examined for inhibition of XBP-1s in these human MCL cell lines. As with wild-type mouse B cells, compounds 21b, 29, and 30 potently suppress the expression of XBP-1s and induce upregulation of IRE-1 in Mino and Jeko cells. N-24 5C).

To establish the dependency of XBP-1s expression on inhibitor concentration, MCL cells were used to determine the whole cell $IC_{50}$ values for 21b, 29, and 30, in comparison to 5, by immunoblots and densitometry (FIG. 40D-FIG. 40G). Compound 30 proved to be the most potent inhibitor of XBP-1s expression in both Mino and Jeko cell lines ($IC_{50}$=0.57 and 0.98 mM, respectively).

Lastly, XTT dose-response experiments to determine approximate $GI_{50}$ concentrations for 30, the most potent inhibitor of XBP-1s expression, was performed. After 48 h treatment, 30 exhibited $GI_{50}$ values of 34 and 19 mM in Mino and Jeko cells, respectively (FIG. 41A). Total growth inhibition by 30 was achieved between 55 and 66 mM for these cell lines. It was shown that growth inhibition is the result of apoptosis by treating Mino and Jeko cells with 30 for 72 h and analyzing cell lysates for cleaved PARP. Consistent with its superior potency in the suppression of XBP-1s, compound 30 induced PARP cleavage more strongly than either 21b or 5 at 50 mM (FIG. 41B). A $GI_{50}$ value of −34 mM in LPS-stimulated wild-type mouse B cells after treatment with 30 for 72 hour was obtained. The results showed that the growths of antibody-secreting plasma cells are also sensitive to inhibition of IRE-1 RNase activity.

CONCLUSION

The synthesis and biological characterization of novel inhibitors of IRE-1 have been demonstrated. Although various salicylaldehydes have been reported to inhibit IRE-1 RNase activity in vitro, the result show that the presence of an o-hydroxy aromatic aldehyde is not sufficient for biological activity. A series of carbamate substituted 2H-chromene-2-ones were prepared. Duff formylation of these substrates resulted in a tandem annelation reaction, giving rise to novel fused tricyclic scaffolds. Tetrahydrochromeno[3,4-c]pyridine 21b served as a lead compound for the synthesis of a family of analogs.

Replacement of the critical aldehyde group in 21b with electrophilic surrogates diminished potency, however, some compounds retained weak to moderate inhibitory activity in vitro. Modifications to the distal N substituent were generally well tolerated. The ability of selected compounds to inhibit XBP-1s expression in wild-type B cells and human MCL cell lines highlights the importance of cell-based assays for this class of inhibitors, as a number of compounds with low- to mid-nanomolar activity in the FRET-suppression assay did not significantly reduce XBP-1s expression in whole cells. The N-methyl analog 30 displayed an in vitro IRE-1 RNase $IC_{50}$ value of 200 nM and potently inhibited the expression of XBP-1s in Mino and Jeko cells ($IC_{50}$=0.57 and 0.98 mM, respectively). Compared to 21b, compound 30 is also more effective at inducing apoptosis in MCL cells. The described tricyclic chromenones thus represent useful compounds for suppressing IRE-1 RNase activity in whole cells and for probing the importance of the IRE-1/XBP-1 pathway of the ER stress response in biological systems.

Example 4: Inhibition of XBP-1s in MCL Cell Lines by C-D06, C-C05, C-D03, and their Respective Prodrug Analogs Over 30 tricyclic B-H09 analogs (FIG. 47A) were synthesized to assess the influence of the electrophile, hydroxyl group, and distal N-substituent on IRE-1 RNase inhibitory activity. All compounds were evaluated by FRET-suppression assay and $IC_{50}$ values and 95% confidence intervals were calculated as a composite of at least 4 separate 10-point dose-response curves (FIG. 47B).

Alkylation of the phenol oxygen resulted in a complete loss of potency below 20 μM. The N-acyl derivative C-C05 exhibited an $IC_{50}$ value of 312 nM while N-alkylated analogs such as C-D06 and C-D03 were generally found to be slightly more potent. Guanidinylation to give C-D01 resulted in a notable increase in potency ($IC_{50}$=47 nM) relative to the parent compound. In order to determine whether new inhibitors could block the expression of XBP- 1s in whole cells, LPS-stimulated wild-type B cells from MD4 mice were incubated with 20 μM of selected compounds for 24 hours, lysed the cells, and analyzed the lysates for the expression of XBP-1s by immunoblots. C-C05, and C-D06 potently suppress the expression of XBP-1, as does C-B06, the active component of B-I09 (FIG. 47C). Despite strong activity in the FRET-suppression assay, compounds C-D01, C-C02, and C-C10 did not effectively inhibit XBP-1s expression in whole cells, presumably due to problems with cell permeability and solubility. Compounds C-CO6, C-C08, and C-D08, which feature alternative electrophilic functional groups, similarly showed little to no effect on XBP-1s expression in B cells at 20 μM. A negative correlation between pharmacological inhibition of XBP-1s and expression level of IRE-1 was shown.

A subset of inhibitors were also evaluated in the MCL cell lines Mino and Jeko at 20 μM, with C-C05, C-D03, C-D06, exhibiting strong suppression of XBP-1s (FIG. 47D and FIG. 47E). The 1,3-dioxane masked analogs of C-C05 and C-D06 (C-G02 and C-G04) also completely inhibited XBP-1s at the protein level in both Mino and Jeko cells. Notably, 1,3-dioxane protection of analogs C-D02 and C-D03 (as C-G06 and C-G05, respectively) enhanced cellular efficacy, consistent with previous data with B-H09 and B-I08. C-C05 and C-D06 potently block the expression of XBP-1s in Mino and Jeko cells cell lines in a dose-dependent manner (FIG. 47F-FIG. 47I), exhibiting IC50 values in the sub-micromolar range.

Other advantages which are obvious and which are inherent to the invention will be evident to one skilled in the art. It will be understood that certain features and sub-combinations are of utility and can be employed without reference to other features and sub-combinations. This is contemplated by and is within the scope of the claims. Since many possible embodiments can be made of the invention without departing from the scope thereof, it is to be understood that all matter herein set forth or shown in the accompanying drawings is to be interpreted as illustrative and not in a limiting sense.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A compound having the following formula:

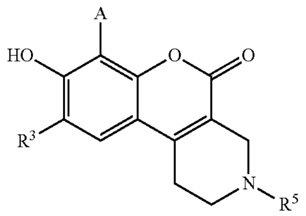

wherein

A is a chalcogen containing moiety;

$R^3$ is hydrogen, halogen, hydroxy, amino, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted alkylaryl, substituted or unsubstituted aryl, substituted or unsubstituted alkylheteroaryl, or substituted or unsubstituted heteroaryl;

$R^5$ is hydrogen, substituted or unsubstituted benzyl, substituted or unsubstituted benzoate, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted haloalkyl, substituted or unsubstituted cycloalkyl, substituted or unsubstituted heterocycloalkyl, substituted or unsubstituted alkylaryl, substituted or unsubstituted aryl, substituted or unsubstituted alkylheteroaryl, or substituted or unsubstituted heteroaryl;

or a pharmaceutically acceptable salt thereof.

2. The compound of claim 1, wherein A is an aldehyde, dioxane or alcohol group.

3. The compound of claim 1, wherein A is a reduced aldehyde, benzoate, ester, ketone, carbonyl, ether, carboxylic acid, alcohol, or alkoxyl.

4. The compound of claim 1, wherein A is an amine, amide, sulfonamide, sulfonyl, sulfinyl, halogenated alkyl, $CH{=}CH{-}CO_2R^6$, or $CH{=}CHSO_2R^6$; where $R^6$ is H, OH, or alkyl.

5. The compound of claim 1, wherein A is a dioxane group.

6. The compound of claim 1, wherein $R^3$ is an alkoxy group.

7. The compound of claim 1, wherein $R^3$ is $-OCH_3$.

8. The compound of claim 1, wherein $R^5$ is chosen from hydrogen, benzyl, substituted benzyl, acetate, alkyl, substituted alkyl, amidine, or substituted amindine.

9. The compound of claim 1, wherein $R^5$ is an alkyl group.

10. The compound of claim 1, wherein $R^5$ is $CH_3$.

11. The compound of claim 1, wherein the compound has the following formula:

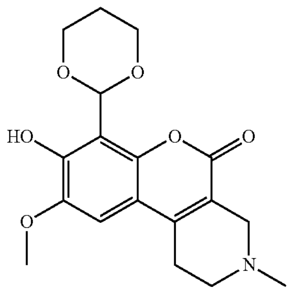 [SMILES: COc1cc2c3c(c(=O)oc2c(C2OCCCO2)c1O)CN(C)CC3]

or a pharmaceutically acceptable salt thereof.

12. A pharmaceutical composition comprising the compound of claim 1.

13. The pharmaceutical composition of claim 12, further comprising ibrutinib.

* * * * *